United States Patent
Kelly

(10) Patent No.: US 11,013,773 B2
(45) Date of Patent: May 25, 2021

(54) LACTIC ACID BACTERIAL STRAINS

(71) Applicant: 4D Pharma Research Limited, Aberdeen (GB)

(72) Inventor: Denise Kelly, Aberdeen (GB)

(73) Assignee: 4D Pharma Research Limited, Aberdeen (GB)

( * ) Notice: Subject to any disclaimer, the term of this patent is extended or adjusted under 35 U.S.C. 154(b) by 0 days.

(21) Appl. No.: 16/206,250

(22) Filed: Nov. 30, 2018

(65) Prior Publication Data

US 2019/0216865 A1 Jul. 18, 2019

Related U.S. Application Data

(60) Continuation of application No. 15/359,144, filed on Nov. 22, 2016, now Pat. No. 10,183,046, which is a division of application No. 14/232,475, filed as application No. PCT/GB2012/051686 on Jul. 13, 2012, now Pat. No. 9,539,293.

(30) Foreign Application Priority Data

Jul. 14, 2011 (GB) .................................... 1112091

(51) Int. Cl.
| | |
|---|---|
| A61K 35/747 | (2015.01) |
| A23L 33/135 | (2016.01) |
| C12R 1/225 | (2006.01) |
| C12R 1/23 | (2006.01) |
| C12R 1/25 | (2006.01) |
| C12N 1/20 | (2006.01) |
| A23K 10/18 | (2016.01) |

(52) U.S. Cl.
CPC ............ *A61K 35/747* (2013.01); *A23K 10/18* (2016.05); *A23L 33/135* (2016.08); *C12N 1/20* (2013.01); *C12R 1/225* (2013.01); *C12R 1/23* (2013.01); *C12R 1/25* (2013.01); *A23V 2002/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio et al. |
| 4,366,241 A | 12/1982 | Tom et al. |
| 4,683,202 A | 7/1987 | Mullis et al. |
| 4,816,567 A | 3/1989 | Cabilly et al. |
| 5,589,168 A | 12/1996 | Allen et al. |
| 5,599,795 A | 2/1997 | McCann et al. |
| 5,674,707 A | 10/1997 | Hintz et al. |
| 5,741,665 A | 4/1998 | Kato et al. |
| 5,925,657 A | 7/1999 | Seed et al. |
| 6,348,452 B1 | 2/2002 | Brown et al. |
| 6,468,964 B1 | 10/2002 | Rowe et al. |
| 6,645,530 B1 | 11/2003 | Borody |
| 7,101,565 B2 | 9/2006 | Monte |
| 7,485,325 B2 | 2/2009 | Swain |
| 7,625,704 B2 | 12/2009 | Fredricks et al. |
| 7,749,494 B2 | 7/2010 | Renaud et al. |
| 7,998,474 B2 | 8/2011 | Kelly |
| 8,197,805 B2 | 6/2012 | Lin et al. |
| 8,287,932 B2 | 10/2012 | Rosales et al. |
| 8,460,648 B2 | 6/2013 | Borody |
| 8,557,233 B2 | 10/2013 | MacSharry et al. |
| 9,011,834 B1 | 4/2015 | McKenzie et al. |

(Continued)

FOREIGN PATENT DOCUMENTS

| | | |
|---|---|---|
| CN | 1863540 A | 11/2006 |
| CN | 1917946 A | 2/2007 |

(Continued)

OTHER PUBLICATIONS

Jan. 17, 2019 First Office Action for CN201680041407.6 (Translated).

(Continued)

*Primary Examiner* — Ralph J Gitomer

(74) *Attorney, Agent, or Firm* — Wilson Sonsini Goodrich & Rosati

(57) ABSTRACT

A first aspect of the invention relates to a porcine lactic acid bacterial strain, wherein said bacterial strain is characterised by one or more of the following characteristics: (i) the ability to exhibit antimicrobial activity against *E. coli*; (ii) the ability to exhibit antimicrobial activity against *S. enteritidis*; (iii) the ability to suppress inflammation in IPEC cells induced by 12-0-tetradecaboylphorbol-13-acetate (PMA); (iv) the ability to block the attachment or invasion of IPEC cells by *S. enteritidis*; (v) the ability to block the attachment or invasion of IPEC cells by *E. coli*; (vi) the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin; and (vii) the ability to exhibit heat stability when subjected to three cycles of heating, each cycle comprising heating at a temperature of 70° C. for a period of 15 minutes. Further aspects of the invention relate to compositions comprising said bacterial strains, and therapeutic uses of said bacterial strains.

20 Claims, 25 Drawing Sheets

Specification includes a Sequence Listing.

(56) References Cited

U.S. PATENT DOCUMENTS

| | | | |
|---|---|---|---|
| 9,314,489 B2 | 4/2016 | Kelly et al. | |
| 9,371,510 B2 | 6/2016 | Moore | |
| 9,376,473 B2 | 6/2016 | Gleiberman et al. | |
| 9,539,293 B2* | 1/2017 | Kelly | A61K 35/747 |
| 9,610,307 B2 | 4/2017 | Berry et al. | |
| 9,662,381 B2 | 5/2017 | Honda et al. | |
| 9,796,762 B2 | 10/2017 | Kelly et al. | |
| 9,808,519 B2 | 11/2017 | Honda et al. | |
| 9,839,655 B2 | 12/2017 | Mulder et al. | |
| 9,855,302 B2 | 1/2018 | Gajewski et al. | |
| 9,937,211 B2 | 4/2018 | Kelly et al. | |
| 9,974,815 B2 | 5/2018 | Mulder et al. | |
| 9,987,311 B2 | 6/2018 | Mulder et al. | |
| 1,004,601 A1 | 8/2018 | Mulder et al. | |
| 1,005,857 A1 | 8/2018 | Grant et al. | |
| 1,008,077 A1 | 9/2018 | Crouzet et al. | |
| 1,008,602 A1 | 10/2018 | Bernalier-Donadille et al. | |
| 1,018,304 A1 | 1/2019 | Kelly | |
| 10,183,046 B2* | 1/2019 | Kelly | A23L 33/135 |
| 10,226,489 B2 | 3/2019 | Patterson et al. | |
| 2003/0147858 A1 | 8/2003 | Renaud et al. | |
| 2004/0106564 A1 | 6/2004 | Nilius et al. | |
| 2006/0073161 A1 | 4/2006 | Breton | |
| 2007/0258953 A1 | 11/2007 | Duncan et al. | |
| 2007/0286913 A1 | 12/2007 | Swain et al. | |
| 2008/0069861 A1 | 3/2008 | Brown et al. | |
| 2008/0206212 A1 | 8/2008 | McMahon et al. | |
| 2008/0260906 A1 | 10/2008 | Stojanovic | |
| 2008/0299098 A1 | 12/2008 | Se et al. | |
| 2010/0028449 A1 | 2/2010 | Prakash et al. | |
| 2010/0047209 A1 | 2/2010 | Stanton et al. | |
| 2010/0247489 A1 | 9/2010 | Saur-Brosch | |
| 2010/0284973 A1 | 11/2010 | Schiffer-Mannioui et al. | |
| 2010/0303782 A1 | 12/2010 | Cobb et al. | |
| 2010/0311686 A1 | 12/2010 | Kasper et al. | |
| 2010/0316617 A1 | 12/2010 | Renaud et al. | |
| 2011/0053829 A1 | 3/2011 | Baumhof et al. | |
| 2011/0086011 A1 | 4/2011 | Kasper et al. | |
| 2011/0280840 A1 | 11/2011 | Blaser et al. | |
| 2012/0020943 A1 | 1/2012 | Lin | |
| 2012/0107279 A1 | 5/2012 | Arigoni et al. | |
| 2013/0022575 A1 | 1/2013 | Cassity | |
| 2013/0130988 A1 | 5/2013 | Blareau et al. | |
| 2013/0195802 A1 | 8/2013 | Moore | |
| 2013/0280724 A1 | 10/2013 | Ramadan et al. | |
| 2013/0316032 A1 | 11/2013 | Itoh et al. | |
| 2013/0336931 A1 | 12/2013 | Wadstroem et al. | |
| 2014/0037716 A1 | 2/2014 | Nowill et al. | |
| 2014/0056852 A1 | 2/2014 | Guglielmetti et al. | |
| 2014/0112897 A1 | 4/2014 | Pyne et al. | |
| 2014/0147425 A1 | 5/2014 | Henn et al. | |
| 2014/0154218 A1 | 6/2014 | Kohno et al. | |
| 2014/0193464 A1 | 7/2014 | Lin et al. | |
| 2014/0199281 A1 | 7/2014 | Henn et al. | |
| 2014/0227227 A1 | 8/2014 | Qin et al. | |
| 2014/0328803 A1 | 11/2014 | McKenzie et al. | |
| 2014/0335131 A1 | 11/2014 | Mazmanian et al. | |
| 2014/0341921 A1 | 11/2014 | Honda et al. | |
| 2014/0363397 A1 | 12/2014 | Allen-Vercoe et al. | |
| 2015/0044173 A1 | 2/2015 | Jones et al. | |
| 2015/0071957 A1 | 3/2015 | Kelly et al. | |
| 2015/0104418 A1 | 4/2015 | Flint et al. | |
| 2015/0132264 A1 | 5/2015 | Kelly et al. | |
| 2015/0284781 A1 | 10/2015 | Klumpp et al. | |
| 2016/0058804 A1 | 3/2016 | Jones et al. | |
| 2016/0067188 A1 | 3/2016 | Cade et al. | |
| 2016/0184370 A1 | 6/2016 | McKenzie et al. | |
| 2016/0199424 A1 | 7/2016 | Berry et al. | |
| 2016/0223553 A1 | 8/2016 | Sears et al. | |
| 2017/0143772 A1 | 5/2017 | Mulder et al. | |
| 2017/0143773 A1 | 5/2017 | Mulder et al. | |
| 2017/0143774 A1 | 5/2017 | Mulder et al. | |
| 2017/0143775 A1 | 5/2017 | Mulder et al. | |
| 2017/0319634 A1 | 11/2017 | Grant et al. | |
| 2017/0326202 A1 | 11/2017 | Kelly | |
| 2017/0354695 A1 | 12/2017 | Grant et al. | |
| 2017/0360856 A1 | 12/2017 | Grant et al. | |
| 2017/0368110 A1 | 12/2017 | Grant et al. | |
| 2018/0072778 A1 | 3/2018 | Kelly et al. | |
| 2018/0078585 A1 | 3/2018 | Mulder et al. | |
| 2018/0078587 A1 | 3/2018 | Crott et al. | |
| 2018/0133265 A1 | 5/2018 | Stevenson | |
| 2018/0207207 A1 | 7/2018 | Bernalier-Donadille et al. | |
| 2018/0207208 A1 | 7/2018 | Jeffery et al. | |
| 2018/0214496 A1 | 8/2018 | Bernalier-Donadille | |
| 2018/0221421 A1 | 8/2018 | Bernalier-Donadille | |
| 2018/0250346 A1 | 9/2018 | Mulder et al. | |
| 2018/0271918 A1 | 9/2018 | Kelly et al. | |
| 2018/0344780 A1 | 12/2018 | Grant et al. | |
| 2018/0369292 A1 | 12/2018 | Bernalier-Donadille et al. | |
| 2018/0369293 A1 | 12/2018 | Jeffery et al. | |
| 2018/0369294 A1 | 12/2018 | Bernalier-Donadille et al. | |
| 2019/0000892 A1 | 1/2019 | Mulder et al. | |
| 2019/0008908 A1 | 1/2019 | Crouzet et al. | |

FOREIGN PATENT DOCUMENTS

| | | |
|---|---|---|
| CN | 1954066 A | 4/2007 |
| CN | 101590081 A | 12/2009 |
| CN | 102304483 A | 1/2012 |
| CN | 102031235 B | 7/2012 |
| CN | 102093967 B | 1/2013 |
| CN | 102905558 A | 1/2013 |
| CN | 102940652 A | 2/2013 |
| CN | 102373172 B | 3/2013 |
| CN | 103037876 A | 4/2013 |
| CN | 103142656 A | 6/2013 |
| CN | 103146620 A | 6/2013 |
| CN | 103156888 A | 6/2013 |
| CN | 103652322 A | 3/2014 |
| CN | 103781487 A | 5/2014 |
| CN | 103820363 A | 5/2014 |
| CN | 103849590 A | 6/2014 |
| CN | 103865846 A | 6/2014 |
| CN | 103981115 A | 8/2014 |
| CN | 103981117 A | 8/2014 |
| CN | 104160014 A | 11/2014 |
| CN | 104195075 A | 12/2014 |
| CN | 103509741 B | 2/2015 |
| CN | 102940652 B | 3/2015 |
| CN | 104435000 A | 3/2015 |
| CN | 103037876 B | 4/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| CN | 104560820 A | 4/2015 |
| CN | 105112333 A | 12/2015 |
| CN | 103820363 B | 2/2016 |
| CN | 103865846 B | 3/2016 |
| CN | 105982919 A | 10/2016 |
| DE | 19826928 A1 | 12/1999 |
| DE | 10206995 A1 | 9/2003 |
| EP | 0120516 A2 | 10/1984 |
| EP | 0238023 A2 | 9/1987 |
| EP | 0449375 A2 | 10/1991 |
| EP | 0581171 A1 | 2/1994 |
| EP | 0778778 A1 | 6/1997 |
| EP | 1141235 A2 | 10/2001 |
| EP | 1227152 A1 | 7/2002 |
| EP | 1448995 A1 | 8/2004 |
| EP | 1481681 A1 | 12/2004 |
| EP | 1675481 B1 | 11/2008 |
| EP | 1997499 A1 | 12/2008 |
| EP | 1997905 A1 | 12/2008 |
| EP | 1997906 A1 | 12/2008 |
| EP | 1997907 A1 | 12/2008 |
| EP | 2133088 A3 | 1/2010 |
| EP | 1280541 B2 | 3/2010 |
| EP | 2308498 A1 | 4/2011 |
| EP | 2217253 B1 | 6/2011 |
| EP | 1940243 B1 | 8/2011 |

(56) References Cited

FOREIGN PATENT DOCUMENTS

| | | |
|---|---|---|
| EP | 2359838 A1 | 8/2011 |
| EP | 1855550 B1 | 10/2011 |
| EP | 1871400 B1 | 10/2011 |
| EP | 2124972 B1 | 6/2012 |
| EP | 1773361 B2 | 9/2012 |
| EP | 1945234 B1 | 12/2012 |
| EP | 2323493 B8 | 12/2012 |
| EP | 2323494 B8 | 12/2012 |
| EP | 1629850 B2 | 5/2013 |
| EP | 2203551 B1 | 8/2013 |
| EP | 2140771 B1 | 12/2013 |
| EP | 2687227 A1 | 1/2014 |
| EP | 2179028 B1 | 8/2014 |
| EP | 2650002 A4 | 8/2014 |
| EP | 2164349 B1 | 9/2014 |
| EP | 2134835 B1 | 10/2014 |
| EP | 2810652 A2 | 12/2014 |
| EP | 2305838 B1 | 1/2015 |
| EP | 2832859 A1 | 2/2015 |
| ES | 2408279 A2 | 6/2013 |
| JP | H08259450 A | 10/1996 |
| JP | 2003261453 A | 9/2003 |
| JP | 2005097280 A | 4/2005 |
| JP | 2006265212 A | 10/2006 |
| JP | 2007084533 A | 4/2007 |
| JP | 2007116991 A | 5/2007 |
| JP | 2008195635 A | 8/2008 |
| JP | 2009507023 A | 2/2009 |
| JP | 2010246523 A | 11/2010 |
| JP | 5031249 B2 | 9/2012 |
| JP | 2013005759 A | 1/2013 |
| JP | 5183848 B2 | 4/2013 |
| JP | 2013527240 A | 6/2013 |
| JP | 2013201912 A | 10/2013 |
| JP | 2014196260 A | 10/2014 |
| JP | 2014534957 A | 12/2014 |
| JP | 2015500792 A | 1/2015 |
| JP | 5710876 B2 | 4/2015 |
| JP | 5792105 B2 | 10/2015 |
| KR | 100468522 B1 | 1/2005 |
| KR | 20100128168 A | 12/2010 |
| KR | 1020100128168 | 12/2010 |
| KR | 101017448 B1 | 2/2011 |
| KR | 101057357 B1 | 8/2011 |
| KR | 20130021764 A | 3/2013 |
| KR | 101250463 B1 | 4/2013 |
| KR | 20140037544 A | 3/2014 |
| KR | 20140061328 A | 5/2014 |
| PL | 229020 B1 | 5/2018 |
| RU | 2078815 C1 | 5/1997 |
| TW | I417054 B | 12/2013 |
| WO | WO-9117243 A1 | 11/1991 |
| WO | WO-9720577 A1 | 6/1997 |
| WO | WO-9730717 A1 | 8/1997 |
| WO | WO-9735956 A1 | 10/1997 |
| WO | WO-9843081 A1 | 10/1998 |
| WO | WO-9855131 A1 | 12/1998 |
| WO | WO-9857631 A1 | 12/1998 |
| WO | WO-9919459 A1 | 4/1999 |
| WO | WO-9942568 A1 | 8/1999 |
| WO | WO-9945955 A1 | 9/1999 |
| WO | WO-0116120 A1 | 3/2001 |
| WO | WO-0158275 A2 | 8/2001 |
| WO | WO-0185187 A1 | 11/2001 |
| WO | WO-0193904 A1 | 12/2001 |
| WO | WO-0207741 A1 | 1/2002 |
| WO | WO-02070670 A1 | 9/2002 |
| WO | WO-02085933 A1 | 10/2002 |
| WO | WO-02094296 A1 | 11/2002 |
| WO | WO-03010297 A1 | 2/2003 |
| WO | WO-03022255 A2 | 3/2003 |
| WO | WO-03045317 A2 | 6/2003 |
| WO | WO-03046580 A1 | 6/2003 |
| WO | WO-03053220 A2 | 7/2003 |
| WO | WO-2004003235 A3 | 6/2004 |
| WO | WO-2004085628 A1 | 10/2004 |
| WO | WO-2005007834 A1 | 1/2005 |
| WO | WO-2005030133 A2 | 4/2005 |
| WO | WO-2005032567 A2 | 4/2005 |
| WO | WO-2005058335 A1 | 6/2005 |
| WO | WO-2005032567 A3 | 7/2005 |
| WO | WO-2005107381 A2 | 11/2005 |
| WO | WO-2006033949 A1 | 3/2006 |
| WO | WO-2006033950 A1 | 3/2006 |
| WO | WO-2006033951 A1 | 3/2006 |
| WO | WO-2006102350 A1 | 9/2006 |
| WO | WO-2006102536 A2 | 9/2006 |
| WO | WO-2006091103 A3 | 10/2006 |
| WO | WO-2006130205 A1 | 12/2006 |
| WO | WO-2007027761 A2 | 3/2007 |
| WO | WO-2007098371 A2 | 8/2007 |
| WO | WO-2007136719 A2 | 11/2007 |
| WO | WO-2007140230 A3 | 2/2008 |
| WO | WO-2008031438 A3 | 5/2008 |
| WO | WO-2008055703 A2 | 5/2008 |
| WO | WO-2008064489 A1 | 6/2008 |
| WO | WO-2008053444 A3 | 7/2008 |
| WO | WO-2008134450 A2 | 11/2008 |
| WO | WO-2008153377 A1 | 12/2008 |
| WO | WO-2009027753 A1 | 3/2009 |
| WO | WO-2009030481 A1 | 3/2009 |
| WO | WO-2009055362 A1 | 4/2009 |
| WO | WO-2009072889 A1 | 6/2009 |
| WO | WO-2009079564 A2 | 6/2009 |
| WO | WO-2009043856 A3 | 7/2009 |
| WO | WO-2009100331 A2 | 8/2009 |
| WO | WO-2009128949 A2 | 10/2009 |
| WO | WO-2009151315 A1 | 12/2009 |
| WO | WO-2009154463 A2 | 12/2009 |
| WO | WO-2009156301 A1 | 12/2009 |
| WO | WO-2010002241 A1 | 1/2010 |
| WO | WO-2010036876 A2 | 4/2010 |
| WO | WO-2010037408 A1 | 4/2010 |
| WO | WO-2010037539 A1 | 4/2010 |
| WO | WO-2010048481 A1 | 4/2010 |
| WO | WO-2010063601 A1 | 6/2010 |
| WO | WO-2010081126 A3 | 9/2010 |
| WO | WO-2010129839 A1 | 11/2010 |
| WO | WO-2010130659 A1 | 11/2010 |
| WO | WO-2010130660 A1 | 11/2010 |
| WO | WO-2010130662 A1 | 11/2010 |
| WO | WO-2010130663 A1 | 11/2010 |
| WO | WO-2010130697 A1 | 11/2010 |
| WO | WO-2010130699 A1 | 11/2010 |
| WO | WO-2010130700 A1 | 11/2010 |
| WO | WO-2010130701 A1 | 11/2010 |
| WO | WO-2010130702 A1 | 11/2010 |
| WO | WO-2010130704 A1 | 11/2010 |
| WO | WO-2010130710 A1 | 11/2010 |
| WO | WO-2010130713 A1 | 11/2010 |
| WO | WO-2010/143940 A1 | 12/2010 |
| WO | WO-2010139531 A1 | 12/2010 |
| WO | WO-2010142504 A1 | 12/2010 |
| WO | WO-2010143961 A1 | 12/2010 |
| WO | WO-2010147714 A1 | 12/2010 |
| WO | WO-2010133475 A3 | 1/2011 |
| WO | WO-2011000620 A1 | 1/2011 |
| WO | WO-2011000621 A1 | 1/2011 |
| WO | WO-2011005756 A1 | 1/2011 |
| WO | WO-2010133472 A3 | 2/2011 |
| WO | WO-2011020748 A1 | 2/2011 |
| WO | WO-2011036539 A1 | 3/2011 |
| WO | WO-2011043654 A1 | 4/2011 |
| WO | WO-2011044208 A1 | 4/2011 |
| WO | WO-2011058535 A1 | 5/2011 |
| WO | WO-2011096808 A1 | 8/2011 |
| WO | WO-2011096809 A1 | 8/2011 |
| WO | WO-2011110918 A1 | 9/2011 |
| WO | WO-2011121379 A1 | 10/2011 |
| WO | WO-2011149335 A1 | 12/2011 |
| WO | WO-2011152566 A2 | 12/2011 |
| WO | WO-2011153226 A2 | 12/2011 |
| WO | WO-2011157816 A1 | 12/2011 |
| WO | WO-2012024638 A2 | 2/2012 |

(56) References Cited

FOREIGN PATENT DOCUMENTS

| | | |
|---|---|---|
| WO | WO-2011153226 A3 | 3/2012 |
| WO | WO-2012062780 A1 | 5/2012 |
| WO | WO-2012071380 A1 | 5/2012 |
| WO | WO-2012105312 A1 | 8/2012 |
| WO | WO-2012122478 A1 | 9/2012 |
| WO | WO-2012140636 A1 | 10/2012 |
| WO | WO-2012142605 A1 | 10/2012 |
| WO | WO-2012145491 A2 | 10/2012 |
| WO | WO-2012158517 A1 | 11/2012 |
| WO | WO-2012165843 A2 | 12/2012 |
| WO | WO-2013005836 A1 | 1/2013 |
| WO | WO-2013008039 A2 | 1/2013 |
| WO | WO-2013037068 A1 | 3/2013 |
| WO | WO-2013050792 A1 | 4/2013 |
| WO | WO-2013053836 A1 | 4/2013 |
| WO | WO-2013080561 A1 | 6/2013 |
| WO | WO-2013124725 A1 | 8/2013 |
| WO | WO-2013144701 A1 | 10/2013 |
| WO | WO-2013153358 A1 | 10/2013 |
| WO | WO-2013154725 A1 | 10/2013 |
| WO | WO-2013181694 A1 | 12/2013 |
| WO | WO-2014001368 A1 | 1/2014 |
| WO | WO-2014020004 A1 | 2/2014 |
| WO | WO-2014032108 A1 | 3/2014 |
| WO | WO-2014036182 A2 | 3/2014 |
| WO | WO-2014043593 A2 | 3/2014 |
| WO | WO-2014064359 A1 | 5/2014 |
| WO | WO-2014067976 A1 | 5/2014 |
| WO | WO-2014070014 A1 | 5/2014 |
| WO | WO-2014070225 A1 | 5/2014 |
| WO | WO-2014075745 A1 | 5/2014 |
| WO | WO-2014078911 A1 | 5/2014 |
| WO | WO-2014082050 A1 | 5/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014130540 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014167338 A1 | 10/2014 |
| WO | WO-2014182966 A1 | 11/2014 |
| WO | WO-2014200334 A1 | 12/2014 |
| WO | WO-2014201037 A2 | 12/2014 |
| WO | WO-2015003001 A1 | 1/2015 |
| WO | WO-2015006355 A2 | 1/2015 |
| WO | WO-2015013214 A2 | 1/2015 |
| WO | WO-2015017625 A1 | 2/2015 |
| WO | WO-2015021936 A1 | 2/2015 |
| WO | WO-201503305 A1 | 3/2015 |
| WO | WO-2015038731 A1 | 3/2015 |
| WO | WO-2015057151 A1 | 4/2015 |
| WO | WO-2015077794 A1 | 5/2015 |
| WO | WO-2015095241 A2 | 6/2015 |
| WO | WO-2015077794 A4 | 7/2015 |
| WO | WO-2015156419 A1 | 10/2015 |
| WO | WO-2015156519 A1 | 10/2015 |
| WO | WO-2015168534 A1 | 11/2015 |
| WO | WO-2015169944 A1 | 11/2015 |
| WO | WO-2015095241 A4 | 12/2015 |
| WO | WO-2016019506 A1 | 2/2016 |
| WO | WO-2016033439 A2 | 3/2016 |
| WO | WO-2016036615 A1 | 3/2016 |
| WO | WO-2016057671 A1 | 4/2016 |
| WO | WO-2016065324 A1 | 4/2016 |
| WO | WO-2016069795 A2 | 5/2016 |
| WO | WO-2016069801 A1 | 5/2016 |
| WO | WO-2016070151 A1 | 5/2016 |
| WO | WO-2016086161 A1 | 6/2016 |
| WO | WO-2016086205 A2 | 6/2016 |
| WO | WO-2016086206 A1 | 6/2016 |
| WO | WO-2016086208 A1 | 6/2016 |
| WO | WO-2016086209 A1 | 6/2016 |
| WO | WO-2016086210 A1 | 6/2016 |
| WO | WO-2016102950 A1 | 6/2016 |
| WO | WO-2016102951 A1 | 6/2016 |
| WO | WO-2016118730 A1 | 7/2016 |
| WO | WO-2016139217 A1 | 9/2016 |
| WO | WO-2016149449 A1 | 9/2016 |
| WO | WO-2016149687 A1 | 9/2016 |
| WO | WO-2016203218 A1 | 12/2016 |
| WO | WO-2016203220 A1 | 12/2016 |
| WO | WO-2017091753 A1 | 6/2017 |
| WO | WO-2017148596 A1 | 9/2017 |
| WO | WO-2018011594 A1 | 1/2018 |
| WO | WO-2018/112365 A2 | 6/2018 |
| WO | WO-2018112363 | 6/2018 |
| WO | WO-2018112363 A1 | 6/2018 |
| WO | WO-2018112365 A2 | 6/2018 |

OTHER PUBLICATIONS

Jan. 17, 2019 Notice of Allowance for U.S. Appl. No. 15/803,721.
Dec. 21, 2018 Notice of Allowance U.S. Appl. No. 15/700,700.
Jan. 30, 2019 Notice of Corrected Allowability for U.S. Appl. No. 15/803,721.
Jan. 30, 2019 Final Rejection for U.S. Appl. No. 15/842,635.
Jan. 1, 2019 Non-Final Office Action U.S. Appl. No. 16/040,356.
Mar. 4, 2019 Final Office Action for U.S. Appl. No. 15/704,245.
4d Pharma Plc: "Clinical Update—RNS—London Stock Exchange", Jul. 19, 2016.
4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].
Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.
Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006.
Altschul et al. 'Basic local alignment search tool.' Journal of Molecular Biology. 1990, vol. 215, No. 3, pp. 403-410.
"Amedei, A. et al. Multiple sclerosis: the role of cytokines in pathogenesis and in therapies. Int J Mol Sci. Oct. 19, 2012;13(10):13438-60. doi: 10.3390/ijms131013438."
Aminov et al. Molecular diversity, cultivation, and improved detection by fluorescent in situ hybridization of a dominant group of human gut bacteria related to *Roseburia* spp. or *Eubacterium rectale*. Applied and environmental microbiology. 2006, vol. 72, No. 9, pp. 6371-6376.
An et al. (1985) "New cloning vehicles for transformation of higher plants," EMBO J. 4:277-284.
An et al. (1988) "Binary Vectors," Plant Molecular Biology Manual. A3:1-19.
An et al. Transformation of Tobacco, Tomato, Potato, and *Arabiodopsis thaliana* Using a Binary Ti Vector System,Plant Physiol. May 1986; 81:301-305.
Anonymous: "4D pharma's Blautix for Irritable Bowel Syndrome shows positive impact—pharmaceutical daily news", Dec. 13, 2016.
Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sep. 8, 2011:DOI:10.1152.ajpg.00167.2011.
Archer et al. (1997) "The Molecular Biology of Secreted Enzyme Production by Fungi," Critical Reviews Biotechnology. 17(4):273-306.
Arenberg, et al., Interferon-γ-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.

(56) References Cited

OTHER PUBLICATIONS

Atarashi et al. Induction of colonic regulatory T cells by indigenous *Clostridium* species. Science 331(6015):337-341 (2011).
Atarashi et al., Th17 Cell Induction by Adhesion of Microbes to Intestinal Epithelial Cells. Cell, vol. 163, No. 2, Oct. 8, 2015. pp. 367-380.
Atarashi, et al., Treg induction by a rationally selected mixture of Clostridia strains from the human microbiota. Supplementary Information. Nature 500, 232-236 (Aug. 8, 2013) doi:10.1038/nature12331.
Atarashi, K. et al., Treg induction by a rationally selected mixture of Clostridia strains from the human microbiota. Nature. 2013; 500(7461):232-236.
ATCC Catalog, https://www.atcc.org/search_results.aspx?dsNav=Ntk:primarysearch%7cbacteroides+thetaiotaomicron%7c3%7c,Ny:true,ro:0,N:1000552&searchterms=bacteroides+thetaiotaomicron&redir=1, Accessed on May 2, 2018.
Atlas, R. Handbook of Microbiological Media, Fourth Edition. CRC Press. 2010.
Ausubel et al. (1999) Short Protocols in Molecular Biology. 4th edition. pp. 7-58 to 7-60, and Chapter 18. pp. 18-1 to 18-23.
Ausubel, et al. Current Protocols in Molecular Biology. 1987. Supplement 30.
Ausubel et al., Short protocols in molecular biology. Fifth edition, 2002.
Awadel-Kariem, Mustafa et al., First report of *Parabacteroides goldsteinii* bacteraemia in a patient with complicated intra-abdominal infection, Anaerobe, vol. 16, Issue 3, Jun. 2010, pp. 223-225.
Azad, M.B. et al., Probiotic supplementation during pregnancy or infancy for the prevention of asthma and wheeze: systematic review and meta-analysis BMJ 2013; 347 :f6471.
Aziz et al. The RAST Server: rapid annotations using subsystems technology. BMC Genomics. 2008, vol. 9, No. 1, pp. 75.
Aziz, R.K., Bartels, D., Best, A.A., DeJongh, M., Disz, T., Edwards, R.A., et al. (2008). The RAST Server: Rapid Annotations using Subsystems Technology. BMC Genomics 9, 75. doi: 10.1186/1471-2164-9-75.
Bagge, et al., Diversity of spore-forming bacteria in cattle manure, slaughterhouse waste and samples from biogas plants. Journal of applied microbiology. 2010;109: 1549-1565.
Balato, et al., Effects of adalimumab therapy in adult subjects with moderate-to-severe psoriasis on Th17 pathway. (2014) J Eur Acad Dermatol Venereol. 28(8):1016-24.
Banfield, J. & Murphy, K.R., Non-Th2, Late-onset, non-allergic asthma. Copd & Asthma for NPs, A peer-reviewed newsletter, Aug. 2016; 14: 8 Pages.
Barcenilla et al. "Phylogenetic relationships of butyrate-producing bacteria from the human gut" Applied and environmental microbiology. 2000, vol. 66, No. 4, pp. 1654-1661.
Barry, et al., Criteria for Disksusceptibility tests and quality control guidelines for the cefoperazone-sulbactam combination, Journal of clinical microbiology, Jan. 1988;26(1):13-17.
Beaucage, et al. Deoxynucleoside phosphoramidites—A new class of key intermediates for deoxypolynucleotide synthesis. Tetrahedron Letters, vol. 22, 1981, pp. 1859-1869.
Beggs (1978) "Transformation of yeast by a replicating hybrid plasmid," Nature. 275:104-109.
Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.
Berg et al. (1996) "Enterocolitis and colon cancer in interleukin-10-deficient mice are associated with aberrant cytokine production and CD4(+) TH1-like responses," The Journal of Clinical Investigation. 98(4):1010-1020.
Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.

Berger, S. Gideon guide to medically important bacteria. Gideon E-book Series. 2017 edition. 4 pages.
Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen Helicobacter pylori. Infect Immun 74(1), 425-434. doi: 10.1128/IAI.74.1.425-434.2006.
Bernalier, A., et al., "Diversity of H2/C02-utilizing acetogenic Bacteria from Feces of Non-Methane-Producing Humans", Current Microbiology vol. 33 (Aug. 1996), pp. 94-99, Springer-Vertag New York Inc., USA.
Bernalier et al., "Acetogenesis from H02 and C0-2 by Methane and Non-Methane-Producing Human Colonic Bacterial Communities" Fems Microbiology Ecology. vol. 19. No. 3. 1996. pp. 193-202. XP000979130.
Bernalier et al. *Ruminococcus hydrogenotrophicus* sp. nov., a new H2/CO2-utilizing acetogenic bacterium isolated from human feces. 1996 Arch. Microbiol. 166 (3), 176-183.
Bertram, J. et al. Establishment of a cloned line of Lewis lung carcinoma cells adapted to cell culture. (1980) Cancer let. 11:63-73.
Birdi, K.S. Handbook of Surface and Colloid Chemistry, 2nd Edition. CRC Press. 1997.
Blandino, G., Fazio, D., DiMarco, R. Probiotics: Overview of microbiological and immunological characteristics (2008). Expert Review of Anti-Infective Therapy, 6 (4), pp. 497-508.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., English Abstract "Carbohydrate substitutes: comparative study of intestinal absorption of fructose, sorbitol und xylitol", "Zuckeraustauschstoffe: Vergleichende Untersuchung zur intestinalen Resorption von Fructose, Sorbit and Xylit", Medizinische Klinik 89, Technischen Universitat Munchen (Munich) Nov. 15, 1994; 89 (11): 575-8 (Article in German), Urban & Vogel, Munich, Germany.
Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.
Bottacini, et al., Comparative genomics of the Bifidobacterium brevetaxon. BMC Genomics, 2014; 15:170. DOI:10.1186/1471-1471-2164-15-170.
Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/s41598-018-28919-4.
Bottacini, F., O'Connell Motherway, M., Kuczynski, J., O'Connell, K.J., Serafini, F., Duranti, S., et al. (2014). Comparative genomics of the Bifidobacterium breve taxon. BMC Genomics 15(1), 170. doi: 10.1186/1471-2164-15-170.
Brand et al., Collagen-induced arthritis, 2007; Protocol 2(5):1269-1275.
Brasel et al. (2000) "Generation of murine dendritic cells from ftl3-ligand-supplemented bone marrow cultures," Blood. 96(9):3029-3039.
Bressa, et al., Differences in gut microbiota profile between women with active lifestyle and sedentary women. Plos One, 2017; 12(2): 1-20.
Bry et al. A model of host-microbial interactions in an open mammalian ecosystem. Science 273(5280):1380-1383 (1996).
Buffie et al., Precision microbiome restoration of bile acid-mediated resistance to Clostridium difficile. Nature, 517(7533):205-208 (2015).
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.

(56) References Cited

OTHER PUBLICATIONS

"Campeau, J.L. et al., Intestinal Epithelial Cells Modulate Antigen-Presenting Cell Responses to Bacterial DNA. Infectionand Immunity. Aug. 2012; 80(8): 2632-2644."

Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292.

Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07.

Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0.

Candela, M., Centanni M Fau—Fiori, J., Fiori J Fau—Biagi, E., Biagi E Fau—Turroni, S., Turroni S Fau—Orrico, C., Orrico C Fau—Bergmann, S., et al. (2010). DnaK from *Bifidobacterium animalis* subsp. lactis is a surface-exposed human plasminogen receptor upregulated in response to bile salts. Microbiology 156(6), 1609-1618.

Caruthers, et al. New chemical methods for synthesizing polynucleotides. Nucleic Acids Symp Ser. 1980;(7):215-23.

Carvalho et al. (Jan. 2011) "TLR5 activation induces secretory interleukin-1 receptor antagonist (sll-1 Ra) and reduces inflammasome-associated tissue damage," Nature. 4(1):102-111.

Casey et al. 'Isolation and characterization of anti-*Salmonella* lactic acid bacteria from the porcine gastrointestinal tract'. Letters in Applied Microbiology. 2004, vol. 39, No. 5, pp. 431-438.

Caspi, P.R. Experimental autoimmune uveoretinitis in the rat and mouse. Curr Protoc Immunol. May 2003;Chapter 15:Unit 15.6. doi: 10.1002/0471142735.im1506s53.

Cekanaviciute, et al., Gut bacteria from multiple sclerosis patients modulate human T cells and exacerbate symptoms in mouse models. PNAS. Jun. 30, 2017; 1-6.

Cereghino et al. (2000) "Heterologous protein expression in the methylotrophic yeast *Pichia pastoris*," FEMS Microbiol Review. 24(1):45-66.

Charriot, et al., Future treatment for ashtma, Eur Respir Rev 2016; 25: 77-92.

Cheluvappa, R. et al., T helper type 17 pathway suppression by appendicitis and appendectomy protects against colitis. Clin Exp Immunol. Feb. 2014;175(2):316-22. doi: 10.1111/cei.12237.

Chen, S. et al., Live combined bacillus subtilis and enterococcus faecium ameliorate murine experimental colitis by immunosuppression. International journal of inflammation. 2014(878054). 7 Pages.

Chevreux et al. 'Genome sequence assembly using trace signals and additional sequence information.' German Conference on Bioinformatics. 1999.

Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.

Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.

Chiu, et al., Monocolonization of germ-free mice with bacteroides fragilis protects against dectran sulfate sodium-induced acute colitis. Biomed Research International 2014. vol. 2014. Article ID 675786. 9 Pages.

Chothia et al. The relation between the divergence of sequence and structure in proteins. EMBO Journal. 1986, 5(4):823-826.

Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111.

Christmann, et al., Human seroreactivity to gut microbiota antigens. J Allergy Clin Immunol 136(5):1378-1386; available online May 23, 2015.

Christou (1994) "Genetic engineering of crop legumes and cereals: current status and recent advances," Agro-Food Industry Hi-Tech. pp. 17-27.

Chung et al. 'Microbiota-stimulated immune mechanisms to maintain gut homeostasis.' Current Opinion in Immunology. 2010, vol. 22, No. 4, pp. 455-460.

Cintas LM, Casaus MP, Herranz C, Nes IF, Hernandez PE. Review: bacteriocins of lactic acid bacteria (2001). Food Sci Technol 7(4):281-305.

Claesson, et al. Gut microbiota composition correlates with diet and health in the elderly. 2012. Nature, 488, 178-184.

Claims to be granted in European Application No. 15817513.3.

Clarridge III, J.E. Impact of 16S rRNA gene sequence analysis for identification of bacteria on clinical microbiology and infectious diseases (2004). Clinical Microbiology Reviews, 17 (4), pp. 840-862.

Clinical Trials for Thetanix, EU Clinical Trials Register, Date of commencement of clinical trial: Oct. 16, 2015. Available at: https://clinicaltrialsregister.eu/ctr-search/search?query=Thetanix.

CN Office Action dated Jan. 17, 2019, for CN 201680041407.6 (translation not yet available).

Colin, et al., GIC-1001, A Clinical Stage, Orally Administered Colonic Analgesic Drug Proposed as a Cost-Effective Alternative to I.V. Sedation Used in Colonoscopy. Canadian Digestive Diseases Week, 2014; 2 pages.

Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.

Colowick, S. and Kaplan, N., Methods of Enzymology. Academic Press, Inc. 1996.

Constantinescu et al. Experimental autoimmune encephalomyelitis (EAE) as a model for multiple sclerosis (MS). 2011. Br J Pharmacol. 164(4):1079-1106.

Co-pending U.S. Appl. No. 15/359,144, filed Nov. 22, 2016.
Co-pending U.S. Appl. No. 15/916,205, filed Mar. 8, 2018.
Co-pending U.S. Appl. No. 16/040,356, filed Jul. 19, 2018.
Co-pending U.S. Appl. No. 16/147,551, filed Sep. 28, 2018.
Co-pending U.S. Appl. No. 16/219,667, filed Dec. 18, 2018.
Co-pending U.S. Appl. No. 16/240,644, filed Jan. 4, 2019.
Co-pending U.S. Appl. No. 16/247,834, filed Jan. 15, 2019.
Co-pending U.S. Appl. No. 16/248,857, filed Jan. 16, 2019.
Co-pending U.S. Appl. No. 16/251,462, filed Jan. 18, 2019.
Co-pending U.S. Appl. No. 16/265,238, filed Feb. 1, 2019.

Cotter, P.O., Hill, C., Ross, R.P. Food microbiology: Bacteriocins: Developing im1ate immunity for food (2005). Nature Reviews Microbiology, 3 (10), pp. 777-788.

Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.

Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.

Cummings, M., Breitling, R., and Takano, E. (2014). Steps towards the synthetic biology of polyketide biosynthesis. Fems Microbiology Letters 351(2), 116-125. doi: 10.1111/1574-6968.12365.

Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.

Darfeuille-Michaud et al. High prevalence of adherent-invasive *Escherichia coli* associated with ileal mucosa in Crohn's disease. .2004. Gastroenterology 127(2):412-21.

Darlington, G.J., Liver Cell Lines. (1987) Meth Enzymol. 151:19-38.

Database UniProt [Online] Jun. 1, 2003 (Jun. 1, 2003), "subname:Full= possible pirin family protein {ECO:0000313|EMBL:AAO75294.1};", XP00275366,retrieved from EBI accession No. UNIPROT:Q8ABC3 Database accession No. Q8ABC3.

(56) References Cited

OTHER PUBLICATIONS

Davis et al. (1971) "Genetic and Microbiological Research Technqiues," Methods Enzymol. 17A:79-143.
Day, J.G. et al., Cryopreservation and Freeze-Drying Protocols. Springer. 2007. 2nd edition.
De Paepe et al. 'Trade-off between bile resistance and nutritional competence drives *Escherichia coli* diversification in the mouse gut.' PLoS Genetics. 2011, vol. 7, No. 6, e1002107.
De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.
Deangelis, M., et al., Selection of potential probiotic lactobacilli from pig feces to be used as additives in pelleted feeding (2006). Research in Microbiology, 157 (8), pp. 792-801.
Delgado, S., Ruiz, L., Hevia, A., Ruas-Madiedo, P., Margolles, A., and Sánchez, B. (2018). "Evidence of the In Vitro and In Vivo Immunological Relevance of Bifidobacteria," in The Bifidobacteria and Related Organisms.), 295-305.
Demarche, et al., Detailed analysis of sputum and systemic inflammation in asthma phenotypes: are paucigranulocytic asthmatics really non-inflammatory?, BMC Pulmonary Medicine, 2016; (16)46: 1-13.
Dennis et al. 'DAVID: database for annotation, visualization, and integrated discovery.' Genome Bioi. 2003, vol. 4, No. 5, pp. 3.
Distrutti, et al., 5-Amino-2-hydroxybenzoic Acid 4-(5-Thioxo-5H-[1,2]dithiol- 3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458.
Distrutti, et al., Gut Microbiota role in irritable bowel syndrome: New therapeutic strategies. World Journal of Gastroenterology. Feb. 21, 2016; 22(7): p. 2219-2241, XP002769875.
Distrutti, et al., Hydrogen sulphide induces u opioid receptor-dependent analgesia in a rodent model of visceral pain. Molecular Pain, 2010; 6(36):1-16.
Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.
DMSZ: Opening of Ampoules and Rehydration of Dried Cultures; (http://web.archive.org/web/20000 52411541 O/www.dsmz.de/open. htm); updated of website on Mar. 2000.
Dong, H., Rowland I Fau—Yaqoob, P., and Yaqoob, P. (2012). Comparative effects of six probiotic strains on immune function in vitro. Br J Nutr 108(3), 459-470. doi: 10.1017/S0007114511005824.
Drago, Lorenzo et al., Immunomodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413.
Duck et al. 'Isolation of flagellated bacteria implicated in Crohn's disease.' Inflammatory Bowel Diseases. 2007, vol. 13, No. 10, pp. 1191-1201.
Duncan et al. (2002) "*Roseburia intestinalis* sp. nov., a novel saccharolytic, butyrate-producing bacterium from human faeces," International Journal Systematic Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Duncan et al. "Lactate-utilizing bacteria, isolated from human feces, that produce butyrate as a major fermentation product" Applied and environmental microbiology. 2004, vol. 70, No. 10, pp. 5810-5817.
Duncan, et al. *Roseburia intestinalis* sp. nov., a novel saccharolytic, butyrate-producing bacterium from human faeces. Int J Syst Evol Microbiol. Sep. 2002;52(Pt 5):1615-20.
Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.
Eckburg, PB. et al., Diversity of the human intestinal microbial flora.Science. Jun. 10, 2005;308(5728):1635-8. Epub Apr. 14, 2005.
Elhenawy et al., Preferential packing of acidic glycosidases and proteases into bacteroides Outer membrane vesicles. mBio 5:e00909-14, pp. 1-12, 2014.
Elkins et al. 'Genes encoding bile salt hydrolases and conjugated bile salt transporters in Lactobacillus johnsonii 100-100 and other *Lactobacillus* species.' Microbiology. 2001, vol. 147, No. 12, pp. 3403-3412.
Elmadfa, 1., Klein, P., Meyer, AL. Immune-stimulating effects oflactic acid bacteria in vivo and in vitro (2010). Proceedings of the Nutrition Society, 69 (3), pp. 416-420.
Ely et al. (2000) "A family of six flagellin genes contributes to the Caulobacter crescentus flagellar filament," Journal of Bacteriology. 182(17):5001-5004.
Embl sequence AAO75294.1 (2003)—provided within the Office Action dated Feb. 16, 2018 in U.S. Appl. No. 15/631,952. 2 Pages.
Eren, A. Murat et al., "A single genus in the gut microbiome reflects host preference and specificity," The ISME Journal (2015) 9, 9-100 (2015).
ESR Dated Dec. 17, 2018, Appl. 18189521.0.
European Communication dated Jun. 14, 2017 for EP Application No. 15817513.3.
Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1.
Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons=evelo&rank=2.
Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons=evelo&rank=3.
Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4.
Evelo Biosciences, Inc. Portfolio: https://evelobio.com/portfolio/.
Evelo Biosciences, Inc. website: https://evelobio.com/science/.
Extended European search report and opinion dated Aug. 23, 2016 for EP Application No. 16166001.4.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Faith et al. Identifying gut microbe-host phenotype relationships using combinatorial communities in gnotobiotic mice. Sci Transl Med 6(220):220ra11 (2014).
Faith et al. The long-term stability of the human gut microbiota. 2013. Science, 341(6141): 1237439.
Falony, et al., Coculture Fermentations of *Bifidobacterium* species and bacteroides thetaiotaomicron Reveal a mechanistic insight into the prebiotic effect of inulin-type Fructans. Applied and environmental microbiology, Apr. 2009;75(8):2312-2319.
Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892.
Fanning, S., Hall, L.J., Cronin, M., Zomer, A., MacSharry, J., Goulding, D., et al. (2012). Bifidobacterial surface-exopolysac-

(56) References Cited

OTHER PUBLICATIONS charide facilitates commensal-host interaction through immune modulation and pathogen protection. Proc Natl Acad Sci U S A 109(6), 2108-2113. doi: 10.1073/pnas.1115621109.
Farmer, et al., Gut pain & visceral hypersensitivity. British journal of pain, 2013;7(1):39-47.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Fenner, et al., *Bacteroides massiliensis* sp. nov., isolated from blood culture of a newborn. International Journal of systematic and evolutionary microbiology, 2005. 55: 1335-1337.
Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056.
Flores-Langarica et al. (2012) "Systemic flagellin immunization stimulates mucosal CD1 03+ dendritic cells and drives Foxp3+ regulatory T Cell and IgA responses in the mesenteric lymph node," Journal of Immunology. 189 (12):57 45-5754.
Fraley et al. (1986) "Genetic Transformation in Higher Plants," Critical Reviews Plant Science. 4:1-46.
Frame et al., Production of fertile transgenic maize plants by silicon carbide whisker-mediated transformation, The Plant Journal. 1994; 6:941-948.
Frank, D. et al., Molecular-phylogenetic characterization of microbial community imbalances in human inflammatory bowel diseases. 2007. PNAS. 104(34):13780-5.
Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497.
Gaboriau-Routhiau et al. 'The key role of segmented filamentous bacteria in the coordinated maturation of gut helper T cell responses.' Immunity. 2009, vol. 31, No. 4, pp. 677-689.
Gait, M.J., (1984) Oligonucleotide Synthesis: A Practical Approach. Irl Press. pp. vii-xiii.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
GB1612190.7 International Search Report dated Apr. 12, 2017.
GB1809729.5 Examination Report dated Oct. 15, 2018.
GenBank Accession No. ABI48297.1 (Jul. 20, 2007) "Fia1 flagellin [Roseburia hominis]".
GenBank Accession No. ABY J02000000 (Nov. 8, 2013) Version 2. "Roseburia intestinal is L 1-82, whole genome shotgun sequencing project".
GenBank Accession Nos. ABY J02000001-ABY J02000409 search results page (Last Updated Apr. 24, 2015).
GenBank accession No. AJ312385 (Oct. 9, 2002) "Roseburia intestinalis 16S rRNA gene, strain L 1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia hom in is Fla2 flagellin gene".
GenBank Accession No. M20983. (Apr. 26, 1993) "R.cecicola ftagellin gene".
GenBank Accession No. NR_044054.1 (Feb. 3, 2015) Blautia wexlerae strain SSM 19850 16S ribsomal RNA gene, partial sequence.
GenBank Accession No. NR_117867.1 (Feb. 3, 2015) Blautia stercoris strain GAM6-1 16S ribsomal RNA gene, partial sequence.
Genbank NCBI Reference Sequence: NR-044054.1, Blautia wexlerae strain DSM 19850 16S ribosomal RNA gene, partial sequence.
Genbank NCBI Reference Sequence: NR_117867.1, Blautia stercoris strain GAMC6-1 16S ribosomal RNA gene, partial sequence.
Genbank NCBI Reference Sequence: NR_026314, Blautia hydrongentrophica strain S5a36 16S ribosomal RNA gene, partial sequence.
Gennaro, A.R. "Quality Assurance and Control," from Remington: The Science and Practice of Pharmacy, 2000, Lippincott Williams & Wilkins, 20th ed., pp. 980-983.
Gennaro, A.R., Remington's Pharmaceutical sciences, Mack publishin co. 1985.
Geraedts et al. 'Release of satiety hormones in response to specific dietary proteins is different between human and murine small intestinal mucosa.' Annals of Nutrition and Metabolism. 2010, vol. 56, No. 4, pp. 3018-3313.
Geuking et al. 'Intestinal bacterial colonization induces mutualistic regulatory T cell responses.' Immunity. 2011, vol. 34, No. 5, pp. 794-806.
Gewirtz et al. (2001) Cutting edge: bacterial flagellin activates basolaterally expressed TLR5 to induce epithelial proinflammatory gene expression. The Journal of Immunology. 167:(4)1882-1885.
Ghadimi, D. et al., Epigenetic imprinting by commensal probiotics inhibits the IL-23/IL-17 axis in an in vitro model of the intestinal mucosal immune system. JLB. 2012;92(4):895-911.
Giraud et al. 'Dissecting the genetic components of adaptation of *Escherichia coli* to the mouse gut.' PLoS Genetics.2008, vol. 4, No. 1, pp. e2.
Goldin, B.R. et al., Clinical indications for probiotics: an overview. Clin Infect Dis. Feb. 1, 2008;46 Suppl 2:S96-100; discussion S144-51. doi: 10.1086/523333.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM. 08024-11.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (200 1 ). International Dairy Journal, 11 (1-2), pp. 19-25.
Gousia, P., et al., Antimicrobial resistance of major foodborne pathogens from major meat products (20II). Foodborne Pathogens and Disease, 8 (1), pp. 27-38.
Greenspan et al., Defining epitopes: It's not as easy as it seems. Nature Biotechnology 7: 936-937, 1999.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487.
GT Biologics obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Guide for the care and use of laboratory animals: 8th edition. The national academic press; 2011.
Haabeth et al. A model for cancer-suppressive inflammation. (2012) OncoImmunology 1(1):1146-1152.
Hammerich, L. et al., Interleukins in chronic liver disease: lessons learned from experimental mouse models. (2014) Clin Exp Gastroenterol. 7:297-306.

(56) References Cited

OTHER PUBLICATIONS

Handbook of Experimental Immunology, vols. I IV (D.M. Weir and C.C. Blackwell, eds, 1986, Blackwell Scientific Publications).
Hansen, et al., The role of mucosal immunity and host genetics in defining intestinal commensal bacteria. 2010. Curr. Opin. Gastroenterol., 26(6): 564-571.
Hapfelmeier et al. 'Reversible microbial colonization of germ-free mice reveals the dynamics of IgA immune responses.' Science. 2010, vol. 328, No. 5986, pp. 1705-1709.
Hayashi et al. The innate immune response to bacterial flagellin is mediated by Toll-like receptor 5. Nature. 2001, vol. 410, No. 6832, pp. 1099-1103.
Heberle, H., Meirelles, G.V., da Silva, F.R., Telles, G.P., and Minghim, R. (2015). InteractiVenn: a web-based tool for the analysis of sets through Venn diagrams. BMC Bioinformatics 16(1), 169. doi: 10.1186/s12859-015-0611-3.
Hedayat et al. (Mar. 1, 2012) "Prophylactic and therapeutic implications of toll-like receptor ligands," Medicinal Research Reviews. 32(2):294-325.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. PLOS One 4(4), e5184. doi: 10.1371/journal.pone.0005184.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of *Bifidobacterium animalis* subsp. lactis confers surface and functional characteristics. Appl Environ Microbiol 81(23), 7960-7968. doi: 10.1128/AEM.02095-15.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in *Bifidobacterium* spp. Appl Environ Microbiol 80(1), 9-18. doi: 10.1128/AEM.02977-13.
Higgins, et al. CLUSTAL: A Package for Performing Multiple Sequence Alignment on a Microcomputer. Gene. 73 (1988): 237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.
Hinnen et al., Transformation of yeast, Proc. Natl. Acad. Sci. USA. Apr. 1978; 75:1929-1933.
Hoekema (1985) The Binary Plant Vector System Offset-drukkerij Kanters BB, Alblasserdam. Chapter V. pp. 63-71.
Hold et al. 'Oligonucleotide probes that detect quantitatively significant groups of butyrate-producing bacteria in human feces.' Applied and environmental microbiology. 2003, vol. 69, No. 7, pp. 4320-4324.
Holdeman, et al., *Eubacterium contortum* (Prevot) comb. nov.: Emendation of description and designation of the type strain. International journal of systematic bacteriology. Oct. 1971;21(4): 304-306.
Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hooper at al. 'Molecular analysis of commensal host-microbial relationships in the intestine.' Science. 2001; vol. 291, No. 5505, pp. 881-884.
Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.

Horwell, et al., The 'peptoid' approach to the design of non-peptide, small molecule agonists and antagonists of neuropeptides. 1995. Trends Biotechnol. 13(4):132-134.
Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.
Hougee, et al., Oral treatment with probiotics reduces allergic symptoms in ovalbumin-sensitized mice:a bacterial strain comparative study. Int Arch Allergy Immunol. 2010; 151:107-117.
Hoyles L. et al. Gastrointestinal Tract, Chapter 56. Handbook of Hydrocarbon and Lipid Microbiology Springer Verlag Berlin 2010, 3120-32.
Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob.160155.
Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.
Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18.
Ibrahim et al., "Method for the isolation of highly purified *Salmonella flagellins*," Journal of Clinical Microbiology. Dec. 1985; 22(6):1040-1044.
Inaba et al., "Generation of large numbers of dendritic cells from mouse bone marrow cultures supplemented with granulocyte/macrophage colony-stimulating factor," J. Exp. Med. Dec. 1992; 176(6):1693-1702.
Interational Search Report for International Application No. PCT/GB2012/052495, dated Mar. 25, 2013.
International Preliminary Report dated Mar. 1, 2017 for International Application No. PCT/GB2015/054113.
International Preliminary Report on Patentability corresponding to International Patent Application No. PCT/GB2014/051123, dated Oct. 13, 2015.
International Preliminary Report on Patentability for International Application No. PCT/GB2012/051686 dated Jan. 14, 2014.
International Search Report dated Jan. 27, 2017 for International Application No. PCT/GB2016/053622.
International Search Report dated Feb. 10, 2016 for International Application No. PCT/GB2015/054113.
International Search Report dated Feb. 17, 2017 for International Application No. PCT/GB2016/053676.
International Search Report dated Mar. 7, 2016 for International Application No. PCT/GB2015/054112.
International Search report dated Mar. 15, 2003 for International Application No. PCT/GB2002/05255.
International Search Report dated Aug. 21, 2014 for International Application No. PCT/GB2014/051123.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International Search Report for International Application No. PCT/GB2012/051686 dated Jan. 31, 2013.
International search report with written opinion dated Feb. 26, 2018 for PCT/GB2017/053722.

(56) References Cited

OTHER PUBLICATIONS

International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Inturri, R., Molinaro, A., Di Lorenzo, F., Blandino, G., Tomasello, B., Hidalgo-Cantabrana, C., et al. (2017). Chemical and biological properties of the novel exopolysaccharide produced by a probiotic strain of Bifidobacterium longum. Carbohydr Polym 174, 1172-1180. doi: 10.1016/j.carbpol.2017.07.039.
Ishikawa, et al., Effect of bifidobacteria to suppress Th17, Food Science and technology institute, 2008, 5 Pages.
Ispirli, H. et al., Characterization of functional properties of Enterococcus faecium strains isolated from human gut.Can. J. Microbiol. 61: 861-870 (2015) dx.doi.org/10.1139/cjm-2015-0446.
Israel, E. et al., Supplementary Appendix, Severe and difficult-to-treat asthma in adults. N. Engl J Med 2017;p. 377:965-76. DOI: 10.1056/NEJMra1608969.
Israel, et al., Severe and difficult-to-treat asthma in adults, The New England Journal of Medicine, Sep. 2017; 377(10):965-976.
Issue Notification dated Feb. 20, 2019 for Co-Pending U.S. Appl. No. 15/631,945.
Ito et al. (1983) "Transformation of Intact Yeast Cells Treated with Alkali Cations," J. Bacteriology. 153:163-168.
Ivanov, D., Emonet, C., Foata, F., Affolter, M., Delley, M., Fisseha, M., et al. (2006). A serpin from the gut bacterium *Bifidobacterium longum* inhibits eukaryotic elastase-like serine proteases. J Biol Chem 281(25), 17246-17252. doi: 10.1074/jbc.M601678200.
Ivanov et al. 'Induction of intestinal Th17 cells by segmented filamentous bacteria.' Cell. 2009, vol. 139, No. 3, pp. 485-498.
Jackson MS, Bird AR, McOrist AL. Comparison of two selective media for the detection and enumeration of Lactobacilli in human faeces (2002). J Microbial Methods. 51 (3), pp. 313-321.
Jarchum et al., "Toll-Like Receptor 5 Stimulation Protects Mice from Acute Clostridium difficile Colitis," Infection and Immunity. Apr. 2011; 79(4):1498-1503.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.
Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714.
Jiao et al., Blockade of Notch Signaling Ameliorates Murine Collagen-Induced Arthritis via Suppressing Th1 and Th17 Cell Responses. 2014; Pathology, 184(4):1085-1093.
Joblin K N., "Ruminal Acetogens and Their Potential to Lower Remnant Methane Emissions." Australian Journal of Agricultural Research. vol. 50. No. 8. 1999, pp. 1307-1313. XP001010439.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. Gastroenterology, 2005;128: p. A281, XP009193489.
Kang et al. (2010) "Dysbiosis of fecal microbiota in Crohn's disease patients as revealed by a custom phylogenetic microarray," Inflammatory Bowel Diseases. 16(12):2034-2042.

Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Karin, M. Nuclear factor-kappaB in cancer development and progression. Nature. May 25, 2006;441(7092):431-6.
Keller et al.. "DNA Probes", 1994. Stockton Press. New York. XP002158943 108660 pp. 594-596.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.
Kelly, et al., Commensal gut bacteria: mechanisms of immune modulation. Trends in immunology, 2005;26(6):326-333.
Kingsley M. A Personalized Approach to Managing 18D. Gastroenterology and Hepatology 12(5)308-315, May 2016.
Kinnebrew et al., Interleukin 23 production by intestinal CD1 03(+)CD11 b(+) dendritic cells in response to Interleukin 23 production by intestinal CD1 03(+)CD11 b(+) dendritic cells in response to bacterial flagellin enhances mucosal innate immune defense, Immunity. 2012; 36(2): 276-287.
Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x.
Kirsty Minton: Mucosal immunology: The ins and outs of gut inflammation, The journal of immunology, 4(2), Feb. 1, 2004: pp. 81-81, XP055252701.
Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001.
Kitahara et al., *Bacteroides plebeius* sp. nov. and *Bacteroides coprocola* sp. nov., isolated from human faeces, 2005; Int J Syst Ev Microbiol 55: 2143-47.
Kitahara, M. et al., *Bacteroides plebeius* sp. nov. and *Bacteroides coprocola* sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.
Kogyo, S. Lactic Acid Bacteria, Intestinal Flora ad Health II; Physiological effects of heat-treated lactococcus "EF-2001" and application to food. Mar. 30, 2001, vol. 44, No. 6, pp. 35-39.
Koh, Gar Yee et al., Parabacteroides distasonis attenuate toll-like receptor 4 signalling and Akt activation and blocks colon tumor formulation in high-fat-diet-fed azoxymethane-treated mice, International Journal of Cancer, pp. 1-30. Accepted Article, doi: 10.1002/ijc.31559.
Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.
Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.
Kverka, M. et al., Oral administration of Parabacteroides distasonis antigens attenuates experimental murine colitis through modulation of immunity and microbiota composition. Clinical & Experimental Immunology. 2010; 163:250-259.
Lahteinen, T., et al., A Pro biotic properties of Lactobacillus isolates originating from porcine intestine and feces (20 10) Anaerobe, 16 (3), pp. 293-300.
Lakhdari, et al. Identification of NF-KB Modulation Capabilities within Human Intestinal Commensal Bacteria. J Biomed Biotechnol. 2011; 2011: 282356.

(56) References Cited

OTHER PUBLICATIONS

Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.

Lavallie et al. (1995) "Gene fusion expression systems in *Escherichia coli*," Current Opinion Biotechnology. 6 (5):501-506.

Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.

Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x.

Lebeer, S., Verhoeven, T.L., Francius, G., Schoofs, G., Lambrichts, I., Dufrene, Y., et al. (2009). Identification of a Gene Cluster for the Biosynthesis of a Long, Galactose-Rich Exopolysaccharide in Lactobacillus rhamnosus GG and Functional Analysis of the Priming Glycosyltransferase. Appl Environ Microbiol 75(11), 3554-3563. doi: 10.1128/AEM.02919-08.

Lee, et al. Intestinal microbiota in pathophysiology and management of irritable bowel syndrome . 2014. World J Gastroenterol. 20(27): 8886-8897.

Lejeune, FJ. et al., Efficiency of Recombinant Human TNF in Human Cancer Therapy. (2006) Cancer Immun. 6:6.

Leser et al. 'Culture-independent analysis of gut bacteria: the pig gastrointestinal tract microbiota revisited'. Applied and Environmental Microbiology. 2002, vol. 68, No. 2, pp. 673-690.

Leslie, et al., Trehalose and sucrose protect both membranes and proteins in intact bacteria during drying. (1995) Appl. Environ. Microbiol. 61, 3592-3597.

Letran et al. 'TLR5-deficient mice lack basal inflammatory and metabolic defects but exhibit impaired CD4 T cell responses to a flagellated pathogen.' The Journal of Immunology. 2011, vol. 186, No. 9, pp. 5406-5412.

Li, C.Y., Lin Hc Fau—Lai, C.-H., Lai Ch Fau—Lu, J.J.-Y., Lu Jj Fau—Wu, S.-F., Wu Sf Fau—Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.

Li, et al,. Screening and Identification of Lactobacillus animalis strain and characteristics of its bacteriostatic protein, Weishengwuxue Tongbao 2009; 36(7): 1001-1007.

Lilley et al., Methods in Enzymology; DNA Structure Part A: Synthesis and Physical Analysis of DNA. 1992; vol. 2011. pp. v-vii.

Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.

Liu, Y., et al., Human-derived probiotic Lactobacillus reuteri strains differentially reduce intestinal inflannuation (20 10). American Journal of Physiology—Gastrointestinal and Liver Physiology, 299 (5), pp. G1087-G1096.

Ljungh, A, Wadstrorn, T. Lactic acid bacteria as probiotics (2006). Current Issues in Intestinal Microbiology, 7 (2), pp. 73-90.

Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.

Lopetuso et al. Commensal Clostridia: leading players in the maintenance of gut homeostasis. 2013. Gut Pathogens, 5: 23.

Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11.

Lopez-Boado, Y. S. et al., Bacterial Exposure Induces and Activates Matrilysin in Mucosal Epithelial Cells. J Cell Biol148, 1305-1315 (2000).

Louis et al. 'Diversity, metabolism and microbial ecology of butyrate-producing bacteria from the human large Intestine.' FEMS Microbiology Letters. 2009, vol. 294, No. 1, pp. 1-8.

Louis et al. 'Diversity of human colonic butyrate-producing bacteria revealed by analysis of the butyryl-GoA: acetate GoA-transferase gene.' Environmental Microbiology. 2010, vol. 12, No. 2, pp. 304-314.

Louis et al. 'Organization of butyrate synthetic genes in human colonic bacteria: phylogenetic conservation and horizontal gene transfer.' FEMS Microbiology Letters. 2007, vol. 269, No. 2, pp. 240-247.

Lozupone. Diversity, stability and resilience of the human gut microbiota. 2012. Nature. Sep. 13, 2012; 489 (7415): 220-230.

López, P., González-Rodriguez, I., Gueimonde, M., Margolles, A., and Suárez, A. (2011). Immune Response to Bifidobacterium bifidum Strains Support Treg/Th17 Plasticity. PLOS One 6(9), e24776. doi: 10.1371/journal.pone.0024776.

López, P., Gueimonde, M., Margolles, A., and Suárez, A. (2010). Distinct Bifidobacterium strains drive different immune responses in vitro. International Journal of Food Microbiology 138(1), 157-165. doi: https://doi.org/10.1016/j.ijfoodmicro.2009.12.023.

Luger, D. and Caspi, R.R., New perspectives on effector mechanisms in uveitis. (2008) Semin. Immunopathol. 30(2): 134-143.

Álvarez-Martín, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/s00253-007-1115-5.

Lyons, et al., Bacterial strain-specific induction of Foxp3 T regulatory cells is protective in murine allergy models. Clinical & Experimental Allergy. 2010; 40:811-819.

Machiels, et al., Predominant dysbiosis in patients with ulcerative colitis is different from Crohn's disease patients, Inflammatory Bowel Diseases, Microbiology 2012. 8th Congress of ECCO. (This Abstract Is in 7th Congress 2012).

Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.

MacPherson, AJ. et al., IgA responses in the intestinal mucosa against pathogenic and non-pathogenic microorganisms. Oct. 2001. 3(12). 1021-1035.

MacPherson, AJ., et al., The functions of mucosal T cells in containing the indigenous commensal flora of the intestine.Cell Mol Life Sci. Dec. 2002;59(12):2088-96.

MacPherson et al. 'IgA adaptation to the presence of commensal bacteria in the intestine.' Gut-Associated Lymphoid Tissues. Springer Berlin Heidelberg, 2006. 117-136.

MacSharry et al., Immunomodulatory effects of feeding with bifidobacterium longum on allergen-induced lung inflammation in the mouse. Pulmonary pharmacology & Therapeutics. 2012; 25:325-334.

Mahowald et al. 'Characterizing a model human gut microbiota composed of members of its two dominant bacterial phyla.' Proceedings of the National Academy of Sciences. 2009, vol. 106, No. 14, pp. 5859-5864.

Maintaining Cultures for Biotechnology and Industry (1996) Jennie C. Hunter-Cevera, Academic Press.

Mallya et al. 'Characterization of the five novel Ly-6 superfamily members encoded in the MHC, and detection of cells expressing their potential ligands.' Protein Science. 2006, vol. 15, No. 10, pp. 2244-2256.

Manni et al., A tale of two cytokines: IL-17 and IL-22 in asthma and infection. Expert Rev Respir Med. Feb. 2014 ; 8(1): 25-42. doi:10.1586/17476348.2014.854167.

Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.

(56) References Cited

OTHER PUBLICATIONS

Martin et al., Cloning, Nucleotide Sequence, and Taxonomic Implications of the Flagellin Gene of Roseburia cecicola, Journal of Bacteriology. Jun. 1988; 170(6):2612-2617.
Martin R. et al., Isolation of lactobacilli from sow milk and evaluation of their probiotic potential. J of dairy research 76(4)418-425. Nov. 2009.
Masco, L., et al., Identification of *Bifidobacterium* Species Using rep-PCR Fingerprinting. Systematic and Applied Microbiology 26(4):557-63 • Dec. 2003.
Matthes, et al., Simultaneous rapid chemical synthesis of over one hundred oligonucleotides on a microscale. Apr. 1984. EMBO Journal, 3(4): p. 801-805.
Maya, J.R. et al., Emerging Therapies for Noninfectious Uveitis: What May Be Coming to the Clinics. (2014) J. Ophthalmology. 310329.
Mazmanian et al. 'An immunomodulatory molecule of symbiotic bacteria directs maturation of the host immune system.' Cell. 2005, vol. 122, No. 1, pp. 107-118.
McCarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17.
McClymont, S.A., Putnam Al Fau—Lee, M.R., Lee Mr Fau—Esensten, J.H., Esensten Jh Fau—Liu, W., Liu W Fau—Hulme, M.A., Hulme Ma Fau—Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.
McIntosh et al. 'Mechanism of conjugated linoleic acid and vaccenic acid formation in human faecal suspensions and pure cultures of intestinal bacteria.' Microbiology. 2009, vol. 155, No. 1, pp. 285-294.
McLaughlin., "McLaughlin et al. Fatty acid chain length determines cholecystokinin secretion and effect on human gastric motility. Gastroenterology. 1999, vol. 116, No. 1, pp. 46-53".
Menard, S., Laharie D Fau—Asensio, C., Asensio C Fau—Vidal-Martinez, T., Vidal-Martinez T Fau—Candalh, C., Candalh C Fau—Rullier, A., Rullier A Fau—Zerbib, F., et al. (2005). Bifidobacterium breve and *Streptococcus thermophilus* secretion products enhance T helper 1 immune response and intestinal barrier in mice. Experimental Biology and Medicine (Maywood) 230(10), 749-756.
Meyer et al. (1992) "The use of cassava mosaic virus as a vector system for plants," Gene. 110:213-217.
Meyza, et al. The BTBR mouse model of idiopathic autism—Current view on mechanisms. 2017. Neurosci Biobehav Rev.;76(Pt A):99-110.
Mikayama, et al., Molecular cloning and functional expression of a cDNA encoding glycosylation-inhibiting factor. Proc.Nati.Acad. Sci. USA, Nov. 1993; vol. 90: 10056-1 0060.
Milani, C., Mangifesta, M., Mancabelli, L., Lugli, G.A., Mancino, W., Viappiani, A., et al. (2017). The Sortase-Dependent Fimbriome of the Genus *Bifidobacterium*: Extracellular Structures with Potential to Modulate Microbe-Host Dialogue. Appl Environ Microbiol 83(19). doi: 10.1128/AEM.01295-17.
Miossec et al., Targeting IL-17 and TH17 cells in chronic inflammation, 2012; Nature Drug Discovery 11, 763-776.
Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.
Mitropoulou, G. et al. Immobilization Technologies in Probiotic Food Production. (2013) Journal Nutr Metab. (2013) 716861.
Miyake, et al., Phylogenetic analysis of the genus *Bifidobacterium* and related genera based on 16S rDNA sequences. Microbiol. Immunol. 1998; 42(10): 661-667.

Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques: An Intensive Laboratory Course, (Ream et al., eds., 1998, Academic Press).
Monteleone et al., IL-10-dependent partial refractoriness to Toll-like receptor stimulation modulates gut mucosal dendritic cell function, European Journal of Immunology. 2008; 38(6):1533-1547.
Monteleone, I. et al., Th17-related cytokines: new players in the control of chronic intestinal inflammation. (2011) BMC Medicine. 2011, 9:122.
Mortaz, E. et, al., Anti-Inflammatory Effects of Lactobacillus Rahmosus and Bifidobacterium Breve on Cigarette Smoke Activated Human Mcrophiages, PLoS One, Apr. 21, 20i15, 10(8):e0136455.DOI:10. 1371, Journal.pone.0136455.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS One 9(8): e105518.
Mulder et al. 'Environmentally-acquired bacteria influence microbial diversity and natural innate immune responses at gut surfaces'. Bmc Biology. 2009, vol. 7, No. 1, pp. 79.
Murofushi, Y., Villena, J., Morie, K., Kanmani, P., Tohno, M., Shimazu, T., et al. (2015). The toll-like receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027.
Narushima, et al., Characterization of the 17 strains of regulatory T cell-inducing human-derived Clostridia. Gut Microbes Mar. 18, 2014; 5:3, 333-339.
Naughton PJ; Grant G. (2005) Modelling of salmonellosis in: Microbial Ecology of the Growing Animal Holzapfel WH, Naughton PJ. (Eds). London, Elsevier. pp. 235-257.
Neeser, J.R., et al., Lactobacillus johnsonii Lal shares carbohydrate-binding specificities with several enteropathogenic bacteria (2000). Glycobiology, 10 (II), pp. II93-II99.
Neish, A. S. et al., Prokaryotic Regulation of Epithelial Responses by Inhibition of IκB-α Ubiquitination. Science 289, 1560 (2000).
Neish et al., TLRS in the Gut. II. Flagellin-induced inftammation and antiapoptosis, American Journal of Physiology—Gastrointestinal and Liver Physiology. 2007;292:G462-466.
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274.
Neville, B.A., Functional genomics of motile commensal intestinal bacteria. PhD Thesis. University College Cork. 2013. 281 Pages.
Neville, et al., Characterization of pro-inflammatory flagellin proteins produced by Lactobacillus ruminis and related motile Lactobacilli. PloS one. Jul. 2012;7(7):e40592.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.
Ng et al., Archaeal flagella, bacterial flagella and type IV pili: a comparison of genes and posttranslation modification, Journal of Molecular Microbiology and Biotechnology. 2006;11:167-191.
Nicolau, D.P. Current challenges in the management of the infected patient (20ll). Current Opinion in Infectious Diseases, 24 (Suppll), pp. SI-S10.
Notice of Allowance dated Feb. 3, 2016 for U.S. Appl. No. 14/349,907.
Notice of Allowance dated Mar. 6, 2017 for U.S. Appl. No. 14/249,710.
Notice of Allowance dated Mar. 30, 2011 for U.S. Appl. No. 10/285,224.
Notice of Allowance dated Apr. 25, 2016 for U.S. Appl. No. 14/232,475.

(56) References Cited

OTHER PUBLICATIONS

Notice of allowance dated Jun. 16, 2017 for U.S. Appl. No. 14/249,710.
Notice of Allowance dated Aug. 23, 2016 for U.S. Appl. No. 14/232,475.
Notice of allowance dated Sep. 1, 2017 for U.S. Appl. No. 15/357,850.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 22, 2017 for U.S. Appl. No. 15/359,988.
Notice of Allowance dated Nov. 24, 2017 for U.S. Appl. No. 15/070,605.
Notice of Publication dated Dec. 27, 2018 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Nutsch et al., T cell tolerance and immunity to commensal bacteria. Current Opinion in Immunology. Aug. 2012; 24 (4):385-391.
O'Connell Motherway, M., Kinsella, M., Fitzgerald, G.F., and Sinderen, D. (2013). Transcriptional and functional characterization of genetic elements involved in galacto-oligosaccharide utilization by Bifidobacterium breve UCC2003. Microbial biotechnology 6(1), 67-79. doi: 10.1111/1751-7915.12011.
O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x.
O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci U S A 108(27), 11217-11222. doi: 10.1073/pnas.1105380108.
Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Office Action dated Mar. 19, 2019 for U.S. Appl. No. 16/031,024.
Ohashi, Y., Ushida, K. Health-beneficial effects ofprobiotics: Its mode of action (2009). Animal Science Journal, 80 (4), pp. 361-371.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325.
O'Sullivan et al., "Bacterial Supplementation in the Irritable Bowel Syndrome. A Randomised Double-Blind Placebo-Controlled Cross-over Study", Digest Liver Dis. 2000. pp. 294-301.
Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.
Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Pang, et al., Crystal structure of human pirin: an iron-binding nuclear protein and transcription cofactor. Journal of Biological Chemistry, 279(2); Jan. 9, 2004:1491-1498.
Parabacteroides distasonis (Eggerth and Gagnon) Sakamoto and Benno (ATCC 8503). Sep. 19, 2017. 2 Pages.
Park, S.K. et al., Blautia stercoris sp. nov., isolated from human faeces. International journal of systematic and evolutionary microbiology. 2012; 62(4): 776-779.
Patel., R. et al., Determination of 16S rRNA sequences of enterococci and application to species identification of nonmotile enterococcus gallinarum isolates. Journal of clinical microbiology, 1998; 36(11):3399-3407.
Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804.
Coakley M et al: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para. of the right-hand col.
PCR (Introduction to Biotechniques Series), 2nd ed. (Newton & Graham eds., 1997, Springer Verlag).
PCT/EP2017/025038 International Preliminary Report on Patentability dated Jun. 6, 2018, 8 Pages.
PCT/EP2017/025038 International Search Report and Written Report dated Jun. 12, 2017.
PCT/EP2017/025038 Written Opinion of the International Preliminary Examining Authority dated Jan. 25, 2018.
PCT/GB2017/052076 Written Opinion of the International Preliminary Examining Authority dated Jun. 21, 2018, 11 Pages.

(56) References Cited

OTHER PUBLICATIONS

PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Database WPI, Week 201801, Thomson Scientific, London, GB; AN 2017-834299, XP002787097, & WO 2017/209156 AI (Morinaga Milk Ind Co. Ltd) Dec. 7, 2017 (Dec. 7, 2017) * abstract * of WO2017/2019156, Kobayashi, Youdai et al.
Pearson, WR. An introduction to sequence similarity ("Homology") searching. Current protocols in bioinformatics/editoral board, Andreas D Baxevanis. [et al]. 2013; 0 3:10. 1002/0471250953.bi0301s42. doi:10.1002/0471250953.bi0301s42.
Petersen et al. Intestinal colonization with phylogenetic group B2 *Escherichia coli* related to inflammatory bowel disease: a systematic review and meta-analysis. 2015. Scand J Gastroenterol. ;50(10):1199-207.
Peterson et al. 'Catecholamines increase conjugative gene transfer between enteric bacteria.' Microbial Pathogensis. 2011, vol. 51, No. 1, pp. 1-8.
Petsuriyawong et al. 'Screening of probiotic lactic acid bacteria from piglet feces'. Nature Science. 2011, vol. 45, pp. 245-253.
Hoarau, Cyrille et al., Supernatant from Bifidobacterium Differentially Modulates Transduction Signaling Pathways for Biological Functions of Human Dendritic Cells, PLOS One, Public Library of Science, US, vol. 3, No. 7, Jul. 1, 2008 (Jul. 1, 2008), pp. e2753-1, XP009139666,ISSN: 1932-6203 *cf. abstract and conclusion, furthermore discussion part at p. 3, col. at the right side*.
Pinto-Sánchez, M.I., Smecuol, E.C., Temprano, M.P., Sugai, E., Gonzalez, A., Moreno, M.L., et al. (2017). Bifidobacterium infantis NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Polak J.M. and McGee J.O., In Situ Hybridization: Principles and Practice, Oxford University Press. 1990; pp. vii-viii.
Potrykus (1991) "Gene Transfer to Plants: Assessment of Published Approaches and Results," Annu. Rev. Plant Physiol. Plant Mol. Bioi. 42:205-225.
Prakash, et al., Complete genome sequences of rat and mouse segmented filamentous bacteria, a potent inducer of th17 cell differentiation. Cell Host & Microbe. Sep. 2011;10(3):273-284.
Pryde et al. 'The microbiology of butyrate formation in the human colon.' FEMS Microbiology Letters. 2002. vol. 217,No. 2, pp. 133-139.
Database WPI,Week 201801, Thomson Scientific, London, GB; AN 2017-834299, XP002787097,& WO 2017/209156 AI (Morinaga Milk Ind Co Ltd) Dec. 7, 2017 (Dec. 7, 2017) * abstract *.
Hoarau et al: "TLR2 Activation by Supernatant From Bifidobacterium Breve Modulates Maturation and Survival of Human DCs via Differential Effects on PI3Kinase, p38 and ERK Pathways",Journal of Allergy and Clinical Immuno, Elsevier, Amsterdam, NL, vol. 119, No. 1, Jan. 1, 2007 (Jan. 1, 2007), p. S258, XP005756921, ISSN: 0091-6749, DOI: 10.1016/J.JACI.2006.12.377 *cf. abs.No. 1008 at p. S258*.
Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.
Matsuda F et al: Evaluation of a probiotics,BBG-01, for enhancement of immunogenicity of an oral inactivated cholera vaccine and safety: A randomized, double-blind, placebo-controlled trial in Bangladeshi children under 5 years of age,Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.
Scuotto, Angelo et al., In silico mining and characterization of bifidobacterial lipoprotein with CHHP domain secreted in an aggregated form, International J. of Biol. Macromolecutes 82(2016), 653-662.

Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Rajilic-Stojanovic, et al. The first 1000 cultures species of the human gastrointestinal micriobiota. FEMS Mlcriobiol Rev, vol. 38, 2014. pp. 996-1047.
Reddy, K.B.P.K., et al., Role of cryoprotectants on the viability and functional properties of pro biotic lactic acid bacteria during freeze drying (2009). Food Biotechnology, 23 (3), pp. 243-265.
Reiff,C. and Kelly,D.,Inflammatory bowel disease, gut bacteria and probiotic therapy. International journal of medical microbiology, 2010;300:25-33.
Remington. Remington: The science and practice of pharmacy. 20th Edition. Gennaro, Eds. Lippincott Williams & Wilkins, 2003.
Reuter, G. (2001). The Lactobacillus and Bifidobacterium microflora of the human intestine: composition and succession. Current Issues in Intestinal Microbiology 2(2), 43-53.
Rhee et al.,Toll-Like Receptor 5 Engagement Modulates Tumor Development and Growth in a Mouse Xenograft Model of Human Colon Cancer. Gastroenterology. Aug. 2008;135(2):518-528.
Rhee, Young-Kyung et al.., Antihumor Activity of *Bifidobacterium* Spp. isolated from a healthy Korean, Arch Pharm Res vol. 23, No. t, 482-487 2000.
Riquelme. Will 4D Pharma be UK's next Microbiome leader? Feb. 2, 2015, LABIOTECH.eu [online].
Robertson, J.M.C., et al., Lack of flagella disadvantages *Salmonella enterica* serovar Enteritidis during the early stages of infection in the rat (2003). Journal of Medical Microbiology, 52 (1), pp. 91-99.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Roe, et al., DNA Isolation and Sequencing: Essential Techniques. John Wiley & Sons, New York, New York. 1996; pp. v-vii.
Rong, Y., Dong, Z., Hong, Z., Jin, Y., Zhang, W., Zhang, B., et al. (2017). Reactivity toward Bifidobacterium longum and Enterococcus hirae demonstrate robust CD8(+) T cell response and better prognosis in HBV-related hepatocellular carcinoma. Experimental Cell Research 358(2), 352-359. doi: 10.1016/j.yexcr.2017.07.009.
Roseburia. Ubiome, 2018. Accessed on Jun. 25, 2018; Available at: https://shop.ubiome.com/pages/roseburia-1.
Round et al. 'The Toll-like receptor 2 pathway establishes colonization by a commensal of the human microbiota.' Science. 2011, vol. 332, No. 6032, pp. 974-977.
Rudinger J, "Characteristics of the amino acids as components of a peptide hormone sequence," Peptide Hormones, JA Parsons Edition, University Park Press, Jun. 1976, pp. 1-7.
Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb.2016.01193.
Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.
Russell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.
Sagar, et al., Bifidobacterium breve and lactobacillus rhamnosus treatment is as effective as budesonide at reducing inflammation in a murine model for chronic asthma. Respiratory Research. 2014; 15(46):1-17.
Saiki, et al., Primer-directed enzymatic amplification of DNA with a thermostable DNA polymerase. 1988. Science, 239. pp. 487-491.
Sakamato, et al., *Parabacteroides faecis* sp. nov., isolated from human faeces. International Journal of Systematic and Evolutionary Microbiology (2015), 65, 1342-1346.

(56) References Cited

OTHER PUBLICATIONS

Sakamoto, et al., *Parabacteroides gordonii* sp. nov., isolated from human blood cultures. International Journal of Systematic and Evolutionary Microbiology (2009), 59, 2843-2847.
Sakamoto, et al., *Parabacteroides johnsonii* sp. nov., isolated from human faeces. International Journal of Systematic and Evolutionary Microbiology (2007), 57, 293-296.
Sakamoto, M. et al., Reclassification of Bacteroides distasonis, Bacteroides goldsteinii and Bacteroides merdae as *Parabacteroides distasonis* gen. nov., comb. nov., *Parabacteroides goldsteinii* comb. nov. and *Parabacteroides merdae* comb. nov. International journal of systematic and evolutionary microbiology. 2006; 56: 1599-1605.
Salix Pharmaceuticals, Inc. FDA Highlights of Prescribing Information—XIFAXAN (rifaximin tablet). Revised Nov. 2015.
Salminen et al., Probiotics: how should they be defined?, Trends in Food Science & Technology 10 (1999) 107-110.
Salonen et al., Gastrointestinal microbia in irritable bowel syndrome: present state and perspectives. Microbiology. 2010; 156: 3205-3215.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.
Schiavi, E., Plattner, S., Rodriguez-Perez, N., Barcik, W., Frei, R., Ferstl, R., et al. (2018). Exopolysaccharide from *Bifidobacterium longum* subsp. longum 35624 modulates murine allergic airway responses. Benef Microbes, 1-14. doi: 10.3920/BM2017.0180.
Schieck, M. et al., Genetic variation in TH17 pathway genes, childhood asthma, and total serum IgE levels.(2014) J Allergy Clin Immunol. 133(3):888-91.
Schleifer, K.H. et al., Transfer of *Streptococcus faecalis* and *Streptococcus faecium* to the Genus *Enterococcus* nom. rev. as *Enterococcus faecalis* comb. nov. and *Enterococcus faecium* comb. nov. Int J Syst Evol Microbiol, Jan. 1984 34: 31-34, doi:10.1099/00207713-34-1-31.
Schmitz, S. et al., A prospective, randomized, blinded, placebo-controlled pilot study on the effect of *Enterococcus faecium* on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.
Schouten, et al., Cow milk allergy symptoms are reduced in mice fed dietary synbiotics during oral sensitization with whey. Nutritional Immunology. 2015; 139(7):1390-403.
Schulke et al. (Aug. 26, 2011) "A fusion protein of ftagellin and ovalbumin suppresses the 25 TH2 response and prevents murine intestinal allergy," The Journal of Allergy and Clinical Immunology. 128(6):1340-1348.
Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.
Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 672-4679.
Sczesnak, et al., The genome of th17 cell-inducing segmented filamentous bacteria reveals extensive auxotrophy and adaptations to the intestinal environment. Cell Host Microbe. Sep. 2011;10 (3):260-272.

Severijnen, A. J. et al., Chronic Arthritis Induced in Rats by Cell Wall Fragments of *Eubacterium* Species from the Human Intestinal Flora. Infection and Immunity, 1990, vol. 58, No. 2, 523-528.
Sgadari, C. et al., Interferon-inducible protein-10 identified as a mediator of tumor necrosis in vivo. (1996) PNAS. 93:13791-6.
Sgadari et al. Mig, the Monokine Induced by Interferon-g, Promotes Tumor Necrosis In Vivo. (1997) Blood. 89:2635-43.
Shabgah, A.G. et al., Interleukin-17 in human inflammatory diseases. Postepy Dermatol Alergol. Aug. 2014; 31(4): 256-261.
Shevach et al., Current Protocols in Immunology. John Wiley & Sons. New York, New York. 1992. Table of Contents only, as accessed online at URL: http://www.4ulr.com/products/currentprotocols/immunology_toc.html. [Last Accessed Jun. 18, 2015].
Simon, et al., Peptoids: A modular approach to drug discover, Oct. 1992. PNAS, 89(20):9367-9371.
Simpson-Herren, L. et al., Kinetic parameters and growth curves for experimental tumor systems. Cancer Chemother Rep. Jun. 1970;54(3):143-74.
Sisson, G. et al., Randomised clinical trial: a liquid multi-strain probiotic vs. placebo in the irritable bowel syndrome—a 12 week double-blind study. Aliment Pharmacol Ther. 2014; 40: 51-62.
Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255.
Sivieri, K. et al., Probiotic enterococcus faecium CRL 183 inhibit chemically induced colon cancer in male wistar rats. Eur Food Res Technol. 2008; 228:231-237.
Skolnick, et al. From genes to protein structure and function: novel applications of computational approaches in the genomic era. Trends Biotechnol. Jan. 2000;18(1):34-9. Review.
Skountzou, et al., *Salmonella flagellins* are potent adjuvants for intranasally administered whole inactivated influenza vaccine. Vaccine. May 2010; 28(24):4103-4112.
Smith, C.L., et al., Lactobacillus fermentum BRII and fructo-oligosaccharide partially reduce jejunal inflammation in a model of intestinal mucositis in rats (2008). Nutrition and Cancer, 60 (6), pp. 757-767.
Smith, et al. Comparison of Biosequences. Advances in Applied Mathematics. 1981;2: 482-489.
Sokol et al. 'Faecalibacterium prausnitzii is an anti-inftammatory commensal bacterium identified by gut microbiota analysis of Crohn disease patients.' Proceedings of the National Academy of Sciences. 2008, vol. 105, No. 43, pp. 6731-16736.
Sokol et al. 'Low counts of Faecalibacterium prausnitzii in colitis microbiota.' Inflammatory bowel diseases. 2009, vol. 15, No. 8, pp. 1183-1189.
Song et al., Impact of Schistosoma japonicum Infection on Collagen-Induced Arthritis in DBA/1 Mice: A Murine Model of Human Rheumatoid Arthritis. 2011; PLoS One 6, e23453, 10 pAGES.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Sonnenburg, et al., Genomic and Metabolic Studies of the Impact of Probiotics on a Model Gut Symbiont and Host. PLoS Biol 4(12): e413. https://doi.org/10.1371/journal.pbio.0040413.
U.S. Appl. No. 15/915,889 Notice of Allowance dated Jun. 4, 2018.
U.S. Appl. No. 15/700,007 Office Action dated Jun. 1, 2018.
Written Opinion for PCT/US2017/066709 (Published as WO2018/112363) owned by Evelo Biosciences, Inc.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.

(56) References Cited

OTHER PUBLICATIONS

Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.
Strasser, S. et al., Influence of lyophilization, fluidized bed drying, addition of protectants, and storage on the viability oflactic acid bacteria (2009). Journal of Applied Microbiology, 107 (1), pp. 167-177.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Strus et al. Distinct effects of Lactobacillus plantarum KL30B and *Escherichia coli* 3A1 on the induction and development of acute and chronic inflammation. 2015. Cent Eur J Immunol.40(4):420-30.
Sun, D. et al., The role of Th17-associated cytokines in the pathogenesis of experimental autoimmune uveitis (EAU). (2015) Cytokine. 74(1):76-80.
Sun, et al., Exploring gut microbes in human health and disease: Pushing the envelope. Genes Dis. Dec. 2014; 1(2):132-139.doi:10.1016/j.gendis.2014.08.001.
Supplement to: Israel, et al., Severe and difficult-to-treat asthma in adults. N Engl J Med 2017; 377:965-76.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.
Tamanai-Shacoori, et al., *Roseburia* spp.: a marker of health?. Future Microbiology Review 12(2), 157-170 (2017).
Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tap et al. Towards the human intestinal microbiota phylogenetic core. 2009. Environ Microbiol, 11(10):2574-84.
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Tatusova et al., BLAST 2 Sequences, a new tool for comparing protein and nucleotidesequences, FEMS Microbiology Letters 174 (1999) 247-250.
Tatusova et al., Erratum to BLAST 2 Sequences, a new tool for comparing protein and nucleotide sequences, FEMS Microbiology Letters 177 (1999) 187-188.
Teng, L. J. et al., PCR Assay for Species-Specific Identification ofBacteroides thetaiotaomicron. J Clin Microbiol38, 1672-1675 (2000).
Terciz, Janos et al., Inflammation and Colon Cancer, Gastroenterology, 2010: 138: 2101-2114.
Tesmer, LA. et al., Th17 cells in human disease. Immunol Rev. 2008;223:87-113.
Tilg, et al., Roseburia hominis: a novel guilty player in ulcerative colitis pathogenesis? Gut, Oct. 14, 2013;63(8)1204-1205.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLOS One 8(3), e59259. doi: 10.1371/journal.pone.0059259.

Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.
Travis, et al. Complete genome sequence of the human gut symbiont Roseburia hominis. Genome announcements. 2015; 3(6):e01286-15.
Tremaroli, et al., A role for the gut microbiota in energy harvesting? Gut. Dec. 2010; 59(12):1589-1590.
Trueman (1995) "Heterologous Expression in Yeast," Methods Molecular Biology. 49:341-354.
Tsukinowa, et al., Fecal microbiota of a dugong (Dugong dugong) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484.
Turnbaugh, et al., An obesity-associated gut microbiome with increased capacity for energy harvest. Nature. Dec. 2006;444(7122):1027-1031.
Turnbaugh et al., Diet-induced obesity is linked to marked but reversible alterations in the mouse distal gut microbiome. Cell Host & Microbe. Apr. 2008;3(4):213-223.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amsterdam, The Netherlands. pp. 641-666.
Turroni, F., Taverniti V Fau—Ruas-Madiedo, P., Ruas-Madiedo P Fau—Duranti, S., Duranti S Fau—Guglielmetti, S., Guglielmetti S Fau—Lugli, G.A., Lugli Ga Fau—Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Ukena, et al., Probiotic *Escherichia coli* Nissle 1917 inhibits leaky gut by enhancing mucosal integrity, PloS one. Dec. 2007;2(12):e1308.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.
U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/359,144 Office Action dated Apr. 10, 2018.
U.S. Appl. No. 15/359,972 Office Action dated Apr. 4, 2018.
U.S. Appl. No. 15/431,393 Office Action dated Jul. 30, 2018.

(56) References Cited

OTHER PUBLICATIONS

U.S. Appl. No. 15/631,945 Office Action dated Jul. 5, 2018.
U.S. Appl. No. 15/631,945 Office Action dated May 15, 2018.
U.S. Appl. No. 15/631,952 Office Action dated Feb. 16, 2018.
U.S. Appl. No. 15/631,952 Office Action dated Jul. 19, 2018.
U.S. Appl. No. 15/673,270 Office Action dated Apr. 10, 2018.
U.S. Appl. No. 15/679,857 Office Action dated Aug. 6, 2018.
U.S. Appl. No. 15/679,857 Office Action dated Feb. 14, 2018.
U.S. Appl. No. 15/704,245 Office Action dated Sep. 17, 2018.
U.S. Appl. No. 15/803,723 Notice of Allowance dated Feb. 13, 2018.
U.S. Appl. No. 15/842,635 Office Action dated Aug. 27, 2018.
Van De Bogert, et al., Immunomodulatory properties of *Streptococcus* and veillonella isolates from the human small intestine microbiota, PLOS One, Dec. 2014: 1-20, DOI:10.1371/journal.pone.0114277.
Van de Pol, M.A. et al., Sybiotics reduce allergen-induced T-helper 2 respond and improve peak expiatory flow in allergic asthmatics, Allergy 2011;66:39-47.
Van De Veerdonk, et al., The Anti-CD20 antibody rituximab reduces the Th17 cell response. Arthritis & Rheumatism. Jun. 2011; 63(6):1507-1516.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.
Van Nevel et al., "Conrol of Rumen Methanogenesis." Environmental Monitoring and Assessment. vol. 42, 1996, pp. 73097, XP000979267.
Van Tilburg, M. Can we treat visceral hypersensitivity in functional abdominal pain? Lancet Gastroenterolhepatol, 2017; 2 Pages.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8.
Vetrovsky, T. and Baldrian, P., The variability of the 16S rRNA gene in bacterial genomes and its consequences for bacterial community analyses. Plos One. Feb. 2013; 8(2): e57923.
Vijay-Kumar, et al., Deletion of TLR5 results in 10 spontaneous colitis in mice. The Journal of Clinical Investigation. Dec. 2007;117(12):3909-3921.
Vijay-Kumar et al., Flagellin Treatment Protects against Chemicals, Bacteria, Viruses, and Radiation. The Journal of Immunology. 2008;180(12):8280-8285.
Walker et al. 'Dominant and diet-responsive groups of bacteria within the human colonic microbiota.' The ISME Journal. 2010, vol. 5, No. 2, pp. 220-230.
Wang, Chun-Sai-Er, et al., VSL#3 can prevent ulcerative colitis-associated carcinogenesis in mice, Oct. 7, 2018, vol. 24, Issue 37, pp. 4254-4262.
Wang et al. 16S rRNA gene-based analysis of fecal microbiota from preterm infants with and without necrotizing enterocolitis. 2009. ISMA J. 3(8): 944-954.
Wang, Feng, Bifidobacterium can mitigate intestinal immunopathology in the context of CTLA-4 blockade, PNA, Jan. 2, 2018 vol. 115, No. 1, pp. 157-161.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22.
Wang, R.F., and Kushner, S.R. (1991). Construction of versatile low-copy-number vectors for cloning, sequencing and gene expression in *Escherichia coli*. Gene 100, 195-199. doi: https://doi.org/10.1016/0378-1119(91)90366-J.
Wang W., Lyophilization and development of solid protein pharmaceuticals. International J. Pharmaceutics 203: 1-60, 2000.
Watson, et al., Signal transduction in Campylobacter jejuni-induced cytokine production. Cellular Microbiology. 2005;7(5):655-665.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038.
Weigel, et al., Comparative analysis of murine marrow-derived dendritic cells generated by Flt3L or GMCSF/IL-4 and matured with immune stimulatory agents on the in vivo induction of antileukemia responses. Blood. Dec. 2002;100(12):4169-4176.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Werth, et al., The transcription factor grainyhead-like 2 regulates the molecular composition of the epithelial apical junctional complex. Development. 2010;37(22):3835-3845.
Westermann, C., Gleinser, M., Cori, S.C., and Riedel, C.U. (2016). A Critical Evaluation of Bifidobacterial Adhesion to the Host Tissue. Front Microbiol 7, 1220. doi: 10.3389/fmicb.2016.01220.
Wilson, et al., The TLR5 ligand flagellin promotes asthma by priming allergic responses to indoor allergens. Nature Medicine. Nov. 2012;18(11):1705-1710.
Workman et al. Guidelines for the welfare and use of animals in cancer research (2010) Br. J. Cancer. 102:1555-77.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11(61):1-13.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921.
Xu, et al., A genomic view of the human-Bacteroides thetaiotaomicron symbiosis. Science. Mar. 28, 2003; 299(5615):2074-6.
Xu, et al., Differential development of murine dendritic cells by GM-CSF versus Flt3 ligand has implications for inflammation and trafficking. J. Immunology. 2007;179(11):7577-7584.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Xu, J. et al., "Message from a human gut symbiont: sensitivity is a prerequisite for sharing", Trends in microbiology, 12(1), Jan. 1, 2004: pp. 21-28, XP055253932.
Yang, Changa et al., Non-invasive imaging of toll-like receptor 5 expressing using 131 labelled mAb in the mice bearing H22 tumors, Oncol. Lett. 2014., 7(6).1919-1924., Published online Apr. 2014.il2. DOI: 10.3892/ol.2014.2025.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Yao, W., et al., Cultivation-Independent Analysis of the Development of the *Lactobacillus* spp. Community in the Intestinal TractofNewbornPiglets (20ll)Agricultural Sciences in China, 10 (3), pp. 438-447.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Yoon, et al., Structural basis of TLR5-flagellin recognition and signaling. Science. Feb. 2012; 335(6070):859-864.
Yq et al. Therapeutic Modulation of the Gut Microbiota in IBD—More Questions to Be Answered. (2016). J. Dig. Dis., Oct. 15, 1751-2980, 12422, Epub ahead of print.

(56) References Cited

OTHER PUBLICATIONS

Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.

Yu, et al., Utilization of major fucosylated and sialylated human milk oligosaccharides by isolated human gut microbes. Glycobiology, 2013; 23(11):1281-1292.

Yu, N.Y., Wagner, J.R., Laird, M.R., Melli, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249.

Yun, J.H., et al., Isolation and characterization of potential pro biotic lactobacilli from pig feces (2009). Journal of Basic Microbiology, 49 (2), pp. 220-226.

Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).

Yurdusev, N. et al., InfectInunun 57,724-731 (1989).

Yutin, N. and Galperin, M.Y., A genomic update on clostridial phylogeny:Gram-negative spore formers and other misplaced clostridia. Environmental microbiology. Oct. 2013; 15(10): 2631-2641.

Zhang, B. et al., Oral administration of enterococcus faecalis FK-23 suppresses Th17 cell development and attenuates allergic airway responses in mice. International journal of molecular medicine. 2012; 30:248-254.

Zhang, B. et al., The Prevalence of Th17 Cells in Patients With Gastric Cancer. 2008. Biochem Biophys Res Commun 374 (3), 533-537.

Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

Zheng, B. et al., Bifidobacteriu breve attenuates murine dextran sodium sulfate-induced colitis and increases regulatory T cell responses. PLOS one. May 2014; 9(5).

Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441.

Zheng, Bin et al., Bifodobacterium breve Attenuates Murine Dexran Doium Sulfate-Induced Colitis and Increases Regulatory T Cell Responses, PLOS One, vol. 9, Isue 5, e95441, May 2014.

Zhongyuan, T. et al., The inflammation regulation effects of enterococcus faecium HDRsEf1 on human enterocyte-like HT-29 cells. Animal cells and systems. Mar. 2016;20(2):70-76.

Zhou et al. Central and peripheral hypersensitivity in the irritable bowel syndrome. 2010. Pain. 148(3): 454-461.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLOS one. 2013; 8(6).

Zitvogel, et al., Type I interferons in anticancer immunity. Nature Reviews. Jul. 2015:405-414.

Casas, Ivan A., et al., Validation of the probiotic concept: Lactobacillus reuteri confers broad-spectrum protection against disease inhuman and animals, Microbial Ecology in Health and Disease, vol. 12, pp. 247-285, (2000), DOI: 10.1080/08910600050216246-1. Published online: Jul. 11, 2009 de Vries, M.C., Analyzing global gene expression of Lactobacillus plantarum in the human gastro-intestinal tract, Thesis, Wageningen University, Wageningen, The Netherlands, pp. 160 p., ISBN: 90/8504-344-1 (Aug. 2, 2006).

Genbank Accession No. AB425917.1, Lactobacillus reuteri gene for 16S ribosomal RNA, partial sequence, strain TB-B11 (= KK18),Murakami, M., et al., submitted Feb. 27, 2008 (Feb. 27, 2008)

Gharei-Fathabad, Eshrat, et al., Isolation and applications of one strain of Lactobacillus paraplantarum from tea leaves (Camellia sinensis), Am. J. Food Technol., vol. 6, No. 5, pp. 429-434, (2011).

Pridmore, R David et al., The genome sequence of the probiotic intestinal bacterium Lactobacillus johnsonii NCC 533, Proceedings of the National Academy of Sciences of the United States of America vol. 101,8 (2004):2512-7. doi:10.1073/pnas.0307327101 (Feb. 24, 2004).

Estelle Devillard et al., Metabolism of Linoleic Acid by Human Gut Bacteria: Different Routes for Biosynthesis of Conjugated Linoleic Acid, Journal of Bacteriology, Mar. 2007, vol. 189, No. 4, pp. 2566-2570, Epub2007 Jan 5.

Federico E. Rey et al., "Dissecting the in Vivo Metabolic Potential of Two Human Gut Acetogens", The Journal of Biological Chemistry, vol. 285, No. 29, pp. 22082-22090, Jul. 16, 2010, Epub2010 May 5.

\* cited by examiner

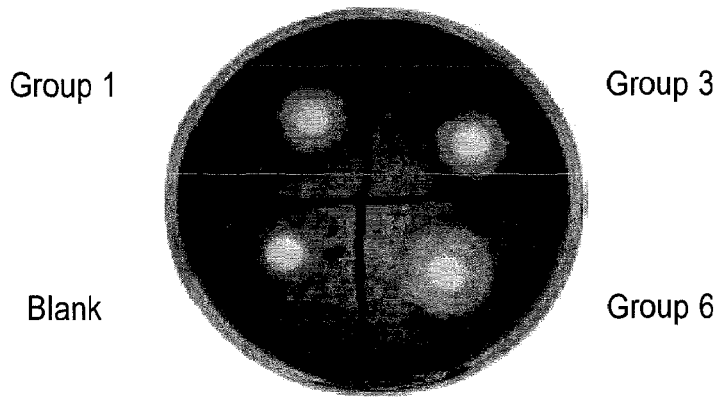

XLD agar containing S. enteritidis S1400 [$10^6$ cfu/ml].
Approximately 5 mm wells cut in agar
An aliquot (60μl) of conditionel media or MRS broth added to the wells.
Plates incubated aerobically for 16 hours at 37°C.
Image captured and area of inhibition measured.

| Group | Inhibition |
|---|---|
| Group 1 | <20000 units of inhibition |
| Group 2 | 20000-40000 units of inhibition |
| Group 3 | 40000-60000 units of inhibition |
| Group 4 | 60000-80000 units of inhibition |
| Group 5 | 80000-100000 units of inhibition |
| Group 6 | >>100000 units of inhibition |

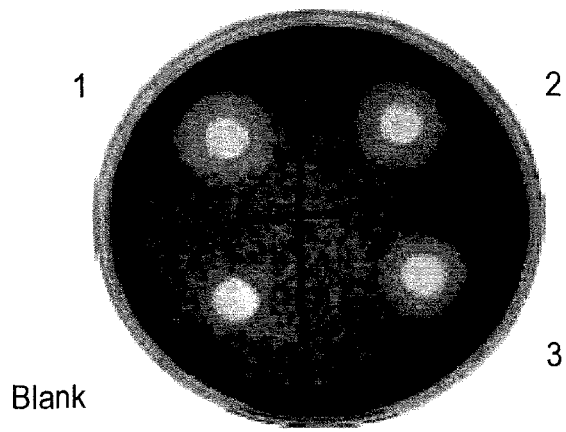

| Bacterial Sample | Inner circle Diameter | Outer circle Diameter | Inhibition Area |
|---|---|---|---|
| 1 | 174 | 366 | 81430 |
| 2 | 174 | 354 | 74644 |
| 3 | 174 | 336 | 64889 |

Inhibition area = $[(\pi R^2) - (\pi r^2)]$

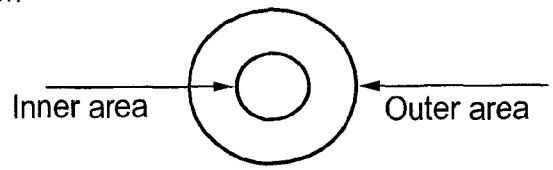

FIG. 1

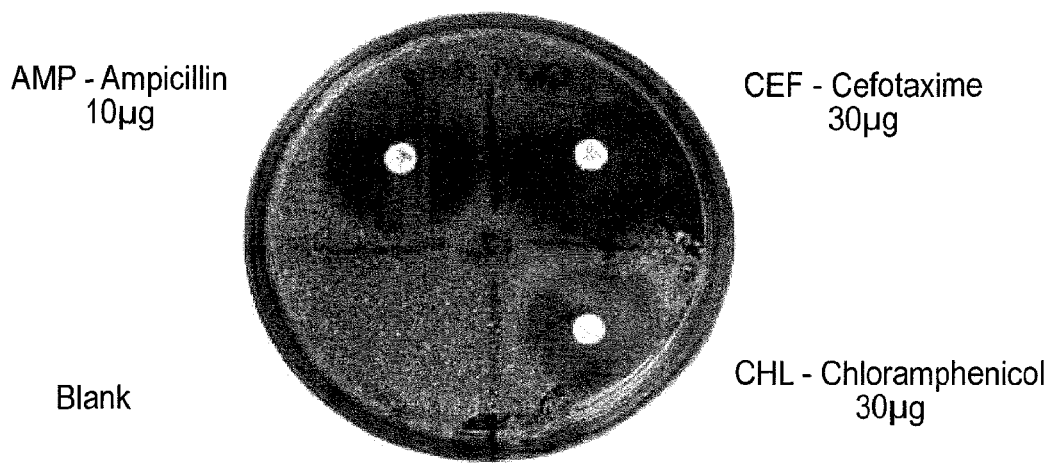
AMP - Ampicillin
10μg
CEF - Cefotaxime
30μg
Blank
CHL - Chloramphenicol
30μg
Inhibition area = $\pi R^2$
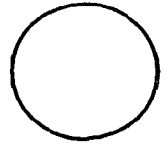
Ampicillin
Cefotaxime
Chloramphenicol
Erythromycin
Tetracycline
Vancomycin
Gentamicin
Kanamycin
Metronizadole
Nalidixic acid
FIG. 5

Bacterium evaluated: Lactobacillus plantarum

| Day | | Control | Salmonella | L. mucosae | L. mucosae + salmonella |
|---|---|---|---|---|---|
| -7 | AM | MRS broth | MRS broth | L. mucosae | L. mucosae |
| -4 | AM | MRS broth | MRS broth | L. mucosae | L. mucosae |
| -2 | AM | MRS broth | MRS broth | L. mucosae | L. mucosae |
| | | ↓ | ↓ | ↓ | ↓ |
| 0 | AM | MRS broth | MRS broth | L. mucosae | L. mucosae |
| | PM | LB media | SE S1400 | LB media | SE S140 |
| | | ↓ | ↓ | ↓ | ↓ |
| 1 | AM | MRS broth | MRS broth | L. mucosae | L. mucosae |
| 2 | AM | MRS broth | MRS broth | L. mucosae | L. mucosae |
| 3 | AM | MRS broth | MRS broth | L. mucosae | L. mucosae |
| 4 | AM | MRS broth | MRS broth | L. mucosae | L. mucosae |
| 5 | AM | MRS broth | MRS broth | L. mucosae | L. mucosae |
| 6 | AM | MRS broth | MRS broth | L. mucosae | L. mucosae |
| 7 | AM | MRS broth | MRS broth | L. mucosae | L. mucosae |
| 8 | AM | MRS broth | MRS broth | L. mucosae | L. mucosae |
| 9 | AM | MRS broth | MRS broth | L. mucosae | L. mucosae |
| 10 | | Euthanase | Euthanase | Euthanase | Euthanase |

SE S1400, S enteritidis S1400. LB media, Luria Bertani broth

FIG. 10

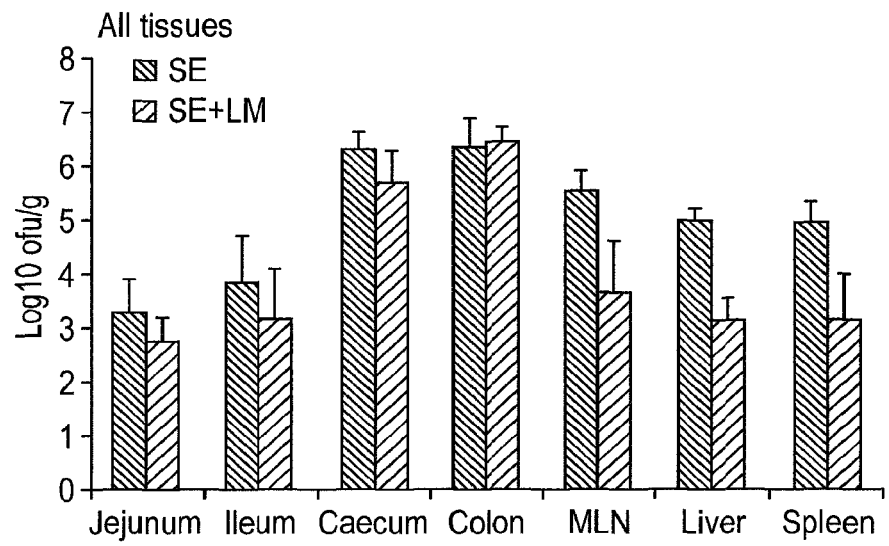
FIG. 11A
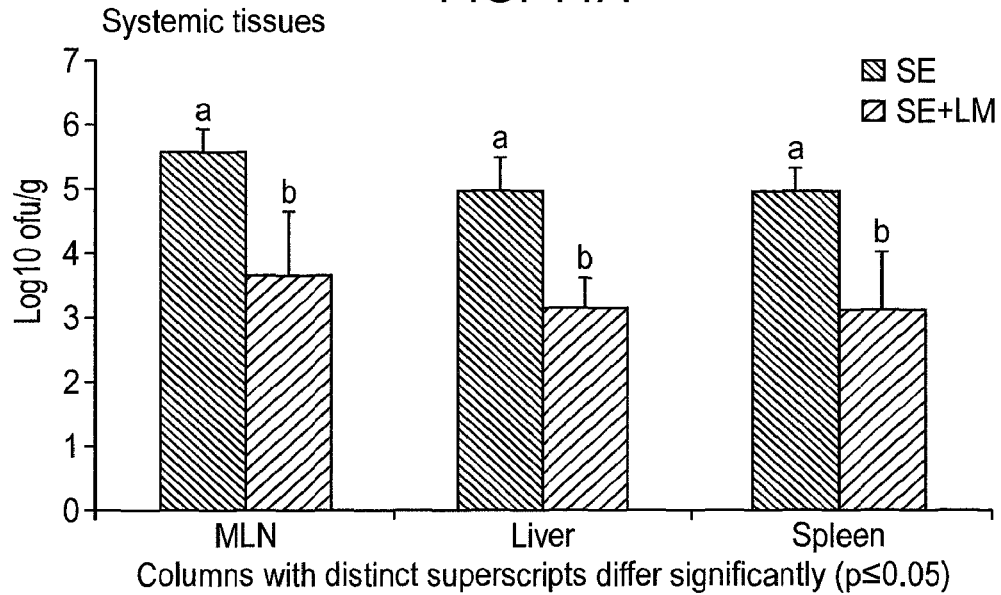
Columns with distinct superscripts differ significantly ($p \leq 0.05$)
FIG. 11B
Statistical analysis
S. enteritidis vs S. enteritidis + L. mucosae
| | |
|---|---|
| Jejunum | p>0.05 |
| Ileum | p>0.05 |
| Caecum | p>0.05 |
| Colon | p>0.05 |
| MLN | p<0.01 |
| Liver | p<0.01 |
| Spleen | p<0.01 |
FIG. 11C Columns with distinct superscripts differ significantly (p≤0.05)

| Day | | Salmonella | L. mucosae + salmonella |
|---|---|---|---|
| -7 | AM | MRS broth | L. mucosae |
| -4 | AM | MRS broth | L. mucosae |
| -2 | AM | MRS broth | L. mucosae |
| 0 | AM | MRS broth | L. mucosae |
|   | PM | SE S1400 | SE S1400 |
| 1 | AM | MRS broth | L. mucosae |
| 2 | AM | MRS broth | L. mucosae |
| 3 | AM | MRS broth | L. mucosae |
| 4 | AM | MRS broth | L. mucosae |
| 5 | AM | MRS broth | L. mucosae |
| 6 |   | Euthanase | Euthanase |

SE S1400, S enteritidis S1400.  LB media, Luria Bertani broth

FIG. 13

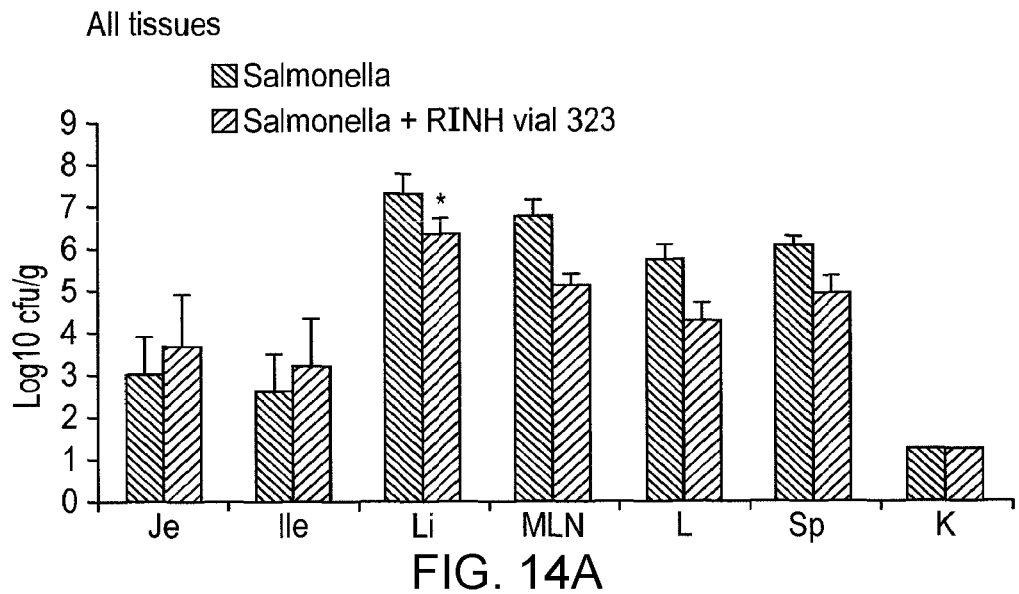
FIG. 14A
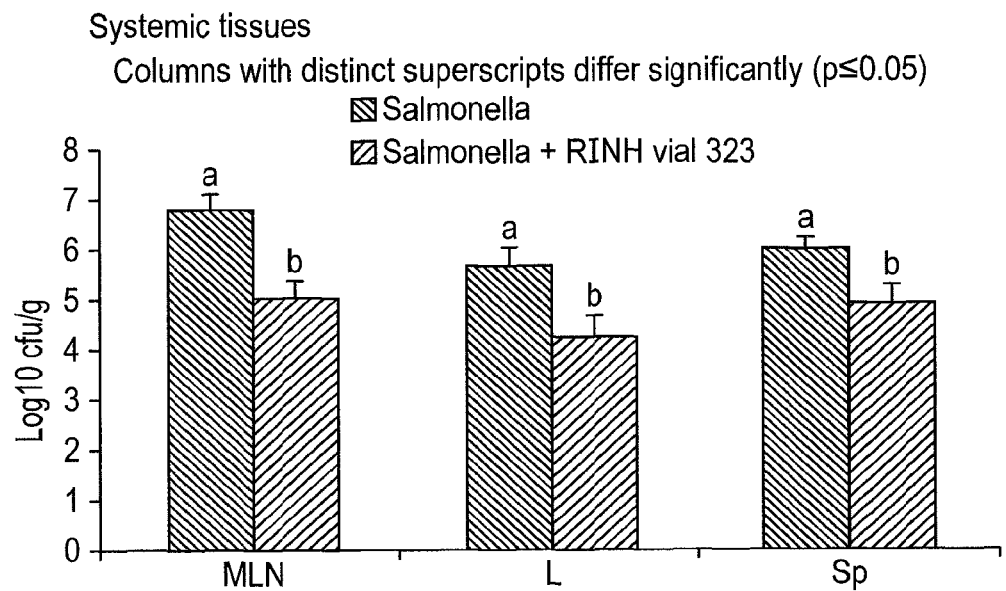
FIG. 14B
Statistical analysis
S. enteritidis vs S. enteritidis + 323
| | |
|---|---|
| Jejunum | p>0.05 |
| Ileum | p>0.05 |
| Large intestine | p<0.05 |
| MLN | p<0.05 |
| Liver | p<0.05 |
| Spleen | p<0.05 |
FIG. 14C

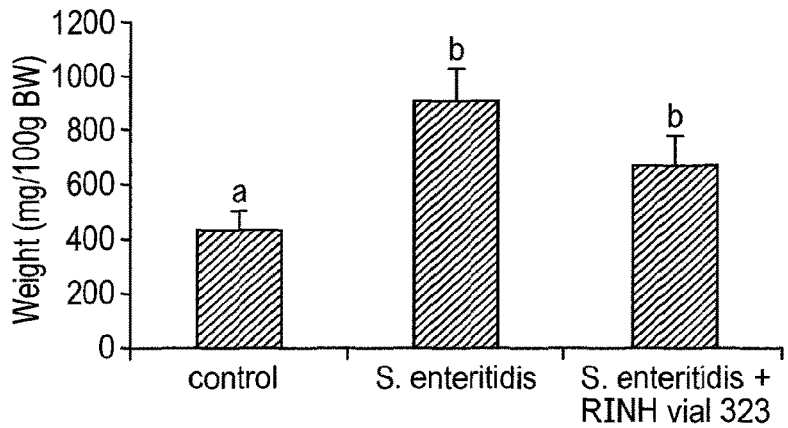

Columns with distinct superscripts differ significantly (p≤0.05)

FIG. 15

| LAB Challenge Day | | Control | Salmonella | Group 6<br>L. reuteri 31<br>Salmonella | Group 6<br>L. reuteri 32<br>Salmonella | Group 3<br>L. mucosae<br>Salmonella | Group 1<br>L. reuteri 46<br>Salmonella | Group 1;<br>L. reuteri 47<br>Salmonella |
|---|---|---|---|---|---|---|---|---|
| -6 | AM | MRS broth | MRS broth | LR 31 | LR 32 | L. mucosae | LR 46 | LR 47 |
| -4 | AM | MRS broth | MRS broth | LR 31 | LR 32 | L. mucosae | LR 46 | LR 47 |
| -2 | AM | MRS broth | MRS broth | LR 31 | LR 32 | L. mucosae | LR 46 | LR 47 |
|  |  | ↓ | ↓ | ↓ | ↓ | ↓ | ↓ | ↓ |
| 0 | AM | MRS broth | MRS broth | LR 31 | LR 32 | L. mucosae | LR 46 | LR 47 |
|  | PM | LB media | SE S1400 | SE S1400 | SE S1400 | SE S1400 | SE S1400 | SE S1400 |
|  |  | ↓ | ↓ | ↓ | ↓ | ↓ | ↓ | ↓ |
| 1 | AM | MRS broth | MRS broth | LR 31 | LR 32 | L. mucosae | LR 46 | LR 47 |
| 2 | AM | MRS broth | MRS broth | LR 31 | LR 32 | L. mucosae | LR 46 | LR 47 |
| 3 | AM | MRS broth | MRS broth | LR 31 | LR 32 | L. mucosae | LR 46 | LR 47 |
| 4 | AM | MRS broth | MRS broth | LR 31 | LR 32 | L. mucosae | LR 46 | LR 47 |
| 5 | AM | MRS broth | MRS broth | LR 31 | LR 32 | L. mucosae | LR 46 | LR 47 |
| 6 | AM | MRS broth | MRS broth | LR 31 | LR 32 | L. mucosae | LR 46 | LR 47 |
| 7 | AM | MRS broth | MRS broth | LR 31 | LR 32 | L. mucosae | LR 46 | LR 47 |
| 8 | AM | MRS broth | MRS broth | LR 31 | LR 32 | L. mucosae | LR 46 | LR 47 |
| 9 | AM | MRS broth | MRS broth | LR 31 | LR 32 | L. mucosae | LR 46 | LR 47 |
| 10 |  | Euthanase | Euthanase | Euthanase | Euthanase | Euthanase | Euthanase | Euthanase |

LR 31, Pig L. reuteri vial 3, LR 32, Pig L. reuteri vial 32. LR 46, Pig L. reuteri vial 46. LR 47, Pig L. reuteri vial 47. SE S1400, S. enteritidis S1400. LB media, Luria Bertani broth

FIG. 16

Columns with distinct superscripts differ significantly ($p \leq 0.05$)

Columns with distinct superscripts differ significantly (p≤0.05)

LACTIC ACID BACTERIAL STRAINS

CROSS REFERENCE

This application is a continuation of U.S. application Ser. No. 15/359,144, filed on Nov. 22, 2016, which is a divisional of U.S. application Ser. No. 14/232,475, filed Oct. 17, 2014, which is a national stage entry of PCT/GB2012/051686, filed Jul. 13, 2012, which claims the benefit of Great Britain Patent Application No. 1112091.2, filed Jul. 14, 2011, the entire contents of which are all incorporated herein by reference.

SEQUENCE LISTING

The instant application contains a Sequence Listing which has been submitted in ASCII format via EFS-Web in U.S. application Ser. No. 14/232,475 and is hereby incorporated by reference in its entirety. Said ASCII copy, is named 553773 (DYT-007US) SEQ.pdf and is 83 002 bytes in size.

The present invention relates to bacterial strains isolated from pigs. More specifically, the invention relates to the isolation of lactic acid bacteria from organically-reared pigs. The claimed lactic acid bacteria have useful probiotic and therapeutic applications.

BACKGROUND TO THE INVENTION

The composition of the microbial flora of pigs, their gut innate immune function and possible susceptibility to infection is greatly influenced by the environment in which they were reared during early life (Mulder et al, 2009). Outdoor-reared pigs generally have a more developed gut immune system, perform better and are healthier than indoor-reared counterparts. The outdoor environment dramatically influences microbial diversity of the gut and is associated with high levels of *Firmicutes*, in particular Lactic Acid Bacteria [LAB].

LAB comprise a clade of gram-positive, low-GC, acid-tolerant, generally non-sporulating, non-respiring bacteria that are associated with certain common metabolic and physiological characteristics. LAB are rod-shaped bacilli or coccus that are characterized by an increased tolerance to a lower pH range. LAB produce lactic acid as the major metabolic end-product of carbohydrate fermentation and are amongst the most important groups of microorganisms used in the food industry.

Lactobacilli are predominant in the gut flora of organically (outdoor) reared pigs. In contrast, the numbers of these bacteria are low in indoor-reared pigs and levels of potentially pathogenic phylotypes are high (Mulder et al, 2009). Furthermore, gut immune development and function of indoor-reared pigs is known to deviate from normal. In particular, expression of Type 1 interferon genes, Major Histocompatibility Complex class I and several chemokines are known to be increased (Mulder et al, 2009).

Lactic acid bacteria may modify the flora and gut structure and function in several ways (Cotter et al, 2005; Ohashi and Ushida, 2009). For example, they may compete with harmful bacteria for key nutrients or attachment sites on the gut, resulting in their exclusion. Alternatively, they can produce bioactive substances that aid or promote colonisation by beneficial bacteria or kill/interfere with the growth of potentially harmful or pathogenic bacteria. Alternatively, these bioactive factors can be immune-modulators that promote immune development and barrier integrity of the gut. Strains of LAB vary greatly in their biological activity. The present invention seeks to provide LAB strains that have therapeutically useful properties. More specifically, the invention seeks to provide LAB strains that are capable of promoting gut and immune development and health, thereby having considerable therapeutic potential as probiotics.

STATEMENT OF INVENTION

The present applicant has shown that the microbiota of out-door reared pigs contain LAB strains that produce potent and specific anti-microbial or cell-/immune-modulating bioactive factors.

Aspects of the invention, together with preferred embodiments, are set forth in the accompanying claims.

A first aspect of the invention relates to a porcine lactic acid bacterial strain, wherein said bacterial strain is characterised by one or more of the following characteristics:

(i) the ability to exhibit antimicrobial activity against *E. coli*;

(ii) the ability to exhibit antimicrobial activity against *S. enteritidis*;

(iii) the ability to suppress inflammation in IPEC cells induced by 12-O-tetradecaboylphorbol-13-acetate (PMA);

(iv) the ability to block the attachment or invasion of IPEC cells by *S. enteritidis*;

(v) the ability to block the attachment or invasion of IPEC cells by *E. coli*;

(vi) the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin; and (vii) the ability to exhibit heat stability when subjected to three cycles of heating, each cycle comprising heating at a temperature of 70° C. for a period of 15 minutes.

A second aspect relates to a composition comprising one or more lactic acid bacterial strains according to the invention and a pharmaceutically acceptable excipient, carrier or diluent.

A third aspect relates to a probiotic composition comprising one or more lactic acid bacterial strains according to the invention.

A fourth aspect relates to one or more lactic acid bacterial strains according to the invention for use in medicine.

A fifth aspect relates to one or more lactic acid bacterial strains according to the invention for use in treating an intestinal disorder in a subject.

A sixth aspect relates to the use of one or more lactic acid bacterial strains according to the invention in the preparation of a medicament for treating an intestinal disorder in a subject.

A seventh aspect relates to a method of treating an intestinal disorder in a subject, said method comprising administering to the subject a pharmaceutically effective amount of one or more lactic acid bacterial strains or composition according to the invention.

An eighth aspect of the invention relates to one or more lactic acid bacterial strains according to the invention for improving intestinal microbiota.

A ninth aspect of the invention relates to a method of improving intestinal microbiota in a subject, said method comprising administering to the subject one or more lactic acid bacterial strains or composition according to the invention.

A tenth aspect relates to a feedstuff comprising one or more lactic acid bacterial strains according to the invention.

An eleventh aspect relates to a food product comprising one or more lactic acid bacterial strains according to the invention.

A twelfth aspect relates to a dietary supplement comprising one or more lactic acid bacterial strains according to the invention.

A thirteenth aspect relates to a food additive comprising one or more lactic acid bacterial strains according to the invention.

A fourteenth aspect relates to a process for producing a probiotic, said process comprising culturing a lactic acid bacterial strain according to the invention.

A fifteenth aspect of the invention relates to a process for obtaining a porcine lactic acid bacterial strain, said process comprising obtaining faeces from an organically reared pig and extracting one or more porcine lactic acid bacterial strains from said faeces.

A sixteenth aspect of the invention relates to one or more porcine lactic acid bacterial strains obtained by, or obtainable by, the process described above.

DETAILED DESCRIPTION OF THE INVENTION

As mentioned above, the present invention relates to one or more porcine lactic acid bacterial strains. The lactic acid bacterial strain is characterised by one or more of the following characteristics:
  (i) the ability to exhibit antimicrobial activity against *E. coli;*
  (ii) the ability to exhibit antimicrobial activity against *S. enteritidis;*
  (iii) the ability to suppress inflammation in IPEC cells induced by 12-O-tetradecaboylphorbol-13-acetate (PMA);
  (iv) the ability to block the attachment or invasion of IPEC cells by *S. enteritidis;*
  (v) the ability to block the attachment or invasion of IPEC cells by *E. coli;*
  (vi) the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin; and
  (vii) the ability to exhibit heat stability when subjected to three cycles of heating, each cycle comprising heating at a temperature of 70° C. for a period of 15 minutes.

As used herein, the term "porcine" means "of or pertaining to swine", i.e. of or pertaining to any of several mammals of the family Suidae, especially the domesticated hog, *Sus scrofa domesticus*, or *Sus domesticus* when young or of comparatively small size.

Preferably, the pig is less than 3 months old, preferably, less than 2 months old. Preferably, the porcine lactic acid bacterial strain is from an organically reared pig. In this regard, preferably, the pigs are reared free range, outside (with exposure to soil) and in the absence of antibiotics, growth promoters and/or growth enhancers.

Preferably, the porcine lactic acid bacterial strain is from an outdoor reared pig. Preferably, the pigs are reared outside for at least 60% of their lives. More preferably, the animals are reared outside for at least 80% of their lives, more preferably, at least 90% of their lives, even more preferably still, 100% of their lives.

In one preferred embodiment, the lactic acid bacterial strain is selected from *L. johnsonii, L. reuteri, L. plantarum, L. gasseri, L. pentosus, L. acidophilus, L. vaginalis* and *L. mucosae.*

In one preferred embodiment, the lactic acid bacterial strain is selected from *L. johnsonii, L. reuteri* and *L. plantarum.*

In another preferred embodiment, the lactic acid bacterial strain is in the form of a live bacterial population, a lyophilized bacterial population, a non-viable bacterial preparation, or the cellular components thereof. Preferably, where the bacterial strain is in the form of a non-viable bacterial preparation, it is selected from heat-killed bacteria, irradiated bacteria and lysed bacteria.

In one preferred embodiment, the lactic acid bacterial strain is in the form of a live bacterium, a dead bacterium, or the cellular components thereof.

In one preferred embodiment, the lactic acid bacterial strain is in isolated form. As used herein, the term "isolated" means isolated from its native environment.

In one preferred embodiment, the lactic acid bacterial strain is in biologically pure form. As used herein the term "biologically pure" refers to a bacterial strain in the form of a laboratory culture that is substantially free from other species of organism. Preferably, the lactic acid bacterial strain is in the form of a culture of a single species of organism.

As used herein, the term "lactic acid bacterial strain" also encompasses mutants of said lactic acid bacterial strain. As used herein, the term "mutant" includes derived bacterial strains having at least 93% homology, preferably at least 96% homology, more preferably 98% homology to the polynucleotide sequence of a referenced strain, but otherwise comprising mutations in other sequences in the bacterial genome. Mutants are obtainable by genetic engineering techniques inferring alteration of the genetic material of the strains of the invention or inferring a recombination of the genetic material of the strains of the invention with other molecules. Typically, in order to obtain such mutant strains, a person skilled in the art can use standard mutagenesis techniques such as UV radiation or exposure to mutagenic chemical products.

As used herein, the term "mutations" includes natural or induced mutations comprising at least single base alterations including deletions, insertions, transversions, and other modifications known to those skilled in the art, including genetic modification introduced into a parent nucleotide or amino acid sequence whilst maintaining at least 50% homology to the parent sequence. Preferably, the sequence comprising the mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http)://www.ncbi.nlm.nih.gov/BLAST/.

As used herein, the term "lactic acid bacterial strain" also encompasses homologues of the lactic acid bacterial strains. As used herein the term "homologue" refers to a lactic acid bacterial strain having a nucleotide sequence having a degree of sequence identity or sequence homology with the nucleotide sequence of the parent lactic acid bacterial strain (hereinafter referred to as a "homologous sequence(s)"). Here, the term "homologous" means an entity having a certain homology with the subject nucleotide sequence. Here, the term "homology" can be equated with "identity".

In the present context, a homologous sequence is taken to include a nucleotide sequence which may be at least 50, 60, 70, 75, 80, 85 or 90% identical, preferably at least 95%, 97%, 98% or 99% identical to the nucleotide sequence of the parent lactic acid bacterial strain (the subject sequence).

Homology comparisons can be conducted by eye, or more usually, with the aid of readily available sequence comparison programs. These commercially available computer programs can calculate % homology between two or more sequences. % homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Preferably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Preferably, the degree of identity with regard to a nucleotide sequence may be determined over the whole sequence.

The traditional identification of bacteria on the basis of phenotypic characteristics is generally not as accurate as identification based on genotypic methods. Comparison of the bacterial 16S rRNA gene sequence has emerged as a preferred genetic technique and allows for new strains to be identified by comparison of sequences with known bacterial DNA sequences using BLAST (http://blast.ncbi.nlm.nih.gov/Blast.cgi). The 16S rRNA gene sequence is universal in bacteria, and so relationships can be measured across many different bacteria. In general, the comparison of the 16S rRNA sequence allows differentiation between organisms at the genus level across all major phyla of bacteria, in addition to classifying strains at multiple levels, including species and sub-species level. The 16S rRNA gene sequence has been determined for a large number of strains. GenBank, the largest databank of nucleotide sequences, has over 20 million deposited sequences, of which over 90,000 are of 16S rRNA genes. This means that there are many previously deposited sequences against which to compare the sequence of an unknown strain.

In one preferred embodiment, the lactic acid bacterial strain has a 16S rRNA gene sequence selected from SEQ ID NOS 1-87, or a homologue or variant thereof. Another embodiment of the invention relates to a lactic acid bacterial strain that comprises a 16S rRNA gene sequence selected from SEQ ID NOS 1-87, or a homologue or variant thereof. Preferred uses/methods apply to this aspect mutatis mutandis.

The term "homologue" is as defined hereinabove. As used herein, the term "variant" includes any variation wherein: (a) one or more nucleotides are substituted by another nucleotide or deleted, (b) the order of two or more nucleotides is reversed, (c) both (a) and (b) are present together. Preferably, the variants arise from one of (a), (b) or (c). More preferably, one or two nucleotides are substituted or deleted. Even more preferably, one nucleotide is substituted by another.

In one preferred embodiment of the invention, the lactic acid bacterial strain is characterised by the ability to exhibit antimicrobial activity against *E. coli*. The observed antimicrobial activity is most likely by virtue of anti-microbial substances produced by the lactic acid bacterial strains of the invention, although nature of these anti-microbial substances has not been determined.

In the context of the present invention, the ability to exhibit antimicrobial activity against *E. coli* can be determined by measuring inhibition of the growth of *E. coli* in an in vitro well diffusion assay. Further details of the well diffusion assay are set forth in the accompanying examples. The assay is carried out using *Escherichia coli* K88 on MacConkey No 3 agar, incubating the plates for 16 hours at 37° C. More specifically, *Escherichia coli* K88 is added to the agar (1 ml of a 1:1000 dilution of an overnight culture of *Escherichia coli* K88 in 200 ml agar to give the equivalent of 106 CFU/ml). The agar is poured into petri dishes and allowed to set. The plates are marked off into quadrants and an approximately 5 mm well cut out in each quadrant. An aliquot (60 μl) of conditioned media or MRS broth is added to the wells. The plates are covered and incubated for 16 hours at 37° C. They are photographed using a digital camera. Images are transferred to Photoshop, and the diameter of the well and zone of inhibition were determined using the measure tool.

In the context of killing *E. coli* in the above well diffusion assay, preferably the lactic acid bacterial strain of the invention exhibits <20000 units of inhibition, more preferably 20000-40000 units, even more preferably 40000-60000 units, more preferably 60000-80000 units, more preferably 80000-100000 units of inhibition, even more preferably still >100000 units of inhibition.

In one preferred embodiment of the invention, the lactic acid bacterial strain is characterised by the ability to exhibit antimicrobial activity against *S. enteritidis*. Again, the observed antimicrobial activity is most likely by virtue of anti-microbial substances produced by the lactic acid bacterial strains of the invention, although nature of these anti-microbial substances has not been determined.

In the context of the present invention, the ability to exhibit antimicrobial activity against *S. enteritidis* can be determined by measuring the ability to inhibit the growth of *S. enteritidis* in an in vitro well diffusion assay. Further details of the well diffusion assay are set forth in the accompanying examples. The assay is carried out using *Salmonella enteritidis* S1400 on XLD agar, incubating the plates for 16 hours at 37° C. XLD agar is prepared as per manufacturer's instructions and cooled to 45° C. *Salmonella enteritidis* S1400 is added to the XLD agar (1 ml of a 1:1000 dilution of an overnight culture of *Salmonella enteritidis* S1400 in 200 ml agar to give the equivalent of 106 CFU/ml). The XLD agar is poured into petri dishes and allowed to set.

The plates are marked off into quadrants and an approximately 5 mm well cut out in each quadrant. An aliquot (60 µl) of conditioned media or MRS broth is added to the wells. The plates are covered and incubated for 16 hours at 37° C. and the data analysed as described above for the *E. coli* assay.

In the context of killing *Salmonella enteritidis* in the above well diffusion assay, preferably the lactic acid bacterial strain of the invention exhibits <20000 units of inhibition, more preferably 20000-40000 units, even more preferably 40000-60000 units, more preferably 60000-80000 units, more preferably 80000-100000 units of inhibition, even more preferably still >100000 units of inhibition.

In an alternative embodiment, the ability to exhibit antimicrobial activity against *S. enteritidis* can be determined by measuring the ability to inhibit *S. enteritidis* in vivo in C3H/HeN or C57Bl/6 mice. Further details of appropriate in vivo assays are set forth in the accompanying examples.

Specifically, C3H/HeN and C57Bl/6 mice are treated with a lactic acid bacterial strain according to the invention prior to and post-challenge with *Salmonella enteritidis*. The mice are euthanased and dissected 6 (C57Bl/6) or 10 (C3H/HeN) days post-infection and viable *salmonella* are detected in systemic tissues (e.g. the mesenteric lymph node, liver and spleen), in the intestine (e.g. caecum, colon) and in the faeces as compared to appropriate controls. The in vivo activity of the lactic acid bacterial strain of the invention can also be measured by determining the level of myeloperoxidase [MPO], a marker for neutrophils, in the intestine of C3H/HeN mice treated with *salmonella* or *salmonella* plus LAB. MPO in the intestine is greatly increased by *salmonella* infection, due to recruitment of neutrophils to the intestine part of the host response to infection. Co-treatment with a lactic acid bacterial strain according to the invention reduces MPO activity in the intestine of *salmonella*-infected mice, indicating that the intestinal inflammatory responses to infection are lowered in these animals, relative to control experiments.

In one preferred embodiment of the invention, the lactic acid bacterial strain is characterised by the ability to suppress inflammation in IPEC cells induced by 12-O-tetradecaboylphorbol-13-acetate (PMA). In the context of the present invention, this refers to the ability of the lactic acid bacterial strain to block interleukin-8 (IL-8) gene expression triggered by PMA. More specifically, it can be determined by measuring the suppression of inflammation in IPEC-J2 cells induced by PMA when incubated for 2 hours at 37° C., 5% $CO_2$, 95% humidity. Following RNA and reverse transcription, real time PCR is carried out on a 7500 Fast Real-time PCR system operating with 7500 Fast System v 1.4.0 Sequence Detection Software version 1.4 (Applied Biosystem), using primers for porcine IL-8 and TNF-α (prepared by Sigma Aldrich). The reaction mix is: 10 µl Power Sybergreen Master mix, 2.5 µl of forward primer, 2.5 µl of reverse primer and 5 µl of cDNA, The Real Time PCR is then run according to the Standard 7500 protocol (95° C., 10 min, 1 cycle. 95° C., 15 sec, 40 cycles. 60° C., 1 min, 40 cycles. 95° C., 15 sec, 1 cycle. 60° C., 1 min, 1 cycle. 95° C., 15 sec, 1 cycle. 60° C., 15 sec, 1 cycle). Expression of IL-8 and TNF-α genes are analysed and compared to that of the 'house-keeping' gene β-actin. For comparison, values are given as the ratio of IL-8 and TNF-α per β-actin or fold-change. Further details of this assay are set forth in the accompanying examples.

In one preferred embodiment of the invention, the lactic acid bacterial strain is characterised by the ability to block the attachment or invasion of IPEC cells by *S. enteritidis*. This can be measured by the assay set forth in the accompanying examples. Specifically, monolayers of IPEC-J2 cells are grown to 3 days post-confluence in 24-well plates and synchronised by the addition of DTS media 24 hrs prior to use. Overnight cultures of pig LAB (10 ml) are centrifuged and the bacteria re-suspended in phosphate buffered saline [PBS]. An aliquot (50 µl) of LAB is added to the wells. The plates are incubated for 2 hours at 37° C., 5% $CO_2$, 95% humidity. An overnight culture of *Salmonella enterica* serovar Enteritidis S1400 [*S. enteritidis* S1400] is sub-cultured (0.5 ml in 10 ml) into Luria Bertani (LB) media and incubated aerobically for 2-3 hours at 37° C. until it reaches an optical density (560 nm) of 0.8 (a concentration equivalent to $1 \times 10^8$ CFU/ml). The culture is centrifuged and the bacteria re-suspended in PBS. An aliquot (50 µl) is added to the wells of IPEC-J2 cells. The plates are incubated for a further 2 hours at 37° C., 5% $CO_2$, 95% humidity. The IPEC-J2 cell monolayers are washed with HBSS. A solution (0.5 ml) of PBS containing Triton-X100 (10 ml/litre) is added to each well, the monolayer scraped off and dispersed. Viable *salmonella* are estimated on XLD agar plates (incubated for 24 hours at 37° C.) by the Miles and Misra method. Lactic acid bacteria are determined by the same procedure (incubated anaerobically for 48 hours at 37° C.).

Preferably, in the context of the adherence/invasion of IPEC cells by *S. enteritidis* the lactic acid bacterial strain of the invention exhibits 0-20% inhibition of adherence/invasion, more preferably 20-40%, even more preferably 40-60%, more preferably still, 60-80%, even more preferably still, 80-100% inhibition of adherence/invasion as measured by the above assay.

In one preferred embodiment of the invention, the lactic acid bacterial strain is characterised by the ability to block the attachment or invasion of IPEC cells by *E. coli*. This can be measured by a similar assay to that described above for *S. enteritidis*, and as set forth in the accompanying examples.

Preferably, in the context of the adherence/invasion of IPEC cells by *E. coli* K88 the lactic acid bacterial strain of the invention exhibits 0-20% inhibition of adherence/invasion, more preferably 20-40%, even more preferably 40-60%, more preferably still, 60-80%, even more preferably still, 80-100% inhibition of adherence/invasion as measured by the above assay.

In one preferred embodiment of the invention, the lactic acid bacterial strain is characterised by the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin. In the context of the present invention, antibiotic resistance can be determined by measuring the effect of various antibiotic-containing discs on an MRS agar plate culture of the lactic acid bacterial strain, when placed in an anaerobic jar and incubated for 24 hours at 37° C. Further details of the assay are set forth in the accompanying examples. More specifically, pig LAB [0.5 ml of a 1:100 dilution of an overnight culture] is spread onto the surface of an MRS agar plate and dried off. The plates are marked off into 4 quadrants and in each quadrant is placed an antibiotic-containing disc [Ampicillin, 10 µg. Cefotaxime, 30 µg. Chloramphenicol, 10 µg. Erythromycin, 15 µg. Gentamicin, 10 µg. Kanamycin, 30 µg. Metronizadole, 50 µg. Nalidixic acid, 30 µg. Tetracycline, 30 µg. Vancomycin, 30 µg]. The plates are covered, placed in an anaerobic jar and incubated for 24 hours at 37° C. The plates are photographed using a digital camera. Images are transferred to Photoshop, and the diameter of the zone of inhibition is determined using the measure tool. For each antibiotic, the exclusion area for the test strain is taken and divided with the maximum area of exclusion obtained for that antibiotic.

Preferably, the LAB of the invention is characterised by the absence of resistance to the antibiotics ampicillin, cefotaxime, chloramphenicol, erythromycin, gentamicin, tetracycline, vancomycin, metronizadole, nalidixic acid and kanamycin. More preferably, the LAB of the invention is characterised by the absence of resistance to the antibiotics ampicillin, cefotaxime, chloramphenicol, erythromycin, gentamicin, tetracycline and vancomycin.

In one preferred embodiment of the invention, the lactic acid bacterial strain is characterised by the ability to exhibit heat stability when subjected to three cycles of heating, each cycle comprising heating at a temperature of 70° C. for a period of 15 minutes. Further details of heat stability studies are set forth in the accompanying examples. More specifically, in the context of the present invention, heat stability is measured by centrifuging an overnight culture (10 ml) of isolated pig LAB and resuspending the pellet in fresh MRS broth (10 ml). An aliquot (1 ml) is heated at 70° C. for 15 min and then plated out (0.5 ml) out on MRS agar and incubated in an anaerobic jar for 48 hours at 37° C. A small number of colonies are detected, picked off, seeded into Hungate tubes containing MRS broth and incubated for 48 hours at 37° C. This culture is centrifuged, re-suspended in MRS broth, heated again at 70° C. for 15 min, plated out on MRS agar, incubated in an anaerobic jar for 48 hours at 37° C., picked off, seeded into Hungate tubes containing MRS broth and incubated for 48 hours at 37° C. This culture is centrifuged, re-suspended in MRS broth, re-heated at 70° C. for 15 min, plated out (0.5 ml) out on MRS agar, incubated in an anaerobic jar for 48 hours at 37° C., picked off, seeded into Hungate tubes containing MRS broth and incubated for 48 hours at 37° C.

In one preferred embodiment, the lactic acid bacterial strain has any two of the characterising features selected from the group consisting of (i), (ii), (iii), (iv), (v), (vi) and (vii) set forth above.

In one preferred embodiment, the lactic acid bacterial strain has any three of the characterising features selected from the group consisting of (i), (ii), (iii), (iv), (v), (vi) and (vii) set forth above.

In one preferred embodiment, the lactic acid bacterial strain has any four of the characterising features selected from the group consisting of (i), (ii), (iii), (iv), (v), (vi) and (vii) set forth above.

In one preferred embodiment, the lactic acid bacterial strain has any five of the characterising features selected from the group consisting of (i), (ii), (iii), (iv), (v), (vi) and (vii) set forth above.

In one preferred embodiment, the lactic acid bacterial strain has any six of the characterising features selected from the group consisting of (i), (ii), (iii), (iv), (v), (vi) and (vii) set forth above.

In one preferred embodiment, the lactic acid bacterial strain has all seven of the characterising features (i), (ii), (iii), (iv), (v), (vi) and (vii) set forth above.

In one particularly preferred embodiment, (A), the lactic acid bacterial strain is characterised by features (i) and (ii) above.

In one particularly preferred embodiment, (B), the lactic acid bacterial strain characterised by features (iv) and (v) above.

In one particularly preferred embodiment, (C), the lactic acid bacterial strain is characterised by features (iv) and (v) above.

In one particularly preferred embodiment, the lactic acid bacterial strain is characterised by features denoted (D) to (G) as follows:
(D) (i) and (iv); or
(E) (i) and (v); or
(F) (ii) and (iv); or
(G) (ii) and (v);

More preferably, the lactic acid bacterial strain is further characterised by feature (vi) in addition to those features recited in any one of embodiments (A) to (G) above.

Even more preferably, the lactic acid bacterial strain is further characterised by feature (iii) in addition to those features recited in any one of embodiments (A) to (G) above.

Even more preferably still, the lactic acid bacterial strain is further characterised by feature (vii) in addition to those features recited in any one of embodiments (A) to (G) above.

Biological Deposits

One embodiment of the invention relates to a lactic acid bacterial strain isolated from the faeces of organically reared pigs and selected from the group consisting of strains deposited on 27 Jun. 2011 under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, under the following accession numbers:

NCIMB 41846: *Lactobacillus reuteri* GGDK31;
NCIMB 41847: *Lactobacillus plantarum/pentosus/paraplantarum* GGDK161;
NCIMB 41848: *Lactobacillus johnsonii/taiwanensis/acidophilus/gasseri* GGDK255;
NCIMB 41849: *Lactobacillus plantarum/pentosus/helveticus/paraplantarum* GGDK258;
NCIMB 41850: *Lactobacillus johnsonii* GGDK266.

The above deposits NCIMB 41846, NCIMB 41847, NCIMB 41848, NCIMB 41849 and NCIMB 41850, were made by Dr George Grant of the Rowett Institute of Nutrition and Health, University of Aberdeen, Greenburn Road, Aberdeen, AB21 9SB on behalf of the Applicant, GT Biologics Limited.

Subsequent studies by the Applicant revealed that the strain deposited as NCIMB 41847 was a mixture of *Lactobacillus paraplantarum* and *Lactobacillus reuteri*. Subsequent studies by the Applicant revealed that the strain deposited as NCIMB 41850 was a mixture of *Lactobacillus johnsonii* and *Lactobacillus reuteri*. Subsequent studies by the Applicant revealed that the strain deposited as NCIMB 41848 was *Lactobacillus reuteri*. Isolated strains for the respective components of strains NCIMB 41847 and NCIMB 41850 were subsequently deposited (see below).

Another embodiment of the invention relates to a lactic acid bacterial strain isolated from the faeces of organically reared pigs and selected from the group consisting of strains deposited on 12 Jul. 2012 under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, under the following accession numbers:

NCI MB 42008 *Lactobacillus johnsonii;*
NCIMB 42009 *Lactobacillus reuteri;*
NCIMB 42010 *Lactobacillus plantarum;*
NCIMB 42011 *Lactobacillus reuteri;*
NCIMB 42012 *Lactobacillus reuteri*

The above deposits NCIMB 42008, NCIMB 42009, NCIMB 42010 and NCIMB 42011 and NCIMB 42012, were made by Professor Denise Kelly of GT Biologics Limited, c/o Institute of Medical Sciences, University of Aberdeen, Foresterhill, Aberdeen, Aberdeensshire, AB25 2ZD, UK, on behalf of the Applicant, GT Biologics Limited.

The invention also encompasses mutant strains, which can be obtained from said strains, and strains exhibiting a DNA-DNA homology of at least 70% and/or a 16S RNA identity of at least 99.5% with a strain selected from those deposited under the above accession numbers.

As used herein the term "16S rRNA identity" refers to the percentage identity with a known bacterial strain. In one preferred embodiment, the lactic acid bacterial strain has a 16S rRNA identity of at least 85% or at least 90%, or at least 95, 96, 97, 98 or 99% with a strain selected from those deposited under the above accession numbers. In one highly preferred embodiment, the lactic acid bacterial strain has a 16S rRNA identity of at least 99.5% with a strain selected from those deposited under the above accession numbers.

In the context of the present invention, the term "DNA-DNA homology" refers to how closely related two or more separate strands of DNA are to each other, based on their nucleotide sequence. Typically, this is measured in terms of their % identity. In one preferred embodiment, the lactic acid bacterial strain has a DNA-DNA homology of at least 70% with a strain selected from those deposited under the above accession numbers, more preferably, at least 80%, or at least 85%, more preferably still, at least 90, 95, 97, 98 or 99% homology with a strain selected from those deposited under the above accession numbers.

In one highly preferred embodiment, the lactic acid bacterial strain has a DNA-DNA homology of at least 70% and a 16S rRNA identity of at least 99.5% with a strain selected from those deposited under the above accession numbers.

Compositions

Another aspect of the invention relates to a composition comprising one or more lactic acid bacterial strains as described above and a pharmaceutically acceptable excipient, carrier or diluent. Suitable excipients, diluents, carriers are described below.

The composition may be any composition, but is preferably a composition to be administered orally, enterally or rectally. For example, the composition may be an edible composition. "Edible" means a material that is approved for human or animal consumption.

Another aspect of the invention relates to a probiotic composition comprising a lactic acid bacterial strain as described above.

Another aspect of the invention relates to combinations of two more lactic acid bacterial strains as described herein. In a particularly preferred embodiment, such combinations exhibit a synergistic functionality, for example, the combination is synergistic, i.e. the resultant effect is greater than the simple additive effects attributable to the individual lactic acid bacterial components in the combination.

One preferred embodiment of the invention relates to a combination of two, three, four or five different lactic acid bacteria, more preferably, two, three or four different lactic acid bacteria, more preferably, two or three different lactic acid bacteria. Where the invention relates to a combination of more than one lactic acid bacterial strain, the individual components of the combination may be present in any ratio.

More preferably still, the invention relates to a combination of two different lactic acid bacteria. Preferably, the two different lactic acid bacteria are present in a ratio of from 1/99.9 to 99.9/1 by weight, for example, 1/99 to 99/1 or 10/90 to 90/10, or 20/80 to 80/20, or 30/70 to 70/30 and the like.

In one highly preferred embodiment, the combination is a mixture of *Lactobacillus johnsonii* and *Lactobacillus reuteri*. Even more preferably, the combination is NCIMB 41850: *Lactobacillus johnsonii* and *Lactobacillus reuteri* GGDK266 as described above. Surprisingly, this particular combination of lactic acid bacteria unexpectedly gives rise to beneficial in vivo responses in early weaned pigs (see Examples).

In another highly preferred embodiment, the combination is a mixture of *Lactobacillus plantarum* and *Lactobacillus reuteri*. Even more preferably, the combination is NCIMB 41847: *Lactobacillus plantarum/pentosus/paraplantarum* and *Lactobacillus reuteri* GGDK161 as described above.

As used herein, the term "probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

Preferably, the probiotic composition is an orally administrable composition of metabolically active, i.e., live and/or or lyophilized, or non-viable heat-killed, irradiated or lysed probiotic bacteria. The probiotic composition may contain other ingredients. The probiotic composition of the invention can be administered orally, i.e., in the form of a tablet, capsule or powder. Alternatively, the probiotic composition of the invention may be administered orally as a food or nutritional product, such as milk or whey based fermented dairy product, or as a pharmaceutical product.

A suitable daily dose of the probiotic bacteria is from about $1\times10^3$ to about $1\times10^{11}$ colony forming units (CFU), more preferably from about $1\times10^7$ to about $1\times10^{10}$ CFU, more preferably, about $1\times10^6$ to about $1\times10^{10}$ CFU.

In one preferred embodiment, the composition contains bacterial strains and/or their cellular components, as active ingredients, in an amount of from about $1\times10^6$ to about $1\times10^{12}$ CFU/g, respect to the weight of the composition, preferably from about $1\times10^8$ to about $1\times10^{10}$ CFU/g. The dose may be of 1 g, 3 g, 5 g, and 10 g, by way of example.

Typically, a probiotic is optionally combined with at least one suitable prebiotic compound. A prebiotic is usually a non-digestible carbohydrate such as an oligo- or polysaccharide, or a sugar alcohol which is not degraded or absorbed in the upper digestive tract. Known prebiotics include commercial products such as inulin and transgalacto-oligosaccharides.

Preferably, the composition of the present invention includes a prebiotic in an amount of from about 1 to about 30% by weight, respect to the total weight composition, preferably from 5 to 20% by weight. Preferred carbohydrates are selected from: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. Particularly preferred prebiotics are the short-chain fructo-oligosaccharides (for simplicity shown hereinbelow as FOSs-c.c); said FOSs-c.c. are not digestable glucides, generally obtained by the conversion of the beet sugar and including a saccharose molecule to which three glucose molecules are bonded.

Preparation of Lactic Acid Bacteria

A further aspect of the invention relates to a process for producing a probiotic, said process comprising culturing a lactic acid bacterial strain according to the invention. The skilled person in the art will be familiar with standard techniques and conditions suitable for culturing a bacterial strain according to the invention.

A further aspect of the invention relates to a method of preparing one or more bacterial strains according to the invention, said method comprising the steps of:
(i) obtaining faeces from an organically reared pig;
(ii) freezing the faeces and dispersing in a suitable diluent;
(iii) applying the dispersed faeces obtained in step (ii) to a suitable agar, optionally in the presence of supplemental pig colostrum carbohydrates, and incubating under an anaerobic conditions;
(v) selecting off distinct colonies of bacteria formed during step (iv) and seeding into a suitable broth, optionally in the presence of supplemental pig colostrum carbohydrates;
(vi) incubating the seeded colonies obtained in step (v).

Suitable agars include, for example, MRS or LAMVAB agar plates. However, other suitable agars can also be used, and would be familiar to the skilled person.

Suitable broths include, for example, MRS broth. However, other suitable broths can also be used, and would be familiar to the skilled person.

Preferably, step (iii) involves incubating the agar for at least 72 hours at a temperature of about 37° C.

Preferably, step (vi) involves incubating the seeded colonies for at least 48 hours at a temperature of about 37° C.

A further aspect of the invention relates to a process for obtaining a porcine lactic acid bacterial strain, said process comprising obtaining faeces from an organically reared pig and extracting one or more porcine lactic acid bacterial strains from said faeces.

Preferably, the process comprises the steps of:
(i) obtaining faeces from an organically reared pig;
(ii) freezing the faeces and dispersing in a suitable diluent;
(iii) applying the dispersed faeces obtained in step (ii) to a suitable agar, optionally in the presence of supplemental pig colostrum carbohydrates, and incubating under an anaerobic conditions;
(v) selecting off distinct colonies of bacteria formed during step (iv) and seeding into a suitable broth, optionally in the presence of supplemental pig colostrum carbohydrates;
(vi) incubating the seeded colonies obtained in step (v).

Another aspect of the invention relates to a porcine lactic acid bacterial strain obtained by, or obtainable by, the process described above.

Therapeutic Applications

Another aspect of the invention relates to one or more lactic acid bacterial strains as defined above for use in medicine.

Another aspect of the invention relates to one or more lactic acid bacterial strains as defined above for use in treating an intestinal disorder.

Another aspect of the invention relates to the use of one or more lactic acid bacterial strains or a composition as defined above in the preparation of a medicament for treating an intestinal disorder.

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Another aspect of the invention relates to a method of treating an intestinal disorder in a subject, said method comprising administering to the subject a pharmaceutically effective amount of one or more lactic acid bacterial strains or a pharmaceutical composition or a probiotic composition as described above.

Preferably, the intestinal disorder is selected from irritable bowel syndrome (IBS), inflammatory bowel disorder (IBD), functional dyspepsia, functional constipation, functional diarrhoea (including antibiotic associated diarrhoea, traveller's diarrhoea and pediatric diarrhoea), functional abdominal pain, functional bloating, Epigastric Pain Syndrome, Postprandial Distress Syndrome, Crohn's disease, ulcerative colitis, gastrointestinal reflux disease (GERD), allergies, atopic diseases e.g. atopic dermatitis, necrotising enterocolitis, other infections, and combinations thereof.

In one preferred embodiment, the intestinal disorder is IBS. The precise pathophysiology of IBS remains to be elucidated. Recent studies have described mucosal inflammation and alterations in intestinal microbiota in IBS patients and a disease correlation with intestinal infections.

In one highly preferred embodiment, the disorder is salmonellosis. Salmonellosis is a disease caused by various strains of *salmonella* that is characterized by fever and intestinal disorders.

Another aspect of the invention relates to one or more lactic acid bacterial strains as defined above for improving intestinal microbiota.

Another aspect of the invention relates to a method of improving intestinal microbiota in a subject, said method comprising administering to the subject a composition comprising one or more lactic acid bacterial strains or a pharmaceutical composition or a probiotic composition according to the invention.

The lactic acid bacterial strains according to the invention may also be used in prophylactic applications. In prophylactic applications, compositions according to the invention are administered to a patient susceptible to, or otherwise at risk of, a particular disease in an amount that is sufficient to at least partially reduce the risk of developing a disease. Such an amount is defined to be "a prophylactic effective dose". The precise amounts depend on a number of patient specific factors such as the patient's state of health and weight.

The lactic acid bacterial strains and probiotic compositions according to the invention may also be used in animal nutrition (e.g. in pig nutrition), particularly in the early-weaned period and growing fattening period. The probiotics are expected to enhance immune function reduce and prevent infectious diseases, beneficially alter the microbiota composition, and improve growth and performance of animals, for example, through increased feed conversion efficiency. The term "animal" includes all animals including humans. Examples of animals are non-ruminants and ruminants. Ruminant animals include for example, sheep, goat, and cattle eg. cow as beef cattle and dairy cows. In a particular embodiment, the animal is a non-ruminant animal. Non-ruminant animals include pet animals, eg horses, cats, and dogs; monogastric eg pigs or swine (including but not limited to, piglets growing pigs and sows); poultry such as turkeys, ducks, and chickens (including but not limited to broiler chicks, layers); fish (including but not limited to salmon, trout, tilapia, catfish and carp); and crustaceans (including but not limited to shrimp and prawn).

Feedstuffs/Products

A further aspect of the invention relates to food products, dietary supplements, nutraceuticals, nutritional formulae, drinks and medicaments containing one or more bacterial strains according to the invention.

In one preferred embodiment, the composition comprises additionally at least one other kind of other food grade bacterium, wherein the food grade bacterium is preferably selected from the group consisting of lactic acid bacteria, bifidobacteria, propionibacteria or mixtures thereof.

One aspect of the invention relates to a food product comprising one or more lactic acid bacterial strains according to the invention. The term "food product" is intended to cover all consumable products that can be solid, jellied or liquid. Suitable food products may include, for example, functional food products, food compositions, pet food, livestock feed, health foods, feedstuffs and the like. In one preferred embodiment, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one preferred embodiment the composition according to the present invention is a food product intended for humans, pets or livestock. The composition may be intended for animals selected from the group consisting of dogs, cats, pigs, cattle, horses, goats, sheep or poultry. In a preferred embodiment, the composition is a food product intended for adult species, in particular human adults.

In the present invention, "milk-based product" means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

One aspect of the invention relates to a feedstuff or animal feed comprising one or more bacterial strains according to the invention.

Feedstuff can be a food additive, a feed premix or an animal feed. Particular examples of feedstuffs according to the invention include the following: animal feed additive comprising (a) porcine lactic acid bacteria according to the present invention (b) at least one fat soluble vitamin (c) at least one water soluble vitamin (d) at least one trace mineral and/or at least one macro mineral; an animal feed composition comprising a porcine lactic acid bacteria according to the present invention and a crude protein content of 50-88 g/kg feed. The so-called premixes are examples of animal feed additives of the invention. A premix designates a preferably uniform mixture of one or more micro-ingredients with diluent and/or carrier. Premixes are used to facilitate uniform dispersion of micro-ingredients in a larger mix.

Further, optional, feed-additive ingredients are coloring agents, e.g. carotenoids such as beta-carotene, astaxanthin, and lutein; aroma compounds; stabilisers; antimicrobial peptides; polyunsaturated fatty acids; reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Usually fat- and water-soluble vitamins, as well as trace minerals form part of a so-called premix intended for addition to the feed, whereas macro minerals are usually separately added to the feed. Either of these composition types, when enriched with a porcine lactic acid bacteria according to the present invention, is an animal feed additive within the scope of the invention.

The following are non-exclusive lists of examples of these components: Examples of fat-soluble vitamins are vitamin A, vitamin D3, vitamin E, and vitamin K, e.g. vitamin K3. Examples of water-soluble vitamins are vitamin B12, biotin and choline, vitamin B1, vitamin B2, vitamin B6, niacin, folic acid and panthothenate, e.g. Ca-D-panthothenate. Examples of trace minerals are manganese, zinc, iron, copper, iodine, selenium, and cobalt. Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A of WO 01/58275.

Animal feed compositions or diets typically have a relatively high content of protein. Poultry and pig diets can be characterized as indicated in Table B of WO 01/58275, columns 2-3. Fish diets can be characterized as indicated in column 4 of this Table B.

Furthermore such fish diets usually have a crude fat content of 200-310 g/kg. WO 01/58275 corresponds to U.S. Ser. No. 09/779,334 which is hereby incorporated by reference.

An animal feed composition according to the invention typically has a crude protein content of 50-800 g/kg, and furthermore comprises a porcine lactic acid bacteria according to the present invention thereof as described and/or claimed herein.

Furthermore, or in the alternative (to the crude protein content indicated above), the animal feed composition of the invention may have a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In certain preferred embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5). Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.). Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In one preferred embodiment, the animal feed composition of the invention contains at least one vegetable protein or protein source. It may also contain animal protein, such as Meat and Bone Meal, and/or Fish Meal, typically in an amount of 0-25%. The term vegetable proteins as used herein refers to any compound, composition, preparation or mixture that includes at least one protein derived from or originating from a vegetable, including modified proteins and protein-derivatives. In certain particularly preferred embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal. In a particular embodiment, the vegetable protein source is material from one or more plants of the family Fabaceae, e.g. soybean, lupine, pea, or bean. Other examples of vegetable protein sources are rapeseed, sunflower seed, cotton seed, and cabbage. Other examples of vegetable protein sources are cereals such as barley, wheat, rye, oat, maize (corn), rice, triticale, and sorghum.

Animal diets can e.g. be manufactured as mash feed (non pelleted) or pelleted feed. Typically, the milled feed-stuffs are mixed and sufficient amounts of essential vitamins and minerals are added according to the specifications for the species in question. A porcine lactic acid bacteria according to the present invention thereof can be added as solid or liquid formulations.

The compositions of the present invention may be—or may be added to—food supplements, also referred to herein as dietary supplements or food additives. Thus, another aspect of the invention relates to a dietary supplement or food additive comprising one or more bacterial strains according to the invention.

Another embodiment of the invention relates to the use of a feedstuff as described above for improving animal growth performance as measured by daily weight gain and/or feed conversion ratio.

In a preferred embodiment, the invention relates to methods for using a feedstuff comprising one or more porcine lactic acid bacteria according to the present invention in animal feed for improving daily weight gain, improving the Feed Conversion Ratio (FCR) and/or for modulation of the gut microflora.

In alternative preferred embodiments, the feedstuff comprising one or more porcine lactic acid bacteria according to the present invention improves animal feed digestibility, and/or maintains animal health by aiding in proper digestion and/or supporting immune system function.

The FCR may be determined on the basis of a piglet growth trial comprising a first treatment in which the feedstuff comprising a porcine lactic acid bacteria according to the present invention is added to the animal feed in a suitable concentration per kg feed, and a second treatment (control) with no addition of a porcine lactic acid bacteria according to the present invention to the animal feed. In the present context, the term Feed Conversion Ratio, or FCR, is used synonymously with the term feed conversion. The FCR is calculated as the feed intake in g/animal relative to the weight gain in g/animal. As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use.

Diluents, Excipients and Carriers

As mentioned above, the invention also relates to compositions, more preferably pharmaceutical compositions, comprising a lactic acid bacterial strain according to the invention. The lactic acid bacterial strains of the present invention are generally administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Administration

The compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. Preferably, the compositions of the present invention are adapted for oral, rectal, vaginal, parenteral, nasal, buccal or sublingual routes of administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The lactic acid bacterial strain can also be incorporated into an ointment consisting of a white wax or white soft paraffin base together with such stabilisers and preservatives as may be required.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The usual effective daily dose in humans or in animals is from about $1\times10^3$ to about $1\times10^{11}$, more preferably, from about $1\times10^7$ to about $1\times10^{11}$, even more preferably, from about $1\times10^6$ to about $1\times10^{10}$ CFU.

Combinations

In one preferred embodiment, the compositions of the invention are administered in any combination, for example, two or more of the lactic acid bacteria may be administered in any combination or ratio.

In another particularly preferred embodiment, the compositions of the invention are administered in combination with one or more other active agents. In such cases, the compositions of the invention may be administered consecutively, simultaneously or sequentially with the one or more other active agents.

Isolation and Characterisation of Bacterial Strains

The LAB strains isolated (total of 436 individual colony picks) from faeces of organically-reared pigs were predominantly L. reuteri, L. johnsonii, L. gasseri, L. pentosus, strains with a small number of L. plantarum, L. acidophilus, L. vaginalis, a single L. mucosae and several uncultured strains.

Most of the LAB produced substances that could inhibit the growth of S. enteritidis and/or E. coli K88 in vitro. The potency of these anti-pathogen effects varied greatly between the individual bacterial strains.

Certain strains were selected on the basis of anti-microbial potency as determined in vitro. These bacteria were further screened for their ability to block adherence/invasion of intestinal pig epithelial cells (IPEC) by pathogens in vitro and their susceptibility to antibiotics.

Certain strains were assayed for substrate range and specificity and their capacity to suppress inflammation in IPEC cells in vitro. From these, fourteen LAB (5 L. johnsonii, 6 L. reuteri and 3 L. plantarum) with favourable properties were identified. Two of these strains [GGDK266 and GGDK31] were prepared in bulk for in vivo evaluation in newly-weaned piglets. Other potentially important candidates were present amongst this set of 14 LAB.

Small losses in viability were evident on freeze drying and storage of LAB dried in skimmed milk powder. A combination of skimmed milk powder and simple sugars was slightly more effective, but difficult to maintain. Bulk preparations of GGDK266 and GGDK31 were freeze-dried and stored in this medium.

Five heat-conditioned cultures of LAB were obtained. However, the biological properties in vitro and probiotic potential of three strains were adversely affected by heat-treatment. Nonetheless, two of the bacteria retained the biological properties of the native non-heat-treated forms.

Oral treatment of mice with pig LAB (L. reuteri or L. mucosae) greatly reduced the pathogenicity of S. enteritidis in acute (C57Bl/6 mouse) and chronic (C3H/HeN mouse) forms of salmonellosis.

The data indicate that LAB from organically-reared pigs have considerable potential as a source of novel and potent probiotics.

Studies carried out by the applicant involved isolating large numbers of LAB from organically-reared pigs and screening for potent probiotic LAB strains by assessing their biological potency and mode of action both in vitro and in vivo.

More specifically, experiments were undertaken to establish cultures of LAB derived from faeces of organically-reared pigs. The LAB strains were screened for anti-microbial activity against a number of pathogens in vitro. Experiments were undertaken to determine whether the LAB strains could block the attachment of pathogens to pig epithelial cells in vitro. Studies were also undertaken to evaluate the capacity of LAB to block inflammatory responses in pig epithelial cells in vitro. Strains demonstrating a good bioactive profile in vitro were selected and cultured in bulk for a large-scale study in vivo.

Further details on the experimental techniques are described in the accompanying examples section. In brief, LAB strains were isolated and cultured from pig faeces using selective microbiological media. Individual bacterial colonies were isolated and 16S rRNA gene sequences were analysed to enable genotypic identification of bacterial strains. Phenotypic characteristic of potential probiotics was further determined following measurement of adherence, anti-bacterial and anti-inflammatory activities, antibiotic susceptibility and finally heat stability. Anti-bacterial activity of conditioned media derived from LAB was evaluated using well-diffusion assays to determine killing activity against the enteric pathogens *Salmonella enteritidis* and *E. coli* K88. The ability of LAB strains to block or interfere with *S. enteritidis* and *E. coli* K88 adherence/invasion of pig epithelial (IPEC) was also evaluated, as was their capacity to suppress inflammation in IPEC cells induced by 12-O-Tetradecaboylphorbol-13-acetate [PMA]. In addition, the metabolic properties of LAB strains (API CH 50 kit) and their susceptibility to antibiotics was further determined. A ranking system, based on scoring the biological properties of LAB was established and used for the selection of candidate LAB strains for probiotic evaluation in vivo.

Further details on the results of the above experiments are described in the accompanying examples.

The LAB (436 individual colony picks) isolated from faeces of organically-reared pigs were predominantly *L. johnsonii* or *L. johnsonii*-related and *L. reuteri* or *L. reuteri*-related with small numbers of *L. plantarum*-related and uncultured strains. This represented a much narrower range of porcine-associated LAB than reported by others (Martin et al, 2009; Yun et al, 2009; Lähteinen et al, 2010; Yao et al, 2011). However, in comparison to conventionally/intensively-reared pigs, out-door organically-reared pigs had high levels of LAB and more developed intestinal immune function (Mulder et al, 2009). The present bacterial data indicate that *L. johnsonii* and *L. reuteri* strains are of particular importance in proper development of the gut and immune system in young pigs. In addition, the inclusion of other lactic acid bacteria derived from the gut or faeces of organically-reared pigs, in particular, *Lactobacillus delbrueckii* and *Lactobacillus amylovorous* may enhance the immune homeostatic properties of *Lactobacillus reuteri*, *Lactobacillus plantarum* and *Lactobacillus johnsonii*.

All of the isolated pig LAB produced substances that could kill or interfere with the growth of *S. enteritidis* in a well-diffusion assay and the majority killed or suppressed growth of *E. coli* K88. The potency of the anti-microbial activities varied greatly between individual colonies, irrespective of whether they were *L. reuteri*, *L. johnsonii* or *L. plantarum*. There was no general correlation between the anti-*salmonella* and anti-*E. coli* K88 potency of each of the LAB. LAB are known to produce a range of active factors, including organic acids, small anti-microbial compounds and anti-bacterial peptides (Cintas et al, 2001). The nature of these anti-microbial substances produced by LAB from organically-reared pigs has not been established.

Thirty three pig LAB strains, selected on the basis of anti-pathogen activity, were tested for the ability to block attachment/invasion of IPEC cells by *S. enteritidis* and *E. coli* K88. They were all able to dramatically reduce attachment/invasion of IPEC cells by *salmonella*. The majority could also block *E. coli* K88. As with pathogen killing, there was no general correlation between the abilities of the LAB to block *salmonella* and *E. coli* K88. Without wishing to be bound by theory, it is believe that the LAB may limit the access of pathogens to the epithelial layer by occupying binding-sites on the cell monolayer or by production of factors that interfere with attachment of the pathogen to the epithelial cells, such as blocking binding sites of surface adhesins (Ljungh and Wadstrom, 2006; Blandino et al, 2008; Williams, 2010).

Pig LAB may also block or suppress inflammatory gene (interleukin-8, IL-8)-expression triggered in IPEC cells by PMA. Individual cultures varied greatly in their ability to affect inflammation, but five strains (RINH vial 29, 30, 31 86 and 266) had potent anti-inflammatory properties. Certain LAB strains are known to have immuno-modulatory or anti-inflammatory properties (Cotter et al, 2005; Blandino et al, 2008; Ohashi and Ushida, 2009; Elmadfa et al, 2010; Liu et al, 2010). The mechanisms involved remain unclear, but are likely to involve modulation of molecular signalling systems by bioactive factors produced by the LAB.

Antibiotic resistance is an increasing problem and can spread between bacteria by gene transfer (Korhonen et al, 2007; Gousia et al, 2011; Nicolau, 2011). Ideally, candidate probiotics should have little or no resistance to antibiotics to minimise the risk of transfer of resistance genes to the host flora. Pig LAB (33 strains) were screened for resistance to 10 individual antibiotics. One strain (RINH vial 266) was susceptible to all the tested antibiotics. Most were susceptible to ampicillin, cefotaxime, chloramphenicol, erythromycin, gentamicin, tetracycline and vancomycin. However, most exhibited resistance to metronizadole, nalidixic acid and to a lesser extent kanamycin. This relatively low incidence of antibiotic resistance amongst these LAB isolates may be linked to the environment in which the source piglets were reared [organic out-door reared] (Mulder et al, 2009).

*L. johnsonii*, *L. reuteri* and *L. plantarum*, as expected, exhibited strain-specific general substrate reaction profiles, when assayed using an API CH 50 kit. However, most genotype strains exhibited fine differences in their substrate reactivity. This indicated that they were unique individual strains of the genotype.

On the basis of their biological activities in vitro, fourteen LAB [4 *L. plantarum*-related, 3 *L. johnsonii*-related and 1 *L. reuteri*] were identified as having potential for testing in vivo. Two of these LAB strains [GGDK266 and GGDK31] were prepared in bulk.

Interestingly, 7 of the fourteen LAB (RINH vials 85, 86, 131, 230, 255, 266) had been isolated from LAB-selective agars supplemented with carbohydrate fractions from pig colostrum. The growth and bioactivity profile of LAB is, in part, dependent on the carbohydrate substrate in which it is grown (Gopal et al, 2001; Tzortzis et al, 2004), The present data may indicate that some of the LAB are host-adapted and require certain pig-associated carbohydrates for optimal growth or bioactivity.

It is advantageous if the LAB can withstand being freeze dried to allow them to be handled and processed as probiotics. However, their viability can be greatly reduced during freezing and drying (Tomas et al, 2009; Strasser et al, 2009;

Reddy et al, 2009). Skimmed milk powder, alone or in combination with simple sugars, is often used as a cryoprotectant to preserve the viability of the bacteria (Tomas et al, 2009; Strasser et al, 2009). In the present study, small losses in viability were evident on drying and storage of pig LAB in skimmed milk powder alone. Sucrose or lactose in combination with skimmed milk powder was slightly more protective. However, the product was hygroscopic and difficult to store or handle. It was therefore decided to dry and store pig LAB in skimmed milk powder.

Supplemental feeds for animal are often given as pellets, production of which involves high temperatures (De Angelis et al, 2006). LAB to be added to animal feeds should therefore have a significant degree of heat-stability to minimise loss of viability during processing. In the present study, five LAB were subject to heating three times for 15 minutes at 70° C. All of the bacteria that were recovered after the third heat-treatment were viable and in most cases grew at rates similar to the native forms of the bacteria. Two of the bacteria retained the biological properties of the native non-heat-treated forms. However, one of the heat-treated strains had lost the ability to block attachment of pathogen to epithelial cells in vitro and another had greatly reduced blocking activity. A further strain was unable to block PMA-induced inflammation in epithelial cells in vitro, although the native form was a potent suppressor of inflammation. Heat-treatment can thus differentially affect the biological properties of individual LAB. This needs to be taken into account when considering inclusion of LAB in pelleted animal feeds.

Experiments demonstrated that the pathogenicity of *S. enteritidis* was attenuated if mice were co-treated with LAB derived from organically-reared pigs. RINH vial 323 (*L. mucosae*) greatly reduced the ability of *S. enteritidis* to invade, spread to and proliferate in systemic tissues in acute (C57BI/6 mouse) and chronic (C3H/Hen mouse) *salmonellosis*. Furthermore, RINH vial 31 [GGDK31], RINH vial 32, RINH vial 46 or RINH vial 47 (all *L. reuteri*) reduced colonisation of the large intestine, invasion and systemic spread and proliferation in C3H/HeN mice by *S. enteritidis*. Overall, RINH vial 31 [GGDK31] and RINH vial 32 were the most effective in this chronic model of salmonellosis. These LAB have potential as novel probiotics to promote gut health or increase resistance to infection in vivo.

Infection by *salmonella* is a multi-factorial process (Naughton and Grant, 2005). *S. enteritidis* colonises the whole gastro-intestinal tract, moves through the mucus layer and attaches to the mucosa. The large intestine acts as a reservoir for the pathogen but invasion is primarily via M cells, present on the Peyer's patches of the ileum. Most invaded *salmonella* spread to the mesenteric lymph nodes and then out to the liver and spleen (Naughton and Grant, 2005). Without wishing to be bound by theory, it is believed that LAB could be blocking *salmonella* at various stages of the infection (Cintas et al, 2001; Cotter et al, 2005; Ohashi and Ushida, 2009). By competing for nutrients, killing of pathogen or blocking of attachment sites, LAB could limit the numbers of *salmonella* in the large intestine reservoir. LAB may also prevent attachment to ileal mucosal cells, in a manner similar to that observed here with IPEC-J2 cells and with Caco-2 cells (Neeser et al, 2000) and thereby limit invasion.

Alternatively, LAB may directly modulate host responses to the infection, in particular suppression of inflammation. By limiting gut damage and preserving barrier integrity (Smith et al, 2008; Schreiber et al, 2009), the ability of *salmonella* to invade and spread would be greatly reduced.

The present invention is further described by way of non-limiting example, and with reference to the following non-limiting figures, wherein:

FIG. 1 shows an assay of antibacterial activity of conditioned media from Lactic Acid Bacteria.

Figure 4A:
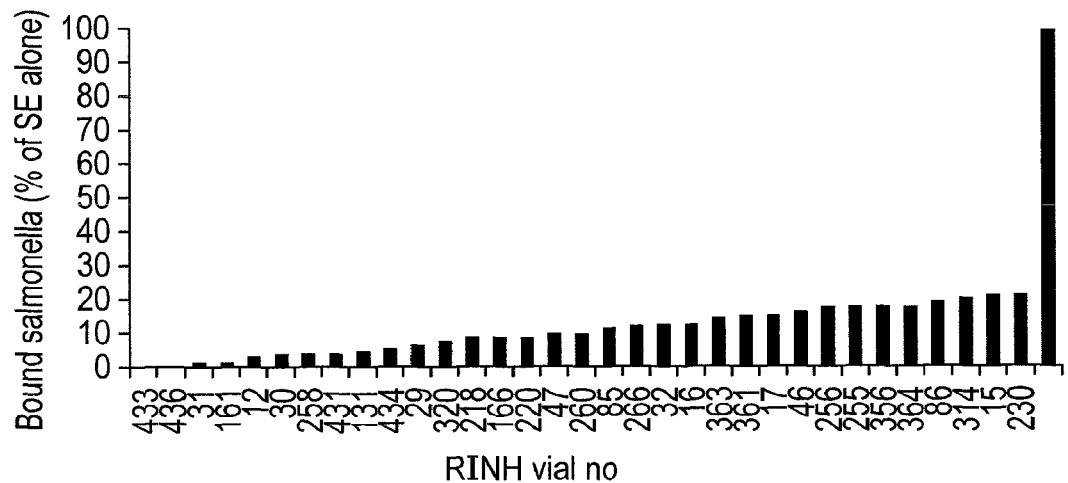
Figure 4B:
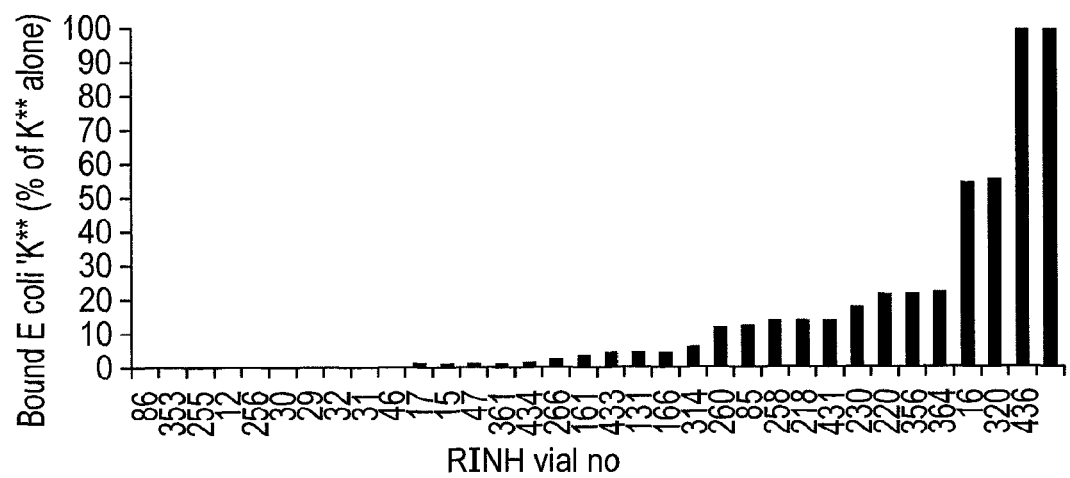
Figure 4C:
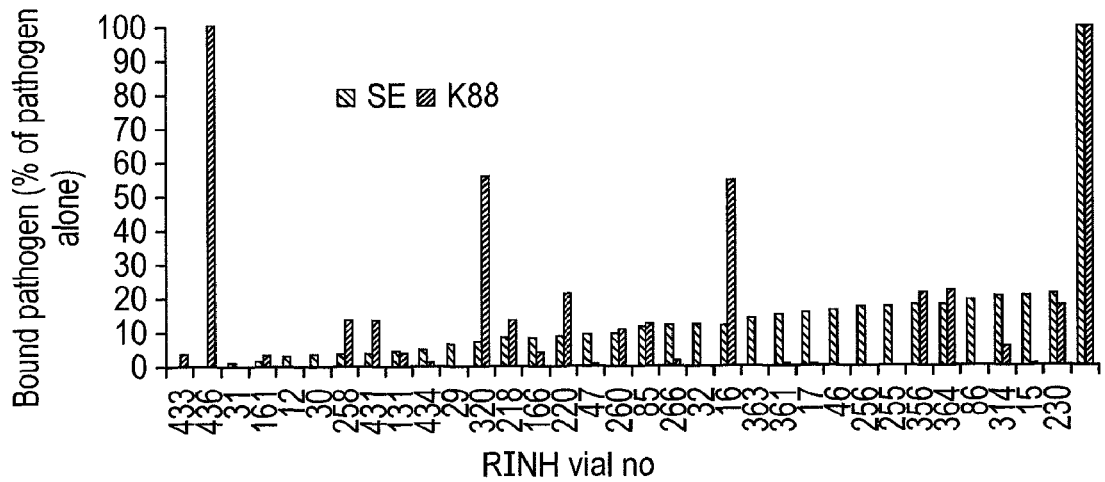

FIGS. 4A, 4B, and 4C shown inhibition of adherence by (FIG. 4A) *S. enteritidis* S1400; and (FIG. 4B) *E. coli* K88 to IPEC cells in culture by LAB cultured from faeces of organically-reared pigs; (FIG. 4C) comparison between inhibition of *S. enteritidis* S1400 and *E. coli* K88.

FIG. 5 shows an assay of the antibiotic susceptibility of Lactic Acid Bacteria using discs impregnated with a defined amount of antibiotic.

Figure 6:
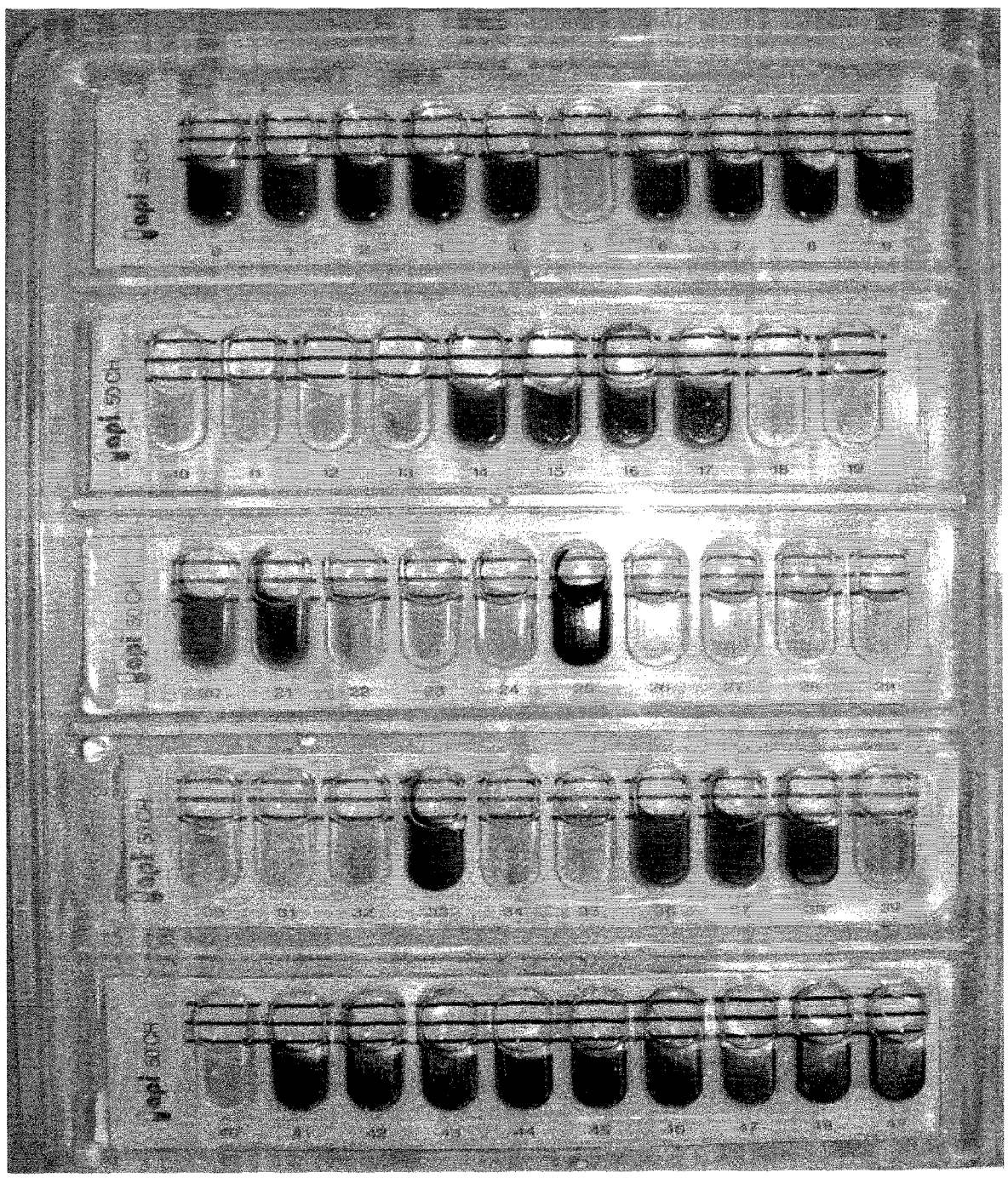

FIG. 6 shows an evaluation of substrate profile of LAB using an API CH 50 kit [49 substrates, pale colour indicated positive reaction, except 25 where positive reaction is black, dark colour indicates no reaction].

Figure 7A:
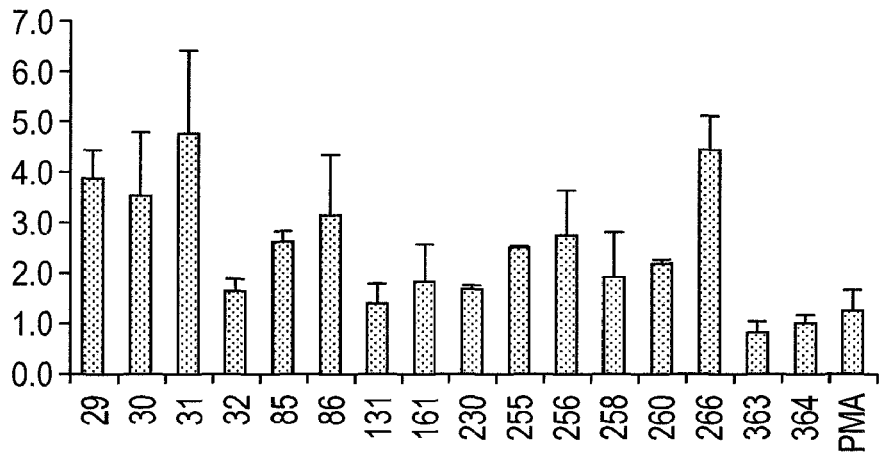
Figure 7B:
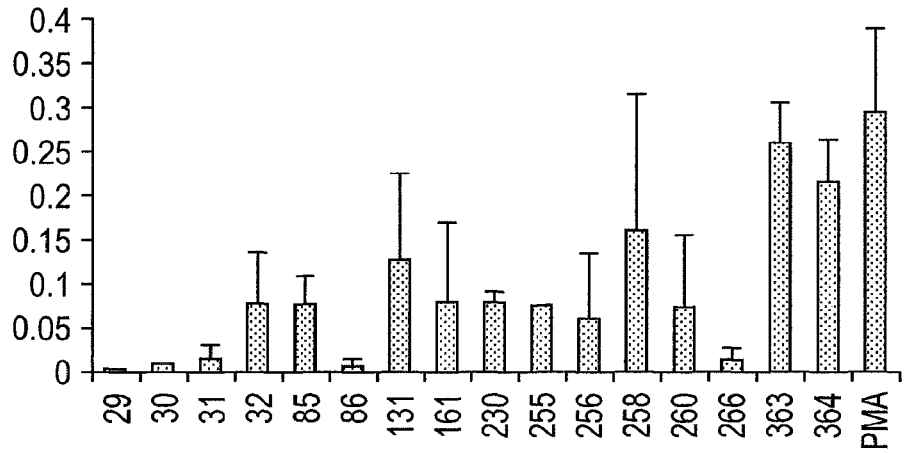
Figure 7C:
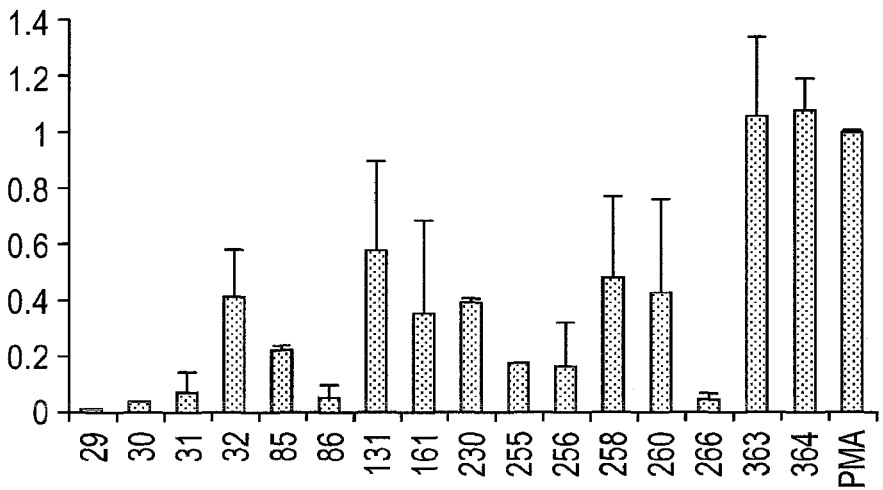

FIGS. 7A-7C show the ΔCt (FIG. 7A]), ratio (FIG. 7B) and fold-change (FIG. 7C) for IL-8 gene expression in IPEC cells treated with PMA and pig LAB.

Figure 8A:
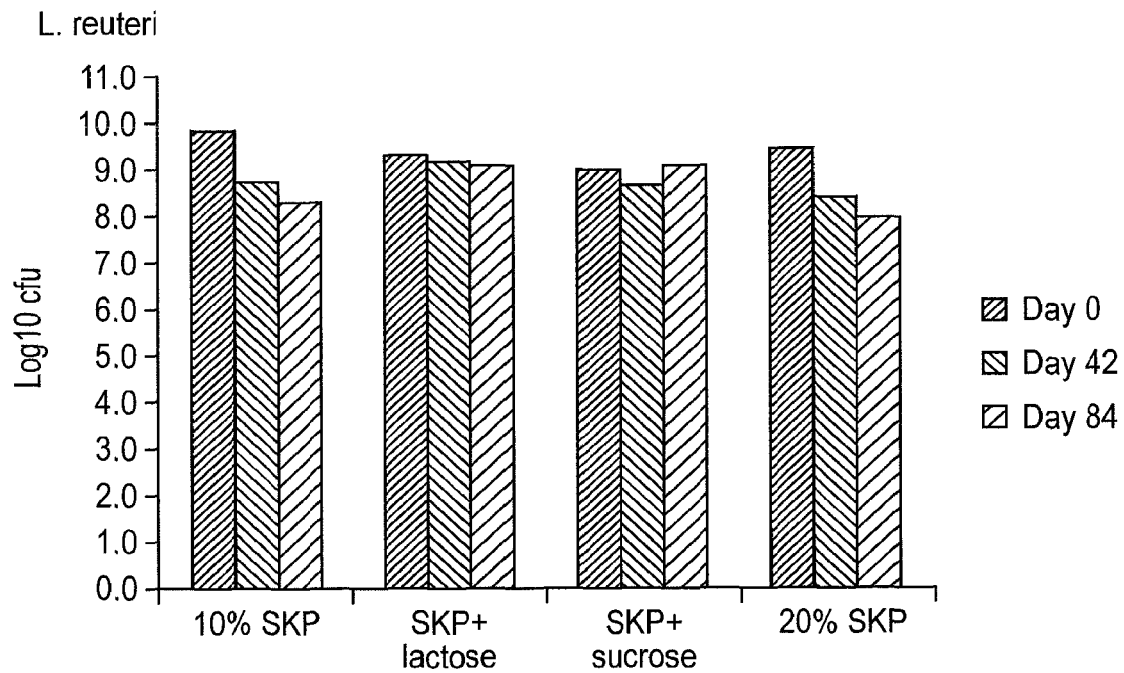
Figure 8B:
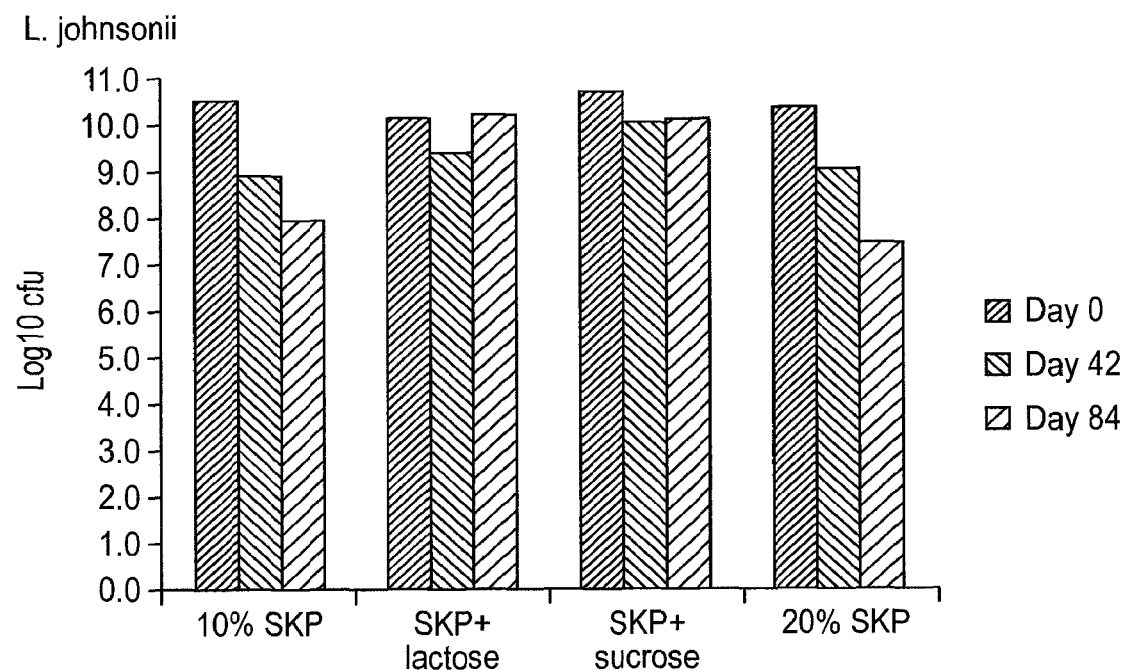

FIGS. 8A and 8B show the stability of *L. reuteri* (FIG. 8A) and *L. johnsonii* (FIG. 8B) after freeze-drying in skimmed milk powder (SKP, (100 g/l), SKP+lactose (both 100 g/l), SKP+sucrose (both 100 g/l) or SKP (200 g/l).

FIGS. 9A-9D show the stability of isolated LAB to heat-treatment (FIG. 9A), the ratio (FIG. 9B) and fold-change (FIG. 9C) for IL-8 gene expression in IPEC cells treated with PMA and naive or heat-treated pig LAB; (FIG. 9D) Antibiotic susceptibility of native and heat-treated RINH vial 31.

FIG. 10 shows a protocol for the C3H/HeN mouse study to evaluate efficacy of vial 323 (*L. mucosae*) to counteract *salmonella* infection in vivo.

FIGS. 11A-11C show the distribution of *S. enteritidis* S1400 in tissues at 10 days post-infection in C3H/HeN mice that had or had not been co-treated with 323 (*L. mucosae*, LM).

Figure 12A:
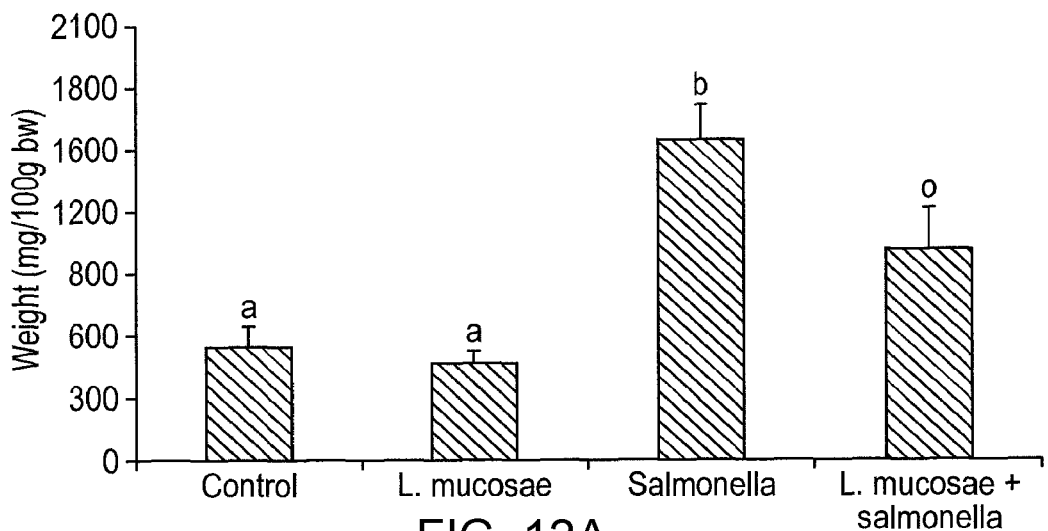
Figure 12B:
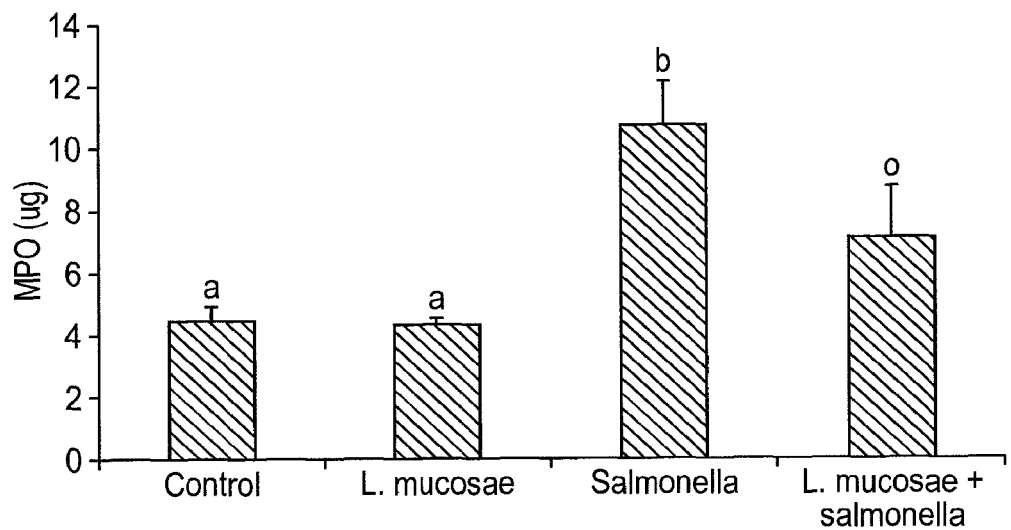

FIGS. 12A-12B show spleen weight (mg/100 g BW) and intestinal (ileal) myeloperoxidase (m) at 10 days post-infection in C3H/HeN mice that had or had not been co-treated with vial 323 (*L. mucosae*).

FIG. 13 shows a protocol for the C57 BI/6 mouse study to evaluate efficacy of vial 323 (*L. mucosae*) to counteract acute *salmonella* infection in vivo.

FIGS. 14A-14C shows the distribution of *S. enteritidis* S1400 in tissues at 6 days post-infection in C57BI/6 mice that had or had not been co-treated with RINH vial 323.

FIG. 15 shows spleen weight (mg/100 g BW) at 6 days post-infection in C57BI/6 mice that had or had not been co-treated with vial 323 (*L. mucosae*).

FIG. 16 shows a protocol for the C3H/HeN mouse study to evaluate efficacy of selected LAB from faeces of organically reared pigs to counteract *salmonella* infection in vivo.

Figure 17A:
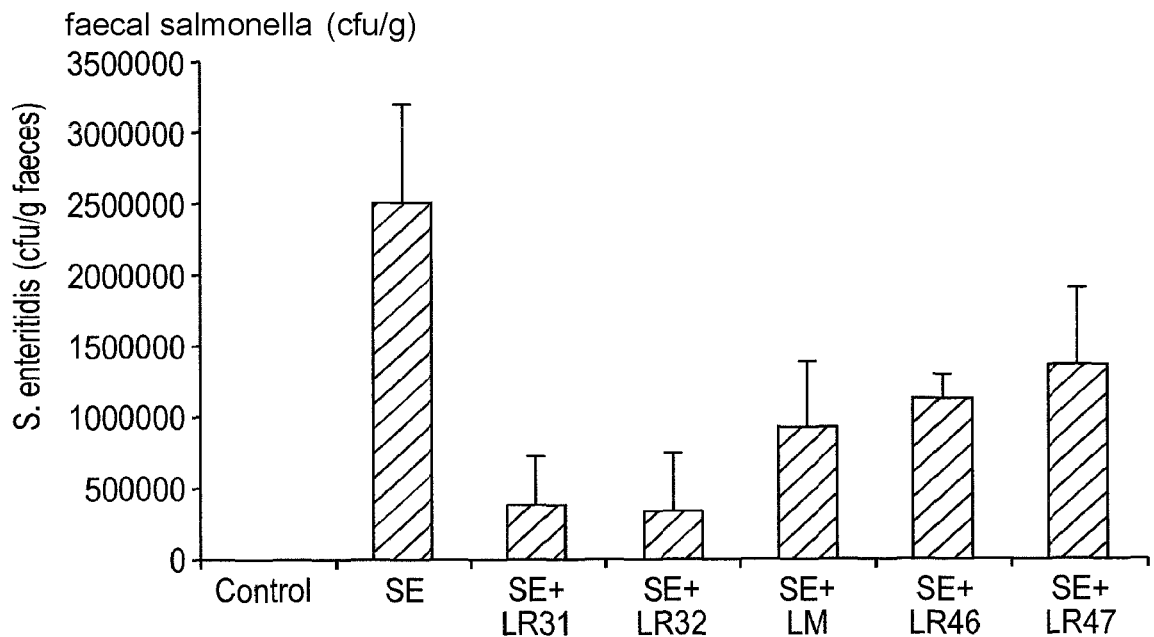
Figure 17B:
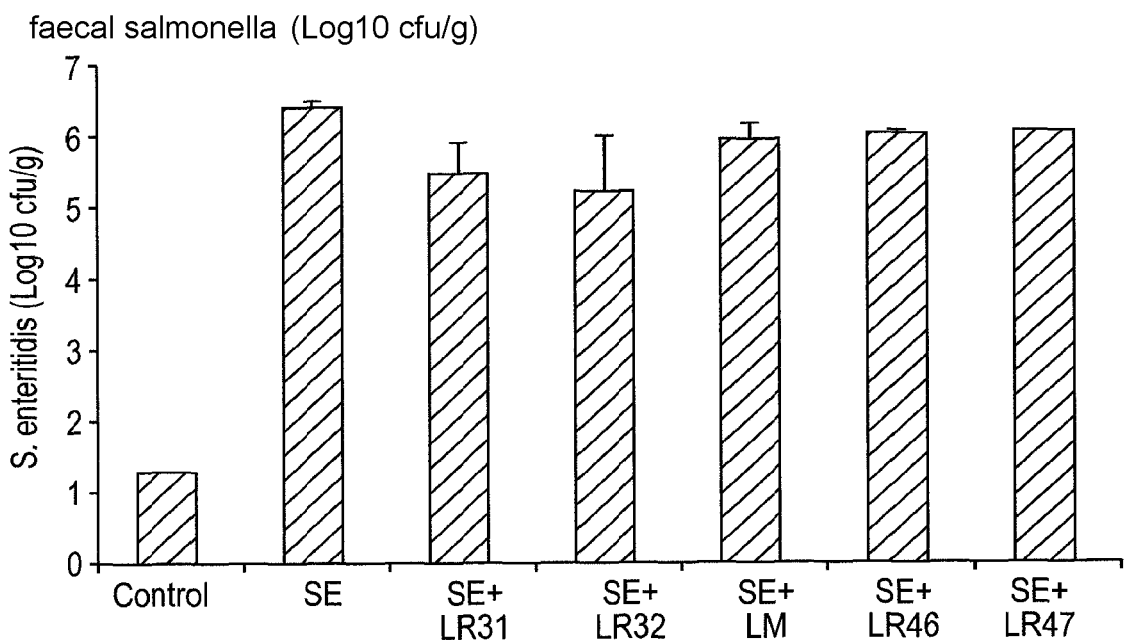

FIGS. 17A & 17B show excretion of *S. enteritidis* in faeces at 7-8 days post-infection by C3H/HeN mice that had or had not been co-treated with selected LAB.

Figure 18A:
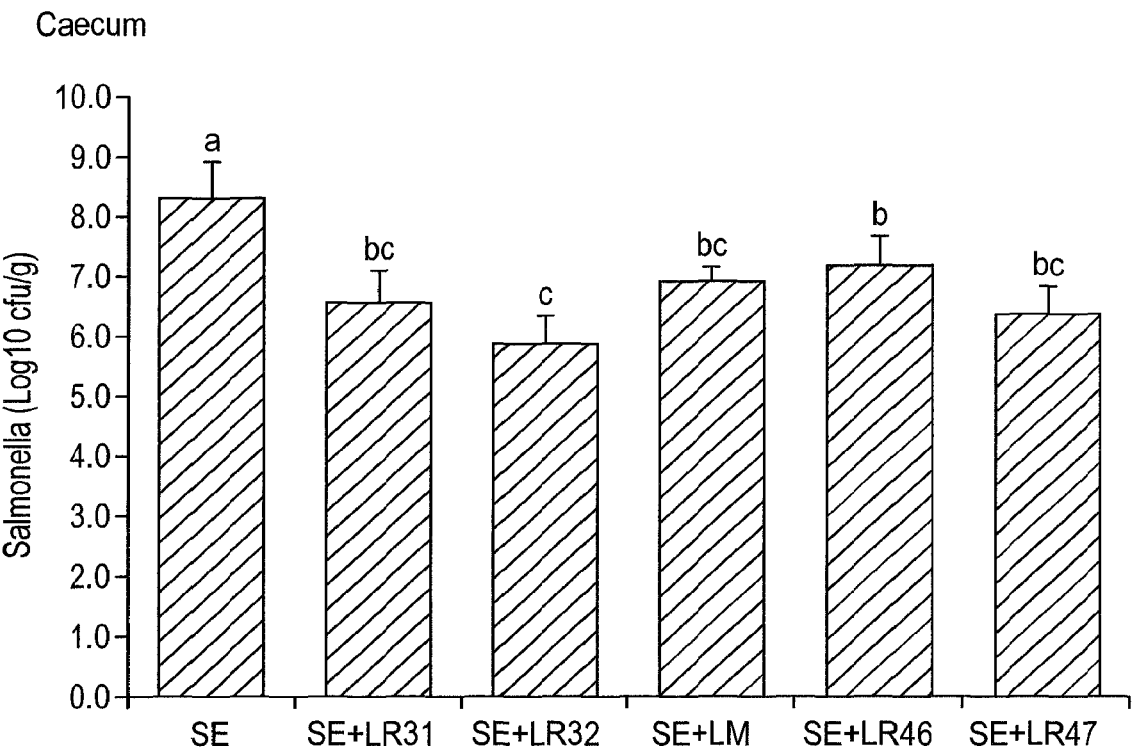
Figure 18B:
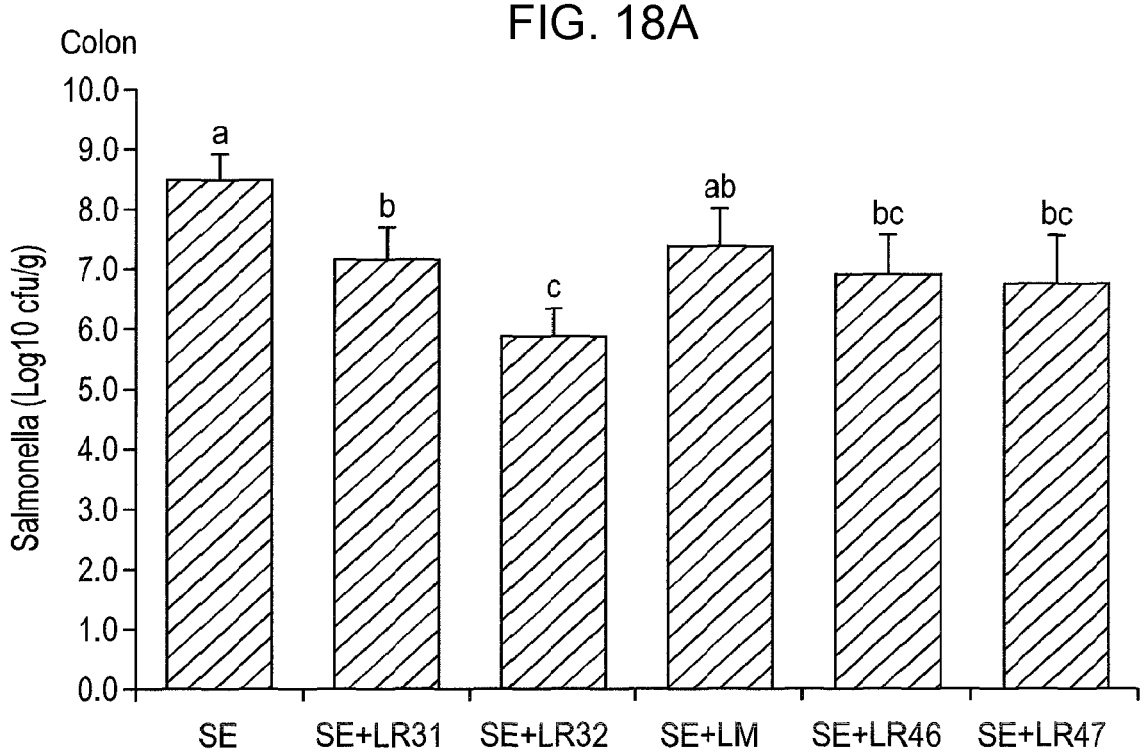

FIGS. 18A-18B show the distribution of *S. enteritidis* (Log 10 CFU/g) in caecum (18A) and colon (18B) at 10 days post-infection of C3H/HeN mice that had or had not been co-treated with selected LAB.

Figure 19A:
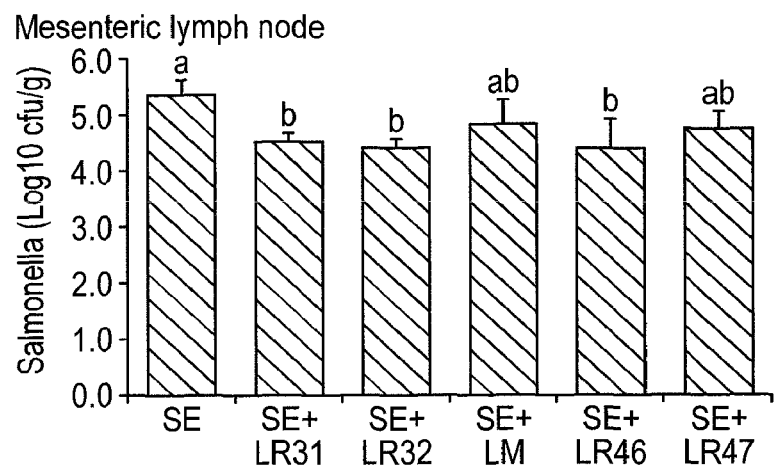
Figure 19B:
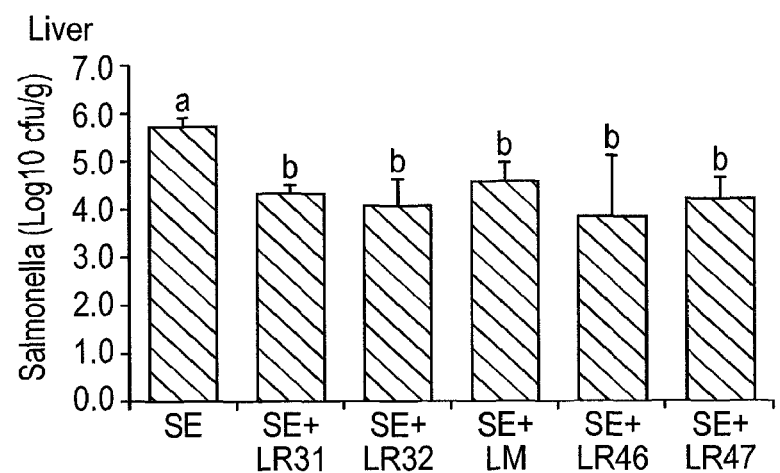
Figure 19C:
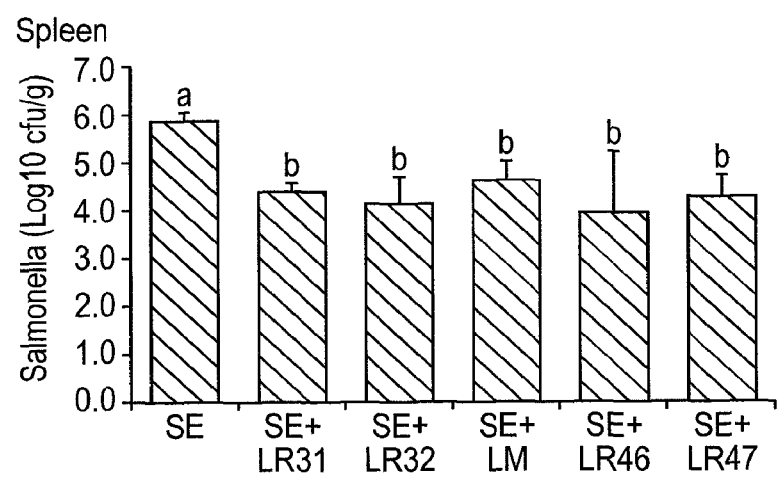

FIGS. 19A-19C show the distribution of *S. enteritidis* (Log 10 CFU/g) in mesenteric lymph node (19A), liver (19B) and spleen (19C) at 10 days post-infection of C3H/HeN mice that had or had not been co-treated with selected LAB.

Figure 20:
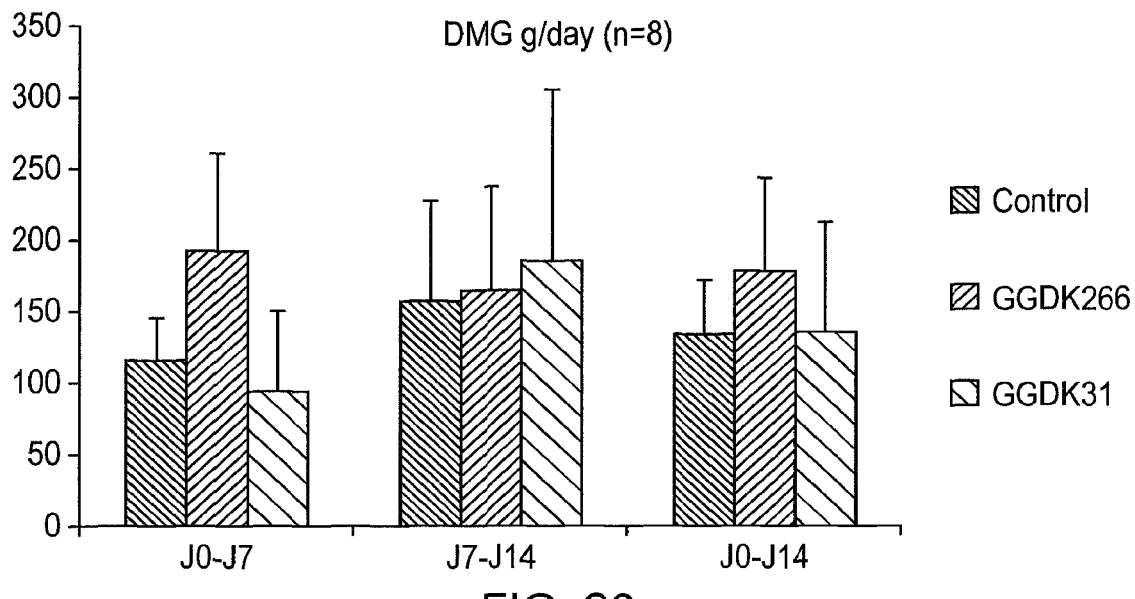

FIG. 20 shows the performance of pigs fed GGDK266 and GGDK31 versus a control (daily weight gain, DWG, in g/day) for days 0-7, 7-14 and 0-14.

Figure 21:
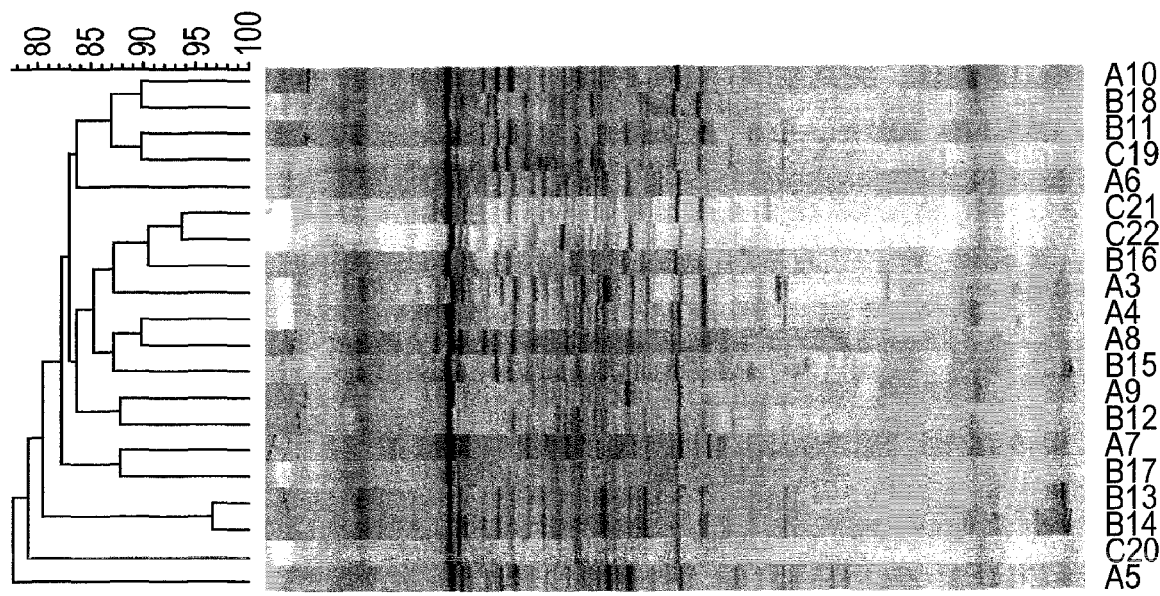

FIG. 21 shows microbial diversity analysis using denaturing gel gradient electrophoresis (DGGE; Trial 1). DGGE using universal primers revealed no differences in overall microbial diversity between the treatments and placebo. Bands on the gel are visualised by silver staining.

Figure 22:
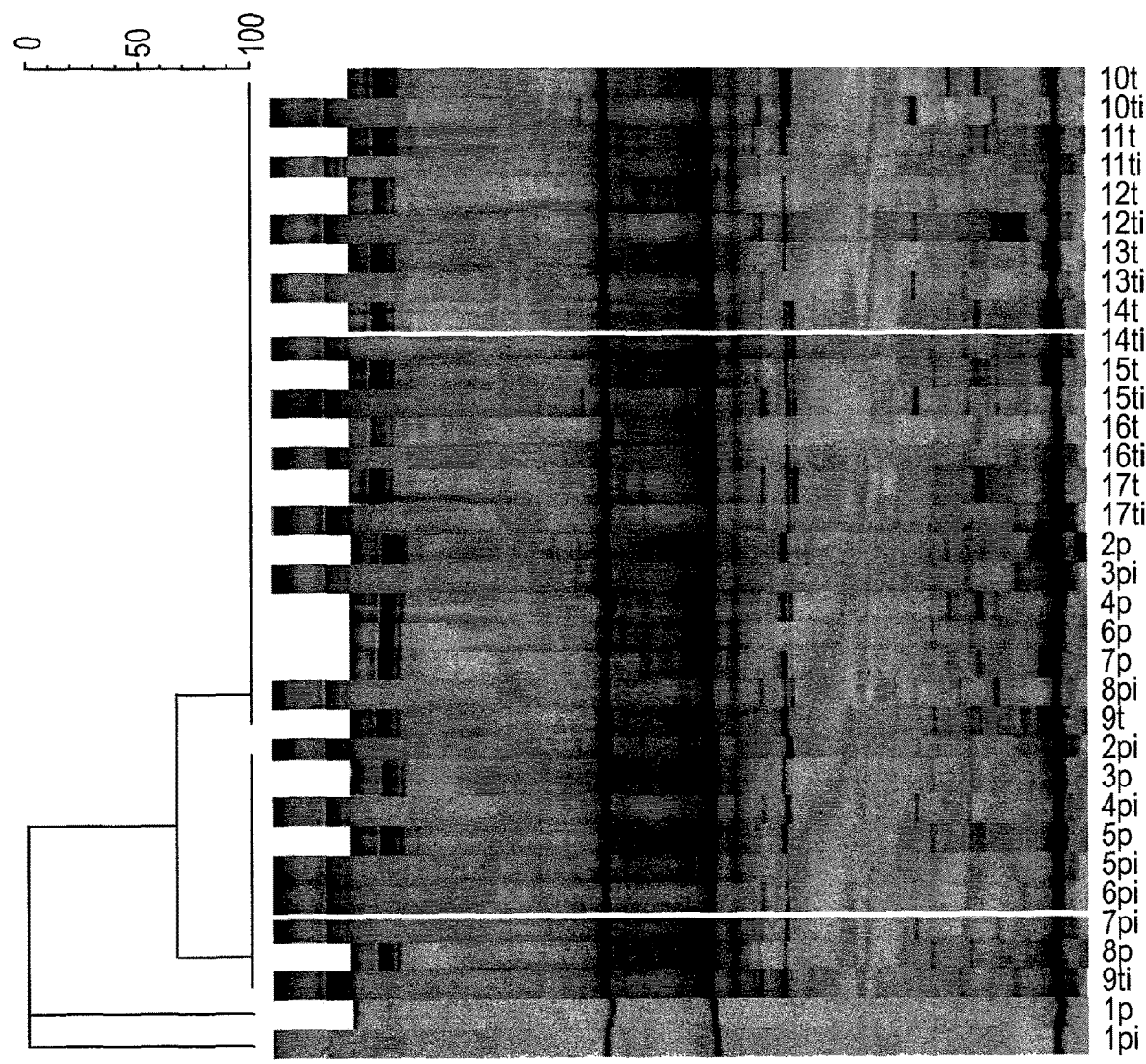

FIG. 22 shows microbial diversity analysis using DGGE. DGGE using lactic acid bacteria (LAB) specific primers revealed significant differences in LAB diversity between treatment with GGDK266 and placebo in both caecal and ileal samples. Bands on the gel are visualised by silver staining.

Figure 23:
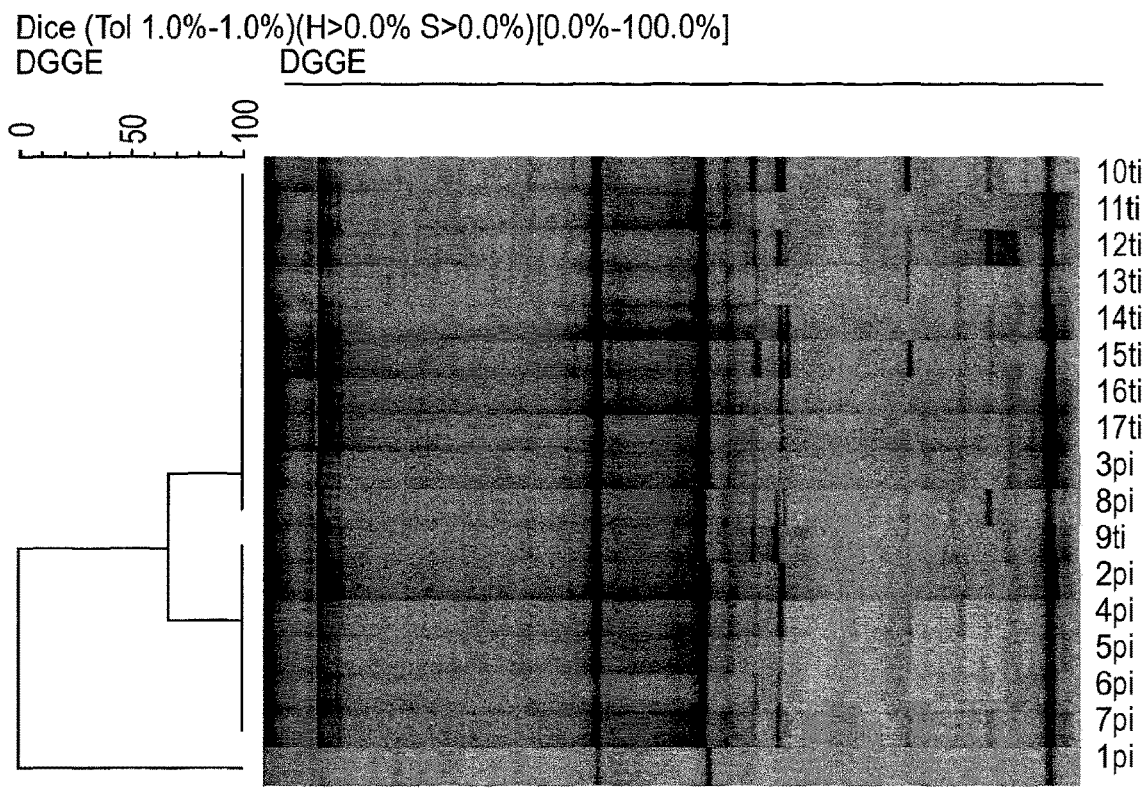

FIG. 23 shows microbial diversity analysis using DGGE. DGGE using lactic acid bacteria (LAB) specific primers revealed significant differences in LAB diversity between treatment with GGDK266 and placebo in ileal samples. Bands on the gel are visualised by silver staining.

Figure 24:
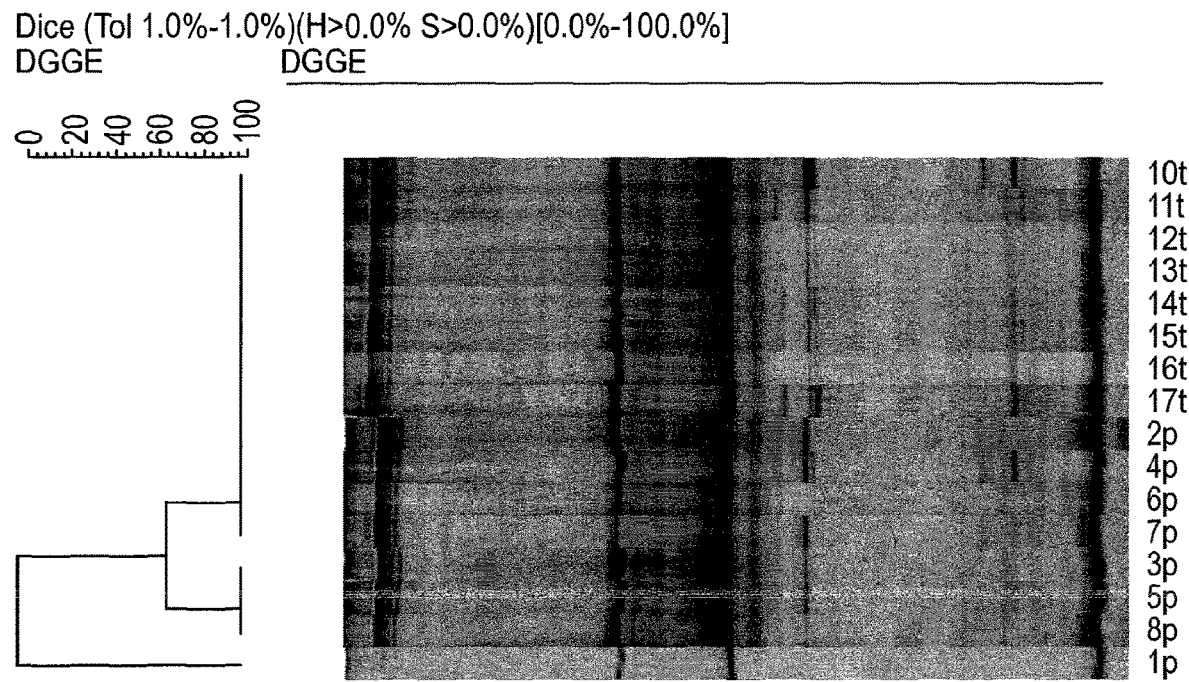

FIG. 24 shows microbial diversity analysis using DGGE. DGGE using lactic acid bacteria (LAB) specific primers revealed significant differences in LAB diversity between treatment with GGDK266 and placebo in caecal samples. Bands on the gel are visualised by silver staining.

Figure 25:
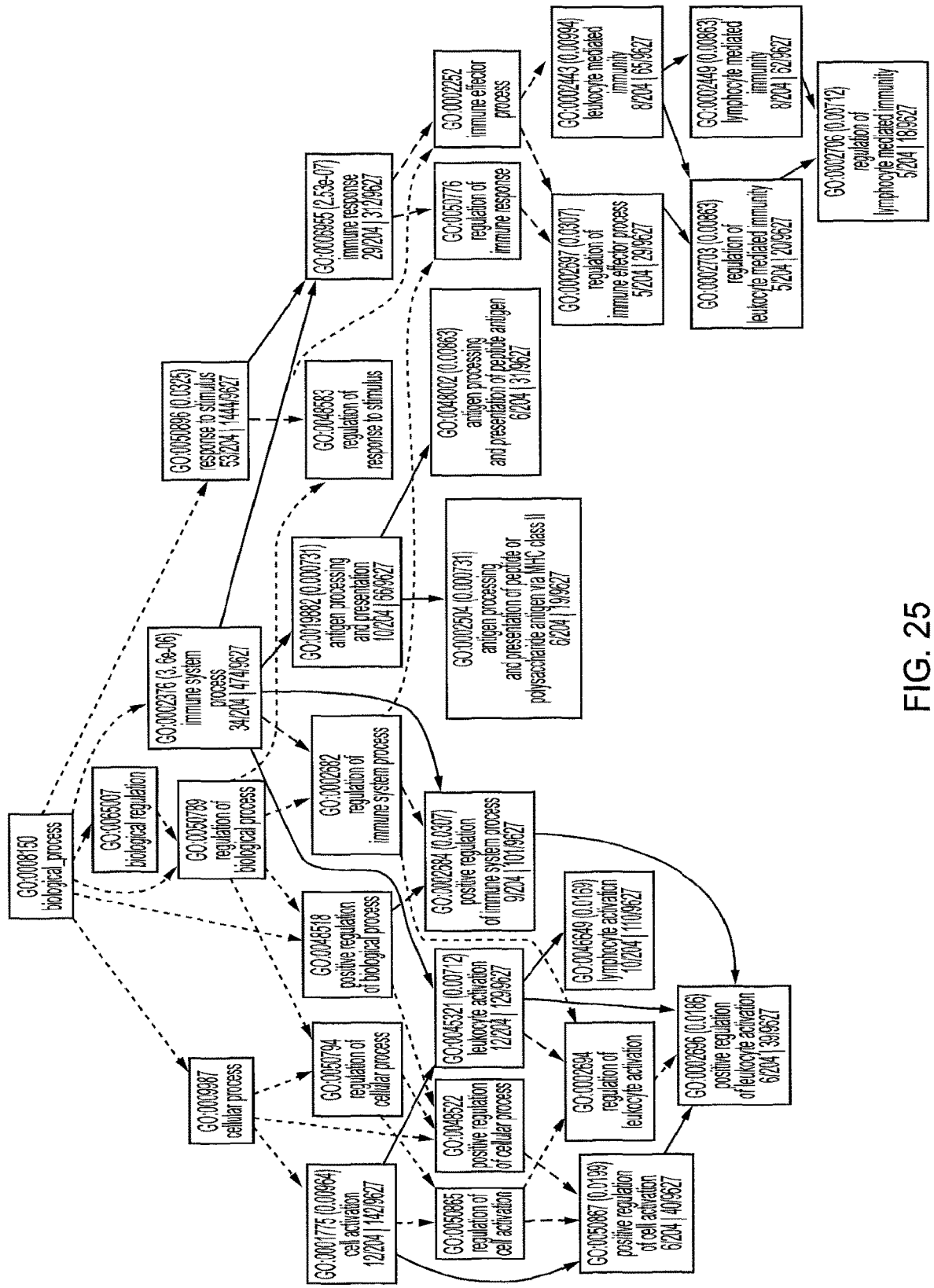

FIG. 25 shows the gene ontology biological processes significantly down-regulated by oral administration of GGDK266.

Figure 26:
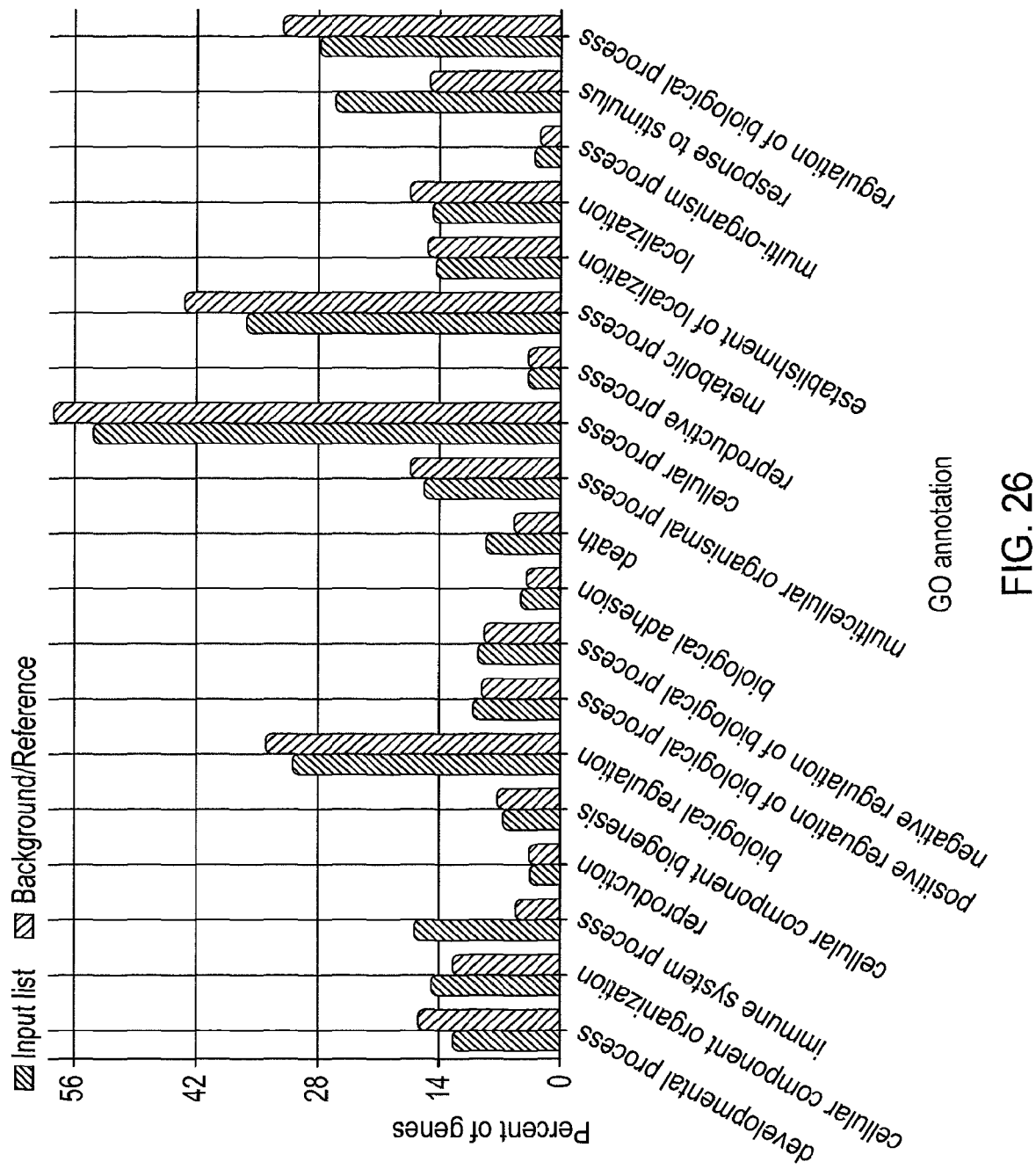

FIG. 26 shows changes in immune response and response to stimuli in animals treated with GGDK266 versus animals treated with placebo (percent of genes versus a range of different GO annotations).

Figure 27:
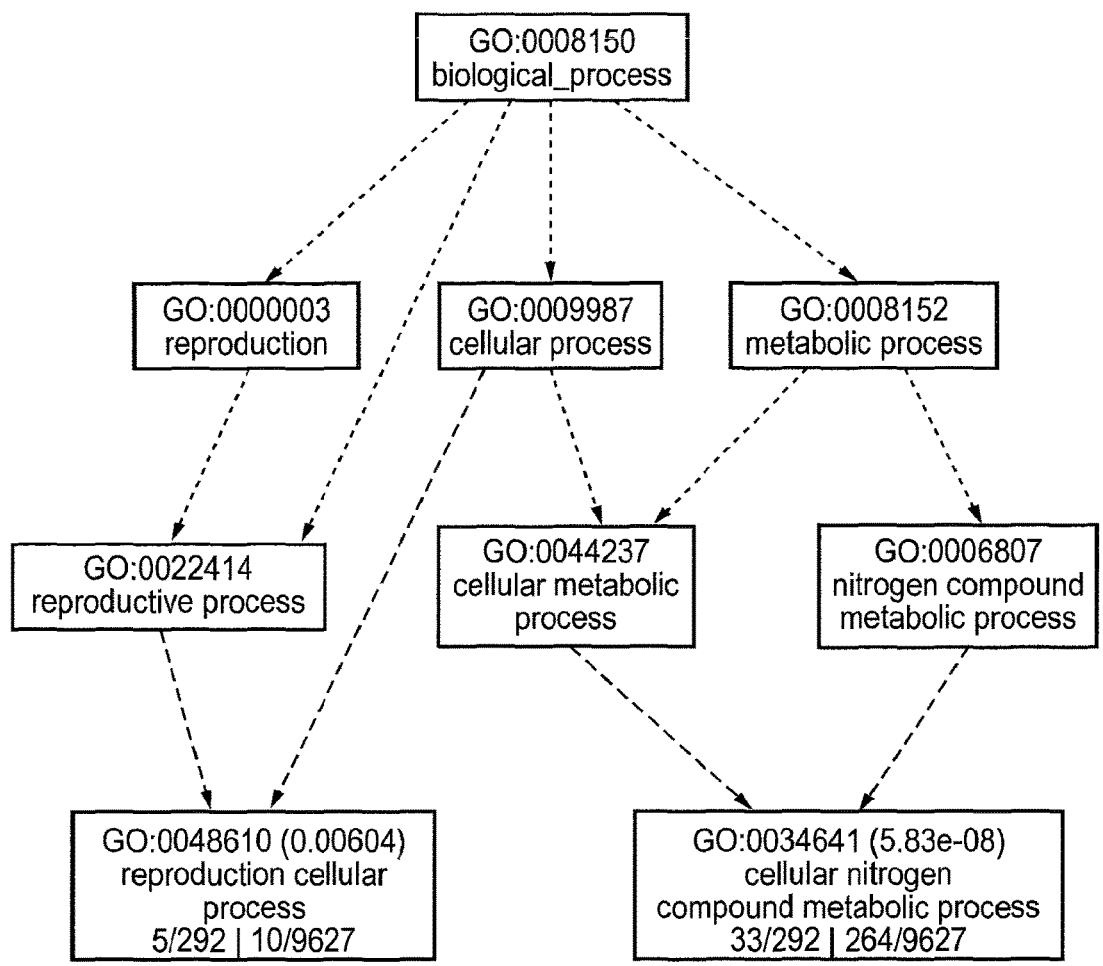

FIG. 27 shows the gene ontology biological processes significantly enriched by oral administration of GGDK266.

EXAMPLES

Materials and Methods

Materials:

Pig faeces samples collected during the course of the study of outdoor- and indoor-reared pigs (Mulder et al, 2009) were used in these studies. The culture collection was based primarily on LAB collected from frozen samples 411, 412 and 416, which were from outdoor-reared pigs with particularly high levels of LAB in their faeces. MRS broth premix, agar and vancomycin, anaerobe gas packs and indicator and antibiotic discs were purchased from Oxoid, anaerobe catalyst from Fisher Scientific and cysteine-HCL, bromocresol green and skimmed milk powder from Sigma-Aldrich. Pig colostrum carbohydrate fractions were prepared as part of the SMART 163 programme of D. Kelly. DNA extraction kits were purchased from MP Biomedicals and PCR reagents and clean-up kits from Promega. API CH 50 kits were purchased from Biomerieux UK Ltd.

Standard Media:

MRS broth and MRS agar were prepared according to the manufacturer's instructions. LAMVAB agar was prepared according to the method of Jackson et al. (2002). Agar plates were prepared immediately before use. MRS broth was decanted (10 ml per tube) into sterile Hungate tubes under anaerobic conditions and stored at room temperature.

Carbohydrate-Supplemented Media:

SMART 163 ammonium sulphate precipitate of pig colostrum: precipitated at 0, 20, 25, 30, 35, 45, 50, 55 or 65% saturation or soluble at 65% saturation were weighed out in proportion to the amounts recovered from 15 ml or 50 ml of colostrum. Carbohydrate fractions were each dispersed in 15 ml of MRS or LAMVAB agar, held at 45° C., and then individual plates were poured for each fraction. They were also dispersed in MRS broth (50 ml) and the supplemented broth decanted to eight (6 ml/tube) sterile Hungate tubes under anaerobic conditions.

Animals:

Female C3H/HeN and C57Bl/6 mice (5-6 weeks old) were purchased from Harlan UK. They were housed as groups or pairs in standard caging within HEPA-filtered flexifilm isolators situated in a class 2 containment facility. They had free access to a high quality rodent chow and sterile deionised water at all times and were allowed to acclimatise for 7 to 10 days prior to commencement of experiments. The Rowett Institute of Nutrition and Health (RINH) is licensed under the UK Animals (Scientific Procedures) Act 1986. Studies herein were carried out under the auspices of an approved Home Office Project License by staff holding the requisite Home Office Personal License (as defined and set out in the UK Animals (Scientific Procedures) Act 1986), and were reviewed and approved by the RINH Ethical Review Committee.

Methods

Culture of LAB:

In initial studies, a small amount of frozen faeces (100 mg) was dispersed in 1 ml of maximum recovery diluent (MRD). Two further sequential ten-fold dilutions were made. All three suspensions were streaked out on MRS or LAMVAB agar plates. In later studies, the faeces sample was dispersed in 5 ml of MRD, further diluted (1:40) in MRD and 0.5 ml of this dilution spread over the surface of MRS or LAMVAB agar plates with or without supplemental pig colostrum carbohydrates. In all cases, the plates were incubated in an anaerobic jar for 72 hours at 37° C. Distinct colonies (at least 8 per plate) were picked off the agar plates and seeded into Hungate tubes containing MRS broth or where appropriate MRS broth containing pig colostral carbohydrates. The tubes were incubated for 48 hours at 37° C.

Frozen Stock:

An aliquot (0.7 ml) of each culture was drawn off with a sterile syringe and needle and dispensed into a plastic tube that was flushed with $CO_2$ and contained 0.3 ml glycerol and 2 mg L-cysteine. The tube was sealed with a plastic stopper, labelled, the contents mixed, frozen and stored at −80° C.

Conditioned Medium:

The remaining culture was transferred to a Corning 15 ml centrifuge tube, centrifuged at 1000 g×5 min at room temperature, the supernatant decanted, aliquoted and frozen. The pellets were either extracted immediately for 16S rRNA gene analysis or frozen.

16S rRNA Gene Analysis (Clarridge, 2004):

Bacterial DNA was extracted using a FastDNA® Spin kit for Soil in conjunction with a Fastprep 120 bead beater system, according to the protocol supplied with the kit. PCR was carried out (reaction mix: buffer, 10 µl. dNTPs (2 mM), 5 µl. 27F Primer (20 pmol/µl), 2 µl. 1492R Primer (20 pmol/µl). 2 µl Go Taq Flexi Polymerase, 0.5 µl. MgCl2, 5 µl. H2O, 23.5 µl and 2 µl of extracted DNA) using MJ Research PTC-200 Peltier Thermal Cycler run through 35 cycles of 95° C. for 3 minutes, 95° C. for 30 seconds, 57° C. for 30 seconds and 72° C. for two minutes. Primer: 27F (F01) AGAGTTTGATCCTGGCTCAG; 1492R (RP2) ACGGCTACCTTGTTACGACTT. PCR product cleanup was done with a Wizard® SV Gel and PCR Clean-up kit (Promega), used according to the manufacturer's instructions. 16S PCR products were sequenced using fully automated genetic analysers based on capillary electrophoresis technology (Genomics Section, RINH, UoA) using the reverse and forward primers 519R and 926F. Bacterial strains were identified by comparison of sequences with known bacterial DNA sequences using BLAST (http://blast.ncbi.nlm.nih.gov/Blast.cgi).

Antibacterial Activity:

XLD agar was prepared as per manufacturer's instructions and cooled to 45° C. *Salmonella enteritidis* S1400 was added to the XLD agar [1 ml of a 1:1000 dilution of an overnight culture of *salmonella* in 200 ml XLD agar to give the equivalent of 106 CFU/ml]. The agar was poured into petri dishes and allowed to set. The plates were marked off into 4 quadrants and an approximately 5 mm well cut out in each quadrant. An aliquot (60 µl) of conditioned media or MRS broth was added to the wells. The plates were covered and incubated for 16 hours at 37° C. They were photographed using a digital camera. Images transferred to Photoshop, and the diameter of the well and zone of inhibition were determined using the measure tool. Values were calculated and stored on an Excel spreadsheet. The same procedure was used with *Escherichia coli* K88, except that MacConkey No 3 agar was used.

Antibiotic Susceptibility:

Pig LAB [0.5 ml of a 1:100 dilution of an overnight culture] was spread onto the surface of an MRS agar [90 mm] plate and dried off. The plates were marked off into 4 quadrants and in each quadrant was placed an antibiotic-containing disc [Ampicillin, 10 µg. Cefotaxime, 30 µg. Chloramphenicol, 10 µg. Erythromycin, 15 µg. Gentamicin, 10 µg. Kanamycin, 30 µg. Metronizadole, 50 µg. Nalidixic acid, 30 µg. Tetracycline, 30 µg. Vancomycin, 30 µg]. The plates were covered, placed in an anaerobic jar and incubated for 24 hours at 37° C. They were photographed using a digital camera. Images transferred to Photoshop, and the diameter of the zone of inhibition was determined using the measure tool. Values were calculated and stored on an Excel spreadsheet.

Prevention of Adherence/Invasion by *Salmonella* In Vitro:

Monolayers of IPEC-J2 cells were grown to 3 days post-confluence in 24-well plates and synchronised by the addition of DTS media 24 hrs prior to use. Overnight cultures of pig LAB (10 ml) were centrifuged [1000 g×5 min at room temperature] and the bacteria re-suspended in 1 ml of phosphate buffered saline [PBS]. An aliquot (50 µl) of LAB was added to the wells. The plates were incubated for 2 hours at 37° C., 5% $CO_2$, 95% humidity. An overnight culture of *Salmonella enterica* serovar Enteritidis S1400 [*S. enteritidis* S1400] was sub-cultured (0.5 ml in 10 ml) into Luria Bertani (LB) media and incubated aerobically for 2-3 hours at 37° C. until it reached an optical density (560 nm) of 0.8. This gave a concentration equivalent to $1 \times 10^8$ CFU/ml. The culture was centrifuged [1000 g×5 min at room temperature], the bacteria re-suspended in 10 ml of PBS. An aliquot (50 µl) was added to the wells of IPEC-J2 cells. Wells treated with PBS were used as controls. The plates were incubated for a further 2 hours at 37° C., 5% $CO_2$, 95% humidity. The IPEC-J2 cell monolayers were washed 5 times with HBSS. A solution (0.5 ml) of PBS containing Triton-X100 (10 ml/litre) was added to each well, the monolayer scraped off and dispersed. Viable *salmonella* were estimated on XLD agar plates [incubated for 24 hours at 37° C.] by the Miles and Misra method [Robertson et al, 2003]. LAB were determined by the same procedure [incubated anaerobically for 48 hours at 37° C.].

Inhibition of Inflammatory Responses:

Monolayers of IPEC-J2 cells were grown to 3 days post-confluence in 24-well plates and synchronised by the addition of DTS media 24 hrs prior to use. Overnight cultures of pig LAB (10 ml) were centrifuged [1000 g×5 min at room temperature] and the bacteria re-suspended in 1 ml of PBS. An aliquot (50 µl) of LAB was added to each well [3 wells for each sample] along with 220 ng 12-O-Tetradecaboylphorbol-13-acetate [PMA] per well. PMA or PBS alone served as controls. The plates were incubated for 2 hours at 37° C., 5% $CO_2$, 95% humidity. Culture media was removed from the dishes and the cells washed twice with PBS. RLT buffer (0.5 ml) containing mercaptoethanol was added to each well, the cells scraped off and transferred to an eppendorf tube [for each sample scrapings from 3 wells were combined]. RNA extraction was done using RNeasy® Mini kit in accordance with the manufacturer's protocols and reverse transcription with a high capacity cDNA Reverse Transcription Kit (Applied Biosystems). Real Time PCR was done on a 7500 Fast Real-time PCR system operating with 7500 Fast System v 1.4.0 Sequence Detection Software version 1.4 (Applied Biosystem). Primers for porcine IL-8 and TNF-α [IPEC-J2, SY100604186-096 IL-8-2 Reverse, SY100604186-090 TNF1 a Reverse, SY100604186-095 IL-8 2 Forward, SY100604186-089 TNFa 1 Forward, and SY100604186-093] were prepared by Sigma Aldrich. The reaction mix was: 10 µl Power Sybergreen Master mix, 2.5 µl of forward primer, 2.5 µl of reverse primer and 5 µl of cDNA, The Real Time PCR was then run according to the Standard 7500 protocol [95° C., 10 min, 1 cycle. 95° C., 15 sec, 40 cycles. 60° C., 1 min, 40 cycles. 95° C., 15 sec, 1 cycle. 60° C., 1 min, 1 cycle. 95° C., 15 sec, 1 cycle. 60° C., 15 sec, 1 cycle]. Expression of IL-8 and TNF-α genes were analysed and compared to that of the 'house-keeping' gene β-actin. For comparison, values were given as the ratio of IL-8 and TNF-α per β-actin or fold-change.

For example:
a. Calculate ΔCt (2 h) for IL-8 [Ct IL-8 minus Ct β-actin]
b. Calculate ΔCt (2 h) for PMA [Ct PMA minus Ct β-actin]
c. Divide ΔCt (IL-8) with ΔCt (PMA)
d. Round up value to whole number Substrate Reactivity:

The carbohydrate reactivity of individual LAB was determined using an API CH 50 kit (Biomerieux UK Ltd). Assays were done according to the manufacturer's instructions and reactions were recorded after incubation for 24 and 48 hours at 37° C. There are 50 capsules on an API CH 50 plate. These contain various potential substrates and negative controls. The range of substrates is as follows: Monosaccharides 16, Monosaccharides/alcohols 4, Disaccharides 8, Trisaccharides 2, Polysaccharides 3, Alcohols 6, Others 7. For each substrate group the number of positive reactions is counted. This is divided by the maximum possible to give the rank for that substrate group. The sum of all the substrate scores gives the overall ranking for the bacterium. High Ranking indicates broad spectrum of substrate reactivity Heat-Treatment of LAB:

A small amount of frozen faeces (100 mg) was dispersed in 5 ml of maximum recovery diluent (MRD). Sediment was allowed to settle out and the upper layer was decanted into eppendorf tubes (1 ml/tube). The tubes were heated at 50° C., 60° C. or 70° C. for 10 min. An aliquot (0.4 ml) of each was plated out on MRS agar and incubated in an anaerobic jar for 72 hours at 37° C. A small number of colonies were detected after heating at 70° C. Distinct colonies were picked off, seeded into Hungate tubes containing MRS broth and incubated for 48 hours at 37° C.

In a second study, a small amount of frozen faeces (100 mg) was dispersed in 5 ml of maximum recovery diluent (MRD). Sediment was allowed to settle out and the upper layer was decanted into eppendorf tubes (1 ml/tube). The tubes were heated at 50° C. for 20 min, 50° C. for 20 min plus 60° C. for 20 min or 50° C. for 20 min plus 60° C. for 20 min plus 70° C. for 20 min. An aliquot (0.5 ml) of each was plated out on MRS agar and incubated in an anaerobic jar for 48 hours at 37° C. A small number of colonies were detected, picked off, seeded into Hungate tubes containing MRS broth and incubated for 48 hours at 37° C.

In the third study, an overnight culture (10 ml) of isolated pig LAB was centrifuged (1000 g×5 min at room temperature), the pellet re-suspended in fresh MRS broth (10 ml). An aliquot (1 ml) was heated at 70° C. for 15 min and then plated out (0.5 ml) out on MRS agar and incubated in an anaerobic jar for 48 hours at 37° C. A small number of colonies were detected, picked off, seeded into Hungate tubes containing MRS broth and incubated for 48 hours at 37° C. This culture was centrifuged, re-suspended in MRS broth, heated again at 70° C. for 15 min, plated out on MRS agar, incubated in an anaerobic jar for 48 hours at 37° C., picked off, seeded into Hungate tubes containing MRS broth and incubated for 48 hours at 37° C. As before, this culture was centrifuged, re-suspended in MRS broth, re-heated at 70° C. for 15 min, plated out (0.5 ml) out on MRS agar, incubated in an anaerobic jar for 48 hours at 37° C., picked off, seeded into Hungate tubes containing MRS broth and incubated for 48 hours at 37° C.

Stability of Freeze Dried Bacteria:

Overnight cultures of LAB were centrifuged (1000 g×5 min at room temperature. Pellets were re-suspended in 2 ml sterile PBS and re-centrifuged. The subsequent pellets were then re-suspended in 5 ml of freezing solution [defatted skimmed milk powder (SKP), 100 g/l; SKP+lactose, both 100 g/l; SKP+sucrose, both 100 g/l; or SKP, 200 g/l]. The samples were frozen at −20° C. (2-3 hours) and then stored at −80° C. overnight. They were freeze-dried for 48 hours and dried material stored at room temperature. Viable bacteria in the samples were determined at 0 and approximately 40 and 80 days after completion of freeze drying. They were plated out on MRS agar and incubated anaerobically for 48 hours at 37° C.

Bulk Preparation of GGDK31 and GGDK266:

Two 500 ml batches of MRS broth were prepared in 500 ml glass screw-top bottles, autoclaved and allowed to cool to room temperature (in proximity to gas flame) whilst being flushed with $CO_2$. Four ml of a 24 hour culture of GGDK31 or GGDK266 was added to each bottles of MRS and the lids lightly closed. The bottles were placed in an anaerobic jar and incubated at 37° C. for 24 hours. The culture was centrifuged [1000 g×5 min at room temperature] in 6 sterile 50 ml centrifuge tubes. The supernatant was discarded, tubes refilled with culture and re-centrifuged until all the bacteria had been recovered. Each of the 6 tubes contained almost equal amounts of bacteria. The bacteria in each tube were re-suspended in 40 ml of sterile PBS, re-centrifuged and the supernatant discarded. The bacteria in each tube was re-suspended in 20 ml of SKM (100 g/l), frozen at −20° C. (2-3 hours) and then overnight at −80° C., freeze-dried for 48-72 hours and stored at 4° C. To evaluate viable bacteria in the sample, one tube of freeze dried material was re-suspended in 20 ml of MRS broth, incubated at room temperature for 2 hours, diluted, plated out on MRS agar and incubated anaerobically for 48 hours at 37° C.

*L. mucosae* In Vivo Study 1:

Sixteen (6 week) old female C3H/HeN mice were dosed with an overnight culture of vial 323 (*L. mucosae*; 50 µl; >109 CFU) at day −7, −4, −2 and 0 and daily thereafter up to day +9. A further 16 mice (control) were given media. On day 0, eight mice (*L. mucosae*-treated) and eight control mice were given, by gavage, a single dose of *Salmonella enteritidis* S1400 (50 µl; ≥108 CFU). In addition, eight mice (*L. mucosae*-treated) and eight control mice were given a single dose of culture medium. Body weight and health score were monitored twice daily post-*salmonella* infection. The mice were euthanased (isoflurane overdose and exsanguination) and dissected at 10 days post-*salmonella* infection. Stomach, representative portions of jejunum and ileum, caecum plus contents, colon plus contents, spleen and liver and one kidney and the mesenteric lymph node were collected under near aseptic conditions for microbiology. Representative portions of upper jejunum, mid jejunum, ileum, caecum and ascending and descending colon were placed in neutral buffered formalin or RNA-later and stored for future analysis.

*L. mucosae* In Vivo Study 2:

Five (6 week) old female C57BI/6 mice were dosed with an overnight culture of vial 323 (*L. mucosae*; 50 µl; >109 CFU) at day −7, −4, −2 and 0 and daily thereafter up to day +5. A further 5 mice were given media. On day 0, all ten mice were given, by gavage, a single dose of *Salmonella enteritidis* S1400 (50 µl; ≥107 CFU). The mice were euthanased and dissected on day 6, according to the procedure for study 1. Novel pig LAB in vivo: Four (6 week) old female C3H/HeN mice were dosed with an overnight culture of RINH vial 31 (*L. reuteri*; 50 µl; >109 CFU), four with RINH vial 32 (*L. reuteri*). Four with vial 323 (*L. mucosae*), four with RINH vial 46 (*L. reuteri*), four with RINH vial 47 (*L. reuteri*) and eight with MRS. This was done at day −6, −4, −2 and 0 and daily thereafter up to day +9. On day 0, all lactobacilli-treated mice and four control mice were given, by gavage, a single dose of *Salmonella enteritidis* S1400 (50 µl; ≥108 CFU). In addition, the remaining four control mice were given a single dose of culture medium. The mice were euthanased and dissected on day 10, according to the procedure for study 1.

Microbiology:

Tissues were homogenised [1:100 w/v] in MRD using a Janke-Kunkel Ultra-Turrax T25 tissue homogeniser at 20,000 rpm for 30 seconds, as were jejunal and ileal contents. Up to eight sequential dilutions (1:10 v/v) of the primary homogenates were made, plated out onto XLD agar and MacConkey No. 3 agar and incubated overnight at 37° C. Viable counts were estimated as before [Robertson et al, 2003].

Statistical analysis: Where appropriate data were initially assessed by one-way analysis of variance (ANOVA) regarding treatment outcome. If ANOVA indicated that there were significant differences ($p<0.05$) amongst all groups, the data was then analysed by the Tukey-Kramer Multiple Comparisons Test or the Kruskal-Wallis Multiple Comparisons Test as appropriate. This was done using the Instat Statistical Package (GraphPad Software Inc., San Diego, USA).

Based on the outputs from the multiple comparison tests, means in tables or graphs were marked with superscript letters. Means that differed significantly from each other (p<0.05) were allocated distinct superscript letters. Means that did not differ significantly from each other were allocated common superscript letters.

Results

1. Isolation of LAB

Faeces from organically-reared piglets were plated out on selective agars and were incubated under anaerobic conditions. From all studies, a total of 436 individual colonies of Lactic Acid Bacteria [LAB] were picked off, seeded into MRS broth and incubated under anaerobic conditions. Each culture was given a unique RINH vial number and an aliquot was frozen down in MRS media containing 30% glycerol and L-cysteine (~2 mg/ml) and stored at −80° C. 16S rRNA gene analysis was done and bacterial strains were identified by comparison of sequences with known bacterial DNA sequences (Table 1).

The majority of the cultured LAB colonies were *L. johnsonii* and *L. johnsonii*-related strains [*L. johnsonii, L. johnsonii/gasseri, L. johnsonii/taiwanensis*] (240/436) and *L. reuteri* or *L. reuteri*-related [*L. reuteri, L. reuteri/pontis, L. reuteri/vaginalis, L. reuteri/acidophilus* (169/436)]. There were 7 *L. plantarum/pentosus* colonies, 19 other species and 5 uncultured strains.

2. Anti-*Salmonella* Activity In Vitro

Conditioned media from isolated LAB were screened for anti-bacterial activity against *Salmonella enteritidis* S1400 using a well-diffusion assay (FIG. 1).

Figure 2A:
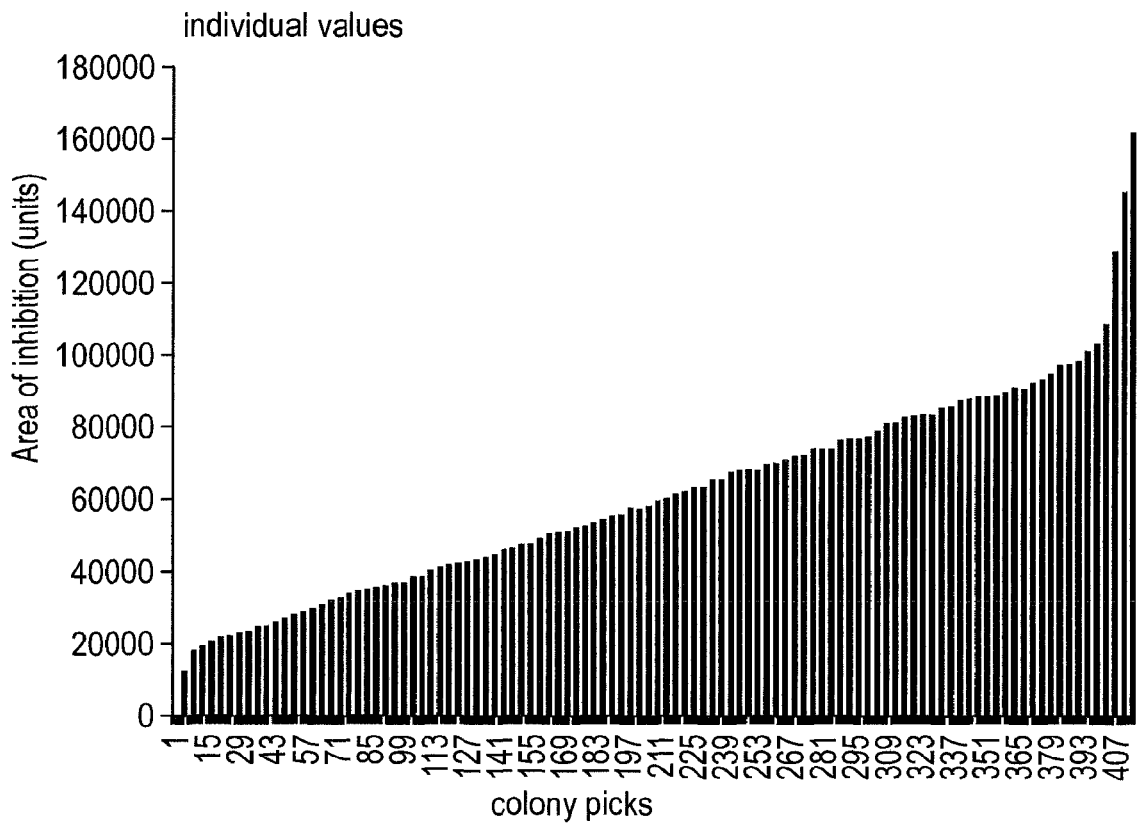
FIGS. 2A and 2B show inhibitory activity against *S. enteritidis* S1400 (expressed as area of inhibition in a well diffusion assay) of conditioned media of all individual LAB cultured from faeces of organically-reared pigs.
Figure 2B:
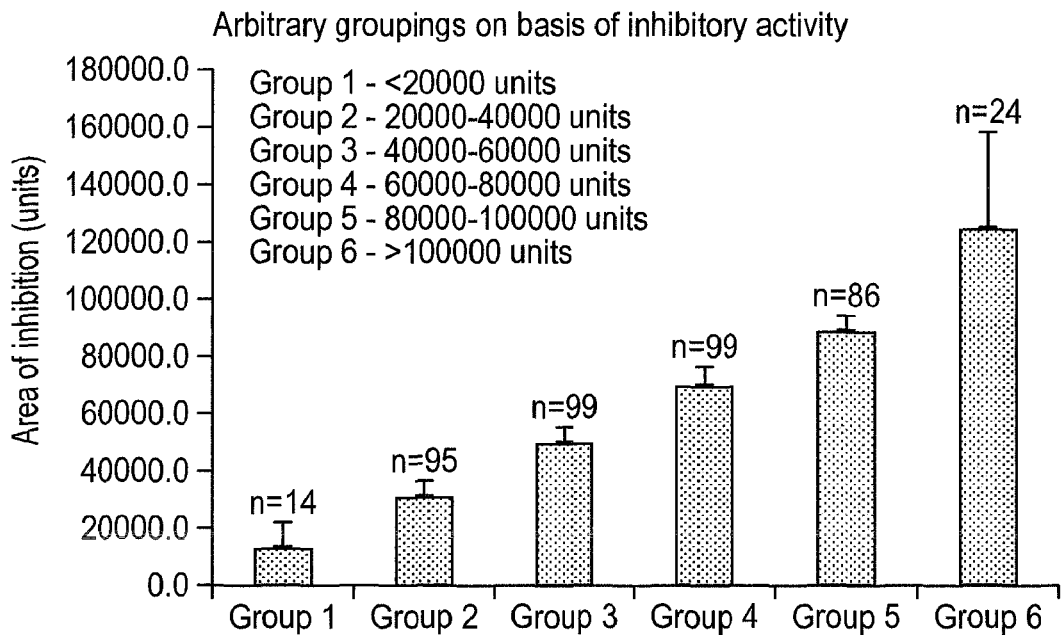

Conditioned media from individual colonies of LAB varied greatly in their activity against *S. enteritidis* (FIG. 2A). This was not strain dependent. The range of anti-*salmonella* activities amongst *L. johnsonii* was similar to that amongst *L. reuteri*. On an arbitrary basis, the cultures were separated into groupings on the basis of their capacity to inhibit *salmonella* in vitro (FIG. 2B). Group 1 had <20000 units of inhibition, Group 2 20000-40000 units of inhibition, Group 3 40000-60000 units of inhibition, Group 4 60000-80000 units of inhibition, Group 5 80000-100000 units of inhibition and Group 6>>100000 units of inhibition (FIG. 2B Group 1 comprised of 14 strains (3.4% of total), Group 2 of 95 strains (22.8%), Group 3 of 99 strains (23.7%), Group 4 of 99 strains (23.7%), Group 5 of 86 strains (20.6%) and Group 6 of 24 strains (5.8%). The latter group comprised of seventeen *L. johnsonii* and *L. johnsonii*-related, six *L. reuteri* or *L. reuteri*-related strains and one uncultured strain.

3. Anti-*E. coli* K88 Activity In Vitro

Figure 3A:
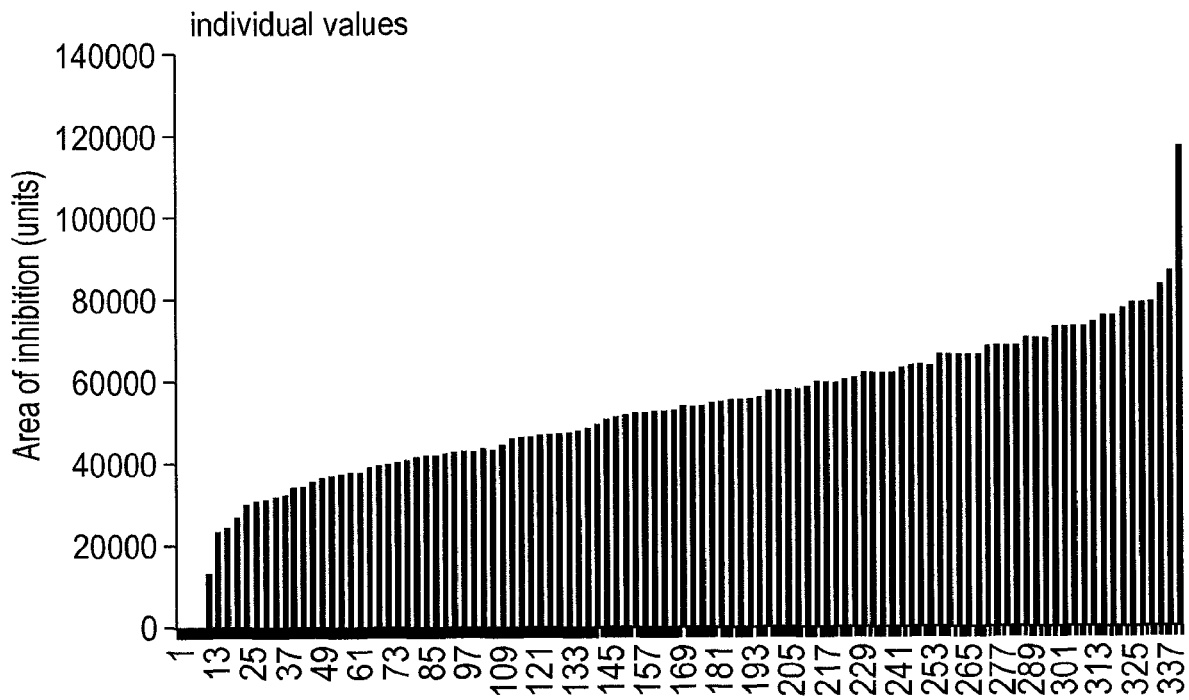
FIGS. 3A and 3B show inhibitory activity against *E. coli* K88 (expressed as area of inhibition in a well diffusion assay) of conditioned media of all individual LAB cultured from faeces of organically-reared pigs.
Figure 3B:
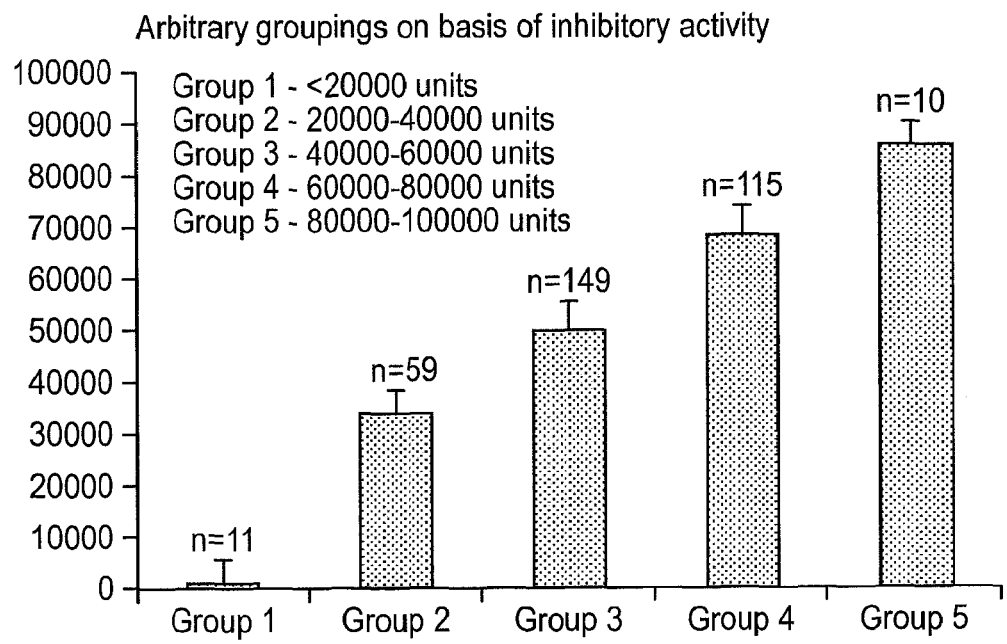
Figure 3C:
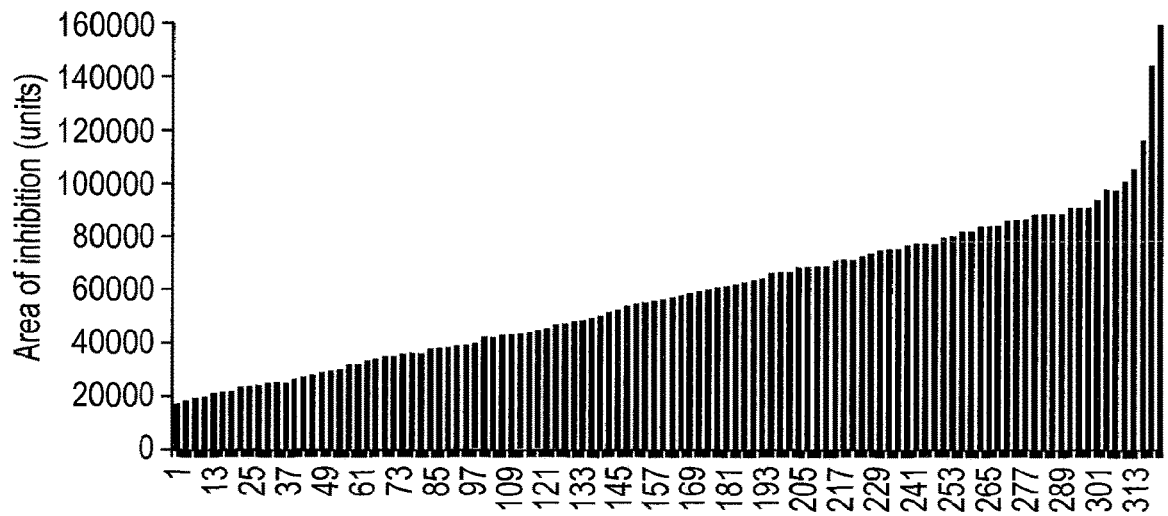
FIGS. 3C and 3D show inhibitory activity (expressed as area of inhibition in a well diffusion assay) of conditioned media of all individual LAB cultured from faeces of organically-reared pigs.
Figure 3D:
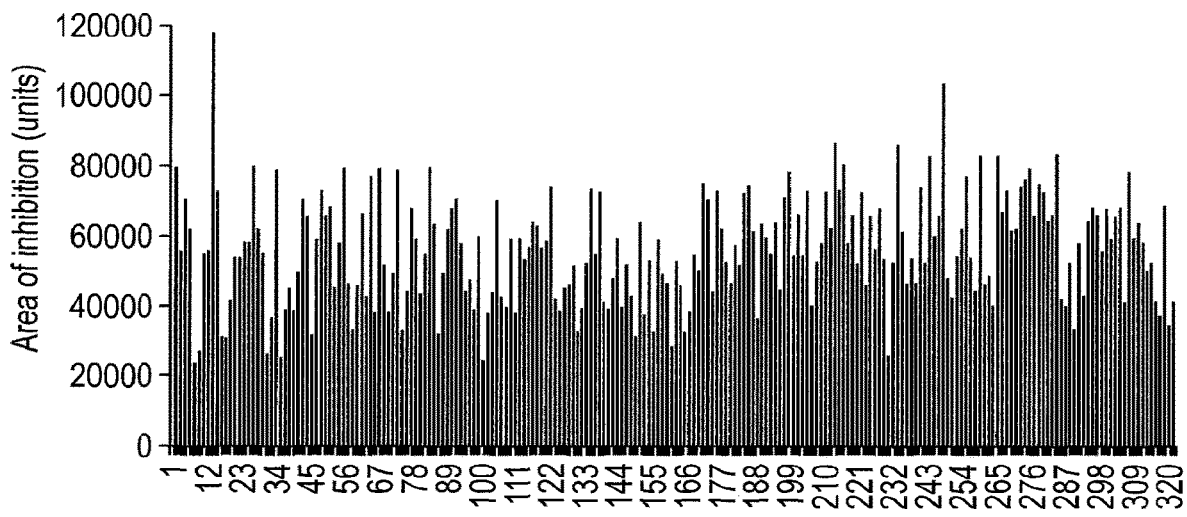

Conditioned media from LAB were also screened for anti-*Escherichia coli* K88 activity by the well diffusion assay. Activity against *E. coli* K88, as with *salmonella*, varied greatly between individual colonies of LAB (FIG. 3A). The range and variation in the activity was similar amongst the *L. johnsonii* and *L. reuteri* strains. In general, there was no direct correlation between the anti-*salmonella* and anti *E. coli* K88 activities for any individual LAB (FIG. 3C, 3D). However of the ten strains in *E. coli* K88 group 5 (FIG. 3B), seven had relatively high activities against both pathogens, two had high activity against *E. coli* K88 but moderate activity against *salmonella* and one was active primarily against *E. coli* K88.

4. Initial Selection of Candidate LAB

Thirty-three strains were identified for further testing in vitro (Table 2).

These comprised 18 *L. johnsonii* and *L. johnsonii*-related strains, 11 *L. reuteri* or *L. reuteri*-related and 4 *L. plantarum* and *L. plantarum*-related strains (Table 2a).

5. Attachment/Invasion of Pig Intestinal Epithelial [IPEC-J2] Cells

The capacity of LAB to block adhesion/invasion of IPEC cells by *S. enteritidis* and *E. coli* K88 was evaluated (FIG. 4A, 4B,). The candidate LAB all greatly reduced attachment and invasion of IPEC cells by *salmonella*. Most of them were also very effective against *E. coli* K88. However, 3 of the strains had only limited effects on adhesion/invasion of IPEC cells by *E. coli* K88.

6. Susceptibility of LAB to Antibiotics.

The susceptibility of the candidate LAB to a range of antibiotics was evaluated (Table 4, FIG. 5). All but one strain (RINH vial 266) exhibited some degree of resistance to individual antibiotics. All were susceptible to ampicillin (10 µg), cefotaxime (30 µg) and chloramphenicol (10 µg). The majority were susceptible to erythromycin (15 µg), gentamicin (10 µg), tetracycline (30 µg) and vancomycin (30 µg). Most strains were resistant to metronizadole (50 µg) and nalidixic acid (30 µg) and to a lesser extent kanamycin (30 µg). 23

7. Refined Selection of Candidate LAB

Twenty-three high ranking strains were identified for further testing in vitro.

8. Substrate Specificity of LAB

The candidate LAB were screened for substrate reactivity using an API CH 50 kit (Table 5, 6, FIG. 6). *L. johnsonii, L. reuteri* and *L. plantarum* each exhibited strain-specific general substrate reaction profiles. In addition, most strains of each genotype exhibited fine differences in their substrate reactivity, indicative that they were unique individual strains.

9. Suppression of Inflammation in Pig Intestinal Epithelial [IPEC-J2] Cells

The ability of candidate LAB to block or suppress inflammatory responses triggered in IPEC cells by 12-O-Tetradecaboylphorbol-13-acetate [PMA] was tested (FIGS. 7A-7C; Table 7). The candidate strains varied greatly in their capacity to block interleukin-8 (IL-8) gene-expression triggered by PMA. Five strains (RINH vial 29, 30, 31 86 and 266) had potent anti-inflammatory effects.

10. Final Selection of Candidate LAB

Fourteen strains were identified having killing and blocking activities against *salmonella* and *E. coli* K88, susceptibility to antibiotics carbohydrate reactivity and capacity to suppress inflammation in vitro. Seven of these were particularly preferred. The latter set comprised 4 *L. plantarum*-related, 3 *L. johnsonii*-related and one *L. reuteri*. Two of these LAB strains [GGDK266 and GGDK31] were prepared in bulk for evaluation in a trial with newly-weaned piglets (Table 8).

11. Freeze Drying and Storage of LAB

The survival and viability of LAB after freeze drying in skimmed milk powder [SKP], SKP plus lactose or SKP plus sucrose was evaluated (FIGS. 8A and 8B). FIG. 8A depicts the stability of *L. reuteri* and FIG. 8B depicts the stability of *L. johnsonii*. Small losses in viability were evident on storage for 42 and 84 days at room temperature of samples dried in SKP. This was less marked when skimmed milk powder and sugars were used in combination. However, the 24 latter preparations tended to be hygroscopic and difficult to maintain. Bulk preparations of GGDK266 and GGDK31 were therefore prepared by drying the bacteria in skimmed milk powder [100 g/l] (Table 8).

12. Heat-Treatment Studies

Suspensions of faeces from organically reared pigs were heat treated for varying periods of time at 50-70° C., plated out on MRS agar, colonies picked off and cultured in MRS broth [RINH vial 417-506]. The strain types recovered were variable and *clostridium* species formed a high proportion, the isolated strains remained sensitive to heat.

Figure 9A:
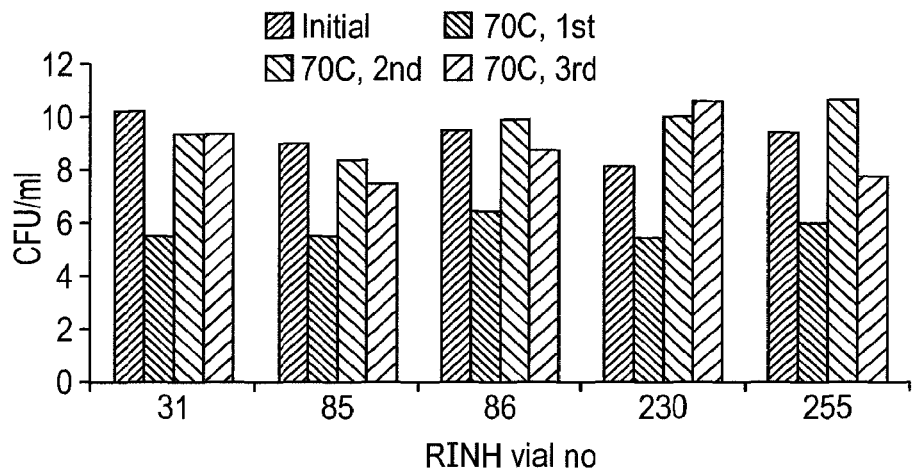
Figure 9B:
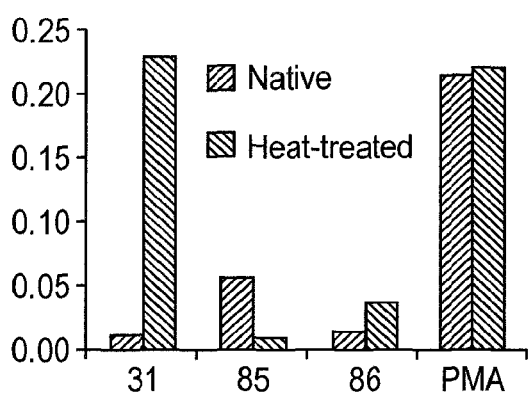
Figure 9C:
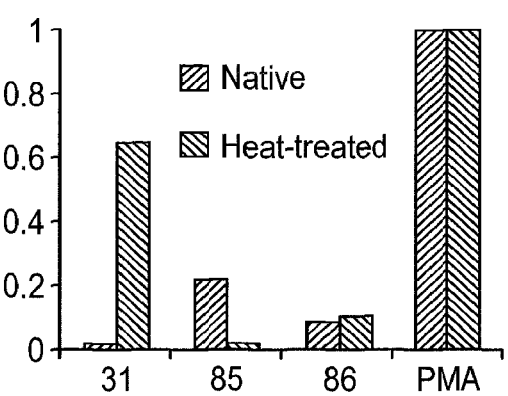
Figure 9D:
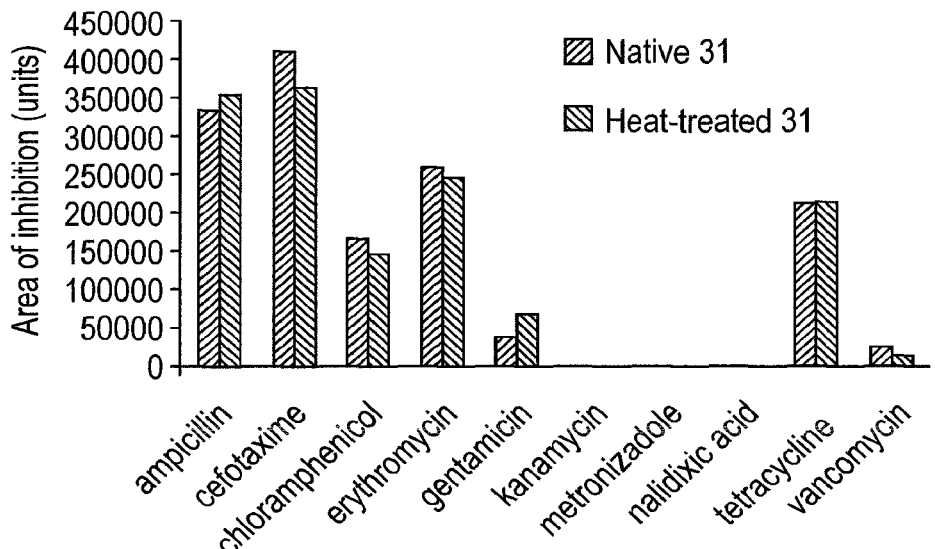

Isolated cultures of LAB were subject to heating three times for 15 minutes at 70° C. (FIGS. 9A-9C). Viable bacteria decreased by 3-4 log orders after heat-treatment for the first time. However, the surviving bacteria had a degree of heat-resistance. With one exception, losses of viable bacteria were low when the bacteria were re-cultured and re-heated a further two times.

Heat-treatment three times at 70° C. altered the biological activities of the strains (FIGS. 9A-9C). RINH vial 521 (vial 255 heat-treated) was not able to block attachment of pathogens to IPEC cells and the capacity of RINH vial 520 (vial 230 heat-treated) to prevent attachment was reduced. The ability of RINH vial 517 (vial 31 heat-treated) to abolish inflammatory responses triggered in IPEC cells was abolished. In contrast, the biological properties of RINH vial 518 (vial 85 heat-treated) and RINH vial 519 (vial 86 heat-treated) were similar to those of the native strains. 13. Mouse infection studies 13.1 *L. mucosae* (RINH Vial 323)

C3H/HeN mice develop a persistent but non-lethal, intestinal and systemic infection, which has many characteristics of the major form of human salmonellosis, when challenged with high levels of *Salmonella enteritidis* S1400. In contrast, C57Bl/6 mice develop a severe primarily systemic, infection, reminiscent of acute infection in humans, when challenged with the same pathogen. To evaluate the capacity of *L. mucosae* (vial 323) to ameliorate salmonellosis, C3H/HeN and C57Bl/6 mice were treated with *L. mucosae* prior to and post-challenge with *Salmonella enteritidis* (FIGS. 10, 13). The mice were euthanased and dissected 6 (C57Bl/6) or 10 (C3H/HeN) days post-infection.

Systemic Tissues:

Oral treatment with *L. mucosae* limited the capacity of *S. enteritidis* to cause systemic infection both in C3H/HeN and C57Bl/6 mice (FIG. 11A-11C; 14A-14C). High numbers of viable *salmonella* were detected in the mesenteric lymph node, liver and spleen of mice. In contrast, the numbers present in these tissues were greatly reduced if the mice had been co-treated with RINH vial 323 (*L. mucosae*). *Salmonella* infection caused enlargement of the spleen (FIGS. 12A; 15). This tissue response was significantly reduced in mice treated with both RINH vial 323 (*L. mucosae*) and *salmonella*.

Intestine:

Intestinal myeloperoxidase [MPO], a marker for neutrophils, was determined in C3H/HeN mice treated with *salmonella* or *salmonella* plus RINH vial 323 (*L. mucosae*). MPO in the intestine was greatly increased by *salmonella* infection, due to recruitment of neutrophils to the intestine part of the host response to infection (FIG. 12B), Co-treatment with RINH vial 323 (*L. mucosae*) reduced MPO activity in the intestine of *salmonella*-infected mice, indicating that the intestinal inflammatory responses to infection were lowered in these animals.

13.2 Novel Pig LAB

Four LAB were selected: RINH vial 31, RINH vial 32, RINH vial 46 and RINH vial 47 (All *L. reuteri*; LR31, LR 32, LR 36 and LR47 respectively). To assess their efficacy to ameliorate a pathogen infection, C3H/HeN mice were treated with these LAB or RINH vial 323 (*L. mucosae*, LM] prior to and post-challenge with *Salmonella enteritidis* (FIG. 16). The mice were euthanased and dissected 10 days post-infection. Faecal excretion of *S. enteritidis* was reduced, if the mice had been co-treated with LAB (FIG. 17A, 17B). LR31 and LR32 tended to have the greatest effects on faecal *salmonella* outputs.

Intestine:

Treatment with LR31, LR32, LM, LR46 or LR47 significantly reduced the numbers of *salmonella* in the caecum (FIG. 18A). Furthermore, LR31, LR32, LR46 and LR47 but not LM lowered *salmonella* numbers in the colon (FIG. 18B). The reductions tended to be greater with LR31 and LR32. In contrast to the large intestine, the LAB had no significant effects on numbers of *salmonella* in the small intestine.

Systemic Tissues:

Treatment with LR31, LR32, LM, LR46 or LR47 greatly reduced the numbers of *salmonella* detected in the spleen and liver (FIGS. 19A-19C). The reductions were more marked with LR31 and LR32 than with LM, LR46, or LR47. *Salmonella* numbers in the mesenteric lymph node were lowered following treatment with LR31, LR32 and LR46 but not with LM or LR47.

Discussion

The LAB strains isolated (total of 436 individual colony picks) from faeces of organically-reared pigs were predominantly *L. reuteri*, *L. johnsonii*, *L. gasseri*, *L. pentosus*, strains with a small number of *L. plantarum*, *L. acidophilus*, *L. vaginalis*, a single *L. mucosae* and several uncultured strains. Most of the LAB produced substances that could inhibit the growth of *S. enteritidis* and/or *E. coli* K88 in vitro. The potency of these anti-pathogen effects varied greatly between the individual bacterial strains. A proportion of LAB had high activity against *S. enteritidis* but low activity against *E. coli* K88 and vice-versa, but the majority had similar activities against both pathogens.

Thirty-three strains were selected on the basis of anti-microbial potency as determined in vitro. These bacteria were further screened for their ability to block adherence/invasion of intestinal pig epithelial cells (IPEC) by pathogens in vitro and their susceptibility to antibiotics.

Twenty-three strains were assayed for substrate range and specificity and their capacity to suppress inflammation in IPEC cells in vitro. From these, fourteen LAB (5 *L. johnsonii*, 6 *L. reuteri* and 3 *L. plantarum*) with particularly favourable properties were identified.

Two LAB strains [GGDK266 and GGDK31] were prepared in bulk for in vivo evaluation in newly-weaned piglets. Other potentially important candidate strains were present in this set of 14 LAB.

The survival and viability of LAB after freeze drying in various solutions was also evaluated. Small losses in viability were evident on prolonged storage of samples dried with skimmed milk powder. This was less marked when skimmed milk powder and sugars were used. However, the latter preparations were hygroscopic and were difficult to maintain. It was therefore decided to use a skimmed milk powder suspension for freeze drying and storage of LAB. The bulk preparations of GGDK266 and GGDK31 were freeze-dried in this medium.

Heat stability is a useful feature for LAB to be used in pelleted animal foods. Five heat-conditioned viable strains of isolated pig LAB were obtained. However, the biological properties in vitro and probiotic potential of three of the strains were adversely affected by heat-treatment. Nonetheless, two of the bacteria retained the biological properties of their native non-heat-treated forms.

Five pig LAB (*L. reuteri* [4] or *L. mucosae* [1]) were tested for ability to ameliorate salmonellosis in vivo. Treatment of mice with these LAB greatly reduced the pathogenicity of *S. enteritidis*.

14. Evaluation of Oral Administration of Organic Lactobacilli Probiotic Strains on the Modulation of the Gut Microbiota and Performance of Early Weaned Pigs In vivo trials were carried out on early weaned piglets to test the effect of two probiotic strains according to the invention, Lactobacilli strains GGDK266 and GGDK31.

Trial Design

Animals:
- 24 Large—White×Redon piglets
- Early weaned (21 days old, ≈7-8 kg), born in a local farm
- Weighted then distributed equally between the different group
- 3 experimental treatments (n=8):
  - A—Basal diet+Placebo
  - B—Basal diet+probiotic GDDK 266—dose 10×10$^{12}$
  - C—Basal diet+probiotic GDDK 31—dose 10×10$^{12}$
- Observation period: 14 days Diet:
Diets based on barley, wheat & soybean meal
Feed composition

|  |  |
|---|---|
| Barley | 36.5 |
| Wheat | 21 |
| SBM 48 | 19 |
| Corn | 10 |
| Soy oil | 4 |
| Sugar | 4 |
| Potato protein | 2 |
| Premix | 3.5 | feed ad libitum in pelleted form

Tissue Sampling and Measurements

Sampling:
- Day 0 Slaughter of 6 "naive" piglets for collection of the caecum Individual collection of faeces (if possible)
- Day 7 individual collection of faeces during weight measurement
- Day 14 Slaughter of 24 piglets for collection of:

| Content (5 g): | Tissus (10 cm): |
|---|---|
| Gastric | Jejunum |
| Jejunum | Ileum |
| Ileum | Caecum |
| Caecum | Lymphatic nodes (distal ileum level) |

Storage:
All samples were weighed, frozen in liquid nitrogen and stored at −80° C.

Performance:
Daily Weight gain (DWG), Feed Intake (FI) and Feed Conversion Ratio (FCR) (1$^{st}$ Step) Analysis:
Determination of the microbiota profile in the different gut content samples by the molecular microbiology technique Denaturing gradient gel electrophoresis (DGGE).

(2$^{nd}$ Step)
Molecular analysis of gene expression data using pig affymetrix gene expression arrays to determine gene modulation patterns.
Determination of immunity markers in intestinal tissues Microbial Analysis Using Denaturing Gel Gradient Electrophoresis DGGE (Trial 1)

DGGE Methodology

DNA is extracted from faecal or tissue samples utilizing the MP Bio FastDNA™ spin kit for soil sample—116560000. The DNA is then amplified using Muyzer primers, as it is essential to use primers with a GC Clamp to be run on the gel. For samples of *lactobacillus*, specialised *lactobacillus* primers with a GC clamp were used.

| Target Group | Primer | Primer Sequence (5'-3') | Amplicon Size (bp) | Annealing temperature (° C.) | DGGE gradient (%) |
|---|---|---|---|---|---|
| All Bacteria | MF | ATTACCGCGGCTGCTGG | 233 | 55 | 35-70 |
|  | MR-GC$^a$ | GC-clamp-CCTACGGGAGGCAGCAG |  |  |  |
| LABs | Lac1 | AGCAGTAGGGAATCTTCCA | 327 | 55 | 30-50 |
|  | Lac2-GC$^a$ | GC-Clamp-ATTYCACCGCTACACATG$^c$ |  |  |  |

Annotations:
$^a$The GC clamp is as follows: CGCCCGCCGCGCGCGGCGGGCGGGGCGGGGGCACGGGGGG
$^c$Y = C or T PCR Program:

| Time | Temperature | Cycles |
|---|---|---|
| 5 minutes | 94° C. | 1 |
| 30 seconds | 94° C. | 35 |
| 30 seconds | 55° C. | |
| 2 minutes | 72° C. | |
| 10 minutes | 72° C. | 1 |

DGGE is a genetic analysis technique in which amplified PCR products are separated by the denaturants formamide and urea within the gel, based on the genetic sequence by as little as a single base difference. DGGE can be utilised to visualise the differences in microbial diversity between samples. DNA obtained from a range of samples can be used in DGGE e.g. tissue and faecal samples. Bands on the gel were visualised using silver staining.

Molecular Analysis and Gene Expression Profiles of Pig Tissues

RNA Extraction and Affymetrix Microarray Analysis

RNA was isolated from both animal tissue and cultured cells for use on Affymetrix GeneChips. For animal tissue, approximately 200 mg tissue sample was removed from RNAlater (Ambion) and lyzed in Trizol (Invitrogen) using a polytron homogenizer. The tissue was further homogenized by passing the lysate through a syringe fitted with a 19 G needle 3-5 times. The samples were incubated for 5 min at RT to permit the complete dissociation of nucleoprotein complexes. Then, chloroform, isopropanol and ethanol steps were performed according to the manufacturer's instructions. Briefly, 0.2 mL of chloroform was added per 1 mL of Trizol, vortexed and incubated at RT for 5 min. The samples were centrifuged at 12,000×g for 15 min at 4° C. The resultant aqueous phase was transferred to a fresh tube, and the RNA was precipitated by the addition of 0.5 mL of isopropanol per 1 mL of Trizol. The tubes were shaken vigorously by hand for 10 s, incubated at 4° C. for 10 min and centrifuged at 12,000×g for 10 min at 4° C.

The RNA precipitate was washed with ice-cold 75% ethanol, adding at least 1 mL of 75% ethanol per 1 mL of Trizol. The samples were vortexed and centrifuged at 7,400×g for 5 min at 4° C. After air-drying the resultant RNA pellet, the RNA was resuspended in up to 100 µL RNase-free water. Total RNA was further extracted with the RNeasy kit (Qiagen) according to the manufacturer's instructions, including an RNase-free DNase I (Qiagen) digestion step.

Cultured cells were homogenized by adding 350 µL Buffer RLT+1% β-mercaptoethanol. The cells were scraped off culture dishes with a filter tip and further homogenized by passing the lysate through a syringe fitted with a 19 G needle 3-5 times. The cell lysate was then further processed using the RNeasy kit (Qiagen) according to the manufacturer's instructions, including an RNase-free DNase I (Qiagen) digestion step.

RNA concentration and integrity was ascertained using a Nanodrop instrument and/or Agilent Bioanalyzer, and purified RNA was stored at −70° C.

250 ng RNA was processed for Affymetrix GeneChips using the GeneChip 3' IVT Express Kit (Affymetrix) according to the manufacturer's instructions. aRNA quality was determined by Agilent 2100 Bioanalyzer. Hybridization to the GeneChip Mouse Genome 430 2.0 and GeneChip Human Genome U133 Plus 2.0 (Affymetrix) on a GeneChip Fluidics Station 450 (Affymetrix) was performed at the Institute of Medical Sciences Microarray Core Facility (University of Aberdeen, UK). Chips were scanned with an Affymetrix GeneChip Scanner 3000 (Affymetrix). Image quality analysis was performed using Gene Chip Operating Software (GCOS) (Affymetrix). Further quality analysis, normalization (gcRMA), statistical analysis and heatmap generation was performed with the freely available software packages R (http://www.r-project.org) and Bioconductor (http://www.bioconductor.org). Microarray data were submitted to the National Center for Biotechnology Information (NCBI) Gene Expression Omnibus (http://www.ncbi.nlm.nih.gov/geo).

Results

Performance of Pigs Fed Probiotics GGDK266 and GGDK31

The results for pigs fed probiotics GGDK266 and GGDK31 are shown in FIG. 20. DWG (Daily weight gain), FI (food intake) and FCR (feed conversion ratio) are shown below:

| GGDK266 | DWG | FI | FCR |
|---|---|---|---|
| d 0-d 7 | +++ (*) | + | + |
| d 7-d 14 | = | + | + |
| d 0-d 14 | + | + | + |

Piglets fed GGDK266 exhibited significantly improved daily weight gain (DWG) during the first week post-weaning relative to GGDK31 and placebo fed piglets.

Microbial Diversity Analysis Using DGGE (Trial 1)

DGGE using universal primers revealed no differences in overall microbial diversity between the treatments and placebo (see FIG. 21).

DGGE using lactic acid bacteria (LAB) specific primers revealed significant differences in LAB diversity between treatment with GGDK 266 and placebo in both caecal and ileal samples (see FIG. 22).

DGGE using LAB specific primers revealed significant differences in LAB diversity between the treatment with GGDK266 and placebo in ileal samples (see FIG. 23).

DGGE using LAB specific primers revealed significant differences in LAB diversity between the treatment with 266 and placebo in caecal samples (see FIG. 24).

Overall the microbial diversity analysis revealed significant clustering of the LAB population in piglets fed GGDK266 indicating that the populations in individual animals on this treatment has a similar and stable microbiota.

Molecular Analysis of Ileal Tissue Samples: Affymetrix Pig Arrays

Downregulated in GDK266 Versus Placebo

Gene ontology analysis of differentially expressed gene revealed that a significant reduction in immune system processes and pro-inflammatory activation in response to feeding young piglets probiotic GGDK266 relative to placebo (see FIG. 25).

Results reveal that GGDK266 had a very specific and targeted effect on the immune system and the functional groups associated with response to stimuli (see FIG. 26).

Upregulated in GGDK266 Versus Placebo

In contrast to the effects on the immune system, GGDK266 promoted metabolic processes particularly in relation to nitrogen (see FIG. 27). Without wishing to be bound by theory, it is believed that these effects may explain the improved DWG in animals fed GGDK266.

Top Differentially Expressed Genes Between GGDK266 and Placebo

| affy. id | Gene Name | Product | FC | p-value |
|---|---|---|---|---|
| Ssc.645.1.S1_at | CSTA | Cystatin A | 44.06 | 0.00000 |
| Ssc.11608.1.A1_at | TIP_HUMAN | T-cell immunomodulatory protein precursor | 28.92 | 0.00030 |
| Ssc.10837.1.A1_at | ROBO1 | Roundabout homolog 1 precursor | 13.35 | 0.00178 |
| Ssc.8960.1.A1_at | BPI | Bactericidal permeability-increasing protein precursor | 11.65 | 0.00476 |
| Ssc.16234.1.S1_at | TCN1 | Transcobalamin 1 precursor | 11.48 | 0.00023 |
| Ssc.1411.1.S1_at | THBS4 | Thrombospondin 4 precursor | 8.92 | 0.00198 |
| Ssc.837.1.A1_at | BPI | Bactericidal permeability-increasing protein precursor | 4.55 | 0.00573 |
| Ssc.30008.1.A1_at | ESR1 | Estrogen receptor | 4.48 | 0.00053 |
| Ssc.13539.1.A1_at | PLAGL1 | Zinc finger protein PLAGL1 | 4.42 | 0.00881 |
| Ssc.26324.1.S1_at | NP_981932 | Iodotyrosine dehalogenase 1 protein | 4.26 | 0.00200 |
| Ssc.29413.1.A1_at | B3GALT2 | UDP-Gal:betaGlcNAc beta 1,3-galactosyltransferase 2 | 4.00 | 0.00046 |
| Ssc.27410.1.S1_at | MYCN | N-myc proto-oncogene protein | 3.80 | 0.00261 |
| Ssc.25176.1.A1_at | GOLPH4 | Golgi phosphoprotein 4 | 3.80 | 0.00009 |
| Ssc.15890.1.S1_at | VNN1 | Pantetheinase precursor | 3.61 | 0.00271 |
| Ssc.23427.1.A1_at | CYB561 | Cytochrome b561 | 3.29 | 0.01512 |
| Ssc.16186.1.S1_at | CD3E | T-cell surface glycoprotein CD3 epsilon chain precursor | −2.62 | 0.00764 |
| Ssc.22676.1.S1_at | CXCR6 | C-X-C chemokine receptor type 6 | −2.63 | 0.01652 |
| Ssc.15565.1.S1_at | LCP2 | Lymphocyte cytosolic protein 2 | −2.76 | 0.00024 |
| Ssc.18652.1.S1_at | IL16 | Interleukin-16 precursor | −2.97 | 0.01132 |
| Ssc.181.1.S1_at | TRGV9 | T-cell receptor gamma chainV region PT-gamma-1/2 precursor | −3.04 | 0.01615 |
| Ssc.23489.1.S1_at | CD8A | T-cell surface glycoprotein CD8 alpha chain precursor | −3.08 | 0.00071 |
| Ssc.428.6.S1_a_at | TCA_HUMAN | T-cell receptor alpha chain C region | −3.15 | 0.00027 |
| Ssc.10357.1.A1_at | FMN2 | Formin 2 | −3.46 | 0.00308 |
| Ssc.27354.1.S1_at | STXBP5 | Tomosyn | −3.88 | 0.02438 |
| Ssc.28609.3.A1_at | TPH2 | Tryptophan 5-hydoxylase 2 | −4.36 | 0.00717 |
| Ssc.25976.1.S1_at | GZMH | Granzyme H precursor | −5.46 | 0.00179 |
| Ssc.11070.1.S1_at | IGHM | Ig alpha-1 chain C region | −9.07 | 0.00115 |
| Ssc.16566.1.S1_at | LCT | Lactase phlorizin hydrolase precursor | −11.31 | 0.00328 |
| Ssc.13273.1.A1_at | GCNT3 | glucosaminyl (N-acetyl) transferase 3, mucin type | −19.75 | 0.00016 |
| Ssc.11098.1.S1_at | IFITM3 | Interferon-induced transmembrane protein 3 | −51.36 | 0.00044 |

Gene expression data revealed that a number of genes were significantly increased including antimicrobial peptides (eg. CSTA, BP1) and immune-regulatory genes (TIP). In contrast GGDK266 reduced the expression of a diverse panel of genes involved in pro-inflammatory immunity (IFITM3, IL-16).

CONCLUSIONS

Cellular and metabolic processes, particularly in relation to nitrogen, are increased in animals treated with GGDK266 relative to placebo.

Immune system processes are downregulated in animals treated with GGDK266 relative to placebo. Examples include T-cell markers CD3 and CD8, T cell receptor chains, chemokines/cytokines and IFN-related genes.

Animals administered with GGDK266 exhibited a stable population of lactic acid bacteria revealed by clustering of the bacterial profile of the individual induced by the administration of probiotic GGDK266.

FCR and performance were significantly improved during the first weeks of post-weaning life.

This improvement in growth performance correlated with the reduction in inflammatory immune responses and the increase in specific metabolic processing.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

| Summary of bacteria colonies selected from cultures of faeces from organically-reared pigs. | |
|---|---|
| Total number of cultured colony picks | 443 |
| Media: | |
| LAMVAB agar | 55 |
| LAMVAB agar + pig colostral carbohydrate | 88 |
| MRS agar | 29 |
| MRS agar + pig colostrum carbohydrate | 176 |
| Glucose-free MRS agar + carbohydrate | 57 |
| MRS agar after heat-treatment at up to 70° C. | 38 |
| Main strains identified: | |
| *Lactobacillus reuteri* | |
| *Lactobacillus johnsonii* | |
| *Lactobacillus plantarum* | |
| Five isolated LAB were heated once, twice or three times at 70° C. for 15 min. | |
| Surviving bacteria were re-grown. | |
| In stock | |
| 5 LAB heated once at 70° C. | |
| 5 LAB heated twice at 70° C. | |
| 5 LAB heated three times at 70° C. | |

TABLE 2

Candidate LAB strains for further study selected on the basis of killing activity in well diffusion assays (note 266 and 161 contain LR)

| RINH Vial no. | | Pathogen killing (units) Well diffusion assay | |
|---|---|---|---|
| | | anti-SE | anti-KSS |
| 85 | LR | 129886 | 60168 |
| 255 | LJ | 101477 | 64390 |
| 266 | LJ | 101335 | 60168 |
| 436 | LJ | 81656 | 85010 |
| 161 | LP | 77894 | 103346 |
| 12 | LJ | 162709 | 42977 |
| 16 | LJ | 117621 | 41365 |
| 29 | LR | 174471 | 45720 |
| 31 | LR | 116867 | 46907 |
| 86 | LR | 98520 | 75147 |
| 230 | LJ | 95705 | 64340 |
| 256 | LJ | 94012 | 77459 |
| 314 | LJ | 103497 | 48936 |
| 361 | LJ | 100770 | 40254 |
| 17 | LJ | 144765 | 23072 |
| 30 | LR | 125463 | 36050 |
| 32 | LR | 168892 | 32572 |
| 258 | LP | 70724 | 68612 |
| 260 | LP | 78197 | 68562 |
| 320 | LJ | 66350 | 78044 |
| 364 | LJ | 99137 | 55123 |
| 433 | LJ | 95083 | 51461 |
| 15 | LP | 77459 | 58669 |
| 218 | LJ | 62329 | 50416 |
| 220 | LJ | 68612 | 53834 |
| 356 | LJ | 72986 | 55302 |
| 363 | LJ | 79125 | 45555 |
| 131 | LR | 42223 | 44108 |
| 434 | LR | 10000 | 81656 |
| 166 | LJ | 17064 | 79621 |
| 431 | LR | 48657 | 31674 |
| 47 | LR | 20722 | 34633 |
| 46 | LR | 19867 | 34633 |

LJ. *L. johnsonii*,
LR. *L. reuteri*,
LP. *L. Plantarum*

TABLE 2a

Identification of candidate LAB strains (by 16S rRNA gene sequence) selected on the basis of killing activity in well diffusion assays (note 266 and 161 contain LR)

| RINH Vial no. | forward sequence | reverse sequence |
|---|---|---|
| 85 | *Lactobacillus reuteri* | *Lactobacillus reuteri* |
| 255 | *Lactobacillus johnsonii, taiwanensis, acidophilus* | *Lactobacillus johnsonii, gasseri* |
| 266 | *Lactobacillus johnsonii* | *Lactobacillus johnsonii* |
| 436 | *lactobacillus johnsonii* str. 466 | *Lactobacillus johnsonii* F19785 |
| 161 | *Lactobacillus plantarum, pentosus, paraplantarum* | *Lactobacillus plantarum, pentosus* |
| 12 | *Lactobacillus johnsonii, gasseri, taiwanensis* | *Lactobacillus johnsonii, gasseri* |
| 16 | *Lactobacillus johnsonii, gasseri, taiwanensis* | *Lactobacillus johnsonii* |
| 29 | *Lactobacillus reuteri, pontis, vaginalis, frumenti* | *Lactobacillus reuteri* |
| 31 | *Lactobacillus reuteri* | *Lactobacillus reuteri* |
| 86 | *Lactobacillus reuteri* | *Lactobacillus reuteri* |
| 230 | *Lactobacillus johnsonii, taiwanensis, acidophilus* | *Lactobacillus johnsonii* |
| 256 | *Lactobacillus johnsonii, taiwanensis, acidophilus* | *Lactobacillus johnsonii* |
| 314 | *lactobacillus johnsonii* BR0315 | uncultured bacterium |
| 361 | *lactobacillus johnsonii* str. NCC2822 | *lactobacillus johnsonii* F19785 |
| 17 | *Lactobacillus johnsonii, gasseri, taiwanensis* | *Lactobacillus johnsonii* |
| 30 | *Lactobacillus reuteri, pontis* | *Lactobacillus reuteri* |
| 32 | *Lactobacillus reuteri* | *Lactobacillus reuteri* |
| 258 | *Lactobacillus plantarum, pentosus, helveticus* | *Lactobacillus plantarum, pentosus, paraplantarum* |
| 260 | *Lactobacillus plantarum, pentosus, paraplantarum* | *Lactobacillus pentosus, plantarum, paraplantarum* |
| 320 | *lactobacillus johnsonii* NCC2822 | *Lactobacillus johnsonii* F19785 |
| 364 | *lactobacillus johnsonii* 466 | *lactobacillus johnsonii* F10785 |
| 433 | *lactobacillus johnsonii* str. CECT 289 | *lactobacillus johnsonii* F19785 |
| 15 | *Lactobacillus plantarum, pentosus* | *Lactobacillus plantarum, pentosus* |
| 218 | *Lactobacillus johnsonii, taiwanensis* | uncultured Firmicutes, *Lactobacillus johnsonii* |
| 220 | *Lactobacillus johnsonii, taiwanensis* | uncultured Firmicutes, *Lactobacillus johnsonii* |
| 356 | *lactobacillus johnsonii* NCC2822 | *lactobacillus johnsonii* F19785 |
| 363 | *lactobacillus johnsonii* 466 | *lactobacillus johnsonii* F10785 |
| 131 | *Lactobacillus reuteri* | *Lactobacillus reuteri* |
| 434 | *Lactobacillus reuteri* NM99-1 | *lactobacillus reuteri* |
| 166 | *Lactobacillus johnsonii, taiwanensis, acidophilus* | *Lactobacillus johnsonii* |
| 431 | *lactobacillus reuteri* str. Probio-16 | *lactobacillus reuteri* JCM 1112 |
| 47 | *Lactobacillus reuteri* | *Lactobacillus reuteri* |
| 46 | *Lactobacillus reuteri* | *Lactobacillus reuteri* |

TABLE 3

Candidate LAB strains for further study selected on the basis of killing activity in well diffusion assays and capacity to block adherence of pathogen to IPEC cells

| RINH Vial no. | Inhibition of adherence (%) | |
|---|---|---|
| | SE | KSS |
| 85 | 88.31 | 87.93 |
| 255 | 82.37 | 99.93 |
| 266 | 88.03 | 98.09 |
| 161 | 98.32 | 96.94 |
| 12 | 96.89 | 99.92 |
| 29 | 93.7 | 99.91 |
| 31 | 98.64 | 99.75 |
| 86 | 81 | 99.98 |
| 256 | 82.47 | 99.92 |
| 361 | 85.07 | 99.44 |
| 17 | 84.56 | 99.66 |
| 30 | 96.44 | 99.91 |
| 32 | 87.74 | 99.86 |
| 230 | 78.89 | 82.45 |
| 258 | 96.37 | 86.5 |
| 260 | 90.22 | 88.79 |
| 314 | 79.68 | 94.2 |
| 433 | 99.99 | 96.23 |
| 16 | 87.68 | 45.38 |
| 218 | 91.53 | 86.49 |
| 363 | 85.61 | 99.93 |
| 364 | 82.13 | 78.12 |
| 15 | 79.19 | 99.52 |

TABLE 3-continued

Candidate LAB strains for further study selected on the basis of killing activity in well diffusion assays and capacity to block adherence of pathogen to IPEC cells

| RINH Vial no. | Inhibition of adherence (%) | |
|---|---|---|
| | SE | KSS |
| 131 | 95.5 | 96.03 |
| 220 | 91.04 | 78.6 |
| 320 | 92.7 | 44.17 |
| 356 | 82.15 | 78.4 |
| 434 | 94.78 | 98.85 |
| 436 | 99.97 | 1 |
| 166 | 91.45 | 95.97 |
| 431 | 96.35 | 86.47 |
| 47 | 90.47 | 99.47 |
| 46 | 83.51 | 99.7 |

TABLE 4

Area of inhibition of LAB by defined amounts of antibiotic (arbitrary units)

| | ampicillin | cefotaxime | chloramphenicol | erythromycin | gentamicin | kanamycin | metronizadole | nal. acid | tetracycline | vancomycin |
|---|---|---|---|---|---|---|---|---|---|---|
| 12 | 244011 | 340402 | 186699 | 13151 | 0 | 0 | 0 | 0 | 37668 | 22581 |
| 15 | 277117 | 311725 | 204282 | 214008 | 0 | 0 | 0 | 0 | 0 | 0 |
| 16 | 266033 | 294166 | 187805 | 64681 | 17000 | 7157 | 0 | 0 | 0 | 105209 |
| 17 | 387224 | 400570 | 235430 | 277145 | 9193 | 0 | 0 | 0 | 50328 | 117741 |
| 29 | 410335 | 444193 | 190293 | 114511 | 0 | 0 | 0 | 0 | 252497 | 11483 |
| 30 | 292728 | 335927 | 77133 | 208117 | 31261 | 0 | 0 | 0 | 187805 | 31402 |
| 31 | 334789 | 410966 | 165904 | 262226 | 38221 | 0 | 0 | 0 | 214037 | 24901 |
| 32 | 404496 | 402291 | 247436 | 350238 | 71608 | 23786 | 0 | 0 | 261979 | 10691 |
| 46 | 359232 | 402588 | 210421 | 251461 | 29550 | 0 | 0 | 0 | 21382 | 25069 |
| 47 | 328283 | 410579 | 185515 | 270105 | 30342 | 0 | 0 | 0 | 211556 | 22231 |
| 85 | 356114 | 369916 | 204992 | 309439 | 0 | 0 | 0 | 0 | 276800 | 3971 |
| 86 | 250812 | 381270 | 183399 | 250805 | 41858 | 0 | 31264 | 0 | 16643 | 13355 |
| 131 | 349955 | 473065 | 248521 | 123562 | 82466 | 14932 | 0 | 0 | 19354 | 7479 |
| 161 | 338497 | 412977 | 258724 | 261133 | 51991 | 4536 | 29126 | 0 | 20435 | 5542 |
| 166 | 268783 | 417393 | 185508 | 251607 | 61136 | 17671 | 0 | 0 | 24606 | 0 |
| 218 | 209117 | 271547 | 148617 | 0 | 0 | 0 | 0 | 0 | 88668 | 122870 |
| 220 | 209371 | 319970 | 165815 | 34230 | 58814 | 32572 | 0 | 0 | 34636 | 111666 |
| 230 | 254614 | 335143 | 164405 | 51078 | 65717 | 45705 | 0 | 0 | 36644 | 41991 |
| 255 | 330364 | 392169 | 217758 | 59224 | 56563 | 8486 | 0 | 0 | 29872 | 0 |
| 256 | 456892 | 502325 | 228531 | 71258 | 93058 | 0 | 0 | 0 | 20955 | 42203 |
| 258 | 401257 | 271932 | 195909 | 233326 | 28608 | 0 | 0 | 0 | 223143 | 0 |
| 260 | 286400 | 364573 | 203796 | 33393 | 78821 | 78364 | 0 | 0 | 21757 | 62792 |
| 266 | 287070 | 322869 | 198614 | 247085 | 54008 | 3079 | 6437 | 2737 | 48286 | 107882 |
| 314 | 297057 | 332853 | 154830 | 44115 | 0 | 0 | 0 | 0 | | 90259 |
| 356 | 291920 | 339895 | 203692 | 62656 | 10472 | 5890 | 0 | 0 | 24194 | 8202 |
| 361 | 320695 | 323713 | 201886 | 234140 | 0 | 0 | 0 | 0 | | 91863 |
| 363 | 275304 | 308159 | 193271 | 44491 | 86683 | 0 | 0 | 0 | 28212 | 18146 |
| 364 | 288514 | 341651 | 194320 | 143978 | 45880 | 0 | 0 | 0 | 18322 | 103995 |
| 431 | 339016 | 380459 | 226484 | 311725 | 74991 | 0 | 0 | 0 | 0 | 26302 |
| 433 | 241710 | 203588 | 174124 | 63381 | 19139 | 0 | 0 | 0 | 19965 | 79034 |
| 434 | 198112 | 261065 | 172223 | 68052 | 6049 | 0 | 0 | 0 | 60344 | 45863 |
| 436 | 290458 | 287331 | 185812 | 142842 | 0 | 0 | 0 | 0 | 52279 | 61810 |

Nal. Acid, naladixie acid.

TABLE 5

Substrates in capsules of API CH 50 Kit

| | Substrates in capules of API CH 50 kit | |
|---|---|---|
| 1 | glycerol | polyol |
| 2 | erythritol | polyol |
| 3 | D-arabinose | monosaccharide |
| 4 | L-arabinose | monosaccharide |
| 5 | D-ribose | monosaccharide |
| 6 | D-xylose | monosaccharide |
| 7 | L-xylose | monosaccharide |
| 8 | D-adonotol | alcohol |
| 9 | Methyl-βD-Xylopyranoside | cyclic |
| 10 | D-galactose | monosaccharide |
| 11 | D-glucose | monosaccharide |
| 12 | D-fructose | monosaccharide |
| 13 | D-mamose | monosaccharide |
| 14 | L-sorbose | monosaccharide |
| 15 | L-rhamose | monosaccharide |
| 16 | dulcitol | monosaccharide/alcohol |
| 17 | inositol | polyol |
| 18 | D-mamitol | polyol |
| 19 | D-sorbitol | sugar/alcohol |
| 20 | Methyl-αD-Mannopyranoside | cyclic |
| 21 | Methyl-αD-Glucopyranoside | cyclic |
| 22 | N-acetylglucosamine | monosaccharide |
| 23 | amygdalin | glycoside |
| 24 | arbutin | glycoside |
| 25 | esculin ferric citrate | |
| 26 | salicin | glycoside |
| 27 | D-cellobiose | disaccharide |
| 28 | D-maltose | disaccharide |
| 29 | D-lactose (bovine) | disaccharide |
| 30 | D-Melibiose | disaccharide |
| 31 | D-saccharose | disaccharide |
| 32 | D-trehalose | disaccharide |
| 33 | inulin | polysaccharide |
| 34 | D-melezitose | trisaccharide |
| 35 | D-rafinose | trisaccharide |

TABLE 5-continued

Substrates in capsules of API CH 50 Kit

| | Substrates in capules of API CH 50 kit | |
|---|---|---|
| 36 | amidon (starch) | polysaccharide |
| 37 | glycogen | polysaccharide |
| 38 | xylitol | monosaccharide/alcohol |
| 39 | gentobiose | disaccharide |
| 40 | D-furanose | disaccharide |
| 41 | D-lyxose | monosaccharide |
| 42 | D-tagatose | monosaccharide |
| 43 | D-fucose | monosaccharide |
| 44 | L-fucose | monosaccharide |
| 45 | D-arabitol | monosaccharide/alcohol |
| 46 | L-arabitol | monosaccharide/alcohol |
| 47 | potassium gluconate | sequestrant |
| 48 | potassium 2-ketogluconate | sequestrant |
| 49 | potassium 5-ketogluconate | sequestrant |

TABLE 6

Substrate profile of LAB using an API CH 50 kit

| | monosaccharides | alcohol/ monosaccharides | disaccharides | trisaccharides | polysaccharides | alcohols | others |
|---|---|---|---|---|---|---|---|
| 17 | 0.4 | 0.0 | 0.8 | 0.5 | 0.3 | 0.0 | 0.4 |
| 30 | 0.2 | 0.0 | 0.0 | 0.0 | 0.0 | 0.0 | 0.3 |
| 31 | 0.3 | 0.0 | 0.6 | 0.5 | 0.0 | 0.0 | 0.6 |
| 32 | 0.3 | 0.0 | 0.5 | 0.5 | 0.0 | 0.0 | 0.3 |
| 46 | 0.2 | 0.0 | 0.5 | 0.5 | 0.0 | 0.0 | 0.4 |
| 47 | 0.2 | 0.3 | 0.5 | 0.5 | 0.0 | 0.0 | 0.4 |
| 85 | 0.1 | 0.0 | 0.3 | 0.0 | 0.0 | 0.0 | 0.4 |
| 86 | 0.3 | 0.0 | 0.5 | 0.5 | 0.0 | 0.0 | 0.4 |
| 131 | 0.4 | 0.0 | 1.0 | 1.0 | 0.3 | 0.3 | 0.9 |
| 161 | 0.7 | 0.3 | 0.9 | 1.0 | 0.0 | 0.3 | 0.9 |
| 166 | 0.4 | 0.0 | 0.6 | 0.0 | 0.7 | 0.0 | 0.3 |
| 220 | 0.1 | 0.0 | 0.5 | 0.5 | 0.0 | 0.0 | 0.4 |
| 230 | 0.3 | 0.0 | 0.8 | 0.5 | 0.0 | 0.0 | 0.4 |
| 255 | 0.1 | 0.0 | 0.6 | 1.0 | 0.3 | 0.0 | 0.4 |
| 256 | 0.2 | 0.0 | 0.5 | 1.0 | 0.0 | 0.2 | 0.6 |
| 258 | 0.6 | 0.3 | 1.0 | 1.0 | 0.7 | 0.7 | 0.9 |
| 260 | 0.4 | 0.3 | 0.9 | 1.0 | 1.0 | 0.0 | 0.6 |
| 266 | 0.3 | 0.0 | 0.9 | 0.5 | 0.3 | 0.0 | 0.4 |
| 320 | 0.3 | 0.0 | 0.5 | 0.5 | 0.3 | 0.0 | 0.3 |
| 363 | 0.4 | 0.0 | 0.8 | 1.0 | 0.3 | 0.0 | 0.4 |
| 364 | 0.4 | 0.0 | 0.8 | 0.5 | 0.3 | 0.0 | 0.4 |
| 433 | 0.2 | 0.0 | 0.5 | 0.0 | 0.0 | 0.2 | 0.3 |

TABLE 7

Candidate LAB strains selected on the basis of killing activity, capacity to block adherence of pathogen to IPEC cells, antibiotic susceptibility, substrate reactivity and ability to suppress inflammation (note 266 and 161 contain LR)

| RINH Vial no. | forward sequence | reverse sequence |
|---|---|---|
| 266 | Lactobacillus johnsonii | Lactobacillus johnsonii |
| 31 | Lactobacillus reuteri | Lactobacillus reuteri |
| 258 | Lactobacillus plantarum, pentosus, helveticus | Lactobacillus plantarum, pentosus, paraplantarum |
| 260 | Lactobacillus plantarum, pentosus, paraplantarum | Lactobacillus pentosus, plantarum, paraplantarum |
| 255 | Lactobacillus johnsonii, taiwanensis, acidophilus | Lactobacillus johnsonii, gasseri |
| 161 | Lactobacillus plantarum, pentosus, paraplantarum | Lactobacillus plantarum, pentosus |
| 256 | Lactobacillus johnsonii, taiwanensis, acidophilus | Lactobacillus johnsonii |
| 86 | Lactobacillus reuteri | Lactobacillus reuteri |
| 85 | Lactobacillus reuteri | Lactobacillus reuteri |
| 32 | Lactobacillus reuteri | Lactobacillus reuteri |
| 230 | Lactobacillus johnsonii, taiwanensis, acidophilus | Lactobacillus johnsonii |
| 131 | Lactobacillus reuteri | Lactobacillus reuteri |
| 30 | Lactobacillus reuteri, pontis | Lactobacillus reuteri |
| 364 | lactobacillus johnsonii 466 | lactobacillus johnsonii F10785 |

TABLE 8

Identity for pig LAB strains selected for bulk preparation (note 266 and 161 contain LR)

| RINH vial no | Seq code primer 926F | Bacteria identified by BLAST | Seq code primer 519R | Bacteria identified by BLAST |
|---|---|---|---|---|
| | | GGDK266 | | |
| 266 | S10CM218 | Lactobacillus johnsonii | S10CM171 | Lactobacillus johnsonii |
| | | GGDK31 | | |
| 31 | S10BL123 | Lactobacillus reuteri | S10BL141 | Lactobacillus reuteri |

31 S10BL123 with 926F

SEQ ID NO: 1
GGTGGAGCATGTGGTTTAATTCGAAGCTACGCGAAGAACCTTACCAGGTC

TTGACATCTTGCGCTAACCTTAGAGATAAGGCGTTCCCTTCGGGGACGCA

-continued

ATGACAGGTGGTGCATGGTCGTCGTCAGCTCGTGTCGTGAGATGTTGGGT

TAAGTCCCGCAACGAGCGCAACCCTTGTTACTAGTTGCCAGCATTAAGTT

GGGCACTCTAGTGAGACTGCCGGTGACAAACCGGAGGAAGGTGGGGACGA

CGTCAGATCATCATGCCCCTTATGACCTGGGCTACACACGTGCTACAATG

GACGGTACAACGAGTCGCAAGCTCGCGAGAGTAAGCTAATCTCTTAAAGC

CGTTCTCAGTTCGGACTGTAGGCTGCAACTCGCCTACACGAAGTCGGAAT

CGCTAGTAATCGCGGATCAGCATGCCGCGGTGAATACGTTCCCGGGCCTT

GTACACACCGCCCGTCACACCATGGGAGTTTGTAACGCCCAAAGTCGGTG

GCCTAACCATTATGGAGGGAGCCGCCTAAGTGCGGGACAGATGACTGGGG

TGAAGTCGTAACAAGGTAGCCTGTATTTTCTTGCGGTTGTTCCCCCCCCN

GGCGGGACTGCCTTACTCCTTTCACCNCCCGCGCCCCTGGAGGGGCCGG

AACCCCCCTCCCAACCCCCCTAACCCACCTCCTTCCTTTTAACCNGCT

31 S10BL141 with 519R

SEQ ID NO: 2
GACTTTCTAGGTTGGATACCGTCACTGCGTGAACAGTTACTCTCACGCAC

GTTCTTCTCCAACAACAGAGCTTTACGAGCCGAAACCCTTCTTCACTCAC

GCGGTGTTGCTCCATCAGGCTTGCGCCCATTGCGGAAGATTCCCTACTGC

TGCCTCCCGTAGGAGTATGGACCGTGTCTCAGTTCCATTGTGGCCGATCA

GTCTCTCAACTCGGCTATGCATCATCGCCTTGGTAAGCCGTTACCTTACC

AACTAGCTAATGCACCGCAGGTCCATCCCAGAGTGATAGCCAAAGCCATC

TTTCAAACAAAAGCCATGTGGACTTTCTTGTTATGCGGTATTAGCATCTG

TTTCCAAATGTTATCCCCGCTCCGGGGCAGGTTACCTACGTGTTACTCA

CCCGTCCGCCACTCACTGGTGATCCATCGTCAATCAGGTGCAAGCACCAT

CAATCAGTTGGGCCAGTGCGTACGACTTGCATGTATTAGGCACACCGCCG

GCGTTCATCCTGAGCCATGATCAAACTCTANGCGTCAGTTTTACGGTCTC

GGCTCGTTTCTCTGTTNTCTGACATCAACGTGCGTTACATTTGCGGTTTA

CGCATTGATTGTACTCCCTCCACATAGGTGGCGGCATACCCTTCGTGCTC

CTCTACTCATCTCGTTCATTACAACTCGCTTTGTTACCTTCCCGGTGGGG

TTCTCTACCTCCTTCGTTTTCTCTCACCTCATTCTCTCTCCCATCCTCTC

NCTTTCCTCTTGCTC

161 S10BL282 with 926F

SEQ ID NO: 3
GGTGGAGCATGTGGTTTAATTCGAAGCTACGCGAAGAACCTTACCAGGTC

TTGACATACTATGCAAATCTAAGAGATTAGACGTTCCCTTCGGGGACATG

GATACAGGTGGTGCATGGTTGTAGTCAGCTCGTGTCGTGAGATGTTGGGT

TAAGTCCCGCAACGAGCGCAACCCTTGTTATCAGTTGCCAGCATTAAGTT

GGGCACTCTGGTGAGACTGCCGGTGACAAACCGGAGGAAGGTGGGGATGA

CGTCAAATCATCATGCCCCTTGATGACCTGGGCTAGACACGTGCTACAAT

GGATGGTACAACGAGTTGCGAACTCGCGAGAGTAAGCTAATCTCTTAAAG

CCATTCTCAGTTACGGATGTGTAGGCTGCAACTCGCCATACATGAAGTCG

GAATCGCTAGTAATCGCGGATACAGCATGCCGCGGTGAATACTGTTCCCG

GGCCTATGTGACACACCGCCCGTCACACCATGAGCAGTTTGTAATCACCC

ACACAGTCGGTGGGGTAACCTTTATAGGAACCAGCCGCCTACAGTGCGGG

ACCGATGATTATGGGTGCACTCGTATCACTGTAACTTAAACCCTTGCGGC

CGTACTCCCCAGGCGGAATGCTTAATACGTTACCTGCAACCCTGAAGGGC

GGAATCCCTCCAACGATTATCAAT

161 S10BL300 with 519R

SEQ ID NO: 4
GTGGCTTTCTGGTTAAATACCGTCAATACCTGAACAGTTACTCTCAGATA

TGTTCTTCTTTAACAACAGAGTTTTACGAGCCGAAACCCTTCTTCACTCA

CGCGGCGTTGCTCCATCAGACTTTCGTCCATTGTGGAAGATTCCCTACTG

CTGCCTCCCGTAGGAGTTTGGGCCGTGTCTCAGTCCCAATGTGGCCGATT

ACCCTCTCAGGTCGGCTACGTATCATTGCCATGGTGAGCCGTTACCCCAC

CATCTAGCTAATACGCCGCGGGACCATCCAAAAGTGATAGCCGAAGCCAT

CTTTCAAGCTCGGACCATGCGGTCCGTTGTTATGCGGTATTAGCATCTGT

TTCCAGGTGTTATCCCCGCTTCTGGGCAGGTTTCCCACGTGTTACTCAC

CAGTTCGCCACTCACTCAAATGTAAATCATGATGAAGCACCAATCAATAC

CAAGTTCGTTCGACTTGCATGTATTAGGCACGCCGCCAGCGTTCGTCGCT

GAGCCATGATCAAACTACTAAAGGCCCCNATGCCTCCCACCCGCTTTGT

TGCCGGGGCCCCCCGTTCCCATACCCTTTTGGACGTTTTCCAGCCCCTT

GGCGGGCCCTGTACCTCCCCCAGGGCGGGGAATGCCTTAATTGCGTTNA

CCTTGCACCCCCTGAAGGGGCGGAATCCCTCCAACGATTACCT

255 S10BL504 with 926F

SEQ ID NO: 5
GGTGGAGCATGTGGTTTAATTCGAAGCAACGCGAAGAACCTTACCAGGTC

TTGACATCCAGTCGCATAACCTAAGAGATTAGGTGTTCCCTTCGGGGACG

CTGAGACAGGTGGTGCATGGCTGTCGTCAGCTCGTGTCGTCACATGTTGG

GTTAAGTCCCGCAACGAGCGCAACCCTTGTCATTAGTTGCCATCATTAAG

TTGGGCACTCTAATGAGACTGCCGGTGACAAACCGGAGGAAGGTGGGGAT

GACGTCAAGATCATCATGCCCCTTATGACCTGGGCTACACACGTGCTAGA

ATGGACGGTACAACGAGATAGCGAACCTGCAAGAGCTAAGCGGATCTCT

TAAAGCCGTTCTCAGTTCGGACTGTAGGCTGCAACTCGCCTACACGAAGC

TTGGAATCGCTAGTAATCGCGGATCAGCACTGCCGCGGTGAATACGTTCC

CGGGCCTTGTACACACCGCCCGTCACACCATGAGAGTCTGTAACTCCCAA

AGTCGGTGGGATAACCTTCTATAGCGAGTGAGTCCGTTCGATGGGTAGGG

ACAAGATGAATGAGCGGTGAAAGGTCGTTAAACCAAGGGTAGCAAGTAAG

GATCCCTTTGGGGGTTTTATCTCCACGGGGGGGGTGTTTCTTTTCTGTCT

TTA

255 S10BL530 with 519R

SEQ ID NO: 6
ACTTTCTAGAGTTAGATGATACCGTTCAACATGACAGATGGCCACGTTTA

CTTACTCTCACTGACTACTGTTCTTTCATCTCACACAACAGAGCTTTACG

AGCCGAAACCCTTCTTCACTCACGCGGCGTTGCTCCATCAGAGCTTTGCG

TCCCATTGTGGAACATTCCCTACTGCTGCCTCCCGTAGGAGTATGGGCCG

TGTCTCAGTCCCATTGTGGCCGATCAGTCTCTCAACTCGGCTATGCATCA

TCGCCTTGGTAAGCCGTTACCTTACCAACTAGCTAATGCACCGCAGGTCC

ATCCAAGAGTGATAGCCGAACCATCTTTCACAACTCTAAACATGCTTGTA

GTGTTGTTATTCCGGTATTAACATTCTGTTTCCAGGTTGTTATTCCCAGC

TGATCTCGGGGCAGGGTTTACCCCAACGTTGGTTTACCTTCACCCCCGGT

TNCGGCCCGGCTTCGNCCTTGGGTTAGTACTNACGATTCTGCTATTATAT

ACGATGGGCTAGACGACCAGCCTAACACAATTTCAATTTCGTNAAGTGTC

GAGAGGNCCTACGGTCGTCCCGTTAACGTGTAGNCNATTTGGCTTATTTG

TTAAGTTGTCCANCGGGCCACCGACCCCCAGGGCCCGGTTGGTCCGGGTT

TCCCCCATTGCAACGTCGCCAAAGTGCGGAAATTTCGAAAATACCCTTAA

CCAATGAAAAAAACATA

258 S10BL414 with 926F

SEQ ID NO: 7

GGTGGAGCATGTGGTTTAATTCGAAGCTACGCGAAGAACCTTACCAGGTC

TTGACATACTATGCAAATCTAAGAGATTAGACGTTCCCTTCGGGGACATG

GATACAGGTGGTGCATGGTTGTCGTCAGCTCGTGTCGTGAGATGTTGGGG

TTAAGTCCCTCAACGAGCGCAACCCTTATTATCAGTTGCCAGCATTAAGT

TGGGCACTCTGGTGAGACTGCCGGTGACAAACCGGAGGAAGGTGGGGATG

ACGTCAAATCATCATGCCCCTTATGACCTGGGCTACACACGTGCTACAAT

GGATGGTACAACGAGTTGCGAACTCGCGAGAGTAAGCTAATCTCTTAAAG

CCATTCTCAGTTCGGATTGTAGGCTGCAACTCGCCTACATGAAGTCGGAA

TCGCTAGTAATCGCGGATCAGCATGCCGCGGTGAATACGTTCCCGGGCCT

TGTACACACCGCCCGTCACACCATGAGAGTTTGTAACACCCAAAGTCGGT

GGGGGTAACCTTTTTAGGAAACCAGCCCGCCCTAAAGGGTGGGGAACAAG

AATGAATTAAGGGGGTTGAAAAGTTCCGTTAAACCAAAAGGGGTTAGCCC

CNGNTNNGANNNNNNNNNNGAC

258 S10BL438 with 519R

SEQ ID NO: 8

GCTTTCTGGTTAAATACCGTCAATACCTGAACAGTTACTCTCAGATATGT

GTCTTCTTTAACAACAGAGTTTTACGAGCCGAAACCCTTCTTCACTCACG

CGGCGTTGCTCCATCAGACTTTCGTCCATTGTGGAAGATTCCCTACTGCT

GCCTCCCGTAGGAGTTTGGGCCGTGTCTCAGTCCCAATGTGGCCGATTAC

CCTCTCAGGTCGGCTACGTATCATTGCCATGGTGAGCCGTTACCCCACCA

TCTAGCTAATACGCCGCGGGACCATCCAAAAGTGATAGCCGAAGCCATCT

TTCAAGCTCGGACCATGCGGTCCAAGTTGTTATGCGGTATTAGCATCTGT

TTCCAGGGTGTTATTCCCCCGCTTCGTGGGCAGGGTTTCCCACGTGTTAC

TCACCAGTTCGCCACTCACTCAAATGTAAATCATGATGCAAGCACCAATC

AATACCAGAGTTCGTTCGACTTGCATGTATTAGGCACGCCGCCAGCGTTC

GTCCTGAGCCATGATCAAACTCNGA

NCIMB 41846 GGDK31—*Lactobacillus reuteri*

S12KG200 GGDK 31-1 27F

SEQ ID NO: 10

TGCCTAATACATGCAAGTCGTACGCACTGGCCCAACTGATTGATGGTGCTTGCACCTGATTGACGATGGATCACCAGTGA

GTGGCGGACGGGTGAGTAACACGTAGGTAACCTGCCCCGGAGCGGGGGATAACATTTGGAAACAGATGCTAATACCGCAT

AACAACAAAAGCCACATGGCTTTTGTTTGAAAGATGGCTTTGGCTATCACTCTGGGATGGACCTGCGGTGCATTAGCTAG

TTGGTAAGGTAACGGCTTACCAAGGCGATGATGCATAGCCGAGTTGAGAGACTGATCGGCCACAATGGAACTGAGACACG

GTCCATACTCCTACGGGAGGCAGCAGTAGGGAATCTTCCACAATGGGCGCAAGCCTGATGGAGCAACACCGCGTGAGTGA

AGAAGGGTTTCGGCTCGTAAAGCTCTGTTGTTGGAGAAGAACGTGCGTGAGAGTAACTGTTCACGCAGTGACGGTATCCA

ACCAGAAAGTCACGGCTAACTACGTGCCAGCAGCCGCGGTAATACGTAGGTGGCAAGCGTTATCCGGATTTATTGGGCGT

AAAGCGAGCGCAGGCGGTTGCTTAGGTCTGATGTGAAAGCCTTCGGCTTAACCGAAGAAGTGCATCGGAAACCGGGCGAC

TTGAGTGCAGAAGAGGACAGTGGAACTC

S12KG201 GGDK 31-1 519F

SEQ ID NO: 11

TCGGATTTATTGGGCGTAAAGCGAGCGCAGGCGGTTGCTTAGGTCTGATGTGAAAGCCTTCGGCTTAACCGAAGAAGTGC

ATCGGAAACCGGGCGACTTGAGTGCAGAAGAGGACAGTGGAACTCCATGTGTAGCGGTGGAATGCGTAGATATATGGAAG

AACACCAGTGGCGAAGGCGGCTGTCTGGTCTGCAACTGACGCTGAGGCTCGAAAGCATGGGTAGCGAACAGGATTAGATA

CCCTGGTAGTCCATGCCGTAAACGATGAGTGCTAGGTGTTGGAGGGTTTCCGCCCTTCAGTGCCGGAGCTAACGCATTAA

GCACTCCGCCTGGGGAGTACGACCGGAAGGTTGAAACTCAAAGGAATTGACGGGGGCCCGCACAAGCGGTGGAGCATGTG

GTTTAATTCGAAGCTACGCGAAGAACCTTACCAGGTCTTGACATCTTGCGCTAACCTTAGAGATAAGGCGTTCCCTTCG

GGGACGCAATGACAGGTGGTGCATGGTCGTCGTCAGCTCGTGTCGTGAGATGTTGGGTTAAGTCCCGCAACGAGCGCAAC

CCTTGTTACTAGTTGCCAGCATTAAGTTGGGCACTCTAGTGAGACTGCCGGTGACAAACCGGAGGAAGGTGGGGACGACG

TCAGATCATCATGCCCCTTATGACCTGGGCTA

-continued

S12KG202 GGDK 31-1 926F
SEQ ID NO: 12
GAGCATGTGGTTTAATTCGAAGCTACGCGAAGAACCTTACCAGGTCTTGACATCTTGCGCTAACCTTAGAGATAAGGCGT

TCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGG

GGACGACGTCAGATCATCATGCCCCTTATGACCTGGGCTACACACGTGCTACAATGGACGGTACAACGAGTCGCAAGCTC

GCGAGAGTAAGCTAATCTCTTAAAGCCGTTCTCAGTTCGGACTGTAGGCTGCAACTCGCCTACACGAAGTCGGAATCGCT

AGTAATCGCGGATCAGCATGCCGCGGTGAATACGTTCCCGGGCCTTGTACACACCGCCCGTCACACCATGGGAGTTTGTA

ACGCCCAAAGTCGGTGGCCTAACCATTATGGAGGGAGCCGCCTAAGGCGGGACAGATGACTGGGGTGAAGTCGTAACAAG

GTAGCCGTA

S12KG203 GGDK 31-1 926R
SEQ ID NO: 13
CTCCCCAGGCGGAGTGCTTAATGCGTTAGCTCCGGCACTGAAGGGCGGAAACCCTCCAACACCTAGCACTCATCGTTTAC

GGCATGGACTACCAGGGTATCTAATCCTGTTCGCTACCCATGCTTTCGAGCCTCAGCGTCAGTTGCAGACCAGACAGCCG

CCTTCGCCACTGGTGTTCTTCCATATATCTACGCATTCCACCGCTACACATGGAGTTCCACTGTCCTCTTCTGCACTCAA

GTCGCCCGGTTTCCGATGCACTTCTTCGGTTAAGCCGAAGGCTTTCACATCAGACCTAAGCAACCGCCTGCGCTCGCTTT

ACGCCCAATAAATCCGGATAACGCTTGCCACCTACGTATTACCGCGGCTGCTGGCACGTAGTTAGCCGTGACTTTCTGGT

TGGATACCGTCACTGCGTGAACAGTTACTCTCACGCACGTTCTTCTCCAACAACAGAGCTTTACGAGCCGAAACCCTTCT

TCACTCACGCGGTGTTGCTCCATCAGGCTTGCGCCCATTGTGGAAGATTCCCTACTGCTGCCTCCCGTAGGAGTATGGAC

CGTGTCTCAGTTCCATTGTGGCCGATCAGTCTCTCAACTCGGCTATGCATCATCGCCTTGGTAAGCCGTTACCTTACCAA

CTAGCTAATGCACCGCAGGTCCATCCCAGAGTGATAGCCAAAGCCATCTTTCAAACAAAAGCCATGTGGCTTTTGTTGT

TATGC

S12KG204 GGDK 31-1 519R
SEQ ID NO: 14
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTGATCCATCGTCAATCAGGTGCAAGCACCATCAATCAGTTGGGCCAGTGCGTACGACTTGCATGT

ATTAGGCACACCGCCGGCGTTCATCCTGAGCCATGATCAAAC

S12KG205 GGDK 31-1 RP2
SEQ ID NO: 15
CCGCCTTAGGCGGCTCCCTCCATAATGGTTAGGCCACCGACTTTGGGCGTTACAAACTCCCATGGTGTGACGGGCGGTGT

GTACAAGGCCCGGGAACGTATTCACCGCGGCATGCTGATCCGCGATTACTAGCGATTCCGACTTCGTGTAGGCGAGTTGC

AGCCTACAGTCCGAACTGAGAACGGCTTTAAGAGATTAGCTTACTCTCGCGAGCTTGCGACTCGTTGTACCGTCCATTGT

AGCACGTGTGTAGCCCAGGTCATAAGGGGCATGATGATCTGACGTCGTCCCCACCTTCCTCCGGTTTGTCACCGGCAGTC

TCACTAGAGTGCCCAACTTAATGCTGGCAACTAGTAACAAGGGTTGCGCTCGTTGCGGGACTTAACCCAACATCTCACGA

CACGAGCTGACGACGACCATGCACCACCTGTCATTGCGTCCCCGAAGGGAACGCCTTATCTCTAAGGTTAGCGCAAGATG

TCAAGACCTGGTAAGGTTCTTCGCGTAGCTTCGAATTAAACCACATGCTCCACCGCTTGTGCGGGCCCCCGTCAATTCCTTT

GAGTTTCCACCTTGCGGTCGTACTCCCCAGGCGGAGTGCTTAATGCGTTAGCTCCGGCACTGAAGGGCGGAAACCCT

CCAACACCTAGCACTCATCGTTTACGGCATGGACTACCAGGG

NCIMB 41847 GGDK161—Contains Both *Lactobacillus plantarum* and *Lactobacillus reuteri*
*Lactobacillus plantarum*

S12KG218 GGDK 161-1 27F

SEQ ID NO: 16

GTGCCTAATACATGCAAGTCGAACGAACTCTGGTATTGATTGGTGCTTGCATCATGATTTACATTTGAGTGAGTGGCGAA

CTGGTGAGTAACACGTGGGAAACCTGCCCAGAAGCGGGGGATAACACCTGGAAACAGATGCTAATACCGCATAACAACTT

GGACCGCATGGTCCGAGTTTGAAAGATGGCTTCGGCTATCACTTTTGGATGGTCCCGCGGCGTATTAGCTAGATGGTGAG

GTAACGGCTCACCATGGCAATGATACGTAGCCGACCTGAGAGGGTAATCGGCCACATTGGGACTGAGACACGGCCCAAAC

TCCTACGGGAGGCAGCAGTAGGGAATCTTCCACAATGGACGAAAGTCTGATGGAGCAACGCCGCGTGAGTGAAGAAGGGT

TTCGGCTCGTAAAACTCTGTTGTTAAAGAAGAACATATCTGAGAGTAACTGTTCAGGTATTGACGGTATTTAACCAGAA

AGCCACGGCTAACTACGTGCCAGCAGCCGCGGTAATACGTAGGTGGCAAGCGTTGTCCGGATTTATTGGGCGTAAAGCGA

GCGCAGGCGGTTTTTTAAGTCTGATGTGAAAGCCTTCGGCTCAACCGAAGAAGTGCATCGGAAACTGGGAAGCTTGAGTG

CAGAAGAGGACAGTGGAACTCCATGTGTAGCGGTGAAATGCGT

S12KG219 GGDK 161-1 519F

SEQ ID NO: 17

CGGATTTATTGGGCGTAAAGCGAGCGCAGGCGGTTTTTTAAGTCTGATGTGAAAGCCTTCGGCTCAACCGAAGAAGTGC

ATCGGAAACTGGGAAACTTGAGTGCAGAAGAGGACAGTGGAACTCCATGTGTAGCGGTGAAATGCGTAGATATATGGAAG

AACACCAGTGGCGAAGGCGGCTGTCTGGTCTGTAACTGACGCTGAGGCTCGAAAGTATGGGTAGCAAACAGGATTAGATA

CCCTGGTAGTCCATACCGTAAACGATGAATGCTAAGTGTTGGAGGGTTTCCGCCCTTCAGTGCTGCAGCTAACGCATTAA

GCATTCCGCCTGGGGAGTACGGCCGCAAGGCTGAAACTCAAAGGAATTGACGGGGGCCCGCACAAGCGGTGGAGCATGTG

GTTTAATTCGAAGCTACGCGAAGAACCTTACCAGGTCTTGACATACTATGCAAATCTAAGAGATTAGACGTTCCCTTCGG

GGACATGGATACAGGTGGTGCATGGTTGTCGTCAGCTCGTGTCGTGAGATGTTGGGTTAAGTCCCGCAACGAGCGCAACC

CTTATTATCAGTTGCCAGCATTAAGTTGGGCACTCTGGTGAGACTGCCGGTGACAAACCGGA

S12KG220 GGDK 161-1 926F

SEQ ID NO: 18

TGGAGCATGTGGTTTAATTCGAAGCTACGCGAAGAACCTTACCAGGTCTTGACATACTATGCAAATCTAAGAGATTAGAC

GTTCCCTTCGGGGACATGGATACAGGTGGTGCATGGTTGTCGTCAGCTCGTGTCGTGAGATGTTGGGTTAAGTCCCGCAA

CGAGCGCAACCCTTATTATCAGTTGCCAGCATTAAGTTGGGCACTCTGGTGAGACTGCCGGTGACAAACCGGAGGAAGGT

GGGGATGACGTCAAATCATCATGCCCCTTATGACCTGGGCTACACACGTGCTACAATGGATGGTACAACGAGTTGCGAAC

TCGCGAGAGTAAGCTAATCTCTTAAAGCCATTCTCAGTTCGGATTGTAGGCTGCAACTCGCCTACATGAAGTCGGAATCG

CTAGTAATCGCGGATCAGCATGCCGCGGTGAATACGTTCCCGGGCCTTGTACACACCGCCCGTCACACCATGAGAGTTTG

TAACACCCAAAGTCGGTGGGGTAACCTTTTAGGAACCAGCCGCCTAAGGTGGGACAGATGATTAGGGTGAAGTCGTAAC

AAGGTAGCCCGTA

S12KG221 GGDK 161-1 926R

SEQ ID NO: 19

ACTCCCCAGGCGGAATGCTTAATGCGTTAGCTGCAGCACTGAAGGGCGGAAACCCTCCAACACTTAGCATTCATCGTTTA

CGGTATGGACTACCAGGGTATCTAATCCTGTTTGCTACCCATACTTTCGAGCCTCAGCGTCAGTTACAGACCAGACAGCC

GCCTTCGCCACTGGTGTTCTTCCATATATCTACGCATTTCACCGCTACACATGGAGTTCCACTGTCCTCTTCTGCACTCA

AGTTTCCCAGTTTCCGATGCACTTCTTCGGTTGAGCCGAAGGCTTTCACATCAGACTTAAAAAACCGCCTGCGCTCGCTT

TACGCCCAATAAATCCGGACAACGCTTGCCACCTACGTATTACCGCGGCTGCTGGCACGTAGTTAGCCGTGGCTTTCTGG

TTAAATACCGTCAATACCTGAACAGTTACTCTCAGATATGTTCTTCTTTAACAACAGAGTTTTACGAGCCGAAACCCTTC

-continued

```
TTCACTCACGCGGCGTTGCTCCATCAGACTTTCGTCCATTGTGGAAGATTCCCTACTGCTGCCTCCCGTAGGAGTTTGGG

CCGTGTCTCAGTCCCAATGTGGCCGATTACCCTCTCAGGTCGGCTACGTATCATTGCCATGGTGAGCCGTTACCCCACCA

TCTAGCTAATACGCCGCGGGACCATCCAAAAGTGATAGCCGAAGCCATCTTTCAAACTCGGACCATGCGGTCCAAGTTGT
```

S12KG222 GGDK 161-1 519R

SEQ ID NO: 20

```
GCTTTCTGGTTAAATACCGTCAATACCTGAACAGTTACTCTCAGATATGTTCTTCTTTAACAACAGAGTTTTACGAGCCG

AAACCCTTCTTCACTCACGCGGCGTTGCTCCATCAGACTTTCGTCCATTGTGGAAGATTCCCTACTGCTGCCTCCCGTAG

GAGTTTGGGCCGTGTCTCAGTCCCAATGTGGCCGATTACCCTCTCAGGTCGGCTACGTATCATTGCCATGGTGAGCCGTT

ACCCCACCATCTAGCTAATACGCCGCGGGACCATCCAAAAGTGATAGCCGAAGCCATCTTTCAAACTCGGACCATGCGGT

CCAAGTTGTTATGCGGTATTAGCATCTGTTTCCAGGTGTTATCCCCCGCTTCTGGGCAGGTTTCCCACGTGTTACTCAC

CAGTTCGCCACTCACTCAAATGTAAATCATGATGCAAGCACCAATCAATACCAAAGTTCGTTCGACTTGCATGTATTAG

GCACGCCGCCAGCGTTCGTCCTGAGCCAGATCAAACTCTAA
```

S32KG223 GGDK 161-1 RP2

SEQ ID NO: 21

```
CCACCTTAGGCGGCTGGTTCCTAAAAGGTTACCCCACCGACTTTGGGTGTTACAAACTCTCATGGTGTGACGGGCGGTGT

GTACAAGGCCCGGGAACGTATTCACCGCGGCATGCTGATCCGCGATTACTAGCGATTCCGACTTCATGTAGGCGAGTTGC

AGCCTACAATCCGAACTGAGAATGGCTTTAAGAGATTAGCTTACTCTCGCGAGTTCGCAACTCGTTGTACCATCCATTGT

AGCACGTGTGTAGCCCAGGTCATAAGGGGCATGATGATTTGACGTCATCCCCACCTTCCTCCGGTTTGTCACCGGCAGTC

TCACCAGAGTGCCCAACTTAATGCTGGCAACTGATAATAAGGGTTGCGCTCGTTGCGGGACTTAACCCAACATCTCACGA

CACGAGCTGACGACAACCATGCACCACCTGTATCCATGTCCCCGAAGGGAACGTCTAATCTCTTAGATTTGCATAGTATG

TCAAGACCTGGTAAGGTTCTTCGCGTAGCTTCGAATTAAACCACATGCTCCACCGCTTGTGCGGGCCCCCGTCAATTCCT

TTGAGTTTCAGCCTTGCGGCCGTACTCCCCAGGCGGAATGCTTAATGCGTTAGCTGCAGCACTGAAGGGCGGAAACCCTC

CAACACTTAGCATTCATCGTTTACGGTATGGACTACCAGGGTATCTA
```

35

NCIMB 41847 GGDK161—contains both *Lactobacillus plantarum* and *Lactobacillus reuteri*
*Lactobacillus reuteri*

S12KG309 cGGDK 161-1 27F

SEQ ID NO: 22

```
ATGCTAGTCGTACGCACTGGCCCAACTGATTGATGGTGCTTGCACCTGATTGACGAT

GGATCACCAGTGAGTGGCGGACGGGTGAGTAACACGTAGGTAACCTGCCCCGGAGCGGGGGATAACATTTGGAAACAGAT

GCTAATACCGCATAACAACAAAAGCCACATGGCTTTTGTTTGAAAGATGGCTTTGGCTATCACTCTGGGATGGACCTGCG

GTGCATTAGCTAGTTGGTAAGGTAACGGCTTACCAAGGCGATGATGCATAGCCGAGTTGAGAGACTGATCGGCCACAATG

GAACTGAGACACGGTCCATACTCCTACGGGAGGCAGCAGTAGGGAATCTTCCACAATGGGCGCAAGCCTGATGGAGCAAC

ACCGCGTGAGTGAAGAAGGGTTTCGGCTCGTAAAGCTCTGTTGTTGGAGAAGAACGTGCGTGAGAGTAACTGTTCACGCA

GTGACGGTATCCAACCAGAAAGTCACGGCTAACTACGTGCCAGCAGCCGCGGTAATACGTAGGTGGCAAGCGTTATCCGG

ATTTATTGGGCGTAAAGCGAGCGCAGGCGGTTGCTTAGGTCTGATGTGAAAGCCTTCGGCTTAACCGAAGAAGTGCATCG

GAAACCGGGCGACTTGAGTGCAGAAGAGGACAGTGGAAC
```

S12KG310 rGGDK 161-1 519F

SEQ ID NO: 23

```
TCCGGATTTATTGGGCGTAAAGCGAGCGCAGGCGGTTGCTTAGGTCTGATGTGAAAGCCTTCGGCTTAACCGAAGAAGTG

CATCGGAAACCGGGCGACTTGAGTGCAGAAGAGGACAGTGGAACTCCATGTGTAGCGGTGGAATGCGTAGATATATGGAA

GAACACCAGTGGCGAAGGCGGCTGTCTGGTCTGCAACTGACGCTGAGGCTCGAAAGCATGGGTAGCGAACAGGATTAGAT

ACCCTGGTAGTCCATGCCGTAAACGATGAGTGCTAGGTGTTGGAGGGTTTCCGCCCTTCAGTGCCGGAGCTAACGCATTA

AGCACTCCGCCTGGGGAGTACGACCGCAAGGTTGAAACTCAAAGGAATTGACGGGGGCCCGCACAAGCGGTGGAGCATGT
```

```
GGTTTAATTCGAAGCTACGCGAAGAACCTTACCAGGTCTTGACATCTTGCGCTAACCTTAGAGATAAGGCGTTCCCTTCG

GGGACGCAATGACAGGTGGTGCATGGTCGTCGTCAGCTCGTGTCGTGAGATGTTGGGTTAAGTCCCGCAACGAGCGCAAC

CCTTGTTACTAGTTGCCAGCATTAAGTTGGGCACTCTAGTGAGACTGCCGGTGACAAACCGGAGGAAGGTGGGGACGACG

TCAGATCATCATGCCCCTTATGACCTGGGCTACACACGTGCTACAATGGACGGTACAACGAGTCGCAAGCTCGCGAGAG
```

S12KG311 cGGDK 161-1 926F
                                                                        SEQ ID NO: 24
```
GGAGCATGTGGTTTAATTCGAAGCTACGCGAAGAACCTTACCAGGTCTTGACATCTTGCGCTAACCTTAGAGATAAGGCG

TTCCCTTCGGGGACGCAATGACAGGTGGTGCATGGTCGTCGTCAGCTCGTGTCGTGAGATGTTGGGTTAAGTCCCGCAAC

GAGCGCAACCCTTGTTACTAGTTGCCAGCATTAAGTTGGGCACTCTAGTGAGACTGCCGGTGACAAACCGGAGGAAGGTG

GGGACGACGTCAGATCATCATGCCCCTTATGACCTGGGCTACACACGTGCTACAATGGACGGTACAACGAGTCGCAAGCT

CGCGAGAGTAAGCTAATCTCTTAAAGCCGTTCTCAGTTCGGACTGTAGGCTGCAACTCGCCTACACGAAGTCGGAATCGC

TAGTAATCGCGGATCAGCATGCCGCGGTGAATACGTTCCCGGGCCTTGTACACACCGCCCGTCACACCATGGGAGTTTGT

AACGCCCAAAGTCGGTGGCCTAACCTTTATGGAGGGAGCCGCCTAAGGCGGGACAGATGACTGGGGTGAAGTCGTAACAA

GGTAGCCGTA
```

S12KG312 cGGDK 161-1 926R
                                                                        SEQ ID NO: 25
```
TCCCCAGGCGGAGTGCTTAATGCGTTAGCTCCGGCACTGAAGGGCGGAAACCCTCCAACACCTAGCACTCATCGTTTACG

GCATGGACTACCAGGGTATCTAATCCTGTTCGCTACCCATGCTTTCGAGCCTCAGCGTCAGTTGCAGACCAGACAGCCGC

CTTCGCCACTGGTGTTCTTCCATATATCTACGCATTCCACCGCTACACATGGAGTTCCACTGTCCTCTTCTGCACTCAAG

TCGCCCGGTTTCCGATGCACTTCTTCGGTTAAGCCGAAGGCTTTCACATCAGACCTAAGCAACCGCCTGCGCTCGCTTTA

CGCCCAATAAATCCGGATAACGCTTGCCACCTACGTATTACCGCGGCTGCTGGCACGTAGTTAGCCGTGACTTTCTGGTT

GGATACCGTCACTGCGTGAACAGTTACTCTCACGCACGTTCTTCTCCAACAACAGAGCTTTACGAGCCGAAACCCTTCTT

CACTCACGCGGTGTTGCTCCATCAGGCTTGCGCCCATTGTGGAAGATTCCCTACTGCTGCCTCCCGTAGGAGTATGGACC

GTGTCTCAGTTCCATTGTGGCCGATCAGTCTCTCAACTCGGCTATGCATCATCGCCTTGGTAAGCCGTTACCTTACCAAC

TAGCTAATGCACCGCAGGTCCATCCCAGAGTGATAGCCAAAGCCATCTTTCAAACAAAAGCCATGTGGCTTTT
```

S12KG313 cGGDK 161-1 519R
                                                                        SEQ ID NO: 26
```
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTAATCCATCGTCAATCAGGTGCAAGCACCATCAATCAGTTGGGCCAGTGCGTACGACTTGCATG

TATTAGGCACACCGCCGGCGTTCATCCTGAGCCATGATCAAAC
```

S12KG314 cGGDK 161-1 RP2
                                                                        SEQ ID NO: 27
```
GCGGCTCCCTCCATAAAGGTTAGCGCCACCGACTTTGGGCGTTACAAACTCCCATGGTGTGACGGGCG

GTGTGTACAAGGCCCGGGAACGTATTCACCGCGGCATGCTGATCCGCGATTACTAGCGATTCCGACTTCGTGTAGGCGAG

TTGCAGCCTACAGTCCGAACTGAGAACGGCTTTAAGAGATTAGCTTACTCTCGCGAGCTTGCGACTCGTTGTACCGTCCA

TTGTAGCACGTGTGTAGCCCAGGTCATAAGGGGCATGATGATCTGACGTCGTCCCCACCTTCCTCCGGTTTGTCACCGGC

AGTCTCACTAGAGTGCCCAACTTAATGCTGGCAACTAGTAACAAGGGTTGCGCTCGTTGCGGGACTTAACCCAACATCTC

ACGACACGAGCTGACGACGACCATGCACCACCTGTCATTGCGTCCCCGAAGGGAACGCCTTATCTCTAAGGTTAGCGCAA

GATGTCAAGACCTGGTAAGGTTCTTCGCGTAGCTTCGAATTAAACCACATGCTCCACCGCTTGTGCGGGCCCCCGTCA

ATTCCTTTGAGTTTCAACCTTGCGGTCGTACTCCCCAGGCGGAGTGCTTAATGCGTTAGCTCCGGCACTGAAGGGCGGAA

ACCCTCCAACACCTAGCACTCATCGTTTACGGCAT
```

NCIMB 41848 GGDK255—*Lactobacillus reuteri*

S12KG237 GGDK 255-1 27F
SEQ ID NO: 28
GTGTGCCTAATACATGCAAGTCGTACGCACTGGCCCAACTGATTGATGGTGCTTGCACCTGATTGACGATGGATCACCAG

TGAGTGGCGGACGGGTGAGTAACACGTAGGTAACCTGCCCCGGAGCGGGGGATAACATTTGGAAACAGATGCTAATACCG

CATAACAACAAAAGCCACATGGCTTTTGTTTGAAAGATGGCTTTGGCTATCACTCTGGGATGGACCTGCGGTGCATTAGC

TAGTTGGTAAGGTAACGGCTTACCAAGGCGATGATGCATAGCCGAGTTGAGAGACTGATCGGCCACAATGGAACTGAGAC

ACGGTCCATACTCCTACGGGAGGCAGCAGTAGGGAATCTTCCACAATGGGCGCAAGCCTGATGGAGCAACACCGCGTGAG

TGAAGAAGGGTTTCGGCTCGTAAAGCTCTGTTGTTGGAGAAGAACGTGCGTGAGAGTAACTGTTCACGCAGTGACGGTAT

CCAACCAGAAAGTCACGGCTAACTACGTGCCAGCAGCCGCGGTAATACGTAGGTGGCAAGCGTTATCCGGATTTATTGGG

CGTAAAGCGAGCGCAGGCGGTTGCTTAGGTCTGATGTGAAAGCCTTCGGCTTAACCGAAGAAGTGCATCGGAAACCGGGC

GACTTGAGTGCAGAAGAGGACAGTGGAACTCCATGTGTAGCGGTGGAATGCGTAGATATATGGAAGAACACCAGTG

S12KG238 GGDK 255-1 519F
SEQ ID NO: 29
TCGGATTTATTGGGCGTAAAGCGAGCGCAGGCGGTTGCTTAGGTCTGATGTGAAAGCCTTCGGCTTAACCGAAGAAGTGC

ATCGGAAACCGGGCGACTTGAGTGCAGAAGAGGACAGTGGAACTCCATGTGTAGCGGTGGAATGCGTAGATATATGGAAG

AACACCAGTGGCGAAGGCGGCTGTCTGGTCTGCAACTGACGCTGAGGCTCGAAAGCATGGGTAGCGAACAGGATTAGATA

CCCTGGTAGTCCATGCCGTAAACGATGAGTGCTAGGTGTTGGAGGGTTTCCGCCCTTCAGTGCCGGAGCTAACGCATTAA

GCACTCCGCCTGGGGAGTACGACCGCAAGGTTGAAACTCAAAGGAATTGACGGGGGCCCGCACAAGCGGTGGAGCATGTG

GTTTAATTCGAAGCTACGCGAAGAACCTTACCAGGTCTTGACATCTTGCGCTAACCTTAGAGATAAGGCGTTCCCTTCGG

GGACGCAATGACAGGTGGTGCATGGTCGTCGTCAGCTCGTGTCGTGAGATGTTGGGTTAAGTCCCGCAACGAGCGCAACC

CTTGTTACTAGTTGCCAGCATTAAGTTGGGCACTCTAGTGAGACTGCCGGTGACAAACCGGAGGAAGGTGGGGACGACG

TCAGATCATCATGCCCCTATGACCTGGGCTACACACGTGCTAC

S12KG239 GGDK 255-1 926F
SEQ ID NO: 30
TGGAGCATGTGGTTTAATTCGAAGCTACGCGAAGAACCTTACCAGGTCTTGACATCTTGCGCTAACCTTAGAGATAAGGC

GTTCCCTTCGGGGACGCAATGACAGGTGGTGCATGGTCGTCGTCAGCTCGTGTCGTGAGATGTTGGGTTAAGTCCCGCAA

CGAGCGCAACCCTTGTTACTAGTTGCCAGCATTAAGTTGGGCACTCTAGTGAGACTGCCGGTGACAAACCGGAGGAAGGT

GGGGACGACGTCAGATCATCATGCCCCTTATGACCTGGGCTACACACGTGCTACAATGGACGGTACAACGAGTCGCAAGC

TCGCGAGAGTAAGCTAATCTCTTAAAGCCGTTCTCAGTTCGGACTGTAGGCTGCAACTCGCCTACACGAAGTCGGAATCG

CTAGTAATCGCGGATCAGCATGCCGCGGTGAATACGTTCCCGGGCCTTGTACACACCGCCCGTCACACCATGGGAGTTTG

TAACGCCCAAAGTCGGTGGCCTAACCTTTATGGAGGGAGCCGCCTAAGGCGGGACAGATGACTGGGGTGAAGTCGTAACA

AGGTAGCCGTA

S12KG240 GGDK 255-1 926R
SEQ ID NO: 31
TACTCCCCAGGCGGAGTGCTTAATGCGTTAGCTCCGGCACTGAAGGGCGGAAACCCTCCAACACCTAGCACTCATCGTTT

ACGGCATGGACTACCAGGGTATCTAATCCTGTTCGCTACCCATGCTTTCGAGCCTCAGCGTCAGTTGCAGACCAGACAGC

CGCCTTCGCCACTGGTGTTCTTCCATATATCTACGCATTCCACCGCTACACATGAGTTCCACTGTCCTCTTCTGCACTC

AAGTCGCCCGGTTTCCGATGCACTTCTTCGGTTAAGCCGAAGGCTTTCACATCAGACCTAAGCAACGCCTGCGCTCGCT

TTACGCCCAATAAATCCGGATAACGCTTGCCACCTACGTATTACCGCGGCTGCTGGCACGTAGTTAGCCGTGACTTTCTG

GTTGGATACCGTCACTGCGTGAACAGTTACTCTCACGCACGTTCTTCTCCAACAACAGAGCTTTACGAGCCGAAACCCTT

CTTCACTCACGCGGTGTTGCTCCATCAGGCTTGCGCCCATTGTGGAAGATTCCCTACTGCTGCCTCCCGTAGGAGTATGG

ACCGTGTCTCAGTTCCATTGTGGCCGATCAGTCTCTCAACTCGGCTATGCATCATCGCCTTGGTAAGCCGTTACCTTACC

AACTAGCTAATGCACCGCAGGTCCATCCCAGAGTGATAGCCAAAGCCATCTTTCAAACAAAAGCCATGTGGCTTTTG

S12KG241 GGDK 255-1 519R

SEQ ID NO: 32

TTTCTGGTTGGATACCGTCACTGCGTGAACAGTTACTCTCACGCACGTTCTTCTCCAACAACAGAGCTTTACGAGCCGAA
ACCCTTCTTCACTCACGCGGTGTTGCTCCATCAGGCTTGCGCCCATTGTGGAAGATTCCCTACTGCTGCCTCCCGTAGGA
GTATGGACCGTGTCTCAGTTCCATTGTGGCCGATCAGTCTCTCAACTCGGCTATGCATCATCGCCTTGGTAAGCCGTTAC
CTTACCAACTAGCTAATGCACCGCAGGTCCATCCCAGAGTGATAGCCAAAGCCATCTTTCAAACAAAAGCCATGTGGCT
TTTGTTGTTATGCGGTATTAGCATCTGTTTCCAAATGTTATCCCCCGCTCCGGGGCAGGTTACCTACGTGTTACTCACC
CGTCCGCCACTCACTGGTGATCCATCGTCAATCAGGTGCAAGCACCATCAATCAGTTGGGCCAGTGCGTACGACTTGCAT
GTATTAGGCACACCGCCGGCGTCCATCCTGAGCCATGATCAAAC

S12KG242 GGDK 255-1 RP2

SEQ ID NO: 33

CCGCCTTAGGCGGCTCCCTCCATAAAGGTTAGGCCACCGACTTTGGGCGTTACAAACTCCCATGGTGTGACGGGCGGTGT
GTACAAGGCCCGGGAACGTATTCACCGCGGCATGCTGATCCGCGATTACTAGCGATTCCGACTTCGTGTAGGCGAGTTGC
AGCCTACAGTCCGAACTGAGAACGGCTTTAAGAGATTAGCTTACTCTCGCGAGCTTGCGACTCGTTGTACCGTCCATTGT
AGCACGTGTGTAGCCCAGGTCATAAGGGGCATGATGATCTGACGTCGTCCCCACCTTCCTCCGGTTTGTCACCGGCAGTC
TCACTAGAGTGCCCAACTTAATGCTGGCAACTAGTAACAAGGGTTGCGCTCGTTGCGGGACTTAACCCAACATCTCACGA
CACGAGCTGACGACGACCATGCACCACCTGTCATTGCGTCCCCGAAGGGAACGCCTTATCTCTAAGGTTAGCGCAAGATG
TCAAGACCTGGTAAGGTTCTTCGCGTAGCTTCGAATTAAACCACATGCTCCACCGCTTGTGCGGGCCCCCGTCAATTCCT
TTGAGTTTCAACCTTGCGGTCGTACTCCCCAGGCGGAGTGCTTAATGCGTTAGCTCCGGCACTGAAGGGCGGAAACCCTCCAA
CACCTAGCACTCATCGTT

NCIMB 41849 GGDK 258—*Lactobacillus plantarum*

S12KG267 GGDK 258-3 27F

SEQ ID NO: 34

GTGCCTAATACATGCAAGTCGAACGAACTCTGGTATTGATTGGTGCTTGCATCATGATTTACATTTGAGTGAGTGGCGAA
CTGGTGAGTAACACGTGGGAAACCTGCCCAGAAGCGGGGGATAACACCTGGAAACAGATGCTAATACCGCATAACAACTT
GGACCGCATGGTCCGAGTTTGAAAGATGGCTTCGGCTATCACTTTTGGATGGTCCCGCGGCGTATTAGCTAGATGGTGAG
GTAACGGCTCACCATGGCAATGATACGTAGCCGACCTGAGAGGGTAATCGGCCACATTGGGACTGAGACACGGCCCAAAC
TCCTACGGGAGGCAGCAGTAGGGAATCTTCCACAATGGACGAAAGTCTGATGGAGCAACGCCGCGTGAGTGAAGAAGGGT
TTCGGCTCGTAAAACTCTGTTGTTAAAGAAGAACATATCTGAGAGTAACTGTTCAGGTATTGACGGTATTTAACCAGAAA
GCCACGGCTAACTACGTGCCAGCAGCCGCGGTAATACGTAGGTGGCAAGCGTTGTCCGGATTTATTGGGCGTAAAGCGAG
CGCAGGCGGTTTTTTAAGTCTGATGTGAAAGCCTTCGGCTCAACCGAAGAAGTGCATCGGAAACTGGGAAACTTGAGTGC
AGAAGAGGACAGTGGAACTC

S12KG268 GGDK 258-3 519F

SEQ ID NO: 35

GGATTTATTGGGCGTAAAGCGAGCGCAGGCGGTTTTTTAAGTCTGATGTGAAAGCCTTCGGCTCAACCGAAGAAGTGCAT
CGGAAACTGGGAAACTTGAGTGCAGAAGAGGACAGTGGAACTCCATGTGTAGCGGTGAAATGCGTAGATATATGGAAGAA
CACCAGTGGCGAAGGCGGCTGTCTGGTCTGTAACTGACGCTGAGGCTCGAAAGTATGGGTAGCAAACAGGATTAGATACC
CTGGTAGTCCATACCGTAAACGATGAATGCTAAGTGTTGGAGGGTTTCCGCCCTTCAGTGCTGCAGCTAACGCATTAAGC
ATTCCGCCTGGGGAGTACGGCCGCAAGGCTGAAACTCAAAGGAATTGACGGGGGCCCGCACAAGCGGTGGAGCATGTGGT
TTAATTCGAAGCTACGCGAAGAACCTTACCAGGTCTTGACATACTATGCAAATCTAAGAGATTAGACGTTCCCTTCGGGG
ACATGGATACAGGTGGTGCATGGTTGTCGTCAGCTCGTGTCGTGAGATGTTGGGTTAAGTCCCGCAACGAGCGCAACCCT
TATTATCAGTTGCCAGCATTAAGTTGGGCACTCTGGTGAGACTGCCGGTGACAAACCGGAGGAAGGTGGGGATGACGTCA
AATCATCATGCCCCTTATGACCTGGGCTAC

S12KG269 GGDK 258-3 926F
SEQ ID NO: 36
GTGGAGCATGTGGTTTAATTCGAAGCTACGCGAAGAACCTTACCAGGTCTTGACATACTATGCAAATCTAAGAGATTAGA

CGTTCCCTTCGGGGACATGGATACAGGTGGTGCATGGTTGTCGTCAGCTCGTGTCGTGAGATGTTGGGTTAAGTCCCGCA

ACGAGCGCAACCCTTATTATCAGTTGCCAGCATTAAGTTGGGCACTCTGGTGAGACTGCCGGTGACAAACCGGAGGAAGG

TGGGGATGACGTCAAATCATCATGCCCCTTATGACCTGGGCTACACACGTGCTACAATGGATGGTACAACGAGTTGCGAA

CTCGCGAGAGTAAGCTAATCTCTTAAAGCCATTCTCAGTTCGGATTGTAGGCTGCAACTCGCCTACATGAAGTCGGAATC

GCTAGTAATCGCGGATCAGCATGCCGCGGTGAATACGTTCCCGGGCCTTGTACACACCGCCCGTCACACCATGAGAGTTT

GTAACACCCAAAGTCGGTGGGGTAACCTTTTAGGAACCAGCCGCCTAAGGTGGGACAGATGATTAGGGTGAAGTCGTAA

CAAGGTAGCCCGTA

S12KG270 GGDK 258-3 926R
SEQ ID NO: 37
ACTCCCCAGGCGGAATGCTTAATGCGTTAGCTGCAGCACTGAAGGGCGGAAACCCTCCAACACTTAGCATTCATCGTTTA

CGGTATGGACTACCAGGGTATCTAATCCTGTTTGCTACCCATACTTTCGAGCCTCAGCGTCAGTTACAGACCAGACAGCC

GCCTTCGCCACTGGTGTTCTTCCATATATCTACGCATTTCACCGCTACACATGGAGTTCCACTGTCCTCTTCTGCACTCA

AGTTTCCCAGTTTCCGATGCACTTCTTCGGTTGAGCCGAAGGCTTTCACATCAGACTTAAAAAACCGCCTGCGCTCGCTT

TACGCCCAATAAATCCGGACAACGCTTGCCACCTACGTATTACCGCGGCTGCGGCACGTAGTTAGCCGTGGCTTTCTGG

TTAAATACCGTCAATACCTGAACAGTTACTCTCAGATATGTTCTTCTTTAACAACAGAGTTTTACGAGCCGAAACCCTTC

TTCACTCACGCGGCGTTGCTCCATCAGACTTTCGTCCATTGTGGAAGATTCCCTACTGCTGCCTCCCGTAGGAGTTTGGG

CCGTGTCTCAGTCCCAATGTGGCCGATTACCCTCTCAGGTCGGCTACGTATCATTGCCATGGTGAGCCGTTACCTCACCA

TCTAGCTAATACGCCGCGGGACCATCCAAAAGTGATAGCCGAAGCCATCTTTCAAACTCGGACCATGCGGTCCAAGTTG

TTATGCGGTATTAGCATCTGTTTC

S12KG271 GGDK 258-3 519R
SEQ ID NO: 38
TTTCTGGTTAAATACCGTCAATACCTGAACAGTTACTCTCAGATATGTTCTTCTTTAACAACAGAGTTTTACGAGCCGAA

ACCCTTCTTCACTCACGCGGCGTTGCTCCATCAGACTTTCGTCCATTGTGGAAGATTCCCTACTGCTGCCTCCCGTAGGA

GTTTGGGCCGTGTCTCAGTCCCAATGTGGCCGATTACCCTCTCAGGTCGGCTACGTATCATTGCCATGGTGAGCCGTTAC

CTCACCATCTAGCTAATACGCCGCGGGACCATCCAAAAGTGATAGCCGAAGCCATCTTTCAAACTCGGACCATGCGGTCC

AAGTTGTTATGCGGTATTAGCATCTGTTTCCAGGTGTTATCCCCCGCTTCTGGGCAGGTTTCCCACGTGTTACTCACCAG

TTCGCCACTCACTCAAATGTAAATCATGATGCAAGCACCAATCAATACCAGAGTTCGTTCGACTTGCATGTATTAGGCAC

GCCGCCAGCGTTCGTCCTGAGCCATGATCAAAC

S12KG272 GGDK 258-3 RP2
SEQ ID NO: 39
CCACCTTAGGCGGCTGGTTCCTAAAAGGTTACCCCACCGACTTTGGGTGTTACAAACTCTCATGGTGTGACGGGCGGTGT

GTACAAGGCCCGGGAACGTATTCACCGCGGCATGCTGATCCGCGATTACTAGCGATTCCGACTTCATGTAGGCGAGTTGC

AGCCTACAATCCGAACTGAGAATGGCTTTAAGAGATTAGCTTACTCTCGCGAGTTCGCAACTCGTTGTACCATCCATTGT

AGCACGTGTGTAGCCCAGGTCATAAGGGGCATGATGATTTGACGTCATCCCCACCTTCCTCCGGTTTGTCACCGGCAGTC

TCACCAGAGTGCCCAACTTAATGCTGGCAACTGATAATAAGGGTTGCGCTCGTTGCGGGACTTAACCCAACATCTCACGA

CACGAGCTGACGACAACCATGCACCACCTGTATCCATGTCCCCGAAGGGAACGTCTAATCTCTTAGATTTGCATAGTATG

TCAAGACCTGGTAAGGTTCTTCGCGTAGCTTCGAATTAAACCACATGCTCCACCGCTTGTGCGGGCCCCCGTCAATTCCT

TTGAGTTTCAGCCTTGCGGCCGTACTCCCCAGGCGGAATGCTTAATGCGTTAGCTGCAGCACTGAAGGGCGGAAACCCTC

CAACACTTAGCATTCATCGTTTACGGTATGGACTACCAGGGTATCTAATCCTGTTTGCTACCCATACTTTCGAGCCTCAGC

GTCAGTTACAGACCAGACAGCCGCCT

NCIMB 41850 GGDK 266—Contains Both *Lactobacillus johnsonii* and *Lactobacillus reuteri*

*Lactobacillus johnsonii*

S12KG273 GGDK 266-1 27F-repeat

SEQ ID NO: 40

GTGCCTAATACATGCAAGTCGAGCGAGCTTGCCTAGATGATTTTAGTGCTTGCACTAAATGAAACTAGATACAAGCGAGC

GGCGGACGGGTGAGTAACACGTGGGTAACCTGCCCAAGAGACTGGGATAACACCTGGAAACAGATGCTAATACCGGATAA

CAACACTAGACGCATGTCTAGAGTTTGAAAGATGGTTCTGCTATCACTCTTGGATGGACCTGCGGTGCATTAGCTAGTTG

GTAAGGTAACGGCTTACCAAGGCAATGATGCATAGCCGAGTTGAGAGACTGATCGGCCACATTGGGACTGAGACACGGCC

CAAACTCCTACGGGAGGCAGCAGTAGGGAATCTTCCACAATGGACGAAAGTCTGATGGAGCAACGCCGCGTGAGTGAAGA

AGGGTTTCGGCTCGTAAAGCTCTGTTGGTAGTGAAGAAAGATAGAGGTAGTAACTGGCCTTTATTTGACGGTAATTACTT

AGAAAGTCACGGCTAACTACGTGCCAGCAGCCGCGGTAATACGTAGGTGGCAAGCGTTGTCCGGATTTATTGGGCGTAA

AGCGAGTGCAGGCGGTTCAATAAGTCTGATGTGAAAGCCTTCGGCTCAACCGGAGAAT

S12KG274 GGDK 266-1 519F

SEQ ID NO: 41

TCCGGATTTATTGGGCGTAAAGCGAGTGCAGGCGGTTCAATAAGTCTGATGTGAAAGCCTTCGGCTCAACCGGAGAATTG

CATCAGAAACTGTTGAACTTGAGTGCAGAAGAGGAGAGTGGAACTCCATGTGTAGCGGTGGAATGCGTAGATATATGGAA

GAACACCAGTGGCGAAGGCGGCTCTCTGGTCTGCAACTGACGCTGAGGCTCGAAAGCATGGGTAGCGAACAGGATTAGAT

ACCCTGGTAGTCCATGCCGTAAACGATGAGTGCTAAGTGTTGGGAGGTTTCCGCCTCTCAGTGCTGCAGCTAACGCATTA

AGCACTCCGCCTGGGGAGTACGACCGCAAGGTTGAAACTCAAAGGAATTGACGGGGGCCCGCACAAGCGGTGGAGCATGT

GGTTTAATTCGAAGCAACGCGAAGAACCTTACCAGGTCTTGACATCCAGTGCAAACCTAAGAGATTAGGTGTTCCCTTC

GGGGACGCTGAGACAGGTGGTGCATGGCTGTCGTCAGCTCGTGT

S12KG275 GGDK 266-1 926F-repeat

SEQ ID NO: 42

GGAGCATGTGGTTTAATTCGAAGCAACGCGAAGAACCTTACCAGGTCTTGACATCCAGTGCAAACCTAAGAGATTAGGTG

TGTCCCTTCGGGGACGCTGAGACAGGTGGTGCATGGCTGTCGTCAGCTCGTGTCGTGAGATGTTGGGTTAAGTCCCGCAA

CGAGCGCAACCCTTGTCATTAGTTGCCATCATTAAGTTGGGCACTCTAATGAGACTGCCGGTGACAAACCGGAGGAAGGT

GGGGATGACGTCAAGTCATCATGCCCCTTATGACCTGGGCTACACACGTGCTACAATGGACGGTACAACGAGAAGCGAAC

CTGCGAAGGCAAGCGGATCTCTTAAAGCCGTTCTCAGTTCGGACTGTAGGCTGCAACTCGCCTACACGAAGCTGGAATCG

CTAGTAATCGCGGATCAGCACGCCGCGGTGAATACGTTCCCGGGCCTTGTACACACCGCCCGTCACACCATGAGAG

TCTGTA

S12KG275 GGDK 266-1 926R

SEQ ID NO: 43

ACTCCCCAGGCGGAGTGCTTAATGCGTTAGCTGCAGCACTGAGAGGCGGAAACCTCCCAACACTTAGCACTCATCGTTTA

CGGCATGGACTACCAGGGTATCTAATCCTGTTCGCTACCCATGCTTTCGAGCCTCAGCGTCAGTTGCAGACCAGAGAGCC

GCCTTCGCCACTGGTGTTCTTCCATATATCTACGCATTCCACCGCTACACATGGAGTTCCACTCTCCTCTTCTGCACTCA

AGTTCAACAGTTTCTGATGCAATTCTCCGGTTGAGCCGAAGGCTTTCACATCAGACTTATTGAACCGCCTGCACTCGCTT

TACGCCCAATAAATCCGGACAACGCTTGCCACCTACGTATTACCGCGGCTGCTGGCACGTAGTTAGCCGTGACTTTCTAA

GTAATTACCGTCAAATAAAGGCCAGTTACTACCTCTATCTTTCTTCACTACCAACAGAGCTTTACGAGCCGAAACCCTTC

TTCACTCACGCGGCGTTGCTCCATCAGACTTTCGTCCATTGTGGAAGATTCCCTACTGCTGCCTCCCGTAGGAGTTTGGG

CCGTGTCTCAGTCCCAATGTGGCCGATCAGTCTCTCAACTCGGCTATGCATCATTGCCTTGGTAAGCCGTTACCTTACCA

ACTAGCTAATGCACCGCAGGTCCATCCAAGAGTGATAGCAGAACCATCTTTCAAACTCTAGACATGCGTCTAGTGTTGT

S12KG277 GGDK 266-1 519R

SEQ ID NO: 44

ACTTTCTAAGTAATTACCGTCAAATAAAGGCCAGTTACTACCTCTATCTTTCTTCACTACCAACAGAGCTTTACGAGCCG

AAACCCTTCTTCACTCACGCGGCGTTGCTCCATCAGACTTTCGTCCATTGTGGAAGATTCCCTACTGCTGCCTCCCGTAG

-continued

```
GAGTTTGGGCCGTGTCTCAGTCCCAATGTGGCCGATCAGTCTCTCAACTCGGCTATGCATCATTGCCTTGGTAAGCCGTT

ACCTTACCAACTAGCTAATGCACCGCAGGTCCATCCAAGAGTGATAGCAGAACCATCTTTCAAACTCTAGACATGCGTCT

AGTGTTGTTATCCGGTATTAGCATCTGTTTCCAGGTGTTATCCCAGTCTCTTGGGCAGGTTACCCACGTGTTACTCACCC

GTCCGCCGCTCGCTTGTATCTAGTTTCATTTAGTGCAAGCACTAAAATCATCTAGGCAAGCTCGCTCGACTTGCATGTAT

TAGGCACGCCGCCAGCGTTCGTCCTGAGCCATGATCAAACT
```

S12KG278 GGDK 266-1 RP2

SEQ ID NO: 45

```
CTACCTTAGACGGCTGACTCCTATAAAGGTTATCCCACCGGCTTTGGGTGTTACAGACTCTCATGGTGTGACGGGCGGTG

TGTACAAGGCCCGGGAACGTATTCACCGCGGCGTGCTGATCCGCGATTACTAGCGATTCCAGCTTCGTGTAGGCGAGTTG

CAGCCTACAGTCCGAACTGAGAACGGCTTTAAGAGATCCGCTTGCCTTCGCAGGTTCGCTTCTCGTTGTACCGTCCATTG

TAGCACGTGTGTAGCCCAGGTCATAAGGGGCATGATGACTTGACGTCATCCCCACCTTCCTCCGGTTTGTCACCGGCAGT

CTCATTAGAGTGCCCAACTTAATGATGGCAACTAATGACAAGGGTTGCGCTCGTTGCGGGACTTAACCCAACATCTCACG

ACACGAGCTGACGACAGCCATGCACCACCTGTCTCAGCGTCCCCGAAGGGAACACCTAATCTCTTAGGTTTGCACTGGAT

GTCAAGACCTGGTAAGGTTCTTCGCGTTGCTTCGAATTAAACCACATGCTCCACCGCTTGTGCGGGCCCCCGTCAATTCC

TTTGAGTTTCAACCTTGCGGTCGTACTCCCCAGGCGGAGTGCTTAATGCGTTAGCTGCAGCACTGAGAGGCGGAAACCTC

CCAACACTTAGCACTCATCGTTTACGGCATGGACTACCAGGGTATCTAATCCTGTTCGCTACCCATGCTTTCGAGCCTCA

GCGTCAGTTGCAGACCAGAGAGCCGCCT
```

NCIMB 41850 GGDK 266—Contains Both *Lactobacillus johnsonii* and *Lactobacillus reuteri*
*Lactobacillus reuteri*

S12KG279 GGDK-266-2 27F

SEQ ID NO: 46

```
GTGTGCCTAATACATGCAAGTCGTACGCACTGGCCCAACTGATTGATGGTGCTTGCACCTGATTGACGATGGATCACCAG

TGAGTGGCGGACGGGTGAGTAACACGTAGGTAACCTGCCCCGGAGCGGGGGATAACATTTGGAAACAGATGCTAATACCG

CATAACAACAAAAGCCACATGGCTTTTGTTTGAAAGATGGCTTCGGCTATCACTCTGGGATGGACCTGCGGTGCATTAGC

TAGTTGGTAAGGTAACGGCTTACCAAGGCGATGATGCATAGCCGAGTTGAGAGACTGATCGGCCACAATGGAACTGAGAC

ACGGTCCATACTCCTACGGGAGGCAGCAGTAGGGAATCTTCCACAATGGGCGCAAGCCTGATGGAGCAACACCGCGTGAG

TGAAGAAGGGTTTCGGCTCGTAAAGCTCTGTTGTTGGAGAAGAACGTGCGTGAGAGTAACTGTTCACGCAGTGACGGTAT

CCAACCAGAAAGTCACGGCTAACTACGTGCCAGCAGCCGCGGTAATACGTAGGTGGCAAGCGTTATCCGGATTTATTGGG

CGTAAAGCGAGCGCAGGCGGTTGCTTAGGTCTGATGTGAAAGCCTTCGGCTTAACCGAAGAAGTGCATCGGAAACCGGGC

GACTTGAGTGCAGAAGAGGACAGTGGAACTCCATGTGTAGCGGTGGAATGCGTA
```

S12G280 GGD-266-2 519F-repeat

SEQ ID NO: 47

```
CGGATTTATTGGGCGTAAAGCGAGCGCAGGCGGTTGCTTAGGTCTGATGTGAAAGCCTTCGGCTTAACCGAAGAAGTGCA

TCGGAAACCGGGCGACTTGAGTGCAGAAGAGGACAGTGGAACTCCATGTGTAGCGGTGGAATGCGTAGATATATGGAAGA

ACACCAGTGGCGAAGGCGGCTGTCTGGTCTGCAACTGACGCTGAGGCTCGAAAGCATGGGTAGCGAACAGGATTAGATAC

CCTGGTAGTCCATGCCGTAAACGATGAGTGCTAGGTGTTGGAGGGTTTCCGCCCTTCAGTGCCGGAGCTAACGCATTAAG

CACTCCGCCTGGGGAGTACGACCGCAAGGTTGAAACTCAAAGGAATTGACGGGGGCCCGCACAAGCGGTGGAGCATGTG

GTTTAATTCG
```

S12KG281 GGDK-266-2 926F-repeat

SEQ ID NO: 48

```
GAGCATGTGGTTTAATTCGAAGCTACGCGAAGAACCTTACCAGGTCTTGACATCTTGCGCTAACCTTAGAGATAAGGCGT

TCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGG
```

-continued

GGACGACGTCAGATCATCATGCCCCTTATGACCTGGGCTACACACGTGCTACAATGGACGGTACAACGAGTCGCAAGCT

CGCGAGAGTAAGCTAATCTCTTAAAGCCGTTCTCAGTTCGGACTGTAGGCTGCAACTCGCCTACACGAAGTCGGAATCGC

TAGTAATCGCGGATCAGCATGCCGCGGTGAATACGTTCCCGGGCCTTGTACACACCGCCCGTCACACC

S12KG282 GGDK-266-2 926R-repeat

SEQ ID NO: 49

ACTCCCCAGGCGGAGTGCTTAATGCGTTAGCTCCGGCACTGAAGGGCGGAAACCCTCCAACACCTAGCACTCATCGTTTA

CGGCATGGACTACCAGGGTATCTAATCCTGTTCGCTACCCATGCTTTCGAGCCTCAGCGTCAGTTGCAGACCAGACAGCC

GCCTTCGCCACTGGTGTTCTTCCATATATCTACGCATTCCACCGCTACACATGGAGCCACTGTCCTCTTCTGCACTCA

AGTCGCCCGGTTTCCGATGCACTTCTTCGGTTAAGCCGAAGGCTTTCACATCAGACCTAAGCAACCGCCTGCGCTCGCTT

TACGCCCAATAAATCCGGATAACGCTTGCCACCTACGTATTACCGCGGCTGCTGGCACGTAGTTAGCCGTGACTTTCTGG

TTGGATACCGTCACTGCGTGAACAGTTACTCTCACGCACGTTCTTCTCCAACAACAGAGCTTTACGAGCCGAAACCCTTC

TTCACTCACGCGGTGTTGCTCCATCAGGCTTGCGCCCATTGTGGAAGATTCCCTACTGCTGCCTCCCGTAGGAGTATGGA

CCGTGTCTCAGTTCCATTGTGGCCGATCAGTCTCTCAACTCGGCTATGCATCATCGCCTTGGTAAGCCGTTACCTTACCA

ACTAGCTAATGCACCGCAGGT

S12KG283 GGDK-266-2 519R

SEQ ID NO: 50

TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTGATCCATCGTCAATCAGGTGCAAGCACCATCAATCAGTTGGGCCAGTGCGTACGACTTGCATGT

ATTAGGCACACCGCCGGCGTTCATCCTGAGCCATGATCAAACTCT

S12KG284 GGDK-266-2 RP2

SEQ ID NO: 51

TCCCGCCTTAGGCGGCTCCCTCCATAATGGTTAGGCCACCGACTTTGGGCGTTACAAACTCCCATGGTGTGACGGGCGGT

GTGTACAAGGCCCGGGAACGTATTCACCGCGGCATGCTGATCCGCGATTACTAGCGATTCCGACTTCGTGTAGGCGAGTT

GCAGCCTACAGTCCGAATGAGAACGGCTTTAAGAGATTAGCTTACTCTCGCGAGCTTGCGACTCGTTGTACCGTCCATT

GTAGCACGTGTGTAGCCCAGGTCATAAGGGGCATGATGATCTGACGTCGTCCCCACCTTCCTCCGGTTTGTCACCGGCAG

TCTCACTAGAGTGCCCAACTTAATGCTGGCAACTAGTAACAAGGGTTGCGCTCGTTGCGGGACTTAACCCAACATCTCAC

GACACGAGCTGACGACGACCATGCACCACCTGTCATTGCGTCCCCGAAGGGAACGCCTTATCTCTAAGGTTAGCGCAAGA

TGTCAAGACCTGGTAAGGTTCTTCGCGTAGCTTCGAATTAAACCACATGCTCCACCGCTTGTGCGGGCCCCCGTCAATTC

CTTTGAGTTTCAACCTTGCGGTCGTACTCCCCAGGCGGAGTGCTTAATGCGTTAGCTCCGGCACTGAAGGGCGGAAACCC

TCCAACACCTAGCACTCATCGTTTACGGCATGGATACCAGGGTATCTAATCCTGTTCGCTACCCATGCTTTCGAGCCTC

AGCGTCAGTTGCAGACCAGACAGCCGCCTTCGCCACTGGTG

NCIMB 41850 GGDK 266—Contains Both *Lactobacillus johnsonii* and *Lactobacillus reuteri*
*Lactobacillus reuteri*

S12KG381 27F

SEQ ID NO: 52

GTGTGCCTAATACATGCAAGTCGTACGCACTGGCCCAACTGATTGATGGTGCTTGCACCTGATTGACGATGGATCACCAGTGAGTGGCGGACG

GGTGAGTAACACGTAGGTAACCTGCCCCGGAGCGGGGGATAACATTTGGAAACAGATGCTAATACCGCATAACAACAAAAGCCACATGGCTTT

TGTTTGAAAGATGGCTTTGGCTATCACTCTGGGATGGACCTGCGGTGCATTAGCTAGTGGTAAGGTAACGGCTTACCAAGGCGATGATGCAT

AGCCGAGTTGAGAGACTGATCGGCCACAATGGAACTGAGACACGGTCCATACTCCTACGGGAGGCAGCAGTAGGGAATCTTCCACAATGGGC

```
GCAAGCCTGATGGAGCAACACCGCGTGAGTGAAGAAGGGTTTCGGCTCGTAAAGCTCTGTTGTTGGAGAAGAACGTGCGTGAGAGTAACTGT

TCACGCAGTGACGGTATCCAACCAGAAAGTCACGGCTAACTACGTGCCAGCAGCCGCGGTAATACGTAGGTGGCAAGCGTTATCCGGATTTAT

TGGGCGTAAAGCGAGCGCAGGCGGTTGCTTAGGTCTGATGTGAAAGCCTTCGGCTTAACCGAAGAAGTGCATCGGAAACCGGGCGACTTGAG

TGC
```

S12KG382 519F                                                                               SEQ ID NO: 53

```
TTATCCGGATTTATTGGGCGTAAAGCGAGCGCAGGCGGTTGCTTAGGTCTGATGTGAAAGCCTTCGGCTTAACCGAAGAAGTGCATCGGAAAC

CGGGCAACTTGAGTGCAGAAGAGGACAGTGGAACTCCATGTGTAGCGGTGGAATGCGTAGATATATGGAAGAACACCAGTGGCGAAGGCGG

CTGTCTGGTCTGCAACTGACGCTGAGGCTCGAAAGCATGGGTAGCGAACAGGATTAGATACCGGTAGTCCATGCCGTAAACGATGAGTGCT

AGGTGTTGGAGGGTTTCCGCCCTTCAGTGCCGGAGCTAACGCATTAAGCACTCCGCCTGGGGAGTACGACCGCAAGGTTGAAACTCAAGGA

ATTGACGGGGGCCCGCACAAGCGGTGGAGCATGTGGTTTAATTCGAAGCTACGCGAAGAACCTTACCAGGTCTTGACATCTTGCGCTAACCTT

AGAGATAAGGCGTCCCTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGGGGACGACGTCA
```

S12KG383 926F                                                                               SEQ ID NO: 54

```
GGTGGAGCATGTGGTTTAATTCGAAGCTACGCGAAGAACCTTACCAGGTCTTGACATCTTGCGCTAACCTTAGAGATAAGGCGTTCCCTTCGGG

GACGCAATGACAGGTGGTGCATGGTCGTCGTCAGCTCGTGTCGTGAGATGTTGGGTTAAGTCCCGCAACGAGCGCAACCCTTGTTACTAGTTG

CCAGCATTAAGTTGGGCACTCTAGTGAGACTGCCGGTGACAAACCGGAGGAAGGTGGGGACGACGTCAGATCATCATGCCCCTTATGACCTG

GGCTACACACGTGCTACAATGGACGGTACAACGAGTCGCAAGCTCGCGAGAGTAAGCTAATCTCTTAAAGCCGTTCTCAGTTCGGACTGTAGG

CTGCAACTCGCCTACACGAAGTCGGAATCGCTAGTAATCGCGGATCAGCATGCCGCGGTGAATACGTTCCCGGGCCTTGTACACACCGCCCGTC

ACACCATGGGAGTTTGTAACGCCCAAAGTCGGTGGCCTAACCATTATGGAGGGAGCCGCCTAAGGCGGGACAGATGACTGGGGTGAAGTCGT

AACAAGGTAGCCGTA
```

S12KG384 926R                                                                               SEQ ID NO: 55

```
TACTCCCCAGGCGGAGTGCTTAATGCGTGAGCTCCGGCACTGAAGGGCGGAAACCCTCCAACACCTAGCACTCATCGTTTACGGCATGGACTA

CCAGGGTATCTAATCCGTTCGCTACCCATGCTTTCGAGCCTCAGCGTCAGTTGCAGACCAGACAGCCGCTTCGCCACTGGTGTTCTTCCATAT

ATCTACGCATTCCACCGCTACACATGGAGTTCCACTGTCCTCTTCTGCACTCAAGTCGCCCGGTTTCCGATGCACTTCTTCGGTTAAGCCGAAGG

CTTTCACATCAGACCTAAGCAACCGCCTGCGCTCGCTTTACGCCCAATAAATCCGGATAACGCTTGCCACCTACGTATTACCGCGGCTGCTGGCA

CGTAGTTAGCCGTGACTTTCTGGTTGGATACCGTCACTGCGTGAACAGTTACTCTCACGCACGTTCTTCTCCAACAACAGAGCTTTACGAGCCGA

AACCCTTCTTCACTCACGCGGTGTTGCTCCATCAGGCTTGCGCCCATTGTGGAAGATTCCCTACTGCTGCCTCCCGTAGGAGTATGGACCGTGTC

TCAGTTCCATTGTGGCCGATCAGTCTCTCAACTCGGCTATGCATCATCGCCTTGGTAAGCCGTTACCTTACCAACTAGCTAATGCACCGCAGGTC

CATCCCAGAGTGATAGCCAAAGCCATCTTTCAAACAAAAGCC
```

S12KG385 519R                                                                               SEQ ID NO: 56

```
GTGACTTTCTGGTTGGATACCGTCACTGCGTGAACAGTTACTCTCACGCACGTGCTTCTCCAACAACAGAGCTTTACGAGCCGAAACCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCGCTCCGGGGC

AGGTTACCTACGTGTTACTCACCCGTCCGCCACTCACTGGTGATCCATCGTCAATCAGGTGCAAGCACCATCAATCAGTTGGGCCAGTGCGTAC

GACTTGCATGTATTAGGCACACCGCCGGCGTTCATCCTGAGCCATGATCAAAC
```

S12KG386 RP2                                                                                SEQ ID NO: 57

```
TCCCGCACTTAGGCGGCTCCCTCCATAATGGTTAGGCCACCGACTTTGGGCGTTACAAACTCCCATGGTGTGACGGGCGGTGTGTACAAGGCC

CGGGAACGTATTCACCGCGGCATGCTGATCCGCGATTACTAGCGATTCCGACTTCGTGTAGGCGAGTTGCAGCCTACAGTCCGAACTGAGAAC

GGCTTTAAGAGATTAGCTTACTCTCGCGAGCTTGCGACTCGTTGTACCGTCCATTGTAGCACGTGTGTAGCCCAGGTCATAAGGGGCATGATGA

TCTGACGTCGTCCCCACCTTCCTCCGGTTTGTCACCGGCAGTCTCACTAGAGTGCCCAACTTAATGCTGGCAACTAGTAACAAGGGTTGCGCTCG
```

-continued

TTGCGGGACTTAACCCAACATCCACGACACGAGCTGACGACGACCATGCACCACCTGTCATTGCGTCCCCGAAGGGAACGCCTTATCTCTAAG

GTTAGCGCAAGATGTCAAGACCTGGTAAGGTTCTTCGCGTAGCTTCGAATTAAACCACATGCTCCACCGCTTGTGCGGGCCCCCGTCAATTCCT

TTGAGTTTCAACCTTGCGGTCGTACTCCCCAGGCGGAGTGCTTAATGCGTTAGCTCCGGCACTGAAGGGCGGAAACCCTCCAACACCTAGCACT

CATCGTTTACGGCATGGACTACCAGGGTATCTAATCCTGTTCGCTACCCATGCTTTCGAGCC

NCIMB 42008 GGDK266a—*L. johnsonii* (Sample 4a)

S12KG399 27F

SEQ ID NO: 58

GCGTGCCTAATACATGCAAGTCGAGCGAGCTTGCCTAGATGATTTTAGTGCTTGCACTAAATGAAACTAGATACAAGCGAGCGGCGGACGGGT

GAGTAACACGTGGGTAACCTGCCCAAGAGACTGGGATAACACCTGGAAACAGATGCTAATACCGGATAACAACACTAGACGCATGTCTAGAG

TTTGAAAGATGGTTCTGCTATCACTCTTGGATGGACCTGCGGTGCATTAGCTAGTTGGTAAGGTAACGGCTTACCAAGGCAATGATGCATAGCC

GAGTTGAGAGACTGATCGGCCACATTGGGACTGAGACACGGCCCAAACTCCTACGGGAGGCAGCAGTAGGGAATCTTCCACAATGGACGAAA

GTCTGATGGAGCCGCCGCGTGAGTGAAGAAGGGTTTCGGCTCGTAAAGCTCTGTTGGTAGTGAAGAAAGATAGAGGTAGTAACTGGCCTT

TATTTGACGGTAATTACTTAGAAAGTCACGGCTAACTACGTGCCAGCAGCCGCGGTAATACGTAGGTGGCAAGCGTTTCCGGATTTATTGGG

CGTAAAGCGAGTGCAGGCGGTTCAATAAGTCTGATGTGAAAGCCTTCGGCTCAACCGGAGAATTGCATCAGAAACTGTTGAACTTGAGTGCAG

AAGAGGAGAGTGGAACTCCATGTGTAGCGGTGGAATGCGTA

S12KG400 519F

SEQ ID NO: 59

TGTCCGGATTTATTGGGCGTAAAGCGAGTGCAGGCGGTTCAATAAGTCTGATGTGAAAGCCTTCGGCTCAACCGGAGAATTGCATCAGAAACT

GTTGAACTTGAGTGCAGAAGAGGAGAGTGGAACTCCATGTGTAGCGGTGGAATGCGTAGATATATGGAAGAACACCAGTGGCGAAGGCGGC

TCTCTGGTCTGCAACTGACGCTGAGGCTCGAAAGCATGGGTAGCGAACAGGATTAGATACCCTGGTAGTCCATGCCGTAAACGATGAGTGCTA

AGTGTTGGGAGGTTTCCGCCTCTCAGTGCTGCAGCTAACGCATTAAGCACTCCGCCTGGGGAGTACGACCGCAAGGTTGAAACTCAAAGGAAT

TGACGGGGGCCCGCACAAGCGGTGGAGCATGTGGTTTAATTCGAAGCAACGCGAAGAACCTTACCAGGTCTTGACATCCAGTGCAAACCTAA

GAGATTAGGTGTTCCCTTCGGGGACGCTGAGACAGGTGGTGCATGGCTGTCGTCAGCTCGTGTCGTGAGATGTTGGGTTAAGTCCCGCAACGA

GCGCAACCTTGTCATTAGTTGCCATCATTAAGTTGGGCACTCTAATGAGACTGCCGGTGACAAACCGGAGGAAGGTGGGGAT

S12KG401 926F

SEQ ID NO: 60

GGTGGAGCATGTGGTTTAATTCGAAGCAACGCGAAGAACCTTACCAGGTCTTGACATCCAGTGCAAACCTAAGAGATTAGGTGTTCCCTTCGG

GGACGCTGAGACAGGTGGTGCATGGCTGTCGTCAGCTCGTGTCGTGAGATGTTGGGTTAAGTCCCGCAACGAGCGCAACCCTTGTCATTAGTT

GCCATCATTAAGTTGGGCACTCTAATGAGACTGCCGGTGACAAACCGGAGGAAGGTGGGGATGACGTCAAGTCATCATGCCCCTTATGACCTG

GGCTACACACGTGCTACAATGGACGGTACAACGAGAAGCGAACCTGCGAAGGCAAGCGGATCTCTTAAAGCCGTTCTCAGTTCGGACTGTAG

GCTGCAACTCGCCTACACGAAGCTGGAATCGCTAGTAATCGCGGATCAGCACGCCGCGGTGAATACGTTCCCGGGCCTTGTACACACCGCCCG

TCACACCATGAGAGTCTGTAACACCCAAAGCCGGTGGGATAACCTTTATAGGAGTCAGCCGTCTAAGGTAGGACAGATGATTAGGGTGAAGTC

GTAACAAGGTAG

S12KG402 926R

SEQ ID NO: 61

TACTCCCCAGGCGGAGTGCTTAATGCGTTAGCTGCAGCACTGAGAGGCGGAAACCTCCCAACACTTAGCACTCATCGTTTACGGCATGGACTAC

CAGGGTATCTAATCCTGTTCGCTACCCATGCTTTCGAGCCTCAGCGTCAGTTGCAGACCAGAGAGCCGCCTCGCCACTGGTGTTCTTCCATATA

TCTACGCATTCCACCGCTACACATGGAGTTCCACTCTCCTCTTCTGCACTCAAGTTCAACAGTTTCTGATGCAATTCTCCGGTTGAGCCGAAGT

TCACATCAGACTTATTGAACCGCCTGCACTCGCTTTACGCCCAATAAATCCGGACAACGCTTGCCACCTACGTATTACCGCGGCTGCTGGCACG

TAGTTAGCCGTGACTTTCTAAGTAATTACCGTCAAATAAAGGCCAGTTACTACCTCTATCTTTCTTCACTACCAACAGAGCTTTACGAGCCGAA

ACCCTTCTTCACTCACGCGGCGTTGCTCCATCAGACTTTCGTCCATTGTGGAAGATTCCCTACTGCTGCTCCCGTAGGAGTTTGGGCCGTGTCT

CAGTCCCAATGTGGCCGATCAGTCTCTCAACTCGGCTATGCATCATTGCCTTGGTAAGCCGTTACTTACCAACTAGCTAATGCACCGCAGGTCC

ATCCAAGAGTGATAGCAGANCCATCTTTCAAACTCTAGACATGCGTCTAGTG

-continued

S12KG403 519R
SEQ ID NO: 62
GTGACTTTCTAAGTAATTACCGTCAAATAAAGGCCAGTTACTACCTCTATCTTTCTTCACTACCAACAGAGCTTTACGAGCAGAAACCTTCTTC
ACTCACGCGGCGTTGCTCCATCAGACTTTCGTCCATTGTGGAAGATTCCCTACTGCTGCCTCCCGTAGGAGTTTGGGCCGTGTCTCAGTCCCAA
TGTGGCCGATCAGTCTCTCAACTCGGCTATGCATCATTGCCTTGGTAAGCCGTTACCTTACCAACTAGCTAATGCACCGCAGGTCCATCCAAGA
GTGATAGCAGAACCATCTTTCAAACTCTAGACATGCGTCTAGTGTTGTTATCCGGTATTAGCATCTGTTTCCAGGTGTTATCCCAGTCTCTTGG
GCAGGTTACCCACGTGTTACTCACCCGTCCGCCGCTCGCTTGTATCTAGTTTCATTTAGTGCAAGCACTAAAATCATCTAGGCAAGCTCGCTCG
ACTTGCATGTATTAGGCACGCCGCCAGCGTTCGTCCTGAGCCA

S12G404 RP2
SEQ ID NO: 63
TCCTACACTTAGACGGCTGACTCCTATAAAGGTTATCCCACCGGCTTTGGGTGTTACAGACTCTCATGGTGTGACGGGCGGTGTGTACAAGGCC
CGGGAACGTATTCACCGCGGCGTGCTGATCCGCGATTACTAGCGATTCCAGCTTCGTGTAGGCGAGTTGCAGCCTACAGTCCGAACTGAGAAC
GGCTTTAAGAGATCCGCTTGCCTTCGCAGGTTCGCTTCTCGTTGTACCGTCCATTGTAGCACGTGTGTAGCCCAGGTCATAAGGGGCATGATGA
CTTGACGTCATCCCCACCTTCCTCCGGTTTGTCACCGGCAGTCTCATTAGAGTGCCCAACTTAATGATGGCAACTAATGACAAGGGTTGCGCTCG
TTGCGGGACTTAACCCAACATCTCACGACACGAGCTGACGACAGCCATGCACCACCTGTCTCAGCGTCCCCGAAGGGAACACCTAATCTCTTAG
GTTTGCACTGGATGTCAAGACCTGGTAAGGTTCTTCGCGTTGCTTCGAATTAAACCACATGCTCCACCGCTTGTGCGGGCCCCCGTCAATTCCTT
TGAGTTTCAACCTTGCGGTCGTACTCCCCAGGCGGAGTGCTTAATGCGTTAGCTGCAGCACTGAGAGGCGGAAACCTCCCAACACTTAGCACTC
ATCGTTTACGGCATGGACTACCAGGGTATCTAATCCTGTTCGCTACCCATGC

NCIMB 42009 GGDK266b - L. reuteri (sample 6a)
S12KG411 27F
SEQ ID NO: 64
GTGTGCCTAATACATGCAAGTCGTACGCACTGGCCCAACTGATTGATGGTGCTTGCACCTGATTGACGATGGATCACCAGTGAGTGGCGGACG
GGTGAGTAACACGTAGGTAACCTGCCCCGGAGCGGGGGATAACATTTGGAAACAGATGCTAATACCGCATAACAACAAAAGCCACATGGCTTT
TGTTTGAAAGATGGCTTTGGCTATCACTCTGGGATGGACCTGCGGTGCATTAGCTAGTTGGTAAGGTAACGGCTTACCAAGGCGATGATGCAT
AGCCGAGTTGAGAGACTGATCGGCCACAATGGAACTGAGACACGGTCCATACTCCTACGGGAGGCAGCAGTAGGGAATCTTCCACAATGGGC
GCAAGCCTGATGGAGCAACACCGCGTGAGTGAAGAAGGGTTTCGGCTCGTAAAGCTCTGTTGTTGGAGAAGAACGTGCGTGAGAGTAACTGT
TCACGCAGTGACGGTATCCAACCAGAAAGTCACGGCTAACTACGTGCCAGCAGCCGCGGTAATACGTAGGTGGCAAGCGT S12KG412 519F
SEQ ID NO: 65
TATCCGGATTTATTGGGCGTAAAGCGAGCGCAGGCGGTTGCTTAGGTCTGATGTGAAAGCCTTCGGCTTAACCGAAGAAGTGCATCGGAAACC
GGGCGACTTGAGTGCAGAAGAGGACAGTGGAACTCCATGTGTAGCGGTGGAATGCGTAGATATATGGAAGAACACCAGTGGCGAAGGCGGC
TGTCTGGTCTGCAACTGACGCTGAGGCTCGAAAGCATGGGTAGCGAACAGGATTAGATACCCTGGTAGTCCATGCCGTAAACGATGAGTGCTA
GGTGTTGGAGGGTTTCCGCCCTTCAGTGCCGGAGCTAACGCATTAAGCACTCCGCCTGGGGAGTACGACCGCAAGGTTGAAACTCAAAGGAAT
TGACGGGGGCCCGCACAAGCGGTGGAGCATGTGGTTTAATTCGAAGCTACGCGAAGAACCTTACCAGGTCTTGACATCTTGCGCTAACCTTAG
AGATAAGGCGTTCCCTTCGGGGACGCAATGACAGGTGGTGCATGGTCGTCGTCAGCTCGTGTCGTGAGATGTTGGGTTAAGTCCCGCAACGA
GCGCAACCCTTGTTACTAGTTGCCAGCATTAAGTTGGGCACTCTAGTGAGACTGCCGGTGACAAACCGGAGGA S12KG413 926F
SEQ ID NO: 66
GTGGAGCATGTGGTTTAATTCGAAGCTACGCGAAGAACCTTACCAGGTCTTGACATCTTGCGCTAACCTTAGAGATAAGGCGTTCCCTTCGGGG
ACGCAATGACAGGTGGTGCATGGTCGTCGTCAGCTCGTGTCGTGAGATGTTGGGTTAAGTCCCGCAACGAGCGCAACCCTTGTTACTAGTTGC
CAGCATTAAGTTGGGCACTCTAGTGAGACTGCCGGTGACAAACCGGAGGAAGGTGGGGACGACGTCAGATCATCATGCCCCTTATGACCTGG
GCTACACACGTGCTACAATGGACGGTACAACGAGTCGCAAGCTCGCGAGAGTAAGCTAATCTCTTAAAGCCGTTCTCAGTTCGGACTGTAGGC
TGCAACTCGCCTACACGAAGTCGGAATCGCTAGTAATCGCGGATCAGCATGCCGCGGTGAATACGTTCCCGGGCCTTGTACACACCGCCCGTC
ACACCATGGGAGTTTGTAACGCCCAAAGTCGGTGGCCTAACCATTATGGAGGGAGCCGCCTAAGGCGGGACAGATGACTGGGGTGAAGTCGT

S12KG414 926R

SEQ ID NO: 67

TACTCCCCAGGCGGAGTGCTTAATGCGTTAGCTCCGGCACTGAAGGGCGGAAACCCTCCAACACCTAGCACTCATCGTTTACGGCATGGACTAC
CAGGGTATCTAATCCTGTTCGCTACCCATGCTTTCGAGCCTCAGCGTCAGTTGCAGACCAGACAGCCGCCTTCGCCACTGGTGTTCTTCCATATA
TCTACGCATTCCACCGCTACACATGGAGTTCCACTGTCCTCTTCTGCACTCAAGTCGCCCGGTTTCCGATGCACTTCTTCGGTTAAGCCGAAGGC
TTTCACATCAGACCTAAGCAACCGCCTGCGCTCGCTTTACGCCCAATAAATCCGGATAACGCTTGCCACCTACGTATTACCGCGGCTGCTGGCAC
GTAGTTAGCCGTGACTTTCTGGTTGGATACCGTCACTGCGTGAACAGTTACTCTCACGCACGTTCTTCTCCAACAACAGAGCTTTACGAGCCGAA
ACCCTTCTTCACTCACGCGGTGTTGCTCCATCAGGCTTGCGCCCATTGTGGAAGATTCCCTACTGCTGCCTCCCGTAGGAGTATGGACCGTGTCT
CAGTTCCATTGTGGCCGATCAGTCTCTCAACTCGGCTATGCATCATCGCC

S12KG415 519R

SEQ ID NO: 68

GTGACTTTCTGGTTGGATACCGTCACTGCGTGAACAGTTACTCTCACGCACGTTCTTCTCCAACAACAGAGCTTTACGAGCCGAAACCCTTCTTC
ACTCACGCGGTGTTGCTCCATCAGGCTTGCGCCCATTGTGGAAGATTCCCTACTGCTGCCTCCCGTAGGAGTATGGACCGTGTCTCAGTTCCATT
GTGGCCGATCAGTCTCTCAACTCGGCTATGCATCATCGCCTTGGTAAGCCGTTACCTTACCAACTAGCTAATGCACCGCAGGTCCATCCCAGAGT
GATAGCCAAAGCCATCTTTCAAACAAAAGCCATGTGGCTTTTGTTGTTATGCGGTATTAGCATCTGTTTCCAAATGTTATCCCCCGCTCCGGGGC
AGGTTACCTACGTGTTACTCACCCGTCCGCCACTCACTGGTGATCCATCGTCAATCAGGTGCAAGCACCATCAATCAGTTGGGCCAGTGCGTAC
GACTTGCATGTATTAGGCACACCGCCGGCGTTCAT

S12KG415 RP2

SEQ ID NO: 69

TCCCGCCTTAGGCGGCTCCCTCCATAATGGTAGGCCACCGACTTTGGGCGTTACAAACTCCCATGGTGTGACGGGCGGTGTGTACAAGGCCC
GGGAACGTATTCACCGCGGCATGCTGATCCGCGATTACTAGCGATTCCGACTTCGTGTAGGCGAGTTGCAGCCTACAGTCCGAACTGAGAACG
GCTTTAAGAGATTAGCTTACTCTCGCGAGCTTGCGACTCGTTGTACCGTCCATTGTAGCACGTGTGTAGCCCAGGTCATAAGGGGCATGATGAT
CTGACGTCGTCCCCACCTTCCTCCGGTTTGTCACCGGCAGTCTCACTAGAGTGCCCAACTTAATGCTGGCAACTAGTAACAAGGGTTGCGCTCGT
TGCGGGACTTAACCCAACATCTCACGACACGAGCTGACGACGACCATGCACCACCTGTCATTGCGTCCCCGAAGGGAACGCCTTATCTCTAAGG
TTAGCGCAAGATGTCAAGACCTGGTAAGGTTCTTCGCGTAGCTTCGAATTAAACCACATGCTCCACCGCTTGTGCGGGCCCCCGTCAATTCCTTT
GAGTTTCAACCTTGCGGTCGTACTCC

NCIMB 42010 GGDK161a - *L. plantarum* (sample 7a)
S12KG417 27F

SEQ ID NO: 70

GTGCCTAATACATGCAAGTCGAACGAACTCTGGTATTGATTGGTGCTTGCATCATGATTTACATTTGAGTGAGTGGCGAACTGGTGAGTAACAC
GTGGGAAACCTGCCCAGAAGCGGGGGATAACACCTGGAAACAGATGCTAATACCGCATAACAACTTGGACCGCATGGTCCGAGTTTGAAAGA
TGGCTTCGGCTATCACTTTTGGATGGTCCCGCGGCGTATTAGCTAGATGGTGAGGTAACGGCTCACCATGGCAATGATACGTAGCCGACCTGA
GAGGGTAATCGGCCACATTGGGACTGAGACACGGCCCAAACTCCTACGGGAGGCAGCAGTAGGGAATCTTCCACAATGGACGAAAGTCTGAT
GGAGCAACGCCGCGTGAGTGAAGAAGGGTTTCGGCTCGTAAAACTCTGTTGTTAAAGAAGAACATATCTGAGAGTAACTGTTCAGGTATTGAC
GGTATTTAACCAGAAAGCCACGGCTAACTACGTGCCAGCAGCCGCGGTAATACGTAGGTGGCAAGCGTTGTCCGGATTTATTGGGCGTAAAGC
GAGCGCAGGCGGTTTTTTAAGTCTGATGTGAAAGCCTTCGGCTCAACCGAAGAAGTGCATCGGAAACTGGGAAACTTGAGTGCAGAAGAGGA
CAGTGGAACTCATGTGT

S12KG418 519F

SEQ ID NO: 71

TCCGGATTTATTGGGCGTAAAGCGAGCGCAGGCGGTTTTTTAAGTCTGATGTGAAAGCCTTCGGCTCAACCGAAGAAGTGCATCGGAAACTGG
GAAACTTGAGTGCAGAAGAGGACAGTGGAACTCCATGTGTAGCGGTGAAATGCGTAGATATATGGAAGAACACCAGTGGCGAAGGCGGCTG
TCTGGTCTGTAACTGACGCTGAGGCTCGAAAGTATGGGTAGCAAACAGGATTAGATACCCTGGTAGTCCATACCGTAAACGATGAATGCTAAG
TGTTGGAGGGTTTCCGCCCTTCAGTGCTGCAGCTAACGCATTAAGCATTCCGCCTGGGGAGTACGGCCGCAAGGCTGAAACTCAAAGGAATTG
ACGGGGGCCCGCACAAGCGGTGGAGCATGTGGTTTAATTCGAAGCTACGCGAAGAACCTTACCAGGTCTGACATACTATGCAAATCTAAGAG

-continued
ATTAGACGTTCCCTTCGGGGACATGGATACAGGTGGTGCATGGTTGTCGTCAGCTCGTGTCGTGAGATGTTGGGTTAAGTCCCGCAACGAGCG CAACCCTTATTATCAGTTGCCAGCATTAAGTTGGGCACTCTGGTGAGACTGCCGGTGACAAACCGGAGGAAGGTGGGGATGACGTCAAATCAT

CATGCCCCTTATGACCTGGGCTACACAC

S12KG419 926F

SEQ ID NO: 72
GGTGGAGCATGTGGTTTAATTCGAAGCTACGCGAAGAACCTTACCAGGTCTTGACATACTATGCAAATCTAAGAGATTAGACGTTCCCTTCGGG

GACATGGATACAGGTGGTGCATGGTTGTCGTCAGCTCGTGTCGTGAGATGTTGGGTTAAGTCCCGCAACGAGCGCAACCCTTATTATCAGTTG

CCAGCATTAAGTTGGGCACTCTGGTGAGACTGCCGGTGACAAACCGGAGGAAGGTGGGGATGACGTCAAATCATCATGCCCCTTATGACCTG

GGCTACACACGTGCTACAATGGATGGTACAACGAGTTGCGAACTCGCGAGAGTAAGCTAATCTCTTAAAGCCATTCTCAGTTCGGATTGTAGG

CTGCAACTCGCCTACATGAAGTCGGAATCGCTAGTAATCGCGGATCAGCATGCCGCGGTGAATACGTTCCCGGGCCTTGTACACACCGCCCGTC

ACACCATGAGAGTTTGTAACACCCAAAGTCGGTGGGGTAACCTTTTAGGAACCAGCCGCCTAAGGTGGGACAGATGATACGGTGAAGTCGTA

ACAAGGTAGCCCGTA

S12KG420 926R

SEQ ID NO: 73
GTACTCCCCAGGCGGAATGCTTAATGCGTTAGCTGCAGCACTGAAGGGCGGAAACCCTCCAACACTTAGCATTCATCGTTTACGGTATGGACTA

CCAGGGTATCTAATCCTGTTTGCTACCCATACTTTCGAGCCTCAGCGTCAGTTACAGACCAGACAGCCGCCTTCGCCACTGGTGTTCTTCCATAT

ATCTACGCATTTCACCGCTACACATGGAGTTCCACTGTCCTCTTCTGCACTCAAGTTTCCCGTTTCCGATGCACTTCTTCGGTTGAGCCGAAGGC

TTTCACATCAGACTTAAAAAACCGCCTGCGCTCGCTTTACGCCCAATAAATCCGGACAACGCTTGCCACCTACGTATTACCGCGGCTGCTGGCAC

GTAGTTAGCCGTGGCTTTCTGGTTAAATACCGTCAATACCTGAACAGTTACTCTCAGATATGTTCTTCTTTAACAACAGAGTTTACGAGCCGAA

ACCCTTCTTCACTCACGCGGCGTTGCTCCATCAGACTTTCGTCCATTGTGGAAGATTCCCTACTGCTGCCTCCCGTAGGAGTTTGGGCCGTGTCT

CAGTCCCAATGTGGCCGATTACCCTCTCAGGTCGGCTACGTATCATTGCCATGGTGAGCCGTTACCTCACCATCTAGCTAATACGCCGCGGGAC

CATCCAAAAGTGATA

S12KG421 519R

SEQ ID NO: 74
TGGCTTTCTGGTTAAATACCGTCAATACCTGAACAGTTACTCTCAGATATGTTCTTCTTTAACAACAGAGTTTTACGAGCCGAAACCCTTCTTCA

CTCACGCGGCGTTGCTCCATCAGACTTTCGTCCATTGTGGAAGATTCCCTACTGCTGCCTCCCGTAGGAGTTTGGGCCGTGTCTCAGTCCCAAT

GTGGCCGATTACCCTCTCAGGTCGGCTACGTATCATTGCCATGGTGAGCCGTTACCTCACCATCTAGCTAATACGCCGCGGGACCATCTAAAAG

TGATAGCCGAAGCCATCTTTCAAACTCGGACCATGCGGTCCAAGTTGTTATGCGGTATTAGCATCTGTTTCCAGGTGTTATCCCCGCTTCTGG

GCAGGTTTCCCACGTGTGCTCACCAGTTCGCCACTCACTCAAATGTAAATCATGATGCAAGCACCAATCAATACCAGAGTTCGTTCGACTTGCA

TGTATTAGGCACGCCGCCAGCGTTCGTCCTGAGCCATGATCAAACTCTA

S12KG422 RP2

SEQ ID NO: 75
ACTTAGGCGGCTGGTTCCTAAAAGGTTACCCCACCGACTTTGGGTGTTACAAACTCTCATGGTGTGACGGGCGGTGTGTACAAGGCCCGGGAA

CGTATTCACCGCGGCATGCTGATCCGCGATTACTAGCGATTCCGACTTCTTGTAGGCGAGTTGCAGCCTACAATCCGAACTGAGAATGGCTTTA

AGAGATTAGCTTACTCTCGCGAGTTCGCAACTCGTTGTACCATCCATTGTAGCACGTGTGTAGCCCAGGTCATAAGGGGCATGATGATTTGACG

TCATCCCCACCTTCCTCCGGTTTGTCACCGGCAGTCTCACCAGAGTGCCCAACTTAATGCTGGCAACTGATAATAAGGGTTGCGCTCGTTGCGG

GACTTAACCCAACATCTCACGACACGAGCTGACGACAACCATGCACCACCTGTATCCATGTCCCGAAGGGAACGTCTAATCTCTTAGATTTGC

ATAGTATGTCAAGACCTGGTAAGGTTCTTCGCGTAGCTTCGAATTAAACCACATGCTCCACCGCTTGTGCGGGCCCCCGTCAATTCCTTTGAGT

TTCAGCCTTGCGGCCGTACTCCCCAGGCGGAATGCTTAATGCGTTAGCTGCAGCACTGAAGGGCGGAAACCCTCCA

NCIMB 42011 GGDK161b —*L. reuteri* (Sample 11a)

S12KG441 27F

SEQ ID NO: 76
TAATACATGCAAGTCGTACGCACTGGCCCAACTGATTGATGGTGCTTGCA

CCTGATTGACGATGGATCACCAGTGAGTGGCGGACGGGTGAGTAACACGT

AGGTAACCTGCCCCGGAGCGGGGGATAACATTTGGAAACAGATGCTAATA

CCGCATAACAACAAAAGCCACATGGCTTTTGTTTGAAAGATGGCTTTGGC

TATCACTCTGGGATGGACCTGCGGTGCATTAGCTAGTTGGTAAGGTAACG

GCTTACCAAGGCGATGATGCATAGCCGAGTTGAGAGACTGATCGGCCACA

```
ATGGAACTGAGACACGGTCCATACTCCTACGGGAGGCAGCAGTAGGGAAT
CTTCCACAATGGGCGCAAGCCTGATGGAGCAACACCGCGTGAGTGAAGAA
GGGTTTCGGCTCGTAAAGCTCTGTTGTTGGAGAAGAACGTGCGTGAGAGT
AACTGTTCACGCAGTGACGGTATCCAACCAGAAAGTCACGGCTAACTACG
TGCCAGCAGCCGCGGTAATACGTAGGTGGCAAGCGTGATCCGGATTTATT
GGGCGTAAAGCGAGCGCAGGCGGTTGCTTAGGTCTGATGTGAAAGCCTTC
GGCTTAACCGAAGAAGTGCATCGGAGACGGGCGACTTGAGTGCA
```

S12KG442 519F

SEQ ID NO: 77
```
TTATCCGGATTTATTGGGCGTAAAGCGAGCGCAGGCGGTTGCTTAGGTCT
GATGTGAAAGCCTTCGGCTTAACCGAAGAAGTGCATCGGAAACCGGGCGA
CTTGAGTGCAGAAGAGGACAGTGGAACTCCATGTGTAGCGGTGGAATGCG
TAGATATATGGAAGAACACCAGTGGCGAAGGCGGCTGTCTGGTCTGCAAC
TGACGCTGAGGCTCGAAAGCATGGGTAGCGAACAGGATTAGATACCCTGG
TAGTCCATGCCGTAAACGATGAGTGCTAGGTGTTGGAGGGTTTCCGCCCT
TCAGTGCCGGAGCTAACGCATTAAGCACTCCGCCTGGGGAGTACGACCGC
AAGGTTGAAACGCAAAGGAATTGACGGGGGCCCGCACAAGCGGTGGAGCA
TGTGGTTTAATTCGAAGCTACGCGAAGAACCTTACCAGGTCTTGACATCT
TGCGCTAACCTTANAAGGCGTCCCCTTCGGGGACTCAATGACAGGTGGTG
CATGGTT
```

S12KG443 926F

SEQ ID NO: 78
```
GGTGGAGCATGTGGTTTAATTCGAAGCTACGCGAAGAACCTTACCAGGTC
TTGACATCTTGCGCTAACCTTAGAGATAAGGCGTTCCCTTCGGGGACGCA
ATGACAGGTGGTGCATGGTCGTCGTCAGCTCGTGTCGTGAGATGTTGGGT
TAAGTCCCGCAACGAGCGCAACCCTTGTTACTAGTTGCCAGCATTAAGTT
GGGCACTCTAGTGAGACTGCCGGTGACAAACCGGAGGAAGGTGGGGACGA
CGTCAGATCATCATGCCCCTTATGACCTGGGCTACACACGTGCTACAATG
GACGGTACAACGAGTCGCAAGCTCGCGAGAGTAAGCTAATCTCTTAAAGC
CGTTCTCAGTTCGGACTGTAGGCTGCAACTCGCCTACACGAAGTCGGAAT
CGCTAGTAATCGCGGATCAGCATGCCGCGGTAATACGTTCCCGGGCCTT
GTACACACCGCCCGTCACACCATGGGAGTTTGTAACGCCCAAAGTCGGTG
```

S12KG444 926R

SEQ ID NO: 79

No results

S12KG445 519R

SEQ ID NO: 80
```
GTGACTTTCTGGTTGGATACCGTCACTGCGTGAACAGTTACTCTCACGCA
CGTTCTTCTCCAACAACAGAGCTTTACGAGCCGAAACCCTTCTTCACTCA
CGCGGTGTTGCTCCATCAGGCTTGCGCCCATTGTGGAAGATTCCCTACTG
CTGCCTCCCGTAGGAGTATGGACCGTGTCTCAGTTCCATTGTGGCCGATC
AGTCTCTCAACTCGGCTATGCATCATCGCCTTGGTAAGCCGTTACCTTAC
CAACTAGCTAATGCACCGCAGGTCCATCCCAGAGTGATAGCCAAAGCCAT
CTTTCAAACAAAAGCCATGTGGCTTTTGTTGTTATGCGGTATTAGCATCT
GTTTCCAAATGTTATCCCCCGCTCCGGGGCAGGTTACCTACGTGTTACTC
ACCCGTCCGCCACTCACTGGTAATCCATCGTCAATCAGGTGCAAGCACCA
TCAATCAGTTGGGCCAGTGCGTACGACTTGCATGTATTAGGCACACCGCC
GGCGTTCATCCTGAGCCA
```

S12KG446 RP2

SEQ ID NO: 81
```
CTCCCTCCATAAAGGTTAGGCCACCGACTTTGGGCGTTACAAACTCCCAT
GGTGTGACGGGCGGTGTGTACAAGGCCCGGGAACGTATTCACCGCGGCAT
GCTGATCCGCGATTACTAGCGATTCCGACTTCGTGTAGGCGAGTTGCAGC
CTACAGTCCGAACTGAGAACGGCTTTAAGAGATTAGCTTACTCTCGCGAG
CTTGCGACTCGTTGTACCGTCCATTGTAGCACGTGTGTAGCCCAGGTCAT
AAGGGGCATGATGATCTGACGTCGTCCCCACCTTCCTCCGGTTTGTCACC
GGCAGTCTCACTAGAGTGCCCAACTTAATGCTGGCAACTAGTAACAAGGG
TTGCGCTCGTTGCGGGACTTAACCCAACATCTCACGACACGAGCTGACGA
CGACCATGCACCACCTGTCATTGCGTCCCCGAAGGGAACGCCTTATCTCT
AAGGTTAGCGCAAGATGTCAAGACCTGGTAAGGTTCTTCGCGTAGCTTCG
AATTAAACCACATGCTCCACCGCTTGTGCGGGCCCCCGTCAATTCCTTTG
AGTTTCAACCTTGGCGGTCGTACTCCCCAGGCGGAGTGCTTAATGCGTTA
GCTCCGGCACTGAAGGGCGGAA
```

NCIMB 42012 GGDKZ66c—*L. reuteri* (Sample 1a)

S12KG381 27F

SEQ ID NO: 82
```
GTGTGCCTAATACATGCAAGTCGTACGCACTGGCCCAACTGATTGATGGTGCTTGCACCTGATTGACGATGGATCACCAGTGAGTGGCGGACG
GGTGAGTAACACGTAGGTAACCTGCCCCGGAGCGGGGATAACATTTGGAAACAGATGCTAATACCGCATAACAACAAAAGCCACATGGCTTT
TGTTTGAAAGATGGCTTTGGCTATCACTCTGGGATGGACCTGCGGTGCATTAGCTAGTTGGTAAGGTAACGGCTTACCAAGGCGATGATGCAT
AGCCGAGTTGAGAGACTGATCGGCCACAATGAACTGAGACACGGTCCATACTCCTACGGGAGGCAGCAGTAGGGAATCTTCCACAATGGGC
GCAAGCCTGATGGAGCAACACCGCGTGAGTGAAGAAGGGTTTCGGCTCGTAAAGCTCTGTTGTTGGAGAAGAACGTGCGTGAGAGTAACTGT
TCACGCAGTGACGGTATCCAACCAGAAAGTCACGGCTAACTACGTGCCAGCAGCCGCGGTAATACGTAGGTGGCAAGCGTTATCCGGATTTAT
TGGGCGTAAAGCGAGCGCAGGCGGTTGCTTAGGTCTGATGTGAAAGCCTTCGGCTTAACCGAAGAAGTGCATCGGAAACCGGGCGACTTGAG
TGC
```

S12KG382 519F

SEQ ID NO: 83

TTATCCGGATTTATTGGGCGTAAAGCGAGCGCAGGCGGTTGCTTAGGTCTGATGTGAAAGCCTTCGGCTTAACCGAAGAAGTGCATCGGAAAC

CGGGCAACTTGAGTGCAGAAGAGGACAGTGGAACTCCATGTGTAGCGGTGGAATGCGTAGATATATGGAAGAACACCAGTGGCGAAGGCGG

CTGTCTGGTCTGCAACTGACGCTGAGGCTCGAAAGCATGGGTAGCGAACAGGATTAGATACCCTGGTAGTCCATGCCGTAAACGATGAGTGCT

AGGTGTTGGAGGGTTTCCGCCCTTCAGTGCCGGAGCTAACGCATTAAGCACTCCGCCTGGGGAGTACGACCGCAAGGTTGAAACTCAAAGGA

ATTGACGGGGGCCCGCACAAGCGGTGGAGCATGTGGTTTAATTCGAAGCTACGCGAAGAACCTTACCAGGTCTTGACATCTTGCGCTAACCTT

AGAGATAAGGCGTCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGGGGACGACGTCA

S12KG383 926F

SEQ ID NO: 84

GGTGGAGCATGTGGTTTAATTCGAAGCTACGCGAAGAACCTTACCAGGTCTTGACATCTTGCGCTAACCTTAGAGATAAGGCGTTCCCTTCGGG

GACGCAATGACAGGTGGTGCATGGTCGTCGTCAGCTCGTGTCGTGAGATGTTGGGTTAAGTCCCGCAACGAGCGCAACCCTTGTTACTAGTTG

CCAGCATTAAGTTGGGCACTCTAGTGAGACTGCCGGTGACAAACCGGAGGAAGGTGGGGACGACGTCAGATCATCATGCCCCTTATGACCTG

GGCTACACACGTGCTACAATGGACGGTACAACGAGTCGCAAGCTCGCGAGAGTAAGCTAATCTCTTAAAGCCGTTCTCAGTTCGGACTGTAGG

CTGCAACTCGCCTACACGAAGTCGGAATCGCTAGTAATCGCGGATCAGCATGCCGCGGTGAATACGTTCCCGGGCCTTGTACACACCGCCCGTC

ACACCATGGGAGTTTGTAACGCCCAAAGTCGGTGGCCTAACCATTATGGAGGGAGCCGCCTAAGGCGGGACAGATGACTGGGGTGAAGTCGT

AACAAGGTAGCCGTA

S12KG384 926R

SEQ ID NO: 85

TACTCCCCAGGCGGAGTGCTTAATGCGTGAGCTCCGGCACTGAAGGGCGGAAACCCTCCAACACCTAGCACTCATCGTTTACGGCATGGACTA

CCAGGGTATCTAATCCTGTTCGCTACCCATGCTTTCGAGCCTCAGCGTCAGTTGCAGACCAGACAGCCGCCTTCGCCACTGGTGTTCTTCCATAT

ATCTACGCATTCCACCGCTACACATGGAGTTCCACTGTCCTCTTCTGCACTCAAGTCGCCCGGTTTCCGATGCACTTCTTCGGTTAAGCCGAAGG

CTTTCACATCAGACCTAAGCAACCGCCTGCGCTCGCTTTACGCCCAATAAATCCGGATAACGCTTGCCACCTACGTATTACCGCGGCTGCTGGCA

CGTAGTTAGCCGTGACTTTCTGGTTGGATACCGTCACTGCGTGAACAGTTACTCTCACGCACGTTCTTCTCCAACAACAGAGCTTTACGAGCCGA

AACCCTTCTTCACTCACGCGGTGTTGCTCCATCAGGCTTGCGCCCATTGTGGAAGATTCCCTACTGCTGCCTCCCGTAGGAGTATGGACCGTGTC

TCAGTTCCATTGTGGCCGATCAGTCTCTCAACTCGGCTATGCATCATCGCCTTGGTAAGCCGTTACCTTACCAACTAGCTAATGCACCGCAGGTC

CATCCCAGAGTGATAGCCAAAGCCATCTTTCAAACAAAAGCC

S12KG385 519R

SEQ ID NO: 86

GTGACTTTCTGGTTGGATACCGTCACTGCGTGAACAGTTACTCTCACGCACGTGCTTCTCCAACAACAGAGCTTTACGAGCCGAAACCCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCCGCTCCGGGC

AGGTTACCTACGTGTTACTCACCCGTCCGCCACTCACTGGTGATCCATCGTCAATCAGGTGCAAGCACCATCAATCAGTTGGGCCAGTGCGTAC

GACTTGCATGTATTAGGCACACCGCCGGCGTTCATCCTGAGCCATGATCAAAC

S12KG386 RP2

SEQ ID NO: 87

TCCCGCACTTAGGCGGCTCCCTCCATAATGGTTAGGCCACCGACTTTGGGCGTTACAAACTCCCATGGTGTGACGGGCGGTGTGTACAAGGCC

CGGGAACGTATTCACCGCGGCATGCTGATCCGCGATTACTAGCGATTCCGACTTCGTGTAGGCGAGTTGCAGCCTACAGTCCGAACTGAGAAC

GGCTTTAAGAGATTAGCTTACTCTCGCGAGCTTGCGACTCGTTGTACCGTCCATTGTAGCACGTGTGTAGCCCAGGTCATAAGGGGCATGATGA

TCTGACGTCGTCCCCACCTTCCTCCGGTTTGTCACCGGCAGTCTCACTAGAGTGCCCAACTTAATGCTGGCAACTAGTAACAAGGGTTGCGCTCG

TTGCGGGACTTAACCCAACATCTCACGACACGAGCTGACGACGACCATGCACCACCTGTCATTGCGTCCCCGAAGGGAACGCCTTATCTCTAAG

```
GTTAGCGCAAGATGTCAAGACCTGGTAAGGTTCTTCGCGTAGCTTCGAATTAAACCACATGCTCCACCGCTTGTGCGGGCCCCCGTCAATTCCT

TTGAGTTTCAACCTTGCGGTCGTACTCCCCAGGCGGAGTGCTTAATGCGTTAGCTCCGGCACTGAAGGGCGGAAACCCTCCAACACCTAGCACT

CATCGTTTACGGCATGGACTACCAGGGTATCTAATCCTGTTCGCTACCCATGCTTTCGAGCC
```

REFERENCES

Blandino, G., Fazio, D., Di Marco, R. Probiotics: Overview of microbiological and immunological characteristics (2008). *Expert Review of Anti-Infective Therapy*, 6 (4), pp. 497-508.

Cintas L M, Casaus M P, Herranz C, Nes I F, Hernandez P E. Review: bacteriocins of lactic acid bacteria (2001). Food Sci Technol Int. 7(4):281-305.

Clarridge III, J. E. Impact of 16S rRNA gene sequence analysis for identification of bacteria on clinical microbiology and infectious diseases (2004). Clinical Microbiology Reviews, 17 (4), pp. 840-862.

Cotter, P. D., Hill, C, Ross, R. P. Food microbiology: Bacteriocins: Developing innate immunity for food (2005). Nature Reviews Microbiology, 3 (10), pp. 777-788.

De Angelis, M., Siragusa, S., Berloco, M., Caputo, L., Settanni, L., Alfonsi, G., Amerio, M., Grandi, A., Ragni, A., Gobbetti, M. Selection of potential probiotic lactobacilli from pig feces to be used as additives in pelleted feeding (2006). *Research in Microbiology*, 157 (8), pp. 792-801

Elmadfa, I., Klein, P., Meyer, A. L. Immune-stimulating effects of lactic acid bacteria in vivo and in vitro (2010). *Proceedings of the Nutrition Society*, 69 (3), pp. 416-420.

Gopal, P. K., Sullivan, P. A., Smart, J. B. Utilisation of galacto-oligosaccharides as selective substrates for growth by lactic acid bacteria including *Bifidobacterium lactis* DR10 and *Lactobacillus rhamnosus* DR20 (2001). International Dairy Journal, 11 (1-2), pp. 19-25.

Gousia, P., Economou, V., Sakkas, H., Leveidiotou, S., Papadopoulou, C. Antimicrobial resistance of major foodborne pathogens from major meat products (2011). *Foodborne Pathogens and Disease*, 8 (1), pp. 27-38.

Jackson M S, Bird A R, McOrist A L. Comparison of two selective media for the detection and enumeration of Lactobacilli in human faeces (2002). J Microbiol Methods. 51(3):313-21.

Korhonen, J. M., Sclivagnotis, Y., Wright, A. V. Characterization of dominant cultivable lactobacilli and their antibiotic resistance profiles from faecal samples of weaning piglets (2007). *Journal of Applied Microbiology*, 103 (6), pp. 2496-2503.

Lähteinen, T., Malinen, E., Koort, J. M. K., Mertaniemi-Hannus, U., Hankimo, T., Karikoski, N., Pakkanen, S., Laine, H., Sillanpää, H., Söderholm, H., Palva, A. Probiotic properties of *Lactobacillus* isolates originating from porcine intestine and feces (2010). Anaerobe, 16 (3), pp. 293-300

Liu, Y., Fatheree, N. Y., Mangalat, N., Rhoads, J. M. Human-derived probiotic *Lactobacillus reuteri* strains differentially reduce intestinal inflammation (2010). *American Journal of Physiology—Gastrointestinal and Liver Physiology*, 299 (5), pp. G1087-G1096.

Ljungh, A., Wadström, T. Lactic acid bacteria as probiotics (2006). *Current Issues in Intestinal Microbiology*, 7 (2), pp. 73-90.

Martin, R, Delgado, S, Maldonado, A, Jiménez, E, Olivares, M, Fernandez, L, Sobrino, O J, Rodriguez, J M. Isolation of lactobacilli from sow milk and evaluation of their probiotic potential (2009). Journal of Dairy Research, 76 (4), pp. 418-425.

Mulder I E, Schmidt B, Stokes C R, Lewis M, Bailey M, Aminov R I, Prosser J I, Gill B P, Pluske J R, Mayer C D, Musk C C, Kelly D. Environmentally-acquired bacteria influence microbial diversity and natural innate immune responses at gut surfaces (2009). BMC Biol. 7:79.

Naughton P J; Grant G. (2005) Modelling of salmonellosis In: Microbial Ecology of the Growing Animal Holzapfel W H, Naughton P J. (Eds). London, Elsevier. pp. 235-257

Neeser, J.-R., Granato, D., Rouvet, M., Servin, A., Teneberg, S., Karlsson, K.-A. *Lactobacillus johnsonii* La1 shares carbohydrate-binding specificities with several enteropathogenic bacteria (2000). Glycobiology, 10 (11), pp. 1193-1199.

Nicolau, D. P. Current challenges in the management of the infected patient (2011). *Current Opinion in Infectious Diseases*, 24 (Suppl 1), pp. S1-S10.

Ohashi, Y., Ushida, K. Health-beneficial effects of probiotics: Its mode of action (2009). Animal Science Journal, 80 (4), pp. 361-371.

Reddy, K. B. P. K., Awasthi, S. P., Madhu, A. N., Prapulla, S. G. Role of cryoprotectants on the viability and functional properties of probiotic lactic acid bacteria during freeze drying (2009). *Food Biotechnology*, 23 (3), pp. 243-265.

Robertson, J. M. C., McKenzie, N. H., Duncan, M., Allen-Vercoe, E., Woodward, M. J., Flint, H. J., Grant, G. Lack of flagella disadvantages *Salmonella enterica* serovar *Enteritidis* during the early stages of infection in the rat (2003). Journal of Medical Microbiology, 52 (1), pp. 91-99.

Schreiber, O., Petersson, J., Phillipson, M., Perry, M., Roos, S., Holm, L. *Lactobacillus reuteri* prevents colitis by reducing P-selectin-associated leukocyte- and platelet-endothelial cell interactions (2009). American Journal of Physiology—Gastrointestinal and Liver Physiology, 296 (3), pp. G534-G542.

Smith, C. L., Geier, M. S., Yazbeck, R., Torres, D. M., Butler, R. N., Howarth, G. S. *Lactobacillus fermentum* BR11 and fructo-oligosaccharide partially reduce jejunal inflammation in a model of intestinal mucositis in rats (2008). Nutrition and Cancer, 60 (6), pp. 757-767.

Strasser, S., Neureiter, M., Geppl, M., Braun, R., Danner, H. Influence of lyophilization, fluidized bed drying, addition of protectants, and storage on the viability of lactic acid bacteria (2009). *Journal of Applied Microbiology*, 107 (1), pp. 167-177.

Tomas, M. S. J., Bru, E., Martos, G., Nader-Macias, M. E. Stability of freeze-dried vaginal *Lactobacillus* strains in the presence of different lyoprotectors (2009). *Canadian Journal of Microbiology*, 55 (5), pp. 544-552.

Tzortzis, G., Baillon, M.-L. A., Gibson, G. R., Rastall, R. A. Modulation of anti-pathogenic activity in canine-derived *Lactobacillus* species by carbohydrate growth substrate (2004). Journal of Applied Microbiology, 96 (3), pp. 552-559.

Williams, N. T. Probiotics (2010). *American Journal of Health-System Pharmacy,* 67 (6), pp. 449-458.

Yao, W., Zhu Wei-yun, W.-Y., Smidt, H., Verstegen, M. W. A. Cultivation-Independent Analysis of the Development of the *Lactobacillus* spp. Community in the Intestinal Tract of Newborn Piglets (2011) *Agricultural Sciences in China,* 10 (3), pp. 438-447.

Yun, J. H., Lee, K. B., Sung, Y. K., Kim, E. B., Lee, H.-G., Choi, Y. J. Isolation and characterization of potential probiotic lactobacilli from pig feces (2009). Journal of Basic Microbiology, 49 (2), pp. 220-226.

The invention claimed is:

1. A solid pharmaceutical composition that comprises at least $10^3$ colony forming units (CFU) of at least one *Lactobacillus* bacteria strain, and a pharmaceutically acceptable excipient, diluent, or carrier,
   wherein the at least one *Lactobacillus* bacteria strain comprises a polynucleotide of a 16S rRNA gene having at least 95% identity to the polynucleotide of SEQ ID NO: 41, as determined by sequence alignment performed using BLAST, and
   wherein the solid pharmaceutical composition is a formulation in unit dose form.

2. The solid pharmaceutical composition of claim 1, wherein the solid pharmaceutical composition is lyophilized.

3. The solid pharmaceutical composition of claim 1, wherein the solid pharmaceutical composition is encapsulated in one or more capsules.

4. The solid pharmaceutical composition of claim 1, wherein the solid pharmaceutical composition further comprises a preservative or stabilizer.

5. The solid pharmaceutical composition of claim 1, wherein the solid pharmaceutical composition comprises from about $10^3$ to about $10^{11}$ colony forming units (CFU) of the at least one *Lactobacillus* bacteria strain per gram of the solid pharmaceutical composition.

6. The solid pharmaceutical composition of claim 1, wherein the at least one *Lactobacillus* bacteria strain exhibits at least one characteristic selected from the group consisting of:
   (i) antimicrobial activity against *E. coli*;
   (ii) antimicrobial activity against *S. enteritidis*;
   (iii) suppression of inflammation in intestinal pig epithelial cells (IPEC) induced by 12-0-tetradecaboylphorbol-13-acetate (PMA);
   (iv) an ability to block the adherence or invasion of the IPEC by *S. enteritidis*;
   (v) an ability to block the adherence or invasion of the IPEC by *E. coli*; and
   (vi) absence of antibiotic resistance to an antibiotic selected from the group consisting of: ampicillin; cefotaxime; chloramphenicol; erythromycin; gentamicin; tetracycline; vancomycin; metronizadole; nalidixic acid; and kanamycin.

7. The solid pharmaceutical composition of claim 1, wherein the at least one *Lactobacillus* bacteria strain exhibits at least two characteristics selected from the group of claim 6.

8. The solid pharmaceutical composition of claim 1, wherein the at least one *Lactobacillus* bacteria strain exhibits at least three characteristics selected from the group of claim 6.

9. The solid pharmaceutical composition of claim 1, wherein the at least one *Lactobacillus* bacteria strain exhibits at least four characteristics selected from the group of claim 6.

10. The solid pharmaceutical composition of claim 1, wherein the at least one *Lactobacillus* bacteria strain is of a species selected from the group consisting of *Lactobacillus johnsonii, Lactobacillus reuteri, Lactobacillus plantarum, Lactobacillus paraplantarum, Lactobacillus gasseri, Lactobacillus pentosus, Lactobacillus helveticus, Lactobacillus acidophilus, Lactobacillus vaginalis, Lactobacillus mucosae*, and any combination thereof.

11. A solid pharmaceutical composition that comprises:
at least $10^3$ colony forming units (CFU) of at least one bacteria strain of a species selected from the group consisting of *Lactobacillus paraplantarum, Lactobacillus pentosus, Lactobacillus helveticus*, and any combination thereof; and
a pharmaceutically acceptable excipient, diluent, or carrier, wherein the solid pharmaceutical composition is a formulation in unit dose form.

12. The solid pharmaceutical composition of claim 11, wherein the solid pharmaceutical composition is lyophilized.

13. The solid pharmaceutical composition of claim 11, wherein the solid pharmaceutical composition is encapsulated in one or more capsules.

14. The solid pharmaceutical composition of claim 11, wherein the solid pharmaceutical composition further comprises a preservative or stabilizer.

15. The solid pharmaceutical composition of claim 11, wherein the solid pharmaceutical composition comprises from about $10^3$ to about $10^{11}$ colony forming units (CFU) of the at least one bacteria strain per gram of the solid pharmaceutical composition.

16. A method of treating an intestinal disorder in a subject, the method comprising administering to the subject a solid pharmaceutical composition that comprises at least $10^3$ colony forming units (CFU) of at least one *Lactobacillus* bacteria strain, and a pharmaceutically acceptable excipient, diluent, or carrier,
wherein the at least one *Lactobacillus* bacteria strain comprises a polynucleotide of a 16S rRNA gene having at least 95% identity to the polynucleotide of SEQ ID NO: 41, as determined by sequence alignment performed using BLAST, and wherein the solid pharmaceutical composition is a formulation in unit dose form.

17. The method of claim 16, wherein the intestinal disorder is selected from the group consisting of *salmonellosis*, irritable bowel syndrome (IBS), inflammatory bowel disease (IBD), functional dyspepsia, functional constipation, functional diarrhea, functional abdominal pain, functional bloating, Epigastric Pain Syndrome, Postprandial Distress Syndrome, Crohn's disease, ulcerative colitis, gastroesophageal reflux disease (GERD), necrotizing enterocolitis, and any combination thereof.

18. The method of claim 16, wherein the at least one *Lactobacillus* bacteria strain is of a species selected from the group consisting of *Lactobacillus johnsonii, Lactobacillus reuteri, Lactobacillus plantarum, Lactobacillus paraplantarum, Lactobacillus gasseri, Lactobacillus pentosus, Lactobacillus helveticus, Lactobacillus acidophilus, Lactobacillus vaginalis, Lactobacillus mucosae*, and any combination thereof.

19. The method of claim 16, wherein the administering is oral.

20. The method of claim 16, wherein the subject is human.

* * * * *

```
                             SEQUENCE LISTING

<160> NUMBER OF SEQ ID NOS: 92

<210> SEQ ID NO 1
<211> LENGTH: 698
<212> TYPE: DNA
<213> ORGANISM: Lactobacillus sp.
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (627)..(627)
<223> OTHER INFORMATION: a, c, t, g, unknown or other
<220> FEATURE:
<221> NAME/KEY: modified_base
<222> LOCATION: (695)..(695)
<223> OTHER INFORMATION: a, c, t, g, unknown or other

<400> SEQUENCE: 1
ggtggagcat gtggtttaat tcgaagctac gcgaagaacc ttaccaggtc ttgacatctt      60
gcgctaacct tagagataag gcgttccctt cggggacgca atgacaggtg gtgcatggtc     120
gtcgtcagct cgtgtcgtga gatgttgggt taagtcccgc aacgagcgca acccttgtta     180
ctagttgcca gcattaagtt gggcactcta gtgagactgc cggtgacaaa ccggaggaag     240
gtggggacga cgtcagatca tcatgcccct tatgacctgg gctacacacg tgctacaatg     300
gacggtacaa cgagtcgcaa gctcgcgaga gtaagctaat ctcttaaagc cgttctcagt     360
tcggactgta ggctgcaact cgcctacacg aagtcggaat cgctagtaat cgcggatcag     420
catgccgcgg tgaatacgtt cccgggcctt gtacacaccg cccgtcacac catgggagtt     480
tgtaacgccc aaagtcggtg gcctaaccat tatggaggga gccgcctaag tgcgggacag     540
atgactgggg tgaagtcgta acaaggtagc ctgtattttc ttgcggttgt tccccccccn     600
ggcgggactg ccttactcct ttcaccnccc gcgccctgg aggggccgg aaccccctc       660 ccaaccccc taacccacct ccttcctttt aaccngct                             698

<210> SEQ ID NO 2
<211> LENGTH: 766
<212> TYPE: DNA
<213> ORGANISM: Lactobacillus sp.
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (538)..(538)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (751)..(751)
<223> OTHER INFORMATION: a, c, t, g, unknown or other

<400> SEQUENCE: 2
```

```
gactttctag gttggatacc gtcactgcgt gaacagttac tctcacgcac gttcttctcc    60
aacaacagag ctttacgagc cgaaacccct cttcactcac gcggtgttgc tccatcaggc   120
ttgcgcccat tgtggaagat tccctactgc tgcctcccgt aggagtatgg accgtgtctc   180
agttccattg tggccgatca gtctctcaac tcggctatgc atcatcgcct tggtaagccg   240
ttaccttacc aactagctaa tgcaccgcag gtccatccca gagtgatagc caaagccatc   300
tttcaaacaa aagccatgtg cttttgttg ttatgcggta ttagcatctg tttccaaatg    360 ttatccccg ctccggggca ggttacctac gtgttactca cccgtccgcc actcactggt    420
gatccatcgt caatcaggtg caagcaccat caatcagttg gccagtgcg tacgacttgc    480 atgtattagg cacaccgccg gcgttcatcc tgagccatga tcaaactcta ngcgtcantt   540
ttacggtctc ggctcgtttc tctgttntct gacatcaacg tgcgttacat ttgcggttta   600
cgcattgatt gtactccctc cacataggtg gcggcatacc cttcgtgctc ctctactcat   660
ctcgttcatt acaactcgct ttgttaccttc ccggtgggg ttctctacct ccttcgtttt   720
ctctcacctc attctctctc ccatcctctc ntctttcctc ttgctc                  766

<210> SEQ ID NO 3
<211> LENGTH: 674
<212> TYPE: DNA
<213> ORGANISM: Lactobacillus sp.

<400> SEQUENCE: 3
ggtggagcat gtggtttaat tcgaagctac gcgaagaacc ttaccaggtc ttgacatact    60
atgcaaatct aagagattag acgttccctt cggggacatg gatacaggtg gtgcatggtt   120
gtcgtcagct cgtgtcgtga gatgttgggt taagtcccgc aacgagcgca acccttatta   180
tcagttgcca gcattaagtt gggcactctg gtgagactgc cggtgacaaa ccggaggaag   240
gtggggatga cgtcaaatca tcatgcccct tgatgacctg ggctacacac gtgctacaat   300
ggatggtaca acgagttgcg aactcgcgag agtaagctaa tctcttaaag ccattctcag   360
ttacggatgt gtaggctgca actcgcctata catgaagtcg gaatcgctag taatcgcgga   420
tacagcatgc cgcggtgaat actgttcccg ggcctatgtg acacaccgcc cgtcacacca   480
tgagcagttt gtaatcaccc acacagtcgg tggggtaacc tttataggaa ccagccgcct   540
acagtgcggg accgatgatt atgggtgcac tcgtatcact gtaacttaaa cccttgcggc   600
cgtactcccc aggcggaatg cttaatacgt tacctgcaac cctgaagggc ggaatccctc   660
caacgattat caat                                                    674

<210> SEQ ID NO 4
<211> LENGTH: 697
<212> TYPE: DNA
<213> ORGANISM: Lactobacillus sp.
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (653)..(653)
<223> OTHER INFORMATION: a, c, t, g, unknown or other

<400> SEQUENCE: 4
gtggctttct ggttaaatac cgtcaatacc tgaacagtta ctctcagata tgttcttctt    60
taacaacaga gttttacgag ccgaaaccct tcttcactca cgcggcgttg ctccatcaga   120
ctttcgtcca ttgtggaaga ttccctactg ctgcctcccg taggagtttg gccgtgtct    180
```

```
cagtcccaat gtggccgatt accctctcag gtcggctacg tatcattgcc atggtgagcc    240
gttaccccac catctagcta atacgccgcg ggaccatcca aaagtgatag ccgaagccat    300
ctttcaagct cggaccatgc ggtccaagtt gttatgcggt attagcatct gtttccaggt    360
gttatccccc gcttctgggc aggtttccca cgtgttactc accagttcgc cactcactca    420
aatgtaaatc atgatgcaag caccaatcaa taccaaagtt cgttcgactt gcatgtatta    480
ggcacgccgc cagcgttcgt cgctgagcca tgatcaaact actaaaggcc ccnatgcct    540 cccacccgct tgttgccgg ggcccccgt tcccataccc cttttggacg ttttccagcc    600
ccttggcggg ccctgtacct cccccagg cggggaatgc cttaattgcg ttnaccttgc    660
accccctgaa ggggcggaat ccctccaacg attacct                            697
```

<210> SEQ ID NO 5
<211> LENGTH: 653
<212> TYPE: DNA
<213> ORGANISM: Lactobacillus sp.

<400> SEQUENCE: 5

```
ggtggagcat gtggtttaat tcgaagcaac gcgaagaacc ttaccaggtc ttgacatcca     60
gtcgcataac ctaagagatt aggtgttccc ttcggggacg ctgagacagg tggtgcatgg    120
ctgtcgtcag ctcgtgtcgt gagatgttgg gttaagtccc gcaacgagcg caacccttgt    180
cattagttgc catcattaag ttgggcactc taatgagact gccggtgaca accggagga    240 aggtggggat gacgtcaaga tcatcatgcc ccttatgacc tgggctacac acgtgctaca    300
atggacggta caacgagata gcgaacctgc gaagagctaa gcggatctct aaagccgtt    360 ctcagttcgg actgtaggct gcaactcgcc tacacgaagc ttggaatcgc tagtaatcgc    420
ggatcagcac tgccgcggtg aatacgttcc cgggccttgt acacaccgcc cgtcacacca    480
tgagagtctg taactcccaa agtcggtggg ataaccttct atagcgagtg agtccgttcg    540
atgggtaggg acaagatgaa tgagcggtga aaggtcgtta aaccaagggt agcaagtaag    600
gatccctttg ggggttttat ctccacgggg ggggtgtttc ttttctgtct tta           653
```

<210> SEQ ID NO 6
<211> LENGTH: 717
<212> TYPE: DNA
<213> ORGANISM: Lactobacillus sp.
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (466)..(466)
<223> OTHER INFORMATION: a, c, t, g, unknown or other
<220> FEATURE:
<221> NAME/KEY: modified_base
<222> LOCATION: (482)..(482)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (557)..(557)
<223> OTHER INFORMATION: a, c, t, g, unknown or other
<220> FEATURE:
<221> NAME/KEY: modified_base
<222> LOCATION: (584)..(584)
<223> OTHER INFORMATION: a, c, t, g, unknown or other
<220> FEATURE:

```
<221> NAME/KEY: modified_base
<222> LOCATION: (586)..(586)
<223> OTHER INFORMATION: a, c, t, g, unknown or other
<220> FEATURE:
<221> NAME/KEY: modified_base
<222> LOCATION: (613)..(613)
<223> OTHER INFORMATION: a, c, t, g, unknown or other

<400> SEQUENCE: 6
actttctaga gttagatgat accgttcaac atgacagatg ccacgttta cttactctca      60
ctgactactg ttctttcatc tcacacaaca gagctttacg agccgaaacc cttcttcact    120
cacgcggcgt tgctccatca gagctttgcg tcccattgtg gaagattccc tactgctgcc    180
tcccgtagga gtatgggccg tgtctcagtc ccattgtggc cgatcagtct ctcaactcgg    240
ctatgcatca tcgccttggt aagccgttac cttaccaact agctaatgca ccgcaggtcc    300
atccaagagt gatagccgaa ccatctttca caactctaaa catgcttgta gtgttgttat    360
tccggtatta acattctgtt tccaggttgt tattcccagc tgctctcggg cagggttta     420
ccccaacgtt ggtttacctt caccccggt tncggcccgg cttcgncctt gggttagtac     480
tnacgattct gctattatat acgatgggct agacgaccag cctaacacaa tttcaatttc    540
gtnaagtgtc gagaggncct acggtcgtcc cgttaacgtg tagncnattt ggcttatttg    600
ttaagttgtc cancgggcca ccgaccccca gggcccggtt ggtccgggtt tcccccattg    660
caacgtcgcc aaagtgcgga aatttcgaaa ataccccttaa ccaatgaaaa aaacata      717

<210> SEQ ID NO 7
<211> LENGTH: 620
<212> TYPE: DNA
<213> ORGANISM: Lactobacillus sp.
<220> FEATURE:
<221> NAME/KEY: modified_base
<222> LOCATION: (601)..(601)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (605)..(606)
<223> OTHER INFORMATION: a, c, t, g, unknown or other
<220> FEATURE:
<221> NAME/KEY: modified_base
<222> LOCATION: (609)..(617)
<223> OTHER INFORMATION: a, c, t, g, unknown or other

<400> SEQUENCE: 7
ggtggagcat gtggtttaat tcgaagctac gcgaagaacc ttaccaggtc ttgacatact      60
atgcaaatct aagagattag acgttccctt cggggacatg gatacaggtg gtgcatggtt    120
gtcgtcagct cgtgtcgtga gatgttgggg ttaagtcccg caacgagcgc aaccccttatt  180
atcagttgcc agcattaagt tgggcactct ggtgagactg ccggtgacaa accggaggaa    240
ggtggggatg acgtcaaatc atcatgcccc ttatgacctg gctacacac gtgctacaat    300
ggatggtaca acgagttgcg aactcgcgag agtaagctaa tctcttaaag ccattctcag    360
ttcggattgt aggctgcaac tcgcctacat gaagtcggaa tcgctagtaa tcgcggatca    420
gcatgccgcg gtgaatacgt tcccgggcct tgtacacacc gcccgtcaca ccatgagagt    480
ttgtaacacc caaagtcggt gggggtaacc ttttaggaa accagccgc cctaaagggt     540
ggggaacaag aatgaattag ggggttgaaa agttccgtta aaccaaaagg ggttagcccc    600
ngntnngann nnnnnnngac                                                620
```

<210> SEQ ID NO 8
<211> LENGTH: 526
<212> TYPE: DNA
<213> ORGANISM: Lactobacillus sp.
<220> FEATURE:
<221> NAME/KEY: modified_base
<222> LOCATION: (524)..(524)
<223> OTHER INFORMATION: a, c, t, g, unknown or other

<400> SEQUENCE: 8

```
gctttctggt taaataccgt caatacctga acagttactc tcagatatgt gtcttcttta      60
acaacagagt tttacgagcc gaaacccttc ttcactcacg cggcgttgct ccatcagact     120
ttcgtccatt gtggaagatt ccctactgct gcctcccgta ggagtttggg ccgtgtctca     180
gtcccaatgt ggccgattac cctctcaggt cggctacgta tcattgccat ggtgagccgt     240
tacccccacc atctagctaa tacgccgcgg gaccatccaa aagtgatagc cgaagccatc     300
tttcaagctc ggaccatgcg gtccaagttg ttatgcggta ttagcatctg tttccagggt     360
gttattcccc cgcttcgtgg gcagggtttc ccacgtgtta ctcaccagtt cgccactcac     420
tcaaatgtaa atcatgatgc aagcaccaat caataccaga gttcgttcga cttgcatgta     480
ttaggcacgc cgccagcgtt cgtcctgagc catgatcaaa ctcnga                    526
```

<210> SEQ ID NO 9
<211> LENGTH: 533
<212> TYPE: DNA
<213> ORGANISM: Lactobacillus sp.

<400> SEQUENCE: 9

```
gtgactttct aagtaattac cgtcaaataa atggccagtt actacctcta tctttcttca      60
ctaccaacag agctttacga gccgaaaccc ttcttcactc acgcggcgtt gctccatcag     120
actttcgtcc attgtggaag attccctact gctgcctccc gtaggagttt gggccgtgtc     180
tcagtcccaa tgtggccgat cagtctctca actcggctat gcatcattgc cttggtaagc     240
cgttacctta ccaactagct aatgcaccgc aggtccatcc aagagtgata gcagaaccat     300
ctttcaaact ctagacatgc gtctagtgtt gttatccggt attagcatct gtttccaggt     360
gttatcccag tctcttgggc aggttaccca cgtgttactc acccgtccgc cgctcgcttg     420
tatctagttt catttagtgc aagcaccaaa atcatctagg caagctcgct cgacttgcat     480
gtattaggca cgccgccagc gttcgtcctg agccaggatc gaactctaac taa            533
```

<210> SEQ ID NO 10
<211> LENGTH: 668
<212> TYPE: DNA
<213> ORGANISM: Lactobacillus reuteri

<400> SEQUENCE: 10

```
tgcctaatac atgcaagtcg tacgcactgg cccaactgat tgatggtgct tgcacctgat      60
tgacgatgga tcaccagtga gtggcggacg ggtgagtaac acgtaggtaa cctgccccgg     120
agcgggggat aacatttgga aacagatgct aataccgcat aacaacaaaa gccacatggc     180
ttttgtttga aagatggctt tggctatcac tctgggatgg acctgcggtg cattagctag     240
ttggtaaggt aacggcttac caaggcgatg atgcatagcc gagttgagag actgatcggc     300
cacaatggaa ctgagacacg gtccatactc ctacgggagg cagcagtagg gaatcttcca     360
caatgggcgc aagcctgatg gagcaacacc gcgtgagtga agaagggttt cggctcgtaa     420
```

```
agctctgttg ttggagaaga acgtgcgtga gagtaactgt tcacgcagtg acggtatcca    480
accagaaagt cacggctaac tacgtgccag cagccgcggt aatacgtagg tggcaagcgt    540
tatccggatt tattgggcgt aaagcgagcg caggcggttg cttaggtctg atgtgaaagc    600
cttcggctta accgaagaag tgcatcggaa accgggcgac ttgagtgcag aagaggacag    660
tggaactc                                                             668

<210> SEQ ID NO 11
<211> LENGTH: 671
<212> TYPE: DNA
<213> ORGANISM: Lactobacillus reuteri

<400> SEQUENCE: 11
tcggatttat tgggcgtaaa gcgagcgcag gcggttgctt aggtctgatg tgaaagcctt     60
cggcttaacc gaagaagtgc atcggaaacc gggcgacttg agtgcagaag aggacagtgg    120
aactccatgt gtagcggtgg aatgcgtaga tatatggaag aacaccagtg gcgaaggcgg    180
ctgtctggtc tgcaactgac gctgaggctc gaaagcatgg gtagcgaaca ggattagata    240
ccctggtagt ccatgccgta aacgatgagt gctaggtgtt ggagggtttc cgcccttcag    300
tgccggagct aacgcattaa gcactccgcc tggggagtac gaccgcaagg ttgaaactca    360
aaggaattga cgggggcccg cacaagcggt ggagcatgtg gtttaattcg aagctacgcg    420
aagaacctta ccaggtcttg acatcttgcg ctaaccttag agataaggcg ttcccttcgg    480
ggacgcaatg acaggtggtg catggtcgtc gtcagctcgt gtcgtgagat gttgggttaa    540
gtcccgcaac gagcgcaacc cttgttacta gttgccagca ttaagttggg cactctagtg    600
agactgccgg tgacaaaccg gaggaaggtg gggacgacgt cagatcatca tgccccttat    660
gacctgggct a                                                         671

<210> SEQ ID NO 12
<211> LENGTH: 569
<212> TYPE: DNA
<213> ORGANISM: Lactobacillus reuteri

<400> SEQUENCE: 12
gagcatgtgg tttaattcga agctacgcga agaaccttac caggtcttga catcttgcgc     60
taaccttaga gataaggcgt tcccttcggg gacgcaatga caggtggtgc atggtcgtcg    120
tcagctcgtg tcgtgagatg ttgggttaag tcccgcaacg agcgcaaccc ttgttactag    180
ttgccagcat taagttgggc actctagtga gactgccggt gacaaaccgg aggaaggtgg    240
ggacgacgtc agatcatcat gccccttatg acctggctgca cacgtgct acaatggacg    300 gtacaacgag tcgcaagctc gcgagagtaa gctaatctct taaagccgtt ctcagttcgg    360
actgtaggct gcaactcgcc tacacgaagt cggaatcgct agtaatcgcg gatcagcatg    420
ccgcggtgaa tacgttcccg ggccttgtac acaccgcccg tcacaccatg ggagtttgta    480
acgcccaaag tcggtggcct aaccattatg agggagccgc ctaaggcgg acagatgac     540 tggggtgaag tcgtaacaag gtagccgta                                      569

<210> SEQ ID NO 13
<211> LENGTH: 724
<212> TYPE: DNA
<213> ORGANISM: Lactobacillus reuteri

<400> SEQUENCE: 13
ctccccaggc ggagtgctta atgcgttagc tccggcactg aagggcggaa accctccaac     60
```

```
acctagcact catcgtttac ggcatggact accagggtat ctaatcctgt tcgctaccca    120
tgctttcgag cctcagcgtc agttgcagac cagacagccg ccttcgccac tggtgttctt    180
ccatatatct acgcattcca ccgctacaca tggagttcca ctgtcctctt ctgcactcaa    240
gtcgcccggt ttccgatgca cttcttcggt taagccgaag gctttcacat cagacctaag    300
caaccgcctg cgctcgcttt acgcccaata atccggata acgcttgcca cctacgtatt     360
accgcggctg ctggcacgta gttagccgtg actttctggt tggataccgt cactgcgtga    420
acagttactc tcacgcacgt tcttctccaa caacagagct ttacgagccg aaacccttct    480
tcactcacgc ggtgttgctc catcaggctt gcgcccattg tggaagattc cctactgctg    540
cctcccgtag gagtatggac cgtgtctcag ttccattgtg ccgatcagt ctctcaactc     600 ggctatgcat catcgccttg gtaagccgtt accttaccaa ctagctaatg caccgcaggt    660
ccatcccaga gtgatagcca aagccatctt tcaaacaaaa gccatgtggc ttttgttgtt    720
atgc                                                                 724

<210> SEQ ID NO 14
<211> LENGTH: 522
<212> TYPE: DNA
<213> ORGANISM: Lactobacillus reuteri

<400> SEQUENCE: 14
tttctggttg gataccgtca ctgcgtgaac agttactctc acgcacgttc ttctccaaca     60
acagagcttt acgagccgaa acccttcttc actcacgcgg tgttgctcca tcaggcttgc    120
gcccattgtg gaagattccc tactgctgcc tcccgtagga gtatggaccg tgtctcagtt    180
ccattgtggc cgatcagtct ctcaactcgg ctatgcatca tcgccttggt aagccgttac    240
cttaccaact agctaatgca ccgcaggtcc atcccagagt gatagccaaa gccatctttc    300
aaacaaaagc catgtggctt tgttgttat gcggtattag catctgtttc caaatgttat     360
cccccgctcc ggggcaggtt acctacgtgt tactcacccg tccgccactc actggtgatc    420
catcgtcaat caggtgcaag caccatcaat cagttgggcc agtgcgtacg acttgcatgt    480
attaggcaca ccgccggcgt tcatcctgag ccatgatcaa ac                       522

<210> SEQ ID NO 15
<211> LENGTH: 681
<212> TYPE: DNA
<213> ORGANISM: Lactobacillus reuteri

<400> SEQUENCE: 15
ccgccttagg cggctccctc cataatggtt aggccaccga ctttgggcgt tacaaactcc     60
catggtgtga cggcggtgt gtacaaggcc cgggaacgta ttcaccgcgg catgctgatc     120
cgcgattact agcgattccg acttcgtgta ggcgagttgc agcctacagt ccgaactgag    180
aacggcttta agagattagc ttactctcgc gagcttgcga ctcgttgtac cgtccattgt    240
agcacgtgtg tagcccaggt cataagggc atgatgatct gacgtcgtcc ccaccttcct     300
ccggtttgtc accggcagtc tcactagagt gcccaactta atgctggcaa ctagtaacaa    360
gggttgcgct cgttgcggga cttaacccaa catctcacga cacgagctga cgacgaccat    420
gcaccacctg tcattgcgtc cccgaaggga acgccttatc tctaaggtta gcgcaagatg    480
tcaagacctg gtaaggttct tcgcgtagct tcgaattaaa ccacatgctc accgcttgt     540 gcgggccccc gtcaattcct ttgagtttcc accttgcggt cgtactcccc aggcggagtg    600
```
cttaatgcgt tagctccggc actgaagggc ggaaaccctc aacacctag cactcatcgt    660 ttacggcatg gactaccagg g    681

<210> SEQ ID NO 16
<211> LENGTH: 682
<212> TYPE: DNA
<213> ORGANISM: Lactobacillus plantarum

<400> SEQUENCE: 16
gtgcctaata catgcaagtc gaacgaactc tggtattgat tggtgcttgc atcatgattt    60
acatttgagt gagtggcgaa ctggtgagta acacgtggga aacctgccca gaagcggggg    120
ataacacctg gaaacagatg ctaataccgc ataacaactt ggaccgcatg gtccgagttt    180
gaaagatggc ttcggctatc acttttggat ggtcccgcgg cgtattagct agatggtgag    240
gtaacggctc accatggcaa tgatacgtag ccgacctgag agggtaatcg ccacattgg    300 gactgagaca cggcccaaac tcctacggga ggcagcagta gggaatcttc cacaatggac    360
gaaagtctga tggagcaacg ccgcgtgagt gaagaagggt ttcggctcgt aaaactctgt    420
tgttaaagaa gaacatatct gagagtaact gttcaggtat tgacggtatt taaccagaaa    480
gccacggcta actacgtgcc agcagccgcg gtaatacgta ggtggcaagc gttgtccgga    540
tttattgggc gtaaagcgag cgcaggcggt tttttaagtc tgatgtgaaa gccttcggct    600
caaccgaaga agtgcatcgg aaactgggaa gcttgagtgc agaagaggac agtggaactc    660
catgtgtagc ggtgaaatgc gt    682

<210> SEQ ID NO 17
<211> LENGTH: 621
<212> TYPE: DNA
<213> ORGANISM: Lactobacillus plantarum

<400> SEQUENCE: 17
cggatttatt gggcgtaaag cgagcgcagg cggttttttta agtctgatgt gaaagccttc    60
ggctcaaccg aagaagtgca tcggaaactg gaaacttga gtgcagaaga ggacagtgga    120
actccatgtg tagcggtgaa atgcgtagat atatggaaga acaccagtgg cgaaggcggc    180
tgtctggtct gtaactgacg ctgaggctcg aaagtatggg tagcaaacag gattagatac    240
cctggtagtc cataccgtaa acgatgaatg ctaagtgttg gagggtttcc gcccttcagt    300
gctgcagcta acgcattaag cattccgcct ggggagtacg gccgcaaggc tgaaactcaa    360
aggaattgac gggggcccgc acaagcggtg gagcatgtgg tttaattcga agctacgcga    420
agaaccttac caggtcttga catactatgc aaatctaaga gattagacgt tcccttcggg    480
gacatggata caggtggtgc atggttgtcg tcagctcgtg tcgtgagatg ttgggttaag    540
tcccgcaacg agcgcaaccc ttattatcag ttgccagcat taagttgggc actctggtga    600
gactgccggt gacaaaccgg a    621

<210> SEQ ID NO 18
<211> LENGTH: 572
<212> TYPE: DNA
<213> ORGANISM: Lactobacillus plantarum

<400> SEQUENCE: 18
tggagcatgt ggtttaattc gaagctacgc gaagaacctt accaggtctt gacatactat    60
gcaaatctaa gagattagac gttcccttcg gggacatgga tacaggtggt gcatggttgt    120
cgtcagctcg tgtcgtgaga tgttgggtta agtcccgcaa cgagcgcaac ccttattatc    180

```
agttgccagc attaagttgg gcactctggt gagactgccg gtgacaaacc ggaggaaggt      240
ggggatgacg tcaaatcatc atgccccta tgacctgggc tacacacgtg ctacaatgga      300
tggtacaacg agttgcgaac tcgcgagagt aagctaatct cttaaagcca ttctcagttc      360
ggattgtagg ctgcaactcg cctacatgaa gtcggaatcg ctagtaatcg cggatcagca      420
tgccgcggtg aatacgttcc cgggccttgt acacaccgcc cgtcacacca tgagagtttg      480
taacacccaa agtcggtggg gtaaccttt aggaaccagc cgcctaaggt gggacagatg      540
attagggtga agtcgtaaca aggtagcccg ta                                    572

<210> SEQ ID NO 19
<211> LENGTH: 720
<212> TYPE: DNA
<213> ORGANISM: Lactobacillus plantarum

<400> SEQUENCE: 19
actccccagg cggaatgctt aatgcgttag ctgcagcact gaagggcgga aaccctccaa       60
cacttagcat tcatcgttta cggtatggac taccagggta tctaatcctg tttgctaccc      120
atactttcga gcctcagcgt cagttacaga ccagacagcc gccttcgcca ctggtgttct      180
tccatatatc tacgcattc accgctacac atggagttcc actgtcctct tctgcactca      240
agtttcccag tttccgatgc acttcttcgg ttgagccgaa ggctttcaca tcagacttaa      300
aaaaccgcct gcgctcgctt tacgcccaat aaatccggac aacgcttgcc acctacgtat      360
taccgcggct gctggcacgt agttagccgt ggctttctgg ttaaataccg tcaatacctg      420
aacagttact ctcagatatg ttcttcttta acaacagagt tttacgagcc gaaaccttc       480 ttcactcacg cggcgttgct ccatcagact ttcgtccatt gtggaagatt ccctactgct      540
gcctcccgta ggagtttggg ccgtgtctca gtcccaatgt ggccgattac cctctcaggt      600
cggctacgta tcattgccat ggtgagccgt taccccacca tctagctaat acgccgcggg      660
accatccaaa agtgatagcc gaagccatct ttcaaactcg gaccatgcgg tccaagttgt      720

<210> SEQ ID NO 20
<211> LENGTH: 519
<212> TYPE: DNA
<213> ORGANISM: Lactobacillus plantarum

<400> SEQUENCE: 20
gctttctggt taaataccgt caatacctga acagttactc tcagatatgt tcttctttaa       60
caacagagtt ttacgagccg aaaaccttct tcactcacgc ggcgttgctc catcagactt      120
tcgtccattg tggaagattc cctactgctg cctcccgtag gagtttgggc cgtgtctcag      180
tcccaatgtg gccgattacc ctctcaggtc ggctacgtat cattgccatg gtgagccgtt      240
accccaccat ctagctaata cgccgcggga ccatccaaaa gtgatagccg aagccatctt      300
tcaaactcgg accatgcggt ccaagttgtt atgcggtatt agcatctgtt ccaggtgtt      360 atccccgct tctgggcagg tttcccacgt gttactcacc agttcgccac tcactcaaat      420
gtaaatcatg atgcaagcac caatcaatac caaagttcgt tcgacttgca tgtattaggc      480
acgccgccag cgttcgtcct gagccagatc aaactctaa                             519

<210> SEQ ID NO 21
<211> LENGTH: 687
<212> TYPE: DNA
<213> ORGANISM: Lactobacillus plantarum
```

<400> SEQUENCE: 21

```
ccaccttagg cggctggttc ctaaaaggtt accccaccga ctttgggtgt tacaaactct    60
catggtgtga cgggcggtgt gtacaaggcc cgggaacgta ttcaccgcgg catgctgatc   120
cgcgattact agcgattccg acttcatgta ggcgagttgc agcctacaat ccgaactgag   180
aatggcttta agagattagc ttactctcgc gagttcgcaa ctcgttgtac catccattgt   240
agcacgtgtg tagcccaggt cataaggggc atgatgattt gacgtcatcc ccaccttcct   300
ccggtttgtc accggcagtc tcaccagagt gcccaactta atgctggcaa ctgataataa   360
gggttgcgct cgttgcggga cttaacccaa catctcacga cacgagctga cgacaaccat   420
gcaccacctg tatccatgtc cccgaaggga acgtctaatc tcttagattt gcatagtatg   480
tcaagacctg gtaaggttct tcgcgtagct tcgaattaaa ccacatgctc caccgcttgt   540
gcgggccccc gtcaattcct ttgagtttca gccttgcggc cgtactcccc aggcggaatg   600
cttaatgcgt tagctgcagc actgaagggc ggaaaccctc caacacttag cattcatcgt   660
ttacggtatg gactaccagg gtatcta                                       687

<210> SEQ ID NO 22
<211> LENGTH: 656
<212> TYPE: DNA
<213> ORGANISM: Lactobacillus reuteri

<400> SEQUENCE: 22
atgctagtcg tacgcactgg cccaactgat tgatggtgct tgcacctgat tgacgatgga    60
tcaccagtga gtggcggacg ggtgagtaac acgtaggtaa cctgccccgg agcgggggat   120
aacatttgga aacagatgct aataccgcat aacaacaaaa gccacatggc ttttgtttga   180
aagatggctt tggctatcac tctgggatgg acctgcggtg cattagctag ttggtaaggt   240
aacggcttac caaggcgatg atgcatagcc gagttgagag actgatcggc cacaatggaa   300
ctgagacacg gtccatactc ctacgggagg cagcagtagg gaatcttcca caatgggcgc   360
aagcctgatg gagcaacacc gcgtgagtga agaagggttt cggctcgtaa agctctgttg   420
ttggagaaga acgtgcgtga gagtaactgt tcacgcagtg acggtatcca accagaaagt   480
cacggctaac tacgtgccag cagccgcggt aatacgtagg tggcaagcgt tatccggatt   540
tattgggcgt aaagcgagcg caggcggttg cttaggtctg atgtgaaagc cttcggctta   600
accgaagaag tgcatcggaa accgggcgac ttgagtgcag aagaggacag tggaac       656

<210> SEQ ID NO 23
<211> LENGTH: 719
<212> TYPE: DNA
<213> ORGANISM: Lactobacillus reuteri

<400> SEQUENCE: 23
tccggattta ttgggcgtaa agcgagcgca ggcggttgct taggtctgat gtgaaagcct    60
tcggcttaac cgaagaagtg catcggaaac cgggcgactt gagtgcagaa gaggacagtg   120
gaactccatg tgtagcggtg gaatgcgtag atatatggaa gaacaccagt ggcgaaggcg   180
gctgtctggt ctgcaactga cgctgaggct cgaaagcatg ggtagcgaac aggattagat   240
accctggtag tccatgccgt aaacgatgag tgctaggtgt tggagggttt ccgcccttca   300
gtgccggagc taacgcatta agcactccgc ctggggagta cgaccgcaag gttgaaactc   360
aaaggaattg acggggccc gcacaagcgg tggagcatgt ggtttaattc gaagctacgc   420
gaagaacctt accaggtctt gacatcttgc gctaacctta gagataaggc gttcccttcg   480
```

```
gggacgcaat gacaggtggt gcatggtcgt cgtcagctcg tgtcgtgaga tgttgggtta      540
agtcccgcaa cgagcgcaac ccttgttact agttgccagc attaagttgg gcactctagt      600
gagactgccg gtgacaaacc ggaggaaggt ggggacgacg tcagatcatc atgcccctta      660
tgacctgggc tacacacgtg ctacaatgga cggtacaacg agtcgcaagc tcgcgagag       719

<210> SEQ ID NO 24
<211> LENGTH: 570
<212> TYPE: DNA
<213> ORGANISM: Lactobacillus reuteri

<400> SEQUENCE: 24
ggagcatgtg gtttaattcg aagctacgcg aagaacctta ccaggtcttg acatcttgcg       60
ctaaccttag agataaggcg ttcccttcgg ggacgcaatg acaggtggtg catggtcgtc      120
gtcagctcgt gtcgtgagat gttgggttaa gtcccgcaac gagcgcaacc cttgttacta      180
gttgccagca ttaagttggg cactctagtg agactgccgg tgacaaaccg gaggaaggtg      240
gggacgacgt cagatcatca tgccccttat gacctgggct acacacgtgc tacaatggac      300
ggtacaacga gtcgcaagct cgcgagagta agctaatctc ttaaagccgt tctcagttcg      360
gactgtaggc tgcaactcgc ctacacgaag tcggaatcgc tagtaatcgc ggatcagcat      420
gccgcggtga atacgttccc gggccttgta cacaccgccc gtcacaccat gggagtttgt      480
aacgcccaaa gtcggtggcc taacctttat ggagggagcc gcctaaggcg ggacagatga      540
ctggggtgaa gtcgtaacaa ggtagccgta                                       570

<210> SEQ ID NO 25
<211> LENGTH: 713
<212> TYPE: DNA
<213> ORGANISM: Lactobacillus reuteri

<400> SEQUENCE: 25
tccccaggcg gagtgcttaa tgcgttagct ccggcactga agggcggaaa ccctccaaca       60
cctagcactc atcgtttacg gcatggacta ccagggtatc taatcctgtt cgctacccat      120
gctttcgagc ctcagcgtca gttgcagacc agacagccgc cttcgccact ggtgttcttc      180
catatatcta cgcattccac cgctacacat ggagttccac tgtcctcttc tgcactcaag      240
tcgcccggtt tccgatgcac ttcttcggtt aagccgaagg ctttcacatc agacctaagc      300
aaccgcctgc gctcgcttta cgcccaataa atccggataa cgcttgccac ctacgtatta      360
ccgcggctgc tggcacgtag ttagccgtga cttctggtt ggataccgtc actgcgtgaa      420
cagttactct cacgcacgtt cttctccaac aacagagctt tacgagccga aacccttctt      480
cactcacgcg gtgttgctcc atcaggcttg cgcccattgt ggaagattcc ctactgctgc      540
ctcccgtagg agtatggacc gtgtctcagt tccattgtgg ccgatcagtc tctcaactcg      600
gctatgcatc atcgccttgg taagccgtta ccttaccaac tagctaatgc accgcaggtc      660
catcccagag tgatagccaa agccatcttt caaacaaaag ccatgtggct ttt            713

<210> SEQ ID NO 26
<211> LENGTH: 522
<212> TYPE: DNA
<213> ORGANISM: Lactobacillus reuteri

<400> SEQUENCE: 26
tttctggttg gataccgtca ctgcgtgaac agttactctc acgcacgttc ttctccaaca       60
```

```
acagagcttt acgagccgaa acccttcttc actcacgcgg tgttgctcca tcaggcttgc    120
gcccattgtg gaagattccc tactgctgcc tcccgtagga gtatggaccg tgtctcagtt    180
ccattgtggc cgatcagtct ctcaactcgg ctatgcatca tcgccttggt aagccgttac    240
cttaccaact agctaatgca ccgcaggtcc atcccagagt gatagccaaa gccatctttc    300
aaacaaaagc catgtggctt tgttgttat gcggtattag catctgtttc caaatgttat     360
cccccgctcc ggggcaggtt acctacgtgt tactcacccg tccgccactc actggtaatc    420
catcgtcaat caggtgcaag caccatcaat cagttgggcc agtgcgtacg acttgcatgt    480
attaggcaca ccgccggcgt tcatcctgag ccatgatcaa ac                       522

<210> SEQ ID NO 27
<211> LENGTH: 661
<212> TYPE: DNA
<213> ORGANISM: Lactobacillus reuteri

<400> SEQUENCE: 27
gcggctccct ccataaaggt tagcgccacc gactttgggc gttacaaact cccatggtgt     60
gacgggcggt gtgtacaagg cccgggaacg tattcaccgc ggcatgctga tccgcgatta    120
ctagcgattc cgacttcgtg taggcgagtt gcagcctaca gtccgaactg agaacggctt    180
taagagatta gcttactctc gcgagcttgc gactcgttgt accgtccatt gtagcacgtg    240
tgtagcccag gtcataaggg gcatgatgat ctgacgtcgt ccccaccttc ctccggtttg    300
tcaccggcag tctcactaga gtgcccaact taatgctggc aactagtaac aagggttgcg    360
ctcgttgcgg gacttaaccc aacatctcac gacacgagct gacgacgacc atgcaccacc    420
tgtcattgcg tccccgaagg gaacgcctta tctctaaggt tagcgcaaga tgtcaagacc    480
tggtaaggtt cttcgcgtag cttcgaatta aaccacatgc tccaccgctt gtgcgggccc    540
ccgtcaattc ctttgagttt caaccttgcg gtcgtactcc ccaggcggag tgcttaatgc    600
gttagctccg gcactgaagg gcggaaaccc tccaacacct agcactcatc gtttacggca    660
t                                                                    661

<210> SEQ ID NO 28
<211> LENGTH: 716
<212> TYPE: DNA
<213> ORGANISM: Lactobacillus reuteri

<400> SEQUENCE: 28
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg ctttggctat cactctggga tggacctgcg gtgcattagc    240
tagttggtaa ggtaacggct taccaaggcg atgatgcata gccgagttga gactgatc     300 ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctg ttgttggaga agaacgtgcg tgagagtaac tgttcacgca gtgacggtat    480
ccaaccagaa agtcacggct aactacgtgc cagcagccgc ggtaatacgt aggtggcaag    540
cgttatccgg atttattggg cgtaaagcga gcgcaggcgg ttgcttaggt ctgatgtgaa    600
agccttcggc ttaaccgaag aagtgcatcg gaaaccgggc gacttgagtg cagaagagga    660
cagtggaact ccatgtgtag cggtggaatg cgtagatata tggaagaaca ccagtg        716
```

<210> SEQ ID NO 29
<211> LENGTH: 683
<212> TYPE: DNA
<213> ORGANISM: Lactobacillus reuteri

<400> SEQUENCE: 29

```
tcggatttat tgggcgtaaa gcgagcgcag gcggttgctt aggtctgatg tgaaagcctt      60
cggcttaacc gaagaagtgc atcggaaacc gggcgacttg agtgcagaag aggacagtgg     120
aactccatgt gtagcggtgg aatgcgtaga tatatggaag aacaccagtg gcgaaggcgg     180
ctgtctggtc tgcaactgac gctgaggctc gaaagcatgg gtagcgaaca ggattagata     240
ccctggtagt ccatgccgta acgatgagt gctaggtgtt ggagggtttc cgcccttcag     300
tgccggagct aacgcattaa gcactccgcc tggggagtac gaccgcaagg ttgaaactca     360
aaggaattga cggggcccg cacaagcggt ggagcatgtg gtttaattcg aagctacgcg     420
aagaaccttcaggtcttg acatcttgcg ctaaccttag agataaggcg ttcccttcgg     480
ggacgcaatg acaggtggtg catggtcgtc gtcagctcgt gtcgtgagat gttgggttaa     540
gtcccgcaac gagcgcaacc cttgttacta gttgccagca ttaagttggg cactctagtg     600
agactgccgg tgacaaaccg gaggaaggtg gggacgacgt cagatcatca tgccccttat     660
gacctgggct acacacgtgc tac                                              683
```

<210> SEQ ID NO 30
<211> LENGTH: 571
<212> TYPE: DNA
<213> ORGANISM: Lactobacillus reuteri

<400> SEQUENCE: 30

```
tggagcatgt ggtttaattc gaagctacgc gaagaaccttaccaggtctt gacatcttgc      60
gctaacctta gagataaggc gttcccttcg ggacgcaat gacaggtggt gcatggtcgt     120
cgtcagctcg tgtcgtgaga tgttgggtta agtcccgcaa cgagcgcaac ccttgttact     180
agttgccagc attaagttgg gcactctagt gagactgccg gtgacaaacc ggaggaaggt     240
ggggacgacg tcagatcatc atgccccttat gacctgggc tacacacgtg ctacaatgga     300
cggtacaacg agtcgcaagc tcgcgagagt aagctaatct cttaaagccg ttctcagttc     360
ggactgtagg ctgcaactcg cctacacgaa gtcggaatcg ctagtaatcg cggatcagca     420
tgccgcggtg aatacgttcc cgggccttgt acaccgcc cgtcacacca tgggagtttg     480
taacgcccaa agtcggtggc ctaaccttta tggaggagc cgcctaaggc gggacagatg     540
actggggtga agtcgtaaca aggtagccgt a                                    571
```

<210> SEQ ID NO 31
<211> LENGTH: 717
<212> TYPE: DNA
<213> ORGANISM: Lactobacillus reuteri

<400> SEQUENCE: 31

```
tactccccag gcggagtgct taatgcgtta gctccggcac tgaagggcgg aaaccctcca      60
acacctagca ctcatcgttt acggcatgga ctaccagggt atctaatcct gttcgctacc     120
catgctttcg agcctcagcg tcagttgcag accagacagc cgccttcgcc actggtgttc     180
ttccatatat ctacgcattc caccgctaca catggagttc cactgtcctc ttctgcactc     240
aagtcgcccg gtttccgatg cacttcttcg gttaagccga aggctttcac atcagaccta     300
```

| | |
|---|---|
| agcaaccgcc tgcgctcgct ttacgcccaa taaatccgga taacgcttgc cacctacgta | 360 |
| ttaccgcggc tgctggcacg tagttagccg tgactttctg gttggatacc gtcactgcgt | 420 |
| gaacagttac tctcacgcac gttcttctcc aacaacagag ctttacgagc cgaaacccc tt | 480 |
| cttcactcac gcggtgttgc tccatcaggc ttgcgcccat tgtggaagat tccctactgc | 540 |
| tgcctcccgt aggagtatgg accgtgtctc agttccattg tggccgatca gtctctcaac | 600 |
| tcggctatgc atcatcgcct tggtaagccg ttaccttacc aactagctaa tgcaccgcag | 660 |
| gtccatccca gagtgatagc caaagccatc tttcaaacaa aagccatgtg gcttttg | 717 |

```
<210> SEQ ID NO 32
<211> LENGTH: 522
<212> TYPE: DNA
<213> ORGANISM: Lactobacillus reuteri

<400> SEQUENCE: 32
```

| | |
|---|---|
| tttctggttg gataccgtca ctgcgtgaac agttactctc acgcacgttc ttctccaaca | 60 |
| acagagcttt acgagccgaa acccttcttc actcacgcgg tgttgctcca tcaggcttgc | 120 |
| gcccattgtg gaagattccc tactgctgcc tcccgtagga gtatggaccg tgtctcagtt | 180 |
| ccattgtggc cgatcagtct ctcaactcgg ctatgcatca tcgccttggt aagccgttac | 240 |
| cttaccaact agctaatgca ccgcaggtcc atcccagagt gatagccaaa gccatctttc | 300 |
| aaacaaaagc catgtggctt tgttgttat gcggtattag catctgtttc caatgttat | 360 |
| cccccgctcc ggggcaggtt acctacgtgt tactcacccg tccgccactc actggtgatc | 420 |
| catcgtcaat caggtgcaag caccatcaat cagttgggcc agtgcgtacg acttgcatgt | 480 |
| attaggcaca ccgccggcgt ccatcctgag ccatgatcaa ac | 522 |

```
<210> SEQ ID NO 33
<211> LENGTH: 661
<212> TYPE: DNA
<213> ORGANISM: Lactobacillus reuteri

<400> SEQUENCE: 33
```

| | |
|---|---|
| ccgccttagg cggctccctc cataaaggtt aggccaccga ctttgggcgt tacaaactcc | 60 |
| catggtgtga cgggcggtgt gtacaaggcc cgggaacgta ttcaccgcgg catgctgatc | 120 |
| cgcgattact agcgattccg acttcgtgta ggcgagttgc agcctacagt ccgaactgag | 180 |
| aacggcttta agagattagc ttactctcgc gagcttgcga ctcgttgtac cgtccattgt | 240 |
| agcacgtgtg tagcccaggt cataagggc atgatgatct gacgtcgtcc ccaccttcct | 300 |
| ccggtttgtc accggcagtc tcactagagt gcccaactta atgctggcaa ctagtaacaa | 360 |
| gggttgcgct cgttgcggga cttaacccaa catctcacga cacgagctga cgacaccat | 420 |
| gcaccacctg tcattgcgtc cccgaaggga acgccttatc tctaaggtta gcgcaagatg | 480 |
| tcaagacctg gtaaggttct tcgcgtagct tcgaattaaa ccacatgctc caccgcttgt | 540 |
| gcgggccccc gtcaattcct ttgagtttca accttgcggt cgtactcccc aggcggagtg | 600 |
| cttaatgcgt tagctccggc actgaagggc ggaaaccctc caacacctag cactcatcgt | 660 |
| t | 661 |

```
<210> SEQ ID NO 34
<211> LENGTH: 660
<212> TYPE: DNA
<213> ORGANISM: Lactobacillus plantarum

<400> SEQUENCE: 34
```

```
gtgcctaata catgcaagtc gaacgaactc tggtattgat tggtgcttgc atcatgattt    60
acatttgagt gagtggcgaa ctggtgagta acacgtggga aacctgccca gaagcggggg   120
ataacacctg gaaacagatg ctaataccgc ataacaactt ggaccgcatg gtccgagttt   180
gaaagatggc ttcggctatc acttttggat ggtcccgcgg cgtattagct agatggtgag   240
gtaacggctc accatggcaa tgatacgtag ccgacctgag agggtaatcg gccacattgg   300
gactgagaca cggcccaaac tcctacggga ggcagcagta gggaatcttc cacaatggac   360
gaaagtctga tggagcaacg ccgcgtgagt gaagaagggt ttcggctcgt aaaactctgt   420
tgttaaagaa gaacatatct gagagtaact gttcaggtat tgacggtatt taaccagaaa   480
gccacggcta actacgtgcc agcagccgcg gtaatacgta ggtggcaagc gttgtccgga   540
tttattgggc gtaaagcgag cgcaggcggt tttttaagtc tgatgtgaaa gccttcggct   600
caaccgaaga agtgcatcgg aaactgggaa acttgagtgc agaagaggac agtggaactc   660
```

<210> SEQ ID NO 35
<211> LENGTH: 670
<212> TYPE: DNA
<213> ORGANISM: Lactobacillus plantarum

<400> SEQUENCE: 35

```
ggatttattg ggcgtaaagc gagcgcaggc ggttttttaa gtctgatgtg aaagccttcg    60
gctcaaccga agaagtgcat cggaaactgg gaaacttgag tgcagaagag gacagtggaa   120
ctccatgtgt agcggtgaaa tgcgtagata tatggaagaa caccagtggc gaaggcggct   180
gtctggtctg taactgacgc tgaggctcga agtatgggt agcaaacagg attagatacc   240
ctggtagtcc ataccgtaaa cgatgaatgc taagtgttgg agggtttccg cccttcagtg   300
ctgcagctaa cgcattaagc attccgcctg gggagtacgg ccgcaaggct gaaactcaaa   360
ggaattgacg ggggcccgca caagcggtgg agcatgtggt ttaattcgaa gctacgcgaa   420
gaaccttacc aggtcttgac atactatgca aatctaagag attagacgtt cccttcgggg   480
acatggatac aggtggtgca tggttgtcgt cagctcgtgt cgtgagatgt tgggttaagt   540
cccgcaacga gcgcaaccct tattatcagt tgccagcatt aagttgggca ctctggtgag   600
actgccggtg acaaaccgga ggaaggtggg gatgacgtca atcatcatg ccccttatga    660
cctgggctac                                                          670
```

<210> SEQ ID NO 36
<211> LENGTH: 573
<212> TYPE: DNA
<213> ORGANISM: Lactobacillus plantarum

<400> SEQUENCE: 36

```
gtggagcatg tggtttaatt cgaagctacg cgaagaacct taccaggtct tgacatacta    60
tgcaaatcta agagattaga cgttcccttc ggggacatgg atacaggtgg tgcatggttg   120
tcgtcagctc gtgtcgtgag atgttgggtt aagtcccgca acgagcgcaa cccttattat   180
cagttgccag cattaagttg gcactctgg tgagactgcc ggtgacaaac cggaggaagg   240
tggggatgac gtcaaatcat catgcccctt atgacctggg ctacacacgt gctacaatgg   300
atggtacaac gagttgcgaa ctcgcgagag taagctaatc tcttaaagcc attctcagtt   360
cggattgtag gctgcaactc gcctacatga agtcggaatc gctagtaatc gcggatcagc   420
atgccgcggt gaatacgttc ccgggccttg tacacaccgc ccgtcacacc atgagagttt   480
```

| | |
|---|---|
| gtaacaccca aagtcggtgg ggtaacccttt taggaaccag ccgcctaagg tgggacagat | 540 |
| gattagggtg aagtcgtaac aaggtagccc gta | 573 |

<210> SEQ ID NO 37
<211> LENGTH: 743
<212> TYPE: DNA
<213> ORGANISM: Lactobacillus plantarum

<400> SEQUENCE: 37

| | |
|---|---|
| actccccagg cggaatgctt aatgcgttag ctgcagcact gaagggcgga aaccctccaa | 60 |
| cacttagcat tcatcgttta cggtatggac taccagggta tctaatcctg tttgctaccc | 120 |
| atactttcga gcctcagcgt cagttacaga ccagacagcc gccttcgcca ctggtgttct | 180 |
| tccatatatc tacgcatttc accgctacac atggagttcc actgtcctct tctgcactca | 240 |
| agtttcccag tttccgatgc acttcttcgg ttgagccgaa ggctttcaca tcagacttaa | 300 |
| aaaaccgcct gcgctcgctt tacgcccaat aaatccggac aacgcttgcc acctacgtat | 360 |
| taccgcggct gctggcacgt agttagccgt ggctttctgg ttaaataccg tcaatacctg | 420 |
| aacagttact ctcagatatg ttcttcttta acaacagagt tttacgagcc gaaacccttc | 480 |
| ttcactcacg cggcgttgct ccatcagact ttcgtccatt gtggaagatt ccctactgct | 540 |
| gcctcccgta ggagtttggg ccgtgtctca gtcccaatgt ggccgattac cctctcaggt | 600 |
| cggctacgta tcattgccat ggtgagccgt tacctcacca tctagctaat acgccgcggg | 660 |
| accatccaaa agtgatagcc gaagccatct ttcaaactcg gaccatgcgg tccaagttgt | 720 |
| tatgcggtat tagcatctgt ttc | 743 |

<210> SEQ ID NO 38
<211> LENGTH: 513
<212> TYPE: DNA
<213> ORGANISM: Lactobacillus plantarum

<400> SEQUENCE: 38

| | |
|---|---|
| tttctggtta ataccgtcaa atacctgaac agttactctc agatatgttc ttctttaaca | 60 |
| acagagtttt acgagccgaa acccttcttc actcacgcgg cgttgctcca tcagactttc | 120 |
| gtccattgtg aagattccc tactgctgcc tcccgtagga gtttgggccg tgtctcagtc | 180 |
| ccaatgtggc cgattaccct ctcaggtcgg ctacgtatca ttgccatggt gagccgttac | 240 |
| ctcaccatct agctaatacg ccgcgggacc atccaaaagt gatagccgaa gccatctttc | 300 |
| aaactcggac catgcggtcc aagttgttat gcggtattag catctgtttc caggtgttat | 360 |
| cccccgcttc tgggcaggtt cccacgtgt tactcaccag ttcgccactc actcaaatgt | 420 |
| aaatcatgat gcaagcacca atcaatacca gagttcgttc gacttgcatg tattaggcac | 480 |
| gccgccagcg ttcgtcctga gccatgatca aac | 513 |

<210> SEQ ID NO 39
<211> LENGTH: 747
<212> TYPE: DNA
<213> ORGANISM: Lactobacillus plantarum

<400> SEQUENCE: 39

| | |
|---|---|
| ccaccttagg cggctggttc ctaaaaggtt accccaccga ctttgggtgt tacaaactct | 60 |
| catggtgtga cggcggtgt gtacaaggcc cgggaacgta ttcaccgcgg catgctgatc | 120 |
| cgcgattact agcgattccg acttcatgta ggcgagttgc agcctacaat ccgaactgag | 180 |
| aatggcttta agagattagc ttactctcgc gagttcgcaa ctcgttgtac catccattgt | 240 |

```
agcacgtgtg tagcccaggt cataagggc atgatgattt gacgtcatcc ccaccttcct    300
ccggtttgtc accggcagtc tcaccagagt gcccaactta atgctggcaa ctgataataa    360
gggttgcgct cgttgcggga cttaacccaa catctcacga cacgagctga cgacaaccat    420
gcaccacctg tatccatgtc cccgaaggga acgtctaatc tcttagattt gcatagtatg    480
tcaagacctg gtaaggttct tcgcgtagct tcgaattaaa ccacatgctc caccgcttgt    540
gcgggccccc gtcaattcct ttgagtttca gccttgcggc cgtactcccc aggcggaatg    600
cttaatgcgt tagctgcagc actgaagggc ggaaaccctc caacacttag cattcatcgt    660
ttacggtatg gactaccagg gtatctaatc ctgtttgcta cccatacttt cgagcctcag    720
cgtcagttac agaccagaca gccgcct                                        747

<210> SEQ ID NO 40
<211> LENGTH: 617
<212> TYPE: DNA
<213> ORGANISM: Lactobacillus johnsonii

<400> SEQUENCE: 40
gtgcctaata catgcaagtc gagcgagctt gcctagatga ttttagtgct tgcactaaat     60
gaaactagat acaagcgagc ggcggacggg tgagtaacac gtgggtaacc tgcccaagag    120
actgggataa cacctggaaa cagatgctaa taccggataa caacactaga cgcatgtcta    180
gagtttgaaa gatggttctg ctatcactct tggatggacc tgcggtgcat tagctagttg    240
gtaaggtaac ggcttaccaa ggcaatgatg catagccgag ttgagagact gatcggccac    300
attgggactg agacacggcc caaactccta cgggaggcag cagtagggaa tcttccacaa    360
tggacgaaag tctgatggag caacgccgcg tgagtgaaga agggtttcgg ctcgtaaagc    420
tctgttggta gtgaagaaag atagaggtag taactggcct ttatttgacg gtaattactt    480
agaaagtcac ggctaactac gtgccagcag ccgcggtaat acgtaggtgg caagcgttgt    540
ccggatttat tgggcgtaaa gcgagtgcag gcggttcaat aagtctgatg tgaaagcctt    600
cggctcaacc ggagaat                                                   617

<210> SEQ ID NO 41
<211> LENGTH: 523
<212> TYPE: DNA
<213> ORGANISM: Lactobacillus johnsonii

<400> SEQUENCE: 41
tccggattta ttgggcgtaa agcgagtgca ggcggttcaa taagtctgat gtgaaagcct     60
tcggctcaac cggagaattg catcagaaac tgttgaactt gagtgcagaa gaggagagtg    120
gaactccatg tgtagcggtg gaatgcgtag atatatggaa gaacaccagt ggcgaaggcg    180
gctctctggt ctgcaactga cgctgaggct cgaaagcatg ggtagcgaac aggattagat    240
accctggtag tccatgccgt aaacgatgag tgctaagtgt tgggaggttt ccgcctctca    300
gtgctgcagc taacgcatta agcactccgc ctggggagta cgaccgcaag gttgaaactc    360
aaaggaattg acgggggccc gcacaagcgg tggagcatgt ggtttaattc gaagcaacgc    420
gaagaacctt accaggtctt gacatccagt gcaaacctaa gagattaggt gttcccttcg    480
gggacgctga cacaggtggt gcatggctgt cgtcagctcg tgt                      523

<210> SEQ ID NO 42
<211> LENGTH: 482
<212> TYPE: DNA
```

<213> ORGANISM: Lactobacillus johnsonii

<400> SEQUENCE: 42

| | | | | | |
|---|---|---|---|---|---|
| ggagcatgtg | gtttaattcg | aagcaacgcg | aagaacctta | ccaggtcttg acatccagtg | 60 |
| caaacctaag | agattaggtg | tgtcccttcg | gggacgctga | gacaggtggt gcatggctgt | 120 |
| cgtcagctcg | tgtcgtgaga | tgttgggtta | agtcccgcaa | cgagcgcaac ccttgtcatt | 180 |
| agttgccatc | attaagttgg | gcactctaat | gagactgccg | gtgacaaacc ggaggaaggt | 240 |
| ggggatgacg | tcaagtcatc | atgcccctta | tgacctgggc | tacacacgtg ctacaatgga | 300 |
| cggtacaacg | agaagcgaac | ctgcgaaggc | aagcggatct | cttaaagccg ttctcagttc | 360 |
| ggactgtagg | ctgcaactcg | cctacacgaa | gctggaatcg | ctagtaatcg cggatcagca | 420 |
| cgccgcggtg | aatacgttcc | cgggccttgt | acaccgcc | cgtcacacca tgagagtctg | 480 |
| ta | | | | | 482 |

<210> SEQ ID NO 43
<211> LENGTH: 719
<212> TYPE: DNA
<213> ORGANISM: Lactobacillus johnsonii

<400> SEQUENCE: 43

| | | | | | |
|---|---|---|---|---|---|
| actccccagg | cggagtgctt | aatgcgttag | ctgcagcact | gagaggcgga aacctcccaa | 60 |
| cacttagcac | tcatcgttta | cggcatggac | taccagggta | tctaatcctg ttcgctaccc | 120 |
| atgctttcga | gcctcagcgt | cagttgcaga | ccagagagcc | gccttcgcca ctggtgttct | 180 |
| tccatatatc | tacgcattcc | accgctacac | atggagttcc | actctcctct ctgcactca | 240 |
| agttcaacag | tttctgatgc | aattctccgg | ttgagccgaa | ggctttcaca tcagacttat | 300 |
| tgaaccgcct | gcactcgctt | tacgcccaat | aaatccggac | aacgcttgcc acctacgtat | 360 |
| taccgcggct | gctggcacgt | agttagccgt | gactttctaa | gtaattaccg tcaaataaag | 420 |
| gccagttact | acctctatct | ttcttcacta | ccaacagagc | tttacgagcc gaaacccttc | 480 |
| ttcactcacg | cggcgttgct | ccatcagact | ttcgtccatt | gtggaagatt ccctactgct | 540 |
| gcctcccgta | ggagtttggg | ccgtgtctca | gtcccaatgt | ggccgatcag tctctcaact | 600 |
| cggctatgca | tcattgcctt | ggtaagccgt | taccttacca | actagctaat gcaccgcagg | 660 |
| tccatccaag | agtgatagca | gaaccatctt | tcaaactcta | gacatgcgtc tagtgttgt | 719 |

<210> SEQ ID NO 44
<211> LENGTH: 521
<212> TYPE: DNA
<213> ORGANISM: Lactobacillus johnsonii

<400> SEQUENCE: 44

| | | | | | |
|---|---|---|---|---|---|
| actttctaag | taattaccgt | caaataaagg | ccagttacta | cctctatctt tcttcactac | 60 |
| caacagagct | ttacgagccg | aaacccttct | tcactcacgc | ggcgttgctc atcagactt | 120 |
| tcgtccattg | tggaagattc | cctactgctg | cctcccgtag | gagtttgggc cgtgtctcag | 180 |
| tcccaatgtg | gccgatcagt | ctctcaactc | ggctatgcat | cattgccttg gtaagccgtt | 240 |
| accttaccaa | ctagctaatg | caccgcaggt | ccatccaaga | gtgatagcag aaccatcttt | 300 |
| caaactctag | acatgcgtct | agtgttgtta | tccggtatta | gcatctgttt ccaggtgtta | 360 |
| tcccagtctc | ttgggcaggt | tacccacgtg | ttactcaccc | gtccgccgct cgcttgtatc | 420 |
| tagtttcatt | tagtgcaagc | actaaaatca | tctaggcaag | ctcgctcgac ttgcatgtat | 480 |
| taggcacgcc | gccagcgttc | gtcctgagcc | atgatcaaac | t | 521 |

<210> SEQ ID NO 45
<211> LENGTH: 748
<212> TYPE: DNA
<213> ORGANISM: Lactobacillus johnsonii

<400> SEQUENCE: 45

```
ctaccttaga cggctgactc ctataaaggt tatcccaccg gctttgggtg ttacagactc      60
tcatggtgtg acgggcggtg tgtacaaggc ccgggaacgt attcaccgcg gcgtgctgat     120
ccgcgattac tagcgattcc agcttcgtgt aggcgagttg cagcctacag tccgaactga     180
gaacggcttt aagagatccg cttgccttcg caggttcgct tctcgttgta ccgtccattg     240
tagcacgtgt gtagcccagg tcataagggg catgatgact tgacgtcatc cccaccttcc     300
tccggtttgt caccggcagt ctcattagag tgcccaactt aatgatggca actaatgaca     360
agggttgcgc tcgttgcggg acttaaccca acatctcacg acacgagctg acgacagcca     420
tgcaccacct gtctcagcgt ccccgaaggg aacacctaat ctcttaggtt tgcactggat     480
gtcaagacct ggtaaggttc ttcgcgttgc ttcgaattaa accacatgct ccaccgcttg     540
tgcgggcccc cgtcaattcc tttgagtttc aaccttgcgg tcgtactccc caggcggagt     600
gcttaatgcg ttagctgcag cactgagagg cggaaacctc ccaacactta gcactcatcg     660
tttacggcat ggactaccag ggtatctaat cctgttcgct acccatgctt tcgagcctca     720
gcgtcagttg cagaccagag agccgcct                                        748
```

<210> SEQ ID NO 46
<211> LENGTH: 694
<212> TYPE: DNA
<213> ORGANISM: Lactobacillus reuteri

<400> SEQUENCE: 46

```
gtgtgcctaa tacatgcaag tcgtacgcac tggcccaact gattgatggt gcttgcacct      60
gattgacgat ggatcaccag tgagtggcgg acgggtgagt aacacgtagg taacctgccc     120
cggagcgggg gataacattt ggaaacagat gctaataccg cataacaaca aaagccacat     180
ggcttttgtt tgaaagatgg cttcggctat cactctggga tggacctgcg gtgcattagc     240
tagttggtaa ggtaacggct taccaaggcg atgatgcata gccgagttga gagactgatc     300
ggccacaatg gaactgagac acggtccata ctcctacggg aggcagcagt agggaatctt     360
ccacaatggg cgcaagcctg atggagcaac accgcgtgag tgaagaaggg tttcggctcg     420
taaagctctg ttgttggaga agaacgtgcg tgagagtaac tgttcacgca gtgacggtat     480
ccaaccagaa agtcacggct aactacgtgc cagcagccgc ggtaatacgt aggtggcaag     540
cgttatccgg atttattggg cgtaaagcga gcgcaggcgg ttgcttaggt ctgatgtgaa     600
agccttcggc ttaaccgaag aagtgcatcg gaaaccgggc gacttgagtg cagaagagga     660
cagtggaact ccatgtgtag cggtggaatg cgta                                 694
```

<210> SEQ ID NO 47
<211> LENGTH: 409
<212> TYPE: DNA
<213> ORGANISM: Lactobacillus reuteri

<400> SEQUENCE: 47

```
cggatttatt gggcgtaaag cgagcgcagg cggttgctta ggtctgatgt gaaagccttc      60
ggcttaaccg aagaagtgca tcggaaaccg ggcgacttga gtgcagaaga ggacagtgga     120
```

```
actccatgtg tagcggtgga atgcgtagat atatggaaga acaccagtgg cgaaggcggc      180
tgtctggtct gcaactgacg ctgaggctcg aaagcatggg tagcgaacag gattagatac      240
cctggtagtc catgccgtaa acgatgagtg ctaggtgttg gagggtttcc gcccttcagt      300
gccggagcta acgcattaag cactccgcct ggggagtacg accgcaaggt tgaaactcaa      360
aggaattgac gggggcccgc acaagcggtg gagcatgtgg tttaattcg                  409

<210> SEQ ID NO 48
<211> LENGTH: 467
<212> TYPE: DNA
<213> ORGANISM: Lactobacillus reuteri

<400> SEQUENCE: 48
gagcatgtgg tttaattcga agctacgcga agaaccttac caggtcttga catcttgcgc       60
taaccttaga gataaggcgt tcccttcggg gacgcaatga caggtggtgc atggtcgtcg      120
tcagctcgtg tcgtgagatg ttgggttaag tcccgcaacg agcgcaaccc ttgttactag      180
ttgccagcat taagttgggc actctagtga gactgccggt gacaaaccgg aggaaggtgg      240
ggacgacgtc agatcatcat gccccttatg acctgggcta cacacgtgct acaatggacg      300
gtacaacgag tcgcaagctc gcgagagtaa gctaatctct aaagccgttc tcagttcgg      360 actgtaggct gcaactcgcc tacacgaagt cggaatcgct agtaatcgcg gatcagcatg      420
ccgcggtgaa tacgttcccg ggccttgtac acaccgcccg tcacacc                    467

<210> SEQ ID NO 49
<211> LENGTH: 661
<212> TYPE: DNA
<213> ORGANISM: Lactobacillus reuteri

<400> SEQUENCE: 49
actccccagg cggagtgctt aatgcgttag ctccggcact gaagggcgga aaccctccaa       60
cacctagcac tcatcgttta cggcatggac taccagggta tctaatcctg ttcgctaccc      120
atgctttcga gcctcagcgt cagttgcaga ccagacagcc gccttcgcca ctggtgttct      180
tccatatatc tacgcattcc accgctacac atggagttcc actgtcctct ctgcactca       240 agtcgcccgg tttccgatgc acttcttcgg ttaagccgaa ggctttcaca tcagacctaa      300
gcaaccgcct gcgctcgctt tacgcccaat aaatccggat aacgcttgcc acctacgtat      360
taccgcggct gctggcacgt agttagccgt gactttctgg ttggataccg tcactgcgtg      420
aacagttact ctcacgcacg ttcttctcca acaacagagc tttacgagcc gaaacccttc      480
ttcactcacg cggtgttgct ccatcaggct tgcgcccatt gtggaagatt ccctactgct      540
gcctcccgta ggagtatgga ccgtgtctca gttccattgt ggccgatcag tctctcaact      600
cggctatgca tcatcgcctt ggtaagccgt taccttacca actagctaat gcaccgcagg      660
t                                                                       661

<210> SEQ ID NO 50
<211> LENGTH: 525
<212> TYPE: DNA
<213> ORGANISM: Lactobacillus reuteri

<400> SEQUENCE: 50
tttctggttg gataccgtca ctgcgtgaac agttactctc acgcacgttc ttctccaaca       60
acagagcttt acgagccgaa acccttcttc actcacgcgg tgttgctcca tcaggcttgc      120
gcccattgtg gaagattccc tactgctgcc tcccgtagga gtatggaccg tgtctcagtt      180
```

```
ccattgtggc cgatcagtct ctcaactcgg ctatgcatca tcgccttggt aagccgttac      240
cttaccaact agctaatgca ccgcaggtcc atcccagagt gatagccaaa gccatctttc      300
aaacaaaagc catgtggctt ttgttgttat gcggtattag catctgtttc caaatgttat      360
cccccgctcc ggggcaggtt acctacgtgt tactcacccg tccgccactc actggtgatc      420
catcgtcaat caggtgcaag caccatcaat cagttgggcc agtgcgtacg acttgcatgt      480
attaggcaca ccgccggcgt tcatcctgag ccatgatcaa actct                     525

<210> SEQ ID NO 51
<211> LENGTH: 761
<212> TYPE: DNA
<213> ORGANISM: Lactobacillus reuteri

<400> SEQUENCE: 51
tcccgcctta ggcggctccc tccataatgg ttaggccacc gactttgggc gttacaaact      60
cccatggtgt gacgggcggt gtgtacaagg cccgggaacg tattcaccgc ggcatgctga     120
tccgcgatta ctagcgattc cgacttcgtg taggcgagtt gcagcctaca gtccgaactg     180
agaacggctt taagagatta gcttactctc gcgagcttgc gactcgttgt accgtccatt     240
gtagcacgtg tgtagcccag gtcataaggg gcatgatgat ctgacgtcgt ccccaccttc     300
ctccggtttg tcaccggcag tctcactaga gtgcccaact taatgctggc aactagtaac     360
aagggttgcg ctcgttgcgg gacttaaccc aacatctcac gacacgagct gacgacgacc     420
atgcaccacc tgtcattgcg tccccgaagg gaacgcctta tctctaaggt tagcgcaaga     480
tgtcaagacc tggtaaggtt cttcgcgtag cttcgaatta aaccacatgc tccaccgctt     540
gtgcgggccc ccgtcaattc ctttgagttt caaccttgcg gtcgtactcc ccaggcggag     600
tgcttaatgc gttagctccg gcactgaagg gcggaaaccc tccaacacct agcactcatc     660
gtttacggca tggactacca gggtatctaa tcctgttcgc tacccatgct ttcgagcctc     720
agcgtcagtt gcagaccaga cagccgcctt cgccactggt g                         761

<210> SEQ ID NO 52
<211> LENGTH: 651
<212> TYPE: DNA
<213> ORGANISM: Lactobacillus reuteri

<400> SEQUENCE: 52
gtgtgcctaa tacatgcaag tcgtacgcac tggcccaact gattgatggt gcttgcacct      60
gattgacgat ggatcaccag tgagtggcgg acgggtgagt aacacgtagg taacctgccc     120
cggagcgggg gataacattt ggaaacagat gctaataccg cataacaaca aaagccacat     180
ggcttttgtt tgaaagatgg ctttggctat cactctggga tggacctgcg gtgcattagc     240
tagttggtaa ggtaacggct taccaaggcg atgatgcata ccgagttgag agactgatc      300 ggccacaatg gaactgagac acggtccata ctcctacggg aggcagcagt agggaatctt     360
ccacaatggg cgcaagcctg atggagcaac accgcgtgag tgaagaaggg tttcggctcg     420
taaagctctg ttgttggaga agaacgtgcg tgagagtaac tgttcacgca gtgacggtat     480
ccaaccagaa agtcacggct aactacgtgc cagcagccgc ggtaatacgt aggtggcaag     540
cgttatccgg atttattggg cgtaaagcga gcgcaggcgg ttgcttaggt ctgatgtgaa     600
agccttcggc ttaaccgaag aagtgcatcg gaaaccgggc gacttgagtg c              651

<210> SEQ ID NO 53
```

```
<211> LENGTH: 645
<212> TYPE: DNA
<213> ORGANISM: Lactobacillus reuteri

<400> SEQUENCE: 53
ttatccggat ttattgggcg taaagcgagc gcaggcggtt gcttaggtct gatgtgaaag      60
ccttcggctt aaccgaagaa gtgcatcgga accgggcaa cttgagtgca gaagaggaca     120
gtggaactcc atgtgtagcg gtggaatgcg tagatatatg gaagaacacc agtggcgaag    180
gcggctgtct ggtctgcaac tgacgctgag gctcgaaagc atgggtagcg aacaggatta   240
gataccctgg tagtccatgc cgtaaacgat gagtgctagg tgttggaggg tttccgccct   300
tcagtgccgg agctaacgca ttaagcactc cgcctgggga gtacgaccgc aaggttgaaa   360
ctcaaaggaa ttgacggggg cccgcacaag cggtggagca tgtggtttaa ttcgaagcta   420
cgcgaagaac cttaccaggt cttgacatct tgcgctaacc ttagagataa ggcgtccctt   480
cggggacgca atgacaggtg gtgcatggtc gtcgtcagct cgtgtcgtga gatgttgggt   540
taagtcccgc aacgagcgca accttgtta  ctagttgcca gcattaagtt gggcactcta   600
gtgagactgc cggtgacaaa ccggaggaag gtggggacga cgtca                    645

<210> SEQ ID NO 54
<211> LENGTH: 573
<212> TYPE: DNA
<213> ORGANISM: Lactobacillus reuteri

<400> SEQUENCE: 54
ggtggagcat gtggtttaat tcgaagctac gcgaagaacc ttaccaggtc ttgacatctt    60
gcgctaacct tagagataag gcgttccctt cggggacgca atgacaggtg gtgcatggtc   120
gtcgtcagct cgtgtcgtga gatgttgggt taagtcccgc aacgagcgca accttgtta    180 ctagttgcca gcattaagtt gggcactcta gtgagactgc cggtgacaaa ccggaggaag   240
gtggggacga cgtcagatca tcatgcccct tatgacctgg gctacacacg tgctacaatg   300
gacggtacaa cgagtcgcaa gctcgcgaga gtaagctaat ctcttaaagc cgttctcagt   360
tcggactgta ggctgcaact cgcctacacg aagtcggaat cgctagtaat cgcggatcag   420
catgccgcgg tgaatacgtt cccgggcctt gtacacaccg cccgtcacac catgggagtt   480
tgtaacgccc aaagtcggtg gcctaaccat tatggaggga ccgcctaag gcgggacaga   540 tgactggggt gaagtcgtaa caaggtagcc gta                                 573

<210> SEQ ID NO 55
<211> LENGTH: 705
<212> TYPE: DNA
<213> ORGANISM: Lactobacillus reuteri

<400> SEQUENCE: 55
tactccccag gcggagtgct taatgcgtga gctccggcac tgaagggcgg aaaccctcca    60
acacctagca ctcatcgttt acggcatgga ctaccagggt atctaatcct gttcgctacc   120
catgctttcg agcctcagcg tcagttgcag accagacagc cgccttcgcc actggtgttc   180
ttccatatat ctacgcattc caccgctaca catggagttc cactgtcctc ttctgcactc   240
aagtcgcccg gtttccgatg cacttcttcg gttaagccga aggctttcac atcagaccta   300
agcaaccgcc tgcgctcgct ttacgcccaa taaatccgga taacgcttgc cacctacgta   360
ttaccgcggc tgctggcacg tagttagccg tgactttctg gttggatacc gtcactgcgt   420
gaacagttac tctcacgcac gttcttctcc aacaacagag ctttacgagc cgaaacccTT   480
```

```
cttcactcac gcggtgttgc tccatcaggc ttgcgcccat tgtggaagat tccctactgc    540
tgcctcccgt aggagtatgg accgtgtctc agttccattg tggccgatca gtctctcaac    600
tcggctatgc atcatcgcct tggtaagccg ttaccttacc aactagctaa tgcaccgcag    660
gtccatccca gagtgatagc caaagccatc tttcaaacaa aagcc                    705

<210> SEQ ID NO 56
<211> LENGTH: 527
<212> TYPE: DNA
<213> ORGANISM: Lactobacillus reuteri

<400> SEQUENCE: 56
gtgactttct ggttggatac cgtcactgcg tgaacagtta ctctcacgca cgtgcttctc     60
caacaacaga gctttacgag ccgaaaccct tcttcactca cgcggtgttg ctccatcagg    120
cttgcgccca ttgtggaaga ttccctactg ctgcctcccg taggagtatg gaccgtgtct    180
cagttccatt gtggccgatc agtctctcaa ctcggctatg catcatcgcc ttggtaagcc    240
gttaccttac caactagcta atgcaccgca ggtccatccc agagtgatag ccaaagccat    300
ctttcaaaca aaagccatgt ggcttttgtt gttatgcggt attagcatct gtttccaaat    360
gttatccccc gctccggggc aggttaccta cgtgttactc acccgtccgc cactcactgg    420
tgatccatcg tcaatcaggt gcaagcacca tcaatcagtt gggccagtgc gtacgacttg    480
catgtattag gcacaccgcc ggcgttcatc ctgagccatg atcaaac                  527

<210> SEQ ID NO 57
<211> LENGTH: 719
<212> TYPE: DNA
<213> ORGANISM: Lactobacillus reuteri

<400> SEQUENCE: 57
tcccgcactt aggcggctcc ctccataatg gttaggccac cgactttggg cgttacaaac     60
tcccatggtg tgacgggcgg tgtgtacaag gcccgggaac gtattcaccg cggcatgctg    120
atccgcgatt actagcgatt ccgacttcgt gtaggcgagt tgcagcctac agtccgaact    180
gagaacggct ttaagagatt agcttactct cgcgagcttg cgactcgttg taccgtccat    240
tgtagcacgt gtgtagccca ggtcataagg ggcatgatga tctgacgtcg tccccacctt    300
cctccggttt gtcaccggca gtctcactag agtgcccaac ttaatgctgg caactagtaa    360
caagggttgc gctcgttgcg ggacttaacc caacatctca cgacacgagc tgacgacgac    420
catgcaccac ctgtcattgc gtccccgaag gaacgccctt atctctaagg ttagcgcaag    480
atgtcaagac ctggtaaggt tcttcgcgta gcttcgaatt aaaccacatg ctccaccgct    540
tgtgcgggcc cccgtcaatt cctttgagtt tcaaccttgc ggtcgtactc ccaggcgga    600 gtgcttaatg cgttagctcc ggcactgaag ggcggaaacc ctccaacacc tagcactcat    660
cgtttacggc atggactacc agggtatcta atcctgttcg ctacccatgc tttcgagcc    719

<210> SEQ ID NO 58
<211> LENGTH: 690
<212> TYPE: DNA
<213> ORGANISM: Lactobacillus johnsonii

<400> SEQUENCE: 58
gcgtgcctaa tacatgcaag tcgagcgagc ttgcctagat gattttagtg cttgcactaa     60
atgaaactag atacaagcga gcggcggacg ggtgagtaac acgtgggtaa cctgcccaag    120
```

| | | |
|---|---|---|
| agactgggat aacacctgga aacagatgct ataccggat aacaacacta gacgcatgtc | 180 | |
| tagagtttga aagatggttc tgctatcact cttggatgga cctgcggtgc attagctagt | 240 | |
| tggtaaggta acggcttacc aaggcaatga tgcatagccg agttgagaga ctgatcggcc | 300 | |
| acattgggac tgagacacgg cccaaactcc tacgggaggc agcagtaggg aatcttccac | 360 | |
| aatggacgaa agtctgatgg agcaacgccg cgtgagtgaa gaagggtttc ggctcgtaaa | 420 | |
| gctctgttgg tagtgaagaa agatagaggt agtaactggc ctttatttga cggtaattac | 480 | |
| ttagaaagtc acggctaact acgtgccagc agccgcggta atacgtaggt ggcaagcgtt | 540 | |
| gtccggattt attgggcgta aagcgagtgc aggcggttca ataagtctga tgtgaaagcc | 600 | |
| ttcggctcaa ccggagaatt gcatcagaaa ctgttgaact tgagtgcaga agaggagagt | 660 | |
| ggaactccat gtgtagcggt ggaatgcgta | 690 | |

<210> SEQ ID NO 59
<211> LENGTH: 638
<212> TYPE: DNA
<213> ORGANISM: Lactobacillus johnsonii

<400> SEQUENCE: 59

| | | |
|---|---|---|
| tgtccggatt tattgggcgt aaagcgagtg caggcggttc aataagtctg atgtgaaagc | 60 | |
| cttcggctca accggagaat tgcatcagaa actgttgaac ttgagtgcag aagaggagag | 120 | |
| tggaactcca tgtgtagcgg tggaatgcgt agatatatgg aagaacacca gtggcgaagg | 180 | |
| cggctctctg gtctgcaact gacgctgagg ctcgaaagca tgggtagcga acaggattag | 240 | |
| ataccctggt agtccatgcc gtaaacgatg agtgctaagt gttgggaggt ttccgcctct | 300 | |
| cagtgctgca gctaacgcat taagcactcc gcctggggag tacgaccgca aggttgaaac | 360 | |
| tcaaaggaat tgacggggc cgcacaagc ggtggagcat gtggtttaat tcgaagcaac | 420 | |
| gcgaagaacc ttaccaggtc ttgacatcca gtgcaaacct aagagattag gtgttccctt | 480 | |
| cggggacgct gagacaggtg gtgcatggct gtcgtcagct cgtgtcgtga gatgttgggt | 540 | |
| taagtcccgc aacgagcgca acccttgtca ttagttgcca tcattaagtt gggcactcta | 600 | |
| atgagactgc cggtgacaaa ccggaggaag gtggggat | 638 | |

<210> SEQ ID NO 60
<211> LENGTH: 569
<212> TYPE: DNA
<213> ORGANISM: Lactobacillus johnsonii

<400> SEQUENCE: 60

| | | |
|---|---|---|
| ggtggagcat gtggtttaat tcgaagcaac gcgaagaacc ttaccaggtc ttgacatcca | 60 | |
| gtgcaaacct aagagattag gtgttccctt cggggacgct gagacaggtg gtgcatggct | 120 | |
| gtcgtcagct cgtgtcgtga gatgttgggt taagtcccgc aacgagcgca acccttgtca | 180 | |
| ttagttgcca tcattaagtt gggcactcta atgagactgc cggtgacaaa ccggaggaag | 240 | |
| gtggggatga cgtcaagtca tcatgcccct tatgacctgg gctacacacg tgctacaatg | 300 | |
| gacggtacaa cgagaagcga acctgcgaag gcaagcggat ctcttaaagc cgttctcagt | 360 | |
| tcggactgta ggctgcaact cgcctacacg aagctggaat cgctagtaat cgcggatcag | 420 | |
| cacgccgcgg tgaatacgtt cccgggcctt gtacacaccg cccgtcacac catgagagtc | 480 | |
| tgtaacaccc aaagccggtg ggataacctt tataggagtc agccgtctaa ggtaggacag | 540 | |
| atgattaggg tgaagtcgta acaaggtag | 569 | |

<210> SEQ ID NO 61
<211> LENGTH: 716
<212> TYPE: DNA
<213> ORGANISM: Lactobacillus johnsonii
<220> FEATURE:
<221> NAME/KEY: modified_base
<222> LOCATION: (684)..(684)
<223> OTHER INFORMATION: a, c, t, g, unknown or other

<400> SEQUENCE: 61

```
tactccccag gcggagtgct taatgcgtta gctgcagcac tgagaggcgg aaacctccca        60
acacttagca ctcatcgttt acggcatgga ctaccagggt atctaatcct gttcgctacc       120
catgctttcg agcctcagcg tcagttgcag accagagagc cgccttcgcc actggtgttc       180
ttccatatat ctacgcattc caccgctaca catggagttc cactctcctc ttctgcactc       240
aagttcaaca gtttctgatg caattctccg gttgagccga aggctttcac atcagactta       300
ttgaaccgcc tgcactcgct ttacgcccaa taaatccgga caacgcttgc cacctacgta       360
ttaccgcggc tgctggcacg tagttagccg tgactttcta agtaattacc gtcaaataaa       420
ggccagttac tacctctatc tttcttcact accaacagag ctttacgagc cgaaaccctt       480
cttcactcac gcggcgttgc tccatcagac tttcgtccat gtggaagat  tccctactgc       540 tgcctcccgt aggagtttgg gccgtgtctc agtcccaatg tggccgatca gtctctcaac       600
tcggctatgc atcattgcct tggtaagccg ttaccttacc aactagctaa tgcaccgcag       660
gtccatccaa gagtgatagc aganccatct ttcaaactct agacatgcgt ctagtg          716
```

<210> SEQ ID NO 62
<211> LENGTH: 514
<212> TYPE: DNA
<213> ORGANISM: Lactobacillus johnsonii

<400> SEQUENCE: 62

```
gtgactttct aagtaattac cgtcaaataa aggccagtta ctacctctat ctttcttcac        60
taccaacaga gctttacgag ccgaaaccct tcttcactca cgcggcgttg ctccatcaga       120
ctttcgtcca tgtggaaga ttccctactg ctgcctcccg taggagtttg gccgtgtct        180 cagtcccaat gtggccgatc agtctctcaa ctcggctatg catcattgcc ttggtaagcc       240
gttaccttac caactagcta atgcaccgca ggtccatcca agagtgatag cagaaccatc       300
tttcaaactc tagacatgcg tctagtgttg ttatccggta ttagcatctg tttccaggtg       360
ttatcccagt ctcttgggca ggttacccac gtgttactca cccgtccgcc gctcgcttgt       420
atctagtttc atttagtgca agcactaaaa tcatctaggc aagctcgctc gacttgcatg       480
tattaggcac gccgccagcg ttcgtcctga gcca                                   514
```

<210> SEQ ID NO 63
<211> LENGTH: 711
<212> TYPE: DNA
<213> ORGANISM: Lactobacillus johnsonii

<400> SEQUENCE: 63

```
tcctacactt agacggctga ctcctataaa ggttatccca ccggctttgg gtgttacaga        60
ctctcatggt gtgacgggcg tgtgtacaa ggcccgggaa cgtattcacc gcggcgtgct       120
gatccgcgat tactagcgat tccagcttcg tgtaggcgag ttgcagccta cagtccgaac       180
tgagaacggc tttaagagat ccgcttgcct tcgcaggttc gcttctcgtt gtaccgtcca       240
ttgtagcacg tgtgtagccc aggtcataag gggcatgatg acttgacgtc atccccacct       300
```

```
tcctccggtt tgtcaccggc agtctcatta gagtgcccaa cttaatgatg gcaactaatg    360
acaagggttg cgctcgttgc gggacttaac ccaacatctc acgacacgag ctgacgacag    420
ccatgcacca cctgtctcag cgtccccgaa gggaacacct aatctcttag gtttgcactg    480
gatgtcaaga cctggtaagg ttcttcgcgt tgcttcgaat taaaccacat gctccaccgc    540
ttgtgcgggc ccccgtcaat tcctttgagt ttcaaccttg cggtcgtact ccccaggcgg    600
agtgcttaat gcgttagctg cagcactgag aggcggaaac ctcccaacac ttagcactca    660
tcgtttacgg catggactac cagggtatct aatcctgttc gctacccatg c             711
```

```
<210> SEQ ID NO 64
<211> LENGTH: 543
<212> TYPE: DNA
<213> ORGANISM: Lactobacillus reuteri

<400> SEQUENCE: 64
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg cttggctat cactctggga tggacctgcg gtgcattagc    240
tagttggtaa ggtaacggct taccaaggcg atgatgcata gccgagttga gagactgatc    300
ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctt tgttggaga agaacgtgcg tgagagtaac tgttcacgca gtgacggtat    480
ccaaccagaa agtcacggct aactacgtgc cagcagccgc ggtaatacgt aggtggcaag    540
cgt                                                                  543
```

```
<210> SEQ ID NO 65
<211> LENGTH: 628
<212> TYPE: DNA
<213> ORGANISM: Lactobacillus reuteri

<400> SEQUENCE: 65
tatccggatt tattgggcgt aaagcgagcg caggcggttg cttaggtctg atgtgaaagc     60
cttcggctta accgaagaag tgcatcggaa accgggcgac ttgagtgcag aagaggacag    120
tggaactcca tgtgtagcgg tggaatgcgt agatatatgg aagaacacca gtggcgaagg    180
cggctgtctg gtctgcaact gacgctgagg ctcgaaagca tgggtagcga acaggattag    240
ataccctggt agtccatgcc gtaaacgatg agtgctaggt gttggagggt ttccgccctt    300
cagtgccgga gctaacgcat taagcactcc gcctggggag tacgaccgca aggttgaaac    360
tcaaaggaat tgacggggc ccgcacaagc ggtggagcat gtggtttaat tcgaagctac    420
gcgaagaacc ttaccaggtc ttgacatctt gcgctaacct agagataag gcgttccctt    480 cggggacgca atgacaggtg gtgcatggtc gtcgtcagct cgtgtcgtga gatgttgggt    540
taagtcccgc aacgagcgca accccttgtta ctagttgcca gcattaagtt gggcactcta    600
gtgagactgc cggtgacaaa ccggagga                                       628
```

```
<210> SEQ ID NO 66
<211> LENGTH: 557
<212> TYPE: DNA
<213> ORGANISM: Lactobacillus reuteri

<400> SEQUENCE: 66
```

```
gtggagcatg tggtttaatt cgaagctacg cgaagaacct taccaggtct tgacatcttg    60
cgctaacctt agagataagg cgttcccttc ggggacgcaa tgacaggtgg tgcatggtcg   120
tcgtcagctc gtgtcgtgag atgttgggtt aagtcccgca acgagcgcaa cccttgttac   180
tagttgccag cattaagttg ggcactctag tgagactgcc ggtgacaaac cggaggaagg   240
tggggacgac gtcagatcat catgcccctt atgacctggg ctacacacgt gctacaatgg   300
acggtacaac gagtcgcaag ctcgcgagag taagctaatc tcttaaagcc gttctcagtt   360
cggactgtag gctgcaactc gcctacacga gtcggaatc gctagtaatc gcggatcagc   420
atgccgcggt gaatacgttc ccgggccttg tacacaccgc ccgtcacacc atgggagttt   480
gtaacgccca agtcggtgg cctaaccatt atggagggag ccgcctaagg cgggacagat   540
gactggggtg aagtcgt                                                  557

<210> SEQ ID NO 67
<211> LENGTH: 619
<212> TYPE: DNA
<213> ORGANISM: Lactobacillus reuteri

<400> SEQUENCE: 67
tactccccag gcggagtgct taatgcgtta gctccggcac tgaagggcgg aaaccctcca    60
acacctagca ctcatcgttt acggcatgga ctaccagggt atctaatcct gttcgctacc   120
catgctttcg agcctcagcg tcagttgcag accagacagc cgccttcgcc actggtgttc   180
ttccatatat ctacgcattc caccgctaca catggagttc cactgtcctc ttctgcactc   240
aagtcgcccg gtttccgatg cacttcttcg gttaagccga aggctttcac atcagaccta   300
agcaaccgcc tgcgctcgct ttacgcccaa taaatccgga taacgcttgc cacctacgta   360
ttaccgcggc tgctggcacg tagttagccg tgactttctg gttggatacc gtcactgcgt   420
gaacagttac tctcacgcac gttcttctcc aacaacagag ctttacgagc cgaaaccctt   480
cttcactcac gcggtgttgc tccatcaggc ttgcgcccat tgtggaagat tccctactgc   540
tgcctcccgt aggagtatgg accgtgtctc agttccattg tggccgatca gtctctcaac   600
tcggctatgc atcatcgcc                                               619

<210> SEQ ID NO 68
<211> LENGTH: 509
<212> TYPE: DNA
<213> ORGANISM: Lactobacillus reuteri

<400> SEQUENCE: 68
gtgactttct ggttggatac cgtcactgcg tgaacagtta ctctcacgca cgttcttctc    60
caacaacaga gctttacgag ccgaaaccct tcttcactca cgcggtgttg ctccatcagg   120
cttgcgccca ttgtggaaga ttccctactg ctgcctcccg taggagtatg gaccgtgtct   180
cagttccatt gtggccgatc agtctctcaa ctcggctatg catcatcgcc ttggtaagcc   240
gttaccttac caactagcta atgcaccgca ggtccatccc agagtgatag ccaaagccat   300
ctttcaaaca aaagccatgt ggcttttgtt gttatgcggt attagcatct gtttccaaat   360
gttatccccc gctccggggc aggttaccta cgtgttactc acccgtccgc cactcactgg   420
tgatccatcg tcaatcaggt gcaagcacca tcaatcagtt gggccagtgc gtacgacttg   480
catgtattag gcacaccgcc ggcgttcat                                    509

<210> SEQ ID NO 69
```

```
<211> LENGTH: 590
<212> TYPE: DNA
<213> ORGANISM: Lactobacillus reuteri

<400> SEQUENCE: 69
tcccgcctta ggcggctccc tccataatgg ttaggccacc gactttgggc gttacaaact    60
cccatggtgt gacgggcggt gtgtacaagg cccgggaacg tattcaccgc ggcatgctga   120
tccgcgatta ctagcgattc cgacttcgtg taggcgagtt gcagcctaca gtccgaactg   180
agaacggctt taagagatta gcttactctc gcgagcttgc gactcgttgt accgtccatt   240
gtagcacgtg tgtagcccag gtcataaggg gcatgatgat ctgacgtcgt ccccaccttc   300
ctccggtttg tcaccggcag tctcactaga gtgcccaact taatgctggc aactagtaac   360
aagggttgcg ctcgttgcgg gacttaaccc aacatctcac gacacgagct gacgacgacc   420
atgcaccacc tgtcattgcg tccccgaagg gaacgcctta tctctaaggt tagcgcaaga   480
tgtcaagacc tggtaaggtt cttcgcgtag cttcgaatta aaccacatgc tccaccgctt   540
gtgcgggccc ccgtcaattc ctttgagttt caaccttgcg gtcgtactcc                590

<210> SEQ ID NO 70
<211> LENGTH: 666
<212> TYPE: DNA
<213> ORGANISM: Lactobacillus plantarum

<400> SEQUENCE: 70
gtgcctaata catgcaagtc gaacgaactc tggtattgat tggtgcttgc atcatgattt    60
acatttgagt gagtggcgaa ctggtgagta acacgtggga aacctgccca gaagcggggg   120
ataacacctg gaaacagatg ctaataccgc ataacaactt ggaccgcatg gtccgagttt   180
gaaagatggc ttcggctatc acttttggat ggtcccgcgg cgtattagct agatggtgag   240
gtaacggctc accatggcaa tgatacgtag ccgacctgag agggtaatcg ccacattgg   300
gactgagaca cggcccaaac tcctacggga ggcagcagta gggaatcttc cacaatggac   360
gaaagtctga tggagcaacg ccgcgtgagt gaagaagggt ttcggctcgt aaaactctgt   420
tgttaaagaa gaacatatct gagagtaact gttcaggtat tgacggtatt taaccagaaa   480
gccacggcta actacgtgcc agcagccgcg gtaatacgta ggtggcaagc gttgtccgga   540
tttattgggc gtaaagcgag cgcaggcggt tttttaagtc tgatgtgaaa gccttcggct   600
caaccgaaga agtgcatcgg aaactgggaa acttgagtgc agaagaggac agtggaactc   660
atgtgt                                                               666

<210> SEQ ID NO 71
<211> LENGTH: 677
<212> TYPE: DNA
<213> ORGANISM: Lactobacillus plantarum

<400> SEQUENCE: 71
tccggattta ttgggcgtaa agcgagcgca ggcggttttt taagtctgat gtgaaagcct    60
tcggctcaac cgaagaagtg catcggaaac tgggaaactt gagtgcagaa gaggacagtg   120
gaactccatg tgtagcggtg aaatgcgtag atatatggaa gaacaccagt ggcgaaggcg   180
gctgtctggt ctgtaactga cgctgaggct cgaaagtatg ggtagcaaac aggattagat   240
accctggtag tccataccgt aaacgatgaa tgctaagtgt tggagggttt ccgcccttca   300
gtgctgcagc taacgcatta agcattccgc ctggggagta cggccgcaag gctgaaactc   360
aaaggaattg acgggggccc gcacaagcgg tggagcatgt ggtttaattc gaagctacgc   420
```

```
gaagaacctt accaggtctt gacatactat gcaaatctaa gagattagac gttcccttcg    480
gggacatgga tacaggtggt gcatggttgt cgtcagctcg tgtcgtgaga tgttgggtta    540
agtcccgcaa cgagcgcaac ccttattatc agttgccagc attaagttgg gcactctggt    600
gagactgccg gtgacaaacc ggaggaaggt ggggatgacg tcaaatcatc atgccctta     660 tgacctgggc tacacac                                                   677
```

```
<210> SEQ ID NO 72
<211> LENGTH: 574
<212> TYPE: DNA
<213> ORGANISM: Lactobacillus plantarum

<400> SEQUENCE: 72
ggtggagcat gtggtttaat tcgaagctac gcgaagaacc ttaccaggtc ttgacatact     60
atgcaaatct aagagattag acgttccctt cggggacatg gatacaggtg gtgcatggtt   120
gtcgtcagct cgtgtcgtga gatgttgggt taagtcccgc aacgagcgca acccttatta   180
tcagttgcca gcattaagtt gggcactctg gtgagactgc cggtgacaaa ccggaggaag   240
gtggggatga cgtcaaatca tcatgcccct tatgacctgg gctacacacg tgctacaatg   300
gatggtacaa cgagttgcga actcgcgaga gtaagctaat ctcttaaagc cattctcagt   360
tcggattgta ggctgcaact cgcctacatg aagtcggaat cgctagtaat cgcggatcag   420
catgccgcgg tgaatacgtt cccgggcctt gtacacaccg cccgtcacac catgagagtt   480
tgtaacaccc aaagtcggtg gggtaacctt ttaggaacca gccgcctaag gtgggacaga   540
tgattacggt gaagtcgtaa caaggtagcc cgta                                574
```

```
<210> SEQ ID NO 73
<211> LENGTH: 679
<212> TYPE: DNA
<213> ORGANISM: Lactobacillus plantarum

<400> SEQUENCE: 73
gtactcccca ggcggaatgc ttaatgcgtt agctgcagca ctgaagggcg gaaaccctcc     60
aacacttagc attcatcgtt tacggtatgg actaccaggg tatctaatcc tgtttgctac   120
ccatactttc gagcctcagc gtcagttaca gaccagacag ccgccttcgc cactggtgtt   180
cttccatata tctacgcatt tcaccgctac acatggagtt ccactgtcct cttctgcact   240
caagtttccc agtttccgat gcacttcttc ggttgagccg aaggctttca catcagactt   300
aaaaaaccgc ctgcgctcgc tttacgccca ataaatccgg acaacgcttg ccacctacgt   360
attaccgcgg ctgctggcac gtagttagcc gtggctttct ggttaaatac cgtcaatacc   420
tgaacagtta ctctcagata tgttcttctt taacaacaga gttttacgag ccgaaaccct   480
tcttcactca cgcggcgttg ctccatcaga ctttcgtcca ttgtggaaga ttccctactg   540
ctgcctcccg taggagtttg ggccgtgtct cagtcccaat gtggccgatt accctctcag   600
gtcggctacg tatcattgcc atggtgagcc gttacctcac catctagcta atacgccgcg   660
ggaccatcca aaagtgata                                                 679
```

```
<210> SEQ ID NO 74
<211> LENGTH: 521
<212> TYPE: DNA
<213> ORGANISM: Lactobacillus plantarum

<400> SEQUENCE: 74
```

-continued

```
tggctttctg gttaaatacc gtcaatacct gaacagttac tctcagatat gttcttcttt    60
aacaacagag ttttacgagc cgaaacccct tcttcactcac gcggcgttgc tccatcagac   120
tttcgtccat tgtggaagat tccctactgc tgcctcccgt aggagtttgg gccgtgtctc   180
agtcccaatg tggccgatta ccctctcagg tcggctacgt atcattgcca tggtgagccg   240
ttacctcacc atctagctaa tacgccgcgg gaccatctaa aagtgatagc cgaagccatc   300
tttcaaactc ggaccatgcg gtccaagttg ttatgcggta ttagcatctg tttccaggtg   360 ttatccccccg cttctgggca ggtttcccac gtgttactca ccagttcgcc actcactcaa   420
atgtaaatca tgatgcaagc accaatcaat accagagttc gttcgacttg catgtattag   480
gcacgccgcc agcgttcgtc ctgagccatg atcaaactct a                        521
```

<210> SEQ ID NO 75
<211> LENGTH: 639
<212> TYPE: DNA
<213> ORGANISM: Lactobacillus plantarum

<400> SEQUENCE: 75

```
acttaggcgg ctggttccta aaaggttacc ccaccgactt tgggtgttac aaactctcat    60
ggtgtgacgg gcggtgtgta caaggcccgg gaacgtattc accgcggcat gctgatccgc   120
gattactagc gattccgact tcatgtaggc gagttgcagc ctacaatccg aactgagaat   180
ggctttaaga gattagctta ctctcgcgag ttcgcaactc gttgtaccat ccattgtagc   240
acgtgtgtag cccaggtcat aaggggcatg atgatttgac gtcatcccca ccttcctccg   300
gtttgtcacc ggcagtctca ccagagtgcc caacttaatg ctggcaactg ataataaggg   360
ttgcgctcgt tgcgggactt aacccaacat ctcacgacac gagctgacga caaccatgca   420
ccacctgtat ccatgtcccc gaagggaacg tctaatctct tagatttgca tagtatgtca   480
agacctggta aggttcttcg cgtagcttcg aattaaacca catgctccac cgcttgtgcg   540
ggcccccgtc aattcctttg agtttcagcc ttgcggccgt actccccagg cggaatgctt   600
aatgcgttag ctgcagcact gaagggcgga aaccctcca                          639
```

<210> SEQ ID NO 76
<211> LENGTH: 644
<212> TYPE: DNA
<213> ORGANISM: Lactobacillus reuteri

<400> SEQUENCE: 76

```
taatacatgc aagtcgtacg cactggccca actgattgat ggtgcttgca cctgattgac    60
gatggatcac cagtgagtgg cggacgggtg agtaacacgt aggtaacctg ccccggagcg   120
ggggataaca tttggaaaca gatgctaata ccgcataaca acaaaagcca catggctttt   180
gtttgaaaga tggctttggc tatcactctg ggatggacct gcggtgcatt agctagttgg   240
taaggtaacg gcttaccaag gcgatgatgc atagccgagt tgagagactg atcggccaca   300
atggaactga gacacggtcc atactcctac gggaggcagc agtagggaat cttccacaat   360
gggcgcaagc ctgatggagc aacaccgcgt gagtgaagaa gggtttcggc tcgtaaagct   420
ctgttgttgg agaagaacgt gcgtgagagt aactgttcac gcagtgacgg tatccaacca   480
gaaagtcacg gctaactacg tgccagcagc cgcggtaata cgtaggtggc aagcgtgatc   540
cggatttatt gggcgtaaag cgagcgcagg cggttgctta ggtctgatgt gaaagccttc   600
ggcttaaccg aagaagtgca tcggagacgg gcgacttgag tgca                    644
```

<210> SEQ ID NO 77
<211> LENGTH: 507
<212> TYPE: DNA
<213> ORGANISM: Lactobacillus reuteri
<220> FEATURE:
<221> NAME/KEY: modified_base
<222> LOCATION: (464)..(464)
<223> OTHER INFORMATION: a, c, t, g, unknown or other

<400> SEQUENCE: 77

```
ttatccggat ttattgggcg taaagcgagc gcaggcggtt gcttaggtct gatgtgaaag    60
ccttcggctt aaccgaagaa gtgcatcgga aaccgggcga cttgagtgca gaagaggaca   120
gtggaactcc atgtgtagcg gtggaatgcg tagatatatg gaagaacacc agtggcgaag   180
gcggctgtct ggtctgcaac tgacgctgag gctcgaaagc atgggtagcg aacaggatta   240
gataccctgg tagtccatgc cgtaaacgat gagtgctagg tgttgagggt ttccgccct    300 tcagtgccgg agctaacgca ttaagcactc cgcctgggga gtacgaccgc aaggttgaaa   360
cgcaaaggaa ttgacggggg cccgcacaag cggtggagca gtggtttaa ttcgaagcta    420 cgcgaagaac cttaccaggt cttgacatct tgcgctaacc ttanaaggcg tccccttcgg   480
ggactcaatg acaggtggtg catggtt                                      507
```

<210> SEQ ID NO 78
<211> LENGTH: 568
<212> TYPE: DNA
<213> ORGANISM: Lactobacillus reuteri

<400> SEQUENCE: 78

```
ggtggagcat gtggtttaat tcgaagctac gcgaagaacc ttaccaggtc ttgacatctt    60
gcgctaacct tagagataag gcgttcccctt cggggacgca atgacaggtg gtgcatggtc   120
gtcgtcagct cgtgtcgtga gatgttgggt taagtcccgc aacgagcgca acccttgtta   180
ctagttgcca gcattaagtt gggcactcta gtgagactgc cggtgacaaa ccggaggaag   240
gtggggacga cgtcagatca tcatgcccct tatgacctgg gctacacacg tgctacaatg   300
gacggtacaa cgagtcgcaa gctcgcgaga gtaagctaat ctcttaaagc cgttctcagt   360
tcggactgta ggctgcaact cgcctacacg aagtcggaat cgctagtaat cgcggatcag   420
catgccgcgg tgaatacgtt cccgggcctt gtacacaccg cccgtcacac catgggagtt   480
tgtaacgccc aaagtcggtg gcctaacctt tatggaggga gccgcctaag gcgggacaga   540
tgactggggt gaagtcgtaa caaggtag                                     568
```

<210> SEQ ID NO 79

<400> SEQUENCE: 79

000

<210> SEQ ID NO 80
<211> LENGTH: 518
<212> TYPE: DNA
<213> ORGANISM: Lactobacillus reuteri

<400> SEQUENCE: 80

```
gtgactttct ggttggatac cgtcactgcg tgaacagtta ctctcacgca cgttcttctc    60
caacaacaga gctttacgag ccgaaaccct tcttcactca cgcggtgttg ctccatcagg   120
cttgcgccca ttgtggaaga ttccctactg ctgcctcccg taggagtatg gaccgtgtct   180
cagttccatt gtggccgatc agtctctcaa ctcggctatg catcatcgcc ttggtaagcc   240
```

```
gttaccttac caactagcta atgcaccgca ggtccatccc agagtgatag ccaaagccat      300
ctttcaaaca aaagccatgt ggcttttgtt gttatgcggt attagcatct gtttccaaat      360
gttatccccc gctccggggc aggttaccta cgtgttactc acccgtccgc cactcactgg      420
taatccatcg tcaatcaggt gcaagcacca tcaatcagtt gggccagtgc gtacgacttg      480
catgtattag gcacaccgcc ggcgttcatc ctgagcca                              518

<210> SEQ ID NO 81
<211> LENGTH: 622
<212> TYPE: DNA
<213> ORGANISM: Lactobacillus reuteri

<400> SEQUENCE: 81
ctccctccat aaaggttagg ccaccgactt tgggcgttac aaactcccat ggtgtgacgg       60
gcggtgtgta caaggcccgg gaacgtattc accgcggcat gctgatccgc gattactagc      120
gattccgact tcgtgtaggc gagttgcagc ctacagtccg aactgagaac ggctttaaga      180
gattagctta ctctcgcgag cttgcgactc gttgtaccgt ccattgtagc acgtgtgtag      240
cccaggtcat aagggcatg atgatctgac gtcgtcccca ccttcctccg gtttgtcacc       300
ggcagtctca ctagagtgcc caacttaatg ctggcaacta gtaacaaggg ttgcgctcgt      360
tgcgggactt aacccaacat ctcacgacac gagctgacga cgaccatgca ccacctgtca      420
ttgcgtcccc gaagggaacg ccttatctct aaggttagcg caagatgtca agacctggta      480
aggttcttcg cgtagcttcg aattaaacca catgctccac cgcttgtgcg gccccccgtc      540
aattcctttg agtttcaacc ttggcggtcg tactccccag gcggagtgct taatgcgtta      600
gctccggcac tgaagggcgg aa                                                622

<210> SEQ ID NO 82
<211> LENGTH: 651
<212> TYPE: DNA
<213> ORGANISM: Lactobacillus reuteri

<400> SEQUENCE: 82
gtgtgcctaa tacatgcaag tcgtacgcac tggcccaact gattgatggt gcttgcacct       60
gattgacgat ggatcaccag tgagtggcgg acgggtgagt aacacgtagg taacctgccc      120
cggagcgggg gataacattt ggaaacagat gctaataccg cataacaaca aaagccacat      180
ggcttttgtt tgaaagatgg ctttggctat cactctggga tggacctgcg gtgcattagc      240
tagttggtaa ggtaacggct taccaaggcg atgatgcata ccgagttga gagactgatc       300 ggccacaatg gaactgagac acggtccata ctcctacggg aggcagcagt agggaatctt      360
ccacaatggg cgcaagcctg atggagcaac accgcgtgag tgaagaaggg tttcggctcg      420
taaagctctg ttgttggaga agaacgtgcg tgagagtaac tgttcacgca gtgacggtat      480
ccaaccagaa agtcacggct aactacgtgc cagcagccgc ggtaatacgt aggtggcaag      540
cgttatccgg atttattggg cgtaaagcga gcgcaggcgg ttgcttaggt ctgatgtgaa      600
agccttcggc ttaaccgaag aagtgcatcg gaaaccgggc gacttgagtg c               651

<210> SEQ ID NO 83
<211> LENGTH: 645
<212> TYPE: DNA
<213> ORGANISM: Lactobacillus reuteri

<400> SEQUENCE: 83
```

```
ttatccggat ttattgggcg taaagcgagc gcaggcggtt gcttaggtct gatgtgaaag      60
ccttcggctt aaccgaagaa gtgcatcgga aaccgggcaa cttgagtgca gaagaggaca     120
gtggaactcc atgtgtagcg gtggaatgcg tagatatatg gaagaacacc agtggcgaag     180
gcggctgtct ggtctgcaac tgacgctgag gctcgaaagc atgggtagcg aacaggatta     240
gataccctgg tagtccatgc cgtaaacgat gagtgctagg tgttggaggg tttccgccct     300
tcagtgccgg agctaacgca ttaagcactc cgcctgggga gtacgaccgc aaggttgaaa     360
ctcaaaggaa ttgacggggg cccgcacaag cggtggagca tgtggtttaa ttcgaagcta     420
cgcgaagaac cttaccaggt cttgacatct gcgctaacct tagagataag gcgtcccctt     480
cggggacgca atgacaggtg gtgcatggtc gtcgtcagct cgtgtcgtga gatgttgggt     540
taagtcccgc aacgagcgca acccttgtta ctagttgcca gcattaagtt gggcactcta     600
gtgagactgc cggtgacaaa ccggaggaag gtggggacga cgtca                    645

<210> SEQ ID NO 84
<211> LENGTH: 573
<212> TYPE: DNA
<213> ORGANISM: Lactobacillus reuteri

<400> SEQUENCE: 84
ggtggagcat gtggtttaat tcgaagctac gcgaagaacc ttaccaggtc ttgacatctt      60
gcgctaacct tagagataag gcgttccctt cggggacgca atgacaggtg gtgcatggtc     120
gtcgtcagct cgtgtcgtga gatgttgggt taagtcccgc aacgagcgca accccttgtta    180 ctagttgcca gcattaagtt gggcactcta gtgagactgc cggtgacaaa ccggaggaag     240
gtggggacga cgtcagatca tcatgcccct tatgacctgg gctacacacg tgctacaatg     300
gacggtacaa cgagtcgcaa gctcgcgaga gtaagctaat ctcttaaagc cgttctcagt     360
tcggactgta ggctgcaact cgcctacacg aagtcggaat cgctagtaat cgcggatcag     420
catgccgcgg tgaatacgtt cccgggcctt gtacacaccg cccgtcacac catgggagtt     480
tgtaacgccc aaagtcggtg gcctaaccat tatggaggga ccgcctaag gcgggacaga     540 tgactggggt gaagtcgtaa caaggtagcc gta                                 573

<210> SEQ ID NO 85
<211> LENGTH: 705
<212> TYPE: DNA
<213> ORGANISM: Lactobacillus reuteri

<400> SEQUENCE: 85
tactccccag gcggagtgct taatgcgtga gctccggcac tgaagggcgg aaaccctcca      60
acacctagca ctcatcgttt acggcatgga ctaccagggt atctaatcct gttcgctacc     120
catgctttcg agcctcagcg tcagttgcag accagacagc cgccttcgcc actggtgttc     180
ttccatatat ctacgcattc caccgctaca catggagttc cactgtcctc ttctgcactc     240
aagtcgcccg gtttccgatg cacttcttcg gttaagccga aggctttcac atcagaccta     300
agcaaccgcc tgcgctcgct ttacgcccaa taaatccgga taacgcttgc cacctacgta     360
ttaccgcggc tgctggcacg tagttagccg tgactttctg gttggatacc gtcactgcgt     420
gaacagttac tctcacgcac gttcttctcc aacaacagag ctttacgagc cgaaacccctt     480 cttcactcac gcggtgttgc tccatcaggc ttgcgcccat tgtggaagat tccctactgc     540
tgcctcccgt aggagtatgg accgtgtctc agttccattg tggccgatca gtctctcaac     600
tcggctatgc atcatcgcct tggtaagccg ttaccttacc aactagctaa tgcaccgcag     660
```

```
gtccatccca gagtgatagc caaagccatc tttcaaacaa aagcc              705
```

<210> SEQ ID NO 86
<211> LENGTH: 527
<212> TYPE: DNA
<213> ORGANISM: Lactobacillus reuteri

<400> SEQUENCE: 86

```
gtgactttct ggttggatac cgtcactgcg tgaacagtta ctctcacgca cgtgcttctc    60
caacaacaga gctttacgag ccgaaaccct tcttcactca cgcggtgttg ctccatcagg   120
cttgcgccca ttgtggaaga ttccctactg ctgcctcccg taggagtatg gaccgtgtct   180
cagttccatt gtggccgatc agtctctcaa ctcggctatg catcatcgcc ttggtaagcc   240
gttaccttac caactagcta atgcaccgca ggtccatccc agagtgatag ccaaagccat   300
ctttcaaaca aagccatgt ggcttttgtt gttatgcggt attagcatct gtttccaaat    360
gttatccccc gctccggggc aggttaccta cgtgttactc acccgtccgc cactcactgg   420
tgatccatcg tcaatcaggt gcaagcacca tcaatcagtt gggccagtgc gtacgacttg   480
catgtattag gcacaccgcc ggcgttcatc ctgagccatg atcaaac                527
```

<210> SEQ ID NO 87
<211> LENGTH: 719
<212> TYPE: DNA
<213> ORGANISM: Lactobacillus reuteri

<400> SEQUENCE: 87

```
tcccgcactt aggcggctcc ctccataatg gttaggccac cgactttggg cgttacaaac    60
tcccatggtg tgacgggcgg tgtgtacaag gcccgggaac gtattcaccg cggcatgctg   120
atccgcgatt actagcgatt ccgacttcgt gtaggcgagt tgcagcctac agtccgaact   180
gagaacggct ttaagagatt agcttactct cgcgagcttg cgactcgttg taccgtccat   240
tgtagcacgt gtgtagccca ggtcataagg ggcatgatga tctgacgtcg tccccacctt   300
cctccggttt gtcaccggca gtctcactag agtgcccaac ttaatgctgg caactagtaa   360
caagggttgc gctcgttgcg ggacttaacc caacatctca cgacacgagc tgacgacgac   420
catgcaccac ctgtcattgc gtccccgaag ggaacgcctt atctctaagg ttagcgcaag   480
atgtcaagac ctggtaaggt tcttcgcgta gcttcgaatt aaaccacatg ctccaccgct   540
tgtgcgggcc cccgtcaatt cctttgagtt tcaaccttgc ggtcgtactc cccaggcgga   600
gtgcttaatg cgttagctcc ggcactgaag ggcggaaacc ctccaacacc tagcactcat   660
cgtttacggc atggactacc agggtatcta atcctgttcg ctacccatgc tttcgagcc   719
```

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 88

```
agagtttgat cctggctcag                                              20
```

<210> SEQ ID NO 89
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 89
acggctacct tgttacgact t                                             21

<210> SEQ ID NO 90
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
attaccgcgg ctgctggcgc ccgccgcgcg cggcgggcgg ggcgggggca cgggggcct    60 acgggaggca gcag                                                     74

<210> SEQ ID NO 91
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagtaggg aatcttccac gcccgccgcg cgcggcgggc ggggcggggg cacgggggga   60
ttycaccgct acacatg                                                  77

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cgcccgccgc gcgcggcggg cggggcgggg gcacgggggg                         40
```